United States Patent
van der Hoek

(10) Patent No.: US 7,803,918 B2
(45) Date of Patent: Sep. 28, 2010

(54) CORONAVIRUS, NUCLEIC ACID, PROTEIN, AND METHODS FOR THE GENERATION OF VACCINE, MEDICAMENTS AND DIAGNOSTICS

(75) Inventor: Cornelia van der Hoek, Diemen (NL)

(73) Assignee: Amsterdam Institute of Viral Genomics B.V., Amsterdam (NL)

( * ) Notice: Subject to any disclaimer, the term of this patent is extended or adjusted under 35 U.S.C. 154(b) by 572 days.

(21) Appl. No.: 10/922,232

(22) Filed: Aug. 18, 2004

(65) Prior Publication Data

US 2006/0024668 A1    Feb. 2, 2006

Related U.S. Application Data

(60) Provisional application No. 60/535,002, filed on Jan. 7, 2004.

(30) Foreign Application Priority Data

Aug. 18, 2003  (EP)  ................................. 03077602
Jan. 7, 2004    (EP)  ................................. 04075050

(51) Int. Cl.
*C07H 21/02* (2006.01)
*C12N 15/00* (2006.01)
*A61K 39/00* (2006.01)
*A61K 39/12* (2006.01)

(52) U.S. Cl. ................ 536/23.1; 435/320.1; 530/185.1; 530/186.1

(58) Field of Classification Search ....................... None
See application file for complete search history.

(56) References Cited

FOREIGN PATENT DOCUMENTS

WO    WO0109290         2/2001
WO    WO 2005/049814 A2 6/2005

OTHER PUBLICATIONS

Thiel V. et al "Infectious RNA transcribed in vitro from a cDNA copy of the human coronavirus genome cloned in vaccinia virus". J Gen Virol. Jun. 2001;82(Pt 6):1273-81.*
Gerna G. et al. "Genetic variability of human coronavirus OC43-, 229E-, and NL63-like strains and their association with lower respiratory tract infections of hospitalized infants and immunocompromised patients". J. Med. Virol. 78:938-949 (2006).*
van der Hoek et al. "Identification of a new human coronavirus". Nat Med. Apr. 2004;10(4):368-73. Epub Mar. 21, 2004.*
Thiel et al., "Infectious RNA transcribed in vitro from a cDNA copy of the human coronavirus genome cloned in vaccinia virus", XP-002203483, Journal of General Virology, vol. 82, pp. 1273-1281, 2001.
XP-002290973, NCBI Protein Accession No, AF304460; VRL Jul. 11, 2001.
XP-002290974, NCBI Accession No. Q05002; VRL Sep. 15, 2003.
XP-002290976, NCBI Protein Accession No. P15423; VRL Jul. 15, 1999.
XP-002290976, NCBI Protein Accession No. P15130; VRL Sep. 15, 2003.
Vabret et al., "Direct diagnosis of human respiratory coronaviruses 229E and O43 by the polymerase chain reaction", XP-002275244, Journal of Virological Methods, vol. 97, pp. 59-66, 2001.
NCBI Accession No. NC_001451; VRL Jun. 24, 2003.
Anand et al., "Coronavirus Main Proteinase (3CLpro) structure: Basis for Design of Anti-SARS Drugs", Science, vol. 300, pp. 1763-1767, 2003.
Ziebuhr et al., "Biosynthesis, Purification, and Characterization of the Human Coronavirus 229E 3C-Like Proteinase", Journal of Virology, vol. 71, No. 5, pp. 3992-3997, 1997.
van der Hoek et al., "Identification of a new human coronavirus", Nature Medicine, vol. 10, No. 4, pp. 368-373, 2004.
Fouchier et al., "A previously undescribed coronavirus associated with respiratory disease in humans", PNAS, vol. 101, No. 16, pp. 6212-6216, 2004.

\* cited by examiner

*Primary Examiner*—Bo Peng
(74) *Attorney, Agent, or Firm*—Hoffmann & Baron, LLP

(57) ABSTRACT

A new coronavirus is disclosed herein with a tropism that includes humans. Means and methods are provided for diagnosing subjects (previously) infected with the virus. Also provided are among others vacines, medicaments, nucleic acids and specific binding members.

26 Claims, 38 Drawing Sheets

Fig. 2
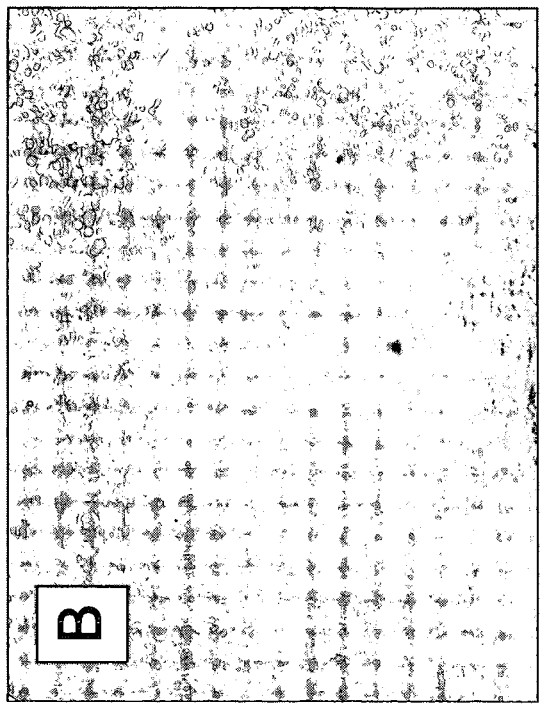
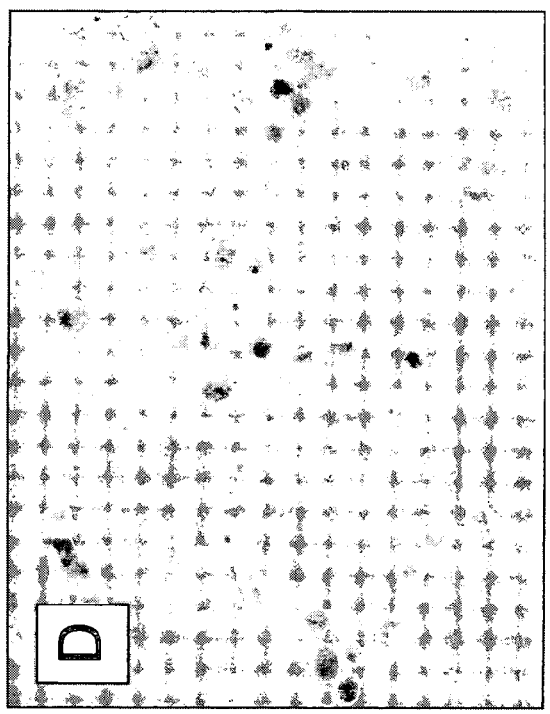
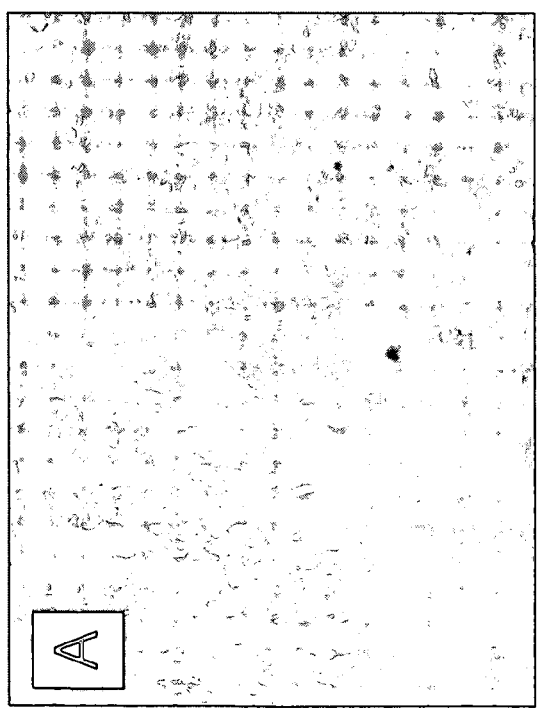
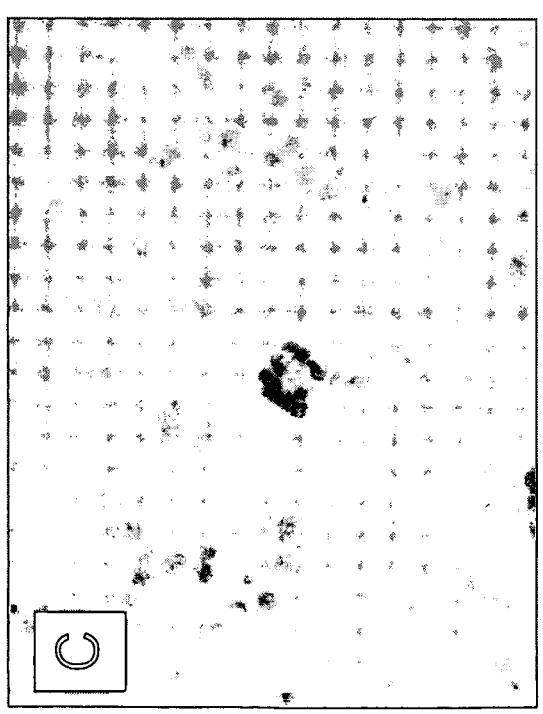

HCoV-NL63

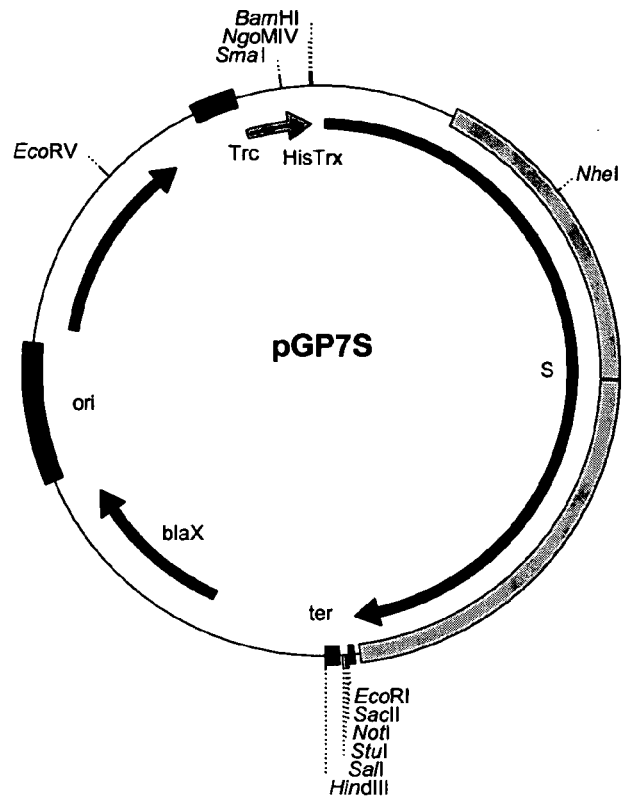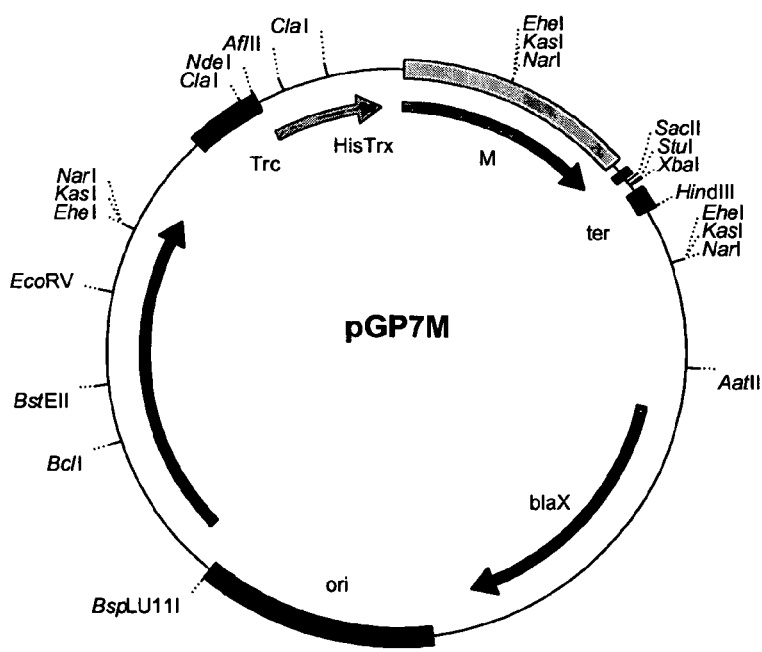
Fig. 8

TCATCCTAATTGTTGTGACTGTTATGATGATATGTGTGTTATACATTGTTCAAATTTTAACA
CACTCTT (SEQ ID NO:38)

Fig. 9

Chimera NL63/229E

CAACGTATGTGTTTGGAACCTTGTAATTTATATAATTATGGGAAGCCAGTTACTTTGCCT
(SEQ ID NO:39)

Fig. 11

Chimera NL63/OC43

Sequence variation in HCoV-NL63 from additional patient samples

```
                    1                                                          60
REF      (1)    TAATAATGCTGTCTATGATGGTGCTCGTTTATTTTCTTCAGATTTGTCTACTTTAGCTGT
223_B    (1)    TAATAATGCTGTCTATGATGGTGCTCGTTTATCTGCTTCAGATTTGTCTACTTTAGCTGT   (SEQ ID NO:41)
246_B    (1)    TAATAATGCTGTCTATGATGGTGCTCGTTTATTTTCTTCAGATTTGTCTACTTTAGCTGT   (SEQ ID NO:42)
248_B    (1)    TAATAATGCTGTCTATGATGGTGCTCGTTTATTTGCTTCAGATTTGTCTACTTTAGCTGT   (SEQ ID NO:43)
251_B    (1)    TAATAATGCTGTCTATGATGGTGCTCGTTTATTTTCTTCAGATTTGTCTACTTTAGCTGT   (SEQ ID NO:44)
466_B    (1)    TAATAATGCTGTCTATGATGGTGCTCGTTTATTTTCTTCAGATTTGTCTACTTTAGCTGT   (SEQ ID NO:40)
496_B    (1)    TAATAATGCTGTCTATGATGGTGCTCGTTTATTTGCTTCAGATTTGTCTACTTTAGCTGT   (SEQ ID NO:45)
                    61                                                         120
REF      (61)   TACAGCTATTGTTGTAGTAGGTGGTTGTGTAACATCTAATGTTCCAACAATTGTTAGTGA
223_B    (61)   TACAGCTATTGTTGTAGTAGGTGGTTGTGTAACATCTAATGTTCCACCAATTGTTAGTGA
246_B    (61)   TACAGCTATTGTTGTAGTAGGTGGTTGTGTAACATCTAATGTTCCACCAATTGTTAGTGA
248_B    (61)   TACAGCTATTGTTGTAGTAGGTGGTTGTGTAACATCTAATGTTCCACCAATTGTTAGTGA
251_B    (61)   TACAGCTATTGTTGTAGTAGGTGGTTGTGTAACATCTAATGTTCCACCAATTGTTAGTGA
466_B    (61)   TACAGCTATTGTTGTAGTAGGTGGTTGTGTAACATCTAATGTTCCAACAATTGTTAGTGA
496_B    (61)   TACAGCTATTGTTGTAGTAGGTGGTTGTGTAACATCTAATGTTCCATCAATTGTTAGTGA
                    121                                                        180
REF      (121)  GAAAATTTCTGTTATGGATAAACTTGATACTGGTGCACAAAAATTTTTCCAATTGGTGA
223_B    (121)  GAAAATTTCTGTTATGGATAAACTTGATACTGGTGCACAAAAATTTTTCCAATTGGTGA
246_B    (121)  GAAAATTTCTGTTATGGATAAACTTGATACTGGTGCACAAAAATTTTTCCAATTGGTGA
248_B    (121)  GAAAATTTCTGTTATGGATAAACTTGATACTGGTGCACAAAAATTTTTCCAATTGGTGA
251_B    (121)  GAAAATTTCTGTTATGGATAAACTTGATACTGGTGCACAAAAATTTTTCCAATTGGTGA
466_B    (121)  GAAAATTTCTGTTATGGATAAACTTGATACTGGTGCACAAAAATTTTTCCAATTGGTGA
496_B    (121)  GAAAATTTCTGTTATGGATAAACTTGATACTGGTGCACAAAAATTTTTCCAATTGGTGA
                    181                                                        240
REF      (181)  TTTTGTTATGAATAACATTGTTCTGTTTTAACTTGGTTGCTTAGTATGTTTAGTCTTT
223_B    (181)  TTTTGTTATGAATAACATTGTTCTGTTTTAACTTGGTTGCTTAGTATGTTTAGTCTTT
246_B    (181)  TTTTGTTATGAATAACATTGTTCTGTTTTAACTTGGTTGCTTAGTATGTTTAGTCTTT
248_B    (181)  TTTTGTTATGAATAACATTGTTCTGTTTTAACTTGGTTGCTTAGTATGTTTAGTCTTT
251_B    (181)  TTTTGTTATGAATAACATTGTTCTGTTTTAACTTGGTTGCTTAGTATGTTTAGTCTTT
466_B    (181)  TTTTGTTATGAATAACATTGTTCTGTTTTAACTTGGTTGCTTAGTATGTTTAGTCTTT
496_B    (181)  TTTTGTTATGAATAACATTGTTCTGTTTTAACTTGGTTGCTTAGTATGTTTAGTCTTT
                    241                                                        300
REF      (241)  ACGTACTTCTATTATGAAGCATGATATTAAAGTTATTGCCAAGGCTCCTAAACGTACAGG
223_B    (241)  ACGTACTTCTATTATGAAGCATGATATTAAAGTTATTGCCAAGGCTCCTAAACGTACAGG
246_B    (241)  ACGTACTTCTATTATGAAGCATGATATTAAAGTTATTGCCAAGGCTCCTAAACGTACAGG
248_B    (241)  ACGTACTTCTATTATGAAGCATGATATTAAAGTTATTGCCAAGGCTCCTAAACGTACAGG
251_B    (241)  ACGTACTTCTATTATGAAGCATGATATTAAAGTTATTGCCAAGGCTCCTAAACGTACAGG
466_B    (241)  ACGTACTTCTATTATGAAGCATGATATTAAAGTTATTGCCAAGGCTCCTAAACGTACAGG
496_B    (241)  ACGTACTTCTATTATGAAGCATGATATTAAAGTTATTGCCAAGGCTCCTAAACGTACAGG
                    301                                                        360
REF      (301)  TGTTATTTTGACACGTAGTTTAAGTATAACATTAGATCTGCTTTGTTTGTTATAAAGCA
223_B    (301)  TGTTATTTTGACACGTAGTTTAAGTATAACATTAGATCTGCTTTGTTTGTTATAAAGCA
246_B    (301)  TGTTATTTTGACACGTAGTTTAAGTATAACATTAGATCTGCTTTGTTTGTTATAAAGCA
248_B    (301)  TGTTATTTTGACACGTAGTTTAAGTATAACATTAGATCTGCTTTGTTTGTTGTAAAGCA
251_B    (301)  TGTTATTTTGACACGTAGTTTAAGTATAACATTAGATCTGCTTTGTTTGTTATAAAGCA
466_B    (301)  TGTTATTTTGACACGTAGTTTAAGTATAACATTAGATCTGCTTTGTTTGTTATAAAGCA
496_B    (301)  TGTTATTTTGACACGTAGTTTAAGTATAACATTAGATCTGCTTTGTTTGTTATAAAGCA
                    361                                                        420
REF      (361)  GAAGTGGTGTGTTATTGTTACTTTGTTTAAGTTCTTATTATTATTATATGCTATTTATGC
223_B    (361)  GAAGTGGTGTGTTATTGTTACTTTGTTTAAGTTCTTATTGTTATTATATGCTATTTATGC
246_B    (361)  GAAGTGGTGTGTTATTGTTACTTTGTTTAAGTTCTTATTGTTATTATATGCTATTTATGC
248_B    (361)  GAAGTGGTGTGTTATTGTTACTTTGTTTAAGTTCTTATTGTTATTATATGCTATTTATGC
251_B    (361)  GAAGTGGTGTGTTATTGTTACTTTGTTTAAGTTCTTATTATTATTATATGCTATTTATGC
466_B    (361)  GAAGTGGTGTGTTATTGTTACTTTGTTTAAGTTCTTATTATTATTATATGCTATTTATGC
496_B    (361)  GAAGTGGTGTGTTATTGTTACTTTGTTTAAGTTCTTATTGTTATTATATGCTATTTATGC
                    421                                       466
REF      (421)  ACTTGTTTTTATGATTGTGCAATTTAGTCCTTTTAATAGTCTTTTA
223_B    (421)  ACTTGTTTTTATGATTGTGCAATTTAGTCCTTTTAATAGTCTTTTA
246_B    (421)  ACTTGTTTTTATGATTGTGCAATTTAGTCCTTTTAATAGTCTTTTA
248_B    (421)  ACTTGTTTTTATGATTGTGCAATTTAGTCCTTTTAATAGTCTTTTA
251_B    (421)  ACTTGTTTTTATGATTGTGCAATTTAGTCCTTTTAATAGTCTTTTA
466_B    (421)  ACTTGTTTTTATGATTGTGCAATTTAGTCCTTTTAATAGTCTTTTA
496_B    (421)  ACTTGTTTTTATGATTGTGCAATTTAGTCCTTTTAATAGTCTTTTA
```

Fig. 17

HCoV-NL63 Nucleocapsid (N) specific PCR primers

| Oligo | Sequence | T$_m$ | Amplicon |
|---|---|---|---|
| NL63NF1 | GCTAGTGTAAATTGGGCCGATG (SEQ ID NO:46) | 55.3 | |
| NL63NR1 | CTTCCAACGAGGTTCTTCAACTG (SEQ ID NO:47) | 56.0 | 708 |
| NL63NF2 | TCCTCCTCCTTCATTTTACATGCC (SEQ ID NO:48) | 57.4 | 372 |
| NL63NR2 | AACTCAAACAACAGAGAGCTCTGGAG (SEQ ID NO:49) | 55.1 | |

Fig. 18

Generic Coronavirus detection primers

| Oligo | Sequence | $T_m$ | Amplicon |
|---|---|---|---|
| COR1F | ATGGGWTGGGAYTATCCIAARTGTGA (SEQ ID NO:50) | 60.6 | 603 |
| COR1R | GYTGKGARCARAAYTCRTGWGGTCC (SEQ ID NO:51) | 60.7 | |
| COR2F | TATKTTAARCCWGGTGGIAC (SEQ ID NO:52) | 46.1 | 362 |
| COR2R | CATRAANACRYYATTYTGRTAATA (SEQ ID NO:53) | 46.7 | |

Fig. 19

Nucleotide sequence HcoV_NL63

```
CTTAAAGAATTTTTCTATCTATAGATAGAGAATTTTCTTATTTAGACTTTGTGTCTACTC
TTCTCAACTAAACGAAATTTTTCTAGTGCTGTCATTTGTTATGGCAGTCCTAGTGTAATT
GAAATTTCGTCAAGTTTGTAAACTGGTTAGGCAAGTGTTGTATTTTCTGTGTCTAAGCAC
TGGTGATTCTGTTCACTAGTGCATACATTGATATTTAAGTGGTGTTCCGTCACTGCTTAT
TGTGGAAGCAACGTTCTGTCGTTGTGGAAACCAATAACTGCTAACCATGTTTTACAATCA
AGTGACACTTGCTGTTGCAAGTGATTCGGAAATTTCAGGTTTTGGTTTTGCCATTCCTTC
TGTAGCCGTTCGCACCTATAGCGAAGCCGCTGCACAAGGTTTTCAGGCATGCCGTTTTGT
TGCTTTTGGCTTACAGGATTGTGTAACCGGTATTAATGATGATGATTATGTCATTGCATT
GACTGGTACTAATCAGCTCTGTGCCAAAATTTTACCTTTTTCTGATAGACCCCTTAATTT
GCGAGGTTGGCTCATTTTTCTAACAGCAATTATGTTCTTCAGGACTTTGATGTTGTTTT
TGGCCATGGTGCAGGAAGTGTGGTTTTTGTGGATAAGTACATGTGTGGTTTTGATGGTAA
ACCTGTGTTACCTAAAAACATGTGGGAATTTAGGGATTACTTTAATAATAATACTGATAG
TATTGTTATTGGTGGTGTCACTTATCAACTAGCATGGGATGTTATACGTAAAGACCTTTC
TTATGAACAGCAAAATGTTTTAGCCATTGAGAGCATTCATTACCTTGGTACTACAGGTCA
TACTTTGAAGTCTGGTTGCAAACTTACTAATGCTAAGCCGCCTAAATATTCTTCTAAGGT
TGTTTTGAGTGGTGAATGGAATGCTGTGTATAGGGCGTTTGGTTCACCATTTATTACAAA
TGGTATGTCATTGCTAGATATAATTGTTAAACCAGTTTTCTTTAATGCTTTTGTTAAATG
CAATTGTGGTTCTGAGAGTTGGAGTGTTGGTGCATGGGATGGTTACTTATCTTCTTGTTG
TGGCACACCTGCTAAGAAACTTTGTGTTGTTCCTGGTAATGTCGTTCCTGGTGATGTGAT
CATCACCTCAACTAGTGCTGGTTGTGGTGTTAAATACTATGCTGGCTTAGTTGTTAAACA
TATTACTAACATTACTGGTGTGTCTTTATGGCGTGTTACAGCTGTTCATTCTGATGGAAT
GTTTGTGGCATCATCTTCTTATGATGCACTCTTGCATAGAAATTCATTAGACCCTTTTTG
CTTTGATGTTAACACTTTACTTTCTAATCAATTACGTCTAGCTTTTCTTGGTGCTTCTGT
TACAGAAGATGTTAAATTTGCTGCTAGCACTGGTGTTATTGACATTAGTGCTGGTATGTT
TGGTCTTTACGATGACATATTGACAAACAATAAACCTTGGTTTGTACGCAAAGCTTCTGG
GCTTTTTGATGCAATCTGGGATGCTTTTGTTGCCGCTATTAAGCTTGTACCAACTACTAC
TGGTGTTTTGGTTAGGTTTGTTAAGTCTATTGCTTCAACTGTTTTAACTGTCTCTAATGG
TGTTATTATTATGTGTGCAGATGTTCCAGATGCTTTTCAATCAGTTTATCGCACATTTAC
ACAAGCTATTTGTGCTGCATTTGATTTTTCTTTAGATGTATTTAAAATTGGTGATGTTAA
ATTTAAACGACTTGGTGATTATGTTCTTACTGAAAACGCTCTTGTTCGTTTGACTACTGA
AGTTGTTCGTGGTGTTCGTGATGCTCGCATAAAGAAAGCCATGTTTACTAAAGTAGTTGT
AGGTCCTACAACTGAAGTTAAGTTTTCTGTTATTGAACTTGCCACTGTTAATTTGCGTCT
TGTTGATTGTGCACCTGTAGTTTGCCCTAAAGGTAAGATTGTTGTTATTGCTGGACAAGC
TTTTTTCTATAGTGGTGGTTTTTATCGTTTATGGTTGATCCTACAACTGTATTAAATGA
TCCTGTTTTTACTGGTGATTTATTCTACACTATTAAGTTTAGTGGTTTTAAGCTTGATGG
TTTTAACCATCAGTTTGTTACTGCTAGTTCTGCTACAGATGCCATTATTGCTGTTGAGCT
GTTGTTATTGGATTTAAAACTGCAGTTTTTGTGTACACATGTGTGGTTGATGGCTGTAG
TGTCATTGTTAGACGTGATGCTACATTCGCTACACATGTGTGTTTAAGGACTGTTATAA
TGTTTGGGAGCAATTCTGCATTGATAATTGTGGTGAGCCATGGTTTTGACTGATTATAA
TGCTATCTTGCAGAGTAATAACCCTCAATGTGCTATTGTTCAAGCATCAGAGTCTAAAGT
TTTGCTTGAGAGGTTTTTACCTAAGTGTCCTGAAATACTGTTGAGTATTGATGATGGCCA
TTTATGGAATCTTTTTGTTGAAAAGTTTAATTTTGTTACAGATTGGTTAAAAACTCTTAA
GCTTACACTTACTTCTAATGGTCTTTTAGGTAATTGTGCCAAACGTTTTAGACGTGTTTT
GGTAAAATTGCTTGATGTCTATAATGGTTTTCTTGAAACTGTCTGTAGTGTCGCATACAC
TGCTGGTGTTTGCATCAAATATTATGCTGTTAATGTTCCATATGTAGTTATTAGTGGTTT
TGTAAGTCGTGTAATTCGTAGAGAAAGGTGTGACATGACTTTTCCTTGTGTTAGTTGTGT
CACCTTTTTCTATGAATTTTAGACACTTGTTTTGGTGTTAGTAAACCTAATGCCATTGA
TGTTGAACATTTAGAGCTTAAAGAAACTGTTTTTGTTGAACCTAAGGATGGTGGTCAATT
TTTTGTTTCTGGTGATTATCTTTGGTATGTTGTAGATGACATTTATTATCCAGCTTCATG
TAATGGTGTATTGCCTGTTGCTTTTACAAAATTAGCTGGTGGTAAAATATCTTTTTCTGA
TGATGTTATAGTTCATGATGTTGAACCTACCCATAAAGTCAAGCTCATATTTGAGTTTGA
AGATGATGTTGTTACCAGTCTTTGTAAGAAGAGTTTTGGTAAGTCCATTATTTATACAGG
```

Fig. 19 cont'd

```
TGATTGGGAAGGTCTACATGAAGTTCTTACATCTGCAATGAATGTCATTGGGCAACATAT
TAAGTTGCCACAATTTTATATTTATGATGAAGAGGGTGGTTATGATGTTTCTAAACCAGT
TATGATTTCACAATGGCCTATTAGTAATGATAGTAATGGTTGTGTTGTTGAAGCGAGCAC
TGATTTTCATCAATTAGAATGTATTGTTGATGACTCTGTTAGAGAAGAGGTTGATATAAT
TGAACAACCTTTTGAAGAAGTTGAACATGTGCTCTCAATTAAGCAACCTTTTTCTTTTTC
TTTTAGAGATGAATTGGGTGTTCGTGTTTTAGATCAATCTGATAATAATTGTTGGATTAG
TACCACACTTGTACAGTTGCAACTTACAAAGCTTTTGGATGATTCTATTGAGATGCAATT
GTTTAAAGTTGGTAAAGTTGATTCAATTGTCCAAAAGTGTTATGAGTTGTCTCATTTAAT
TAGTGGTTCACTTGGTGATAGTGGTAAACTTCTTAGTGAACTTCTTAAAGAAAAATATAC
ATGTTCTATAACTTTTGAGATGTCTTGTGATTGTGGTAAAAAGTTTGATGATCAGGTTGG
TTGTTTGTTTTGGATTATGCCTTACACAAAACTTTTTCAAAAAGGTGAGTGTTGTATTTG
TCATAAAATGCAGACTTATAAGCTTGTTAGTATGAAAGGTACTGGTGTGTTTGTACAGGA
TCCAGCACCTATTGACATTGATGCTTTCCCTGTGAAACCTATATGTTCATCTGTATATTT
AGGTGTTAAGGGTTCTGGTCATTATCAAACAAATTTATACAGTTTTAACAAAGCTATTGA
TGGTTTTGGTGTCTTTGACATTAAAAATAGTAGTGTTAATACTGTTTGTTTTGTTGATGT
TGATTTTCATAGTGTAGAAATAGAAGCTGGTGAAGTTAAACCTTTTGCTGTATATAAAAA
TGTTAAATTTTATTTAGGTGATATTTCACACCTTGTAAACTGTGTTTCTTTTGACTTTGT
TGTCAATGCTGCTAATGAAAATCTCTTGCATGGAGGCGGTGTTGCACGTGCTATTGATAT
TTTGACTGAAGGTCAACTTCAGTCACTATCTAAAGATTACATTAGTAGTAATGGTCCACT
TAAGGTTGGAGCAGGTGTTATGTTGGAGTGTGAAAAATTCAACGTATTTAATGTTGTTGG
TCCGCGAACTGGTAAACATGAGCATTCATTACTTGTTGAAGCTTATAATTCTATTTTATT
TGAAAATGGTATTCCACTTATGCCTCTTCTTAGTTGTGGTATTTTTGGTGTAAGGATTGA
AAATTCTCTTAAAGCTTTGTTTAGTTGTGACATTAATAAACCATTGCAAGTTTTTGTTTA
TTCTTCAAATGAAGAACAAGCTGTTCTTAAGTTTTTAGATGGTTTAGATTTAACACCAGT
CATTGATGATGTTGATGTTGTTAAACCTTTTAGAGTTGAAGGTAATTTTTCATTCTTTGA
TTGTGGTGTCAATGCCTTGGATGGTGATATTTACTTATTATTTACTAACTCTATTTTAAT
GTTGGATAAACAAGGACAATTATTGGACACAAAACTTAATGGTATTTTGCAACAGGCAGC
TCTTGATTATCTTGCTACAGTTAAAACTGTACCAGCTGGTAATTTGGTTAAACTTTTTGT
TGAGAGTTGTACCATTTATATGTGTGTTGTACCATCGATAAATGATCTTTCTTTTGATAA
AAATCTTGGTCGTTGTGTGCGTAAACTTAATAGATTGAAAACTTGTGTTATTGCCAATGT
TCCTGCTATTGATGTTTTGAAAAAGCTTCTTTCAAGTTTGACTTTAACTGTTAAATTTGT
TGTAGAGAGTAATGTTATGGATGTTAACGACTGTTTTAAGAATGATAATGTAGTTTTGAA
AATTACTGAAGATGGTATTAATGTTAAAGATGTTGTTGTTGAGTCTTCTAAGTCACTTGG
TAAACAATTGGGTGTTGTGAGTGATGGTGTTGACTCTTTTGAAGGTGTTTTACCTATTAA
TACTGATACTGTCTTATCTGTAGCTCCAGAAGTTGACTGGGTTGCTTTTTACGGTTTTGA
AAAGGCAGCACTTTTTGCTTCTTTGGATGTAAAGCCATATGGTTACCCTAATGATTTTGT
TGGTGGTTTTAGAGTTCTTGGGACCACCGACAATAATTGTTGGGTTAATGCAACTTGTAT
AATTTTACAGTATCTTAAGCCTACTTTTAAATCTAAGGGTTTAAATGTTCTTTGGAACAA
ATTTGTTACAGGTGATGTTGGACCTTTTGTTAGTTTTATTTATTTTATAACTATGTCTTC
AAAGGGTCAAAAGGGTGATGCTGAAGAGGCATTATCTAAATTGTCAGAGTATTTGATTAG
TGATTCTATTGTTACTCTTGAACAATATTCAACTTGTGACATTTGTAAAAGTACTGTAGT
TGAAGTTAAAAGTGCTATTGTCTGTGCTAGTGTGCTTAAAGATGGTTGTGATGTTGGTTT
TTGTCCACACAGACATAAATTGCGTTCACGTGTTAAGTTTGTTAATGGACGTGTTGTTAT
TACCAATGTTGGTGAACCTATAATTTCACAACCTTCTAAGTTGCTTAATGGTATTGCTTA
TACAACATTTTCAGGTTCTTTTGATAACGGTCACTATGTAGTTTATGATGCTGCTAATAA
TGCTGTCTATGATGGTGCTCGTTTATTTTCTTCAGATTTGTCTACTTTAGCTGTTACAGC
TATTGTTAGTAGGTGGTTGTGTAACATCTAATGTTCCAACAATTGTTAGTGAGAAAAT
TTCTGTTATGATAAACTTGATACTGGTGCACAAAAATTTTTCCAATTTGGTGATTTTGT
TATGAATAACATTGTTCTGTTTTTAACTTGGTTGCTTAGTATGTTTAGTCTTTTACGTAC
TTCTATTATGAAGCATGATATTAAAGTTATTGCCAAGGCTCCTAAACGTACAGGTGTTAT
TTTGACACGTAGTTTTAAGTATAACATTAGATCTGCTTTGTTTGTTATAAAGCAGAAGTG
GTGTGTTATTGTTACTTTGTTTAAGTTCTTATTATTATTATATGCTATTTATGCACTTGT
TTTTATGATTGTGCAATTTAGTCCTTTTAATAGTCTTTTATGTGGTGACATTGTAAGTGG
TTATGAAAAATCCACTTTTAATAAGGATATTTATTGTGGTAATTCTATGGTTTGTAAGAT
GTGTTTGTTCAGTTATCAAGAGTTTAATGATTTGGATCATACTAGTCTTGTTTGGAAGCA
CATTCGTGATCCTATATTAATCAGTTTACAACCATTTGTTATACTTGTTATTTTGTTAAT
```

Fig. 19 cont'd

```
TTTTGGTAATATGTATTTGCGTTTTGGACTTTTATATTTTGTTGCACAATTTATTAGTAC
TTTTGGTTCTTTCTTAGGCTTTCATCAGAAACAGTGGTTTTTACATTTTGTGCCGTTTGA
TGTTTTATGTAATGAGTTTTTAGCTACATTTATTGTCTGCAAAATCGTTTTATTTGTTAG
ACATATTATTGTTGGCTGTAATAATGCTGACTGTGTAGCTTGTTCTAAAAGTGCTAGACT
TAAACGTGTACCACTTCAAACTATTATTAATGGTATGCATAAATCATTCTATGTTAATGC
TAATGGTGGTACTTGTTTCTGTAATAAACATAACTTCTTTTGTGTTAATTGTGATTCTTT
TGGGCCTGGTAATACTTTTATTAATGGTGATATTGCAAGAGAGCTTGGTAATGTTGTTAA
AACAGCTGTTCAACCCACAGCTCCTGCATATGTTATTATTGATAAGGTAGATTTTGTTAA
TGGATTTTATCGTCTTTATAGTGGTGACACTTTTTGGCGGTATGACTTTGACATTACTGA
ATCTAAGTATAGTTGTAAAGAGGTTCTGAAGAATTGTAATGTTTTAGAAAATTTTATTGT
TTACAATAATAGTGGTAGTAACATTACACAGATTAAAAATGCTTGTGTTTATTTTTCTCA
ATTGTTGTGTGAACCTATAAAGTTGGTAAATTCAGAGTTGTTGTCAACTTTATCTGTTGA
TTTTAATGGTGTTTTGCATAAGGCATATGTTGATGTTTTGTGTAATAGTTTTTTTAAGGA
GTTAACTGCTAACATGTCCATGGCTGAATGTAAAGCTACACTTGGTTTGACTGTTTCTGA
TGATGATTTTGTTTCAGCTGTTGCCAATGCACATAGGTATGACGTTTTGCTTTCAGATTT
GTCATTTAATAATTTTTTATTTCTTATGCTAAACCTGAAGATAAGTTGTCCGTTTATGA
CATTGCTTGTTGTATGCGTGCCGGTTCTAAGGTTGTTAACCATAATGTTTTAATTAAAGA
GTCAATACCTATTGTTTGGGGTGTCAAGGACTTTAATACTCTTTCTCAAGAAGGTAAGAA
GTACCTTGTTAAAACAACTAAAGCAAAGGGTTTGACTTTTTTATTAACTTTTAATGATAA
CCAAGCAATTACACAAGTTCCTGCTACTAGTATAGTTGCAAAACAGGGTGCTGGTTTTAA
ACGTACTTATAATTTTCTGTGGTATGTATGTTTATTTGTTGTTGCATTGTTTATTGGTGT
CTCATTTATTGATTATACAACCACTGTAACTAGCTTTCATGGTTATGATTTTAAGTACAT
TGAGAATGGTCAGTTGAAGGTGTTTGAAGCACCTTTACACTGTGTTCGTAATGTTTTTGA
TAATTTTAATCAATGGCATGAGGCTAAGTTTGGTGTTGTTACTACTAATAGTGATAAATG
TCCTATAGTTGTTGGTGTTTCAGAGCGTATTAATGTTGTTCCTGGTGTTCCAACAAATGT
ATATTTGGTAGGAAAGACTCTTGTTTTTACATTACAGGCTGCTTTTGGAAACACAGGTGT
TTGTTATGACTTTGATGGTGTTACCACTAGTGATAAGTGTATTTTTAATTCTGCTTGTAC
TAGGTTGGAAGGTTTGGGTGGTGACAATGTTTATTGTTACAACACTGATCTTATTGAAGG
TTCTAAACCTTATAGTACTTTACAGCCCAATGCGTATTATAAGTATGATGCTAAAAATTA
TGTACGTTTTCCAGAAATTTTAGCTAGAGGTTTTGGCTTACGTACTATTAGAACTTTGGC
TACACGTTATTGTAGAGTTGGTGAATGCCGTGACTCACATAAAGGTGTTTGTTTTGGTTT
TGATAAATGGTATGTTAATGATGGACGTGTTGATGACGGTTACATTTGTGGTGATGGTCT
TATAGACCTTCTTGTTAATGTACTCTCAATCTTTAGTTCATCTTTTAGCGTTGTGGCTAT
GTCTGGACATATGTTGTTTAATTTTCTTTTTGCAGCATTTATTACATTTTGTGCTTTTT
AGTTACTAAATTTAAACGTGTTTTTGGTGATCTTTCTTATGGTGTTTTTACTGTTGTTTG
TGCAACTTTGATTAATAACATTTCTTATGTTGTTACTCAAAATTTATTTTTTATGTTGCT
TTATGCTATTTTGTATTTTGTTTTACTAGGACAGTGCGTTATGCTTGGATTTGGCATAT
TGCATACATTGTTGCATACTTCTTGTTAATACCATGGTGGCTTCTCACATGGTTTAGTTT
TGCTGCATTTTTAGAGCTTTTACCTAATGTTTTAAGTTAAAAATCTCTACTCAATTGTT
TGAAGGTGATAAGTTTATAGGTACTTTTGAGAGTGCTGCTGCAGGTACATTTGTTCTTGA
CATGCGTTCTTATGAAAGGCTGATAAATACTATTTCACCTGAGAAACTTAAGAATTATGC
TGCAAGTTATAATAAATATAAATATTATAGTGGTAGTGCTAGTGAGGCTGATTATCGTTG
TGCTTGTTATGCTCATTTAGCCAAGGCTATGTTAGATTATGCAAAAGATCATAATGACAT
GTTATATTCTCCACCTACTATTAGCTACAATTCCACCTTACAATCTGGTCTTAAGAAGAT
GGCACAACCATCTGGTTGTGTTGAGATGTGTGGTTCGCGTCTGTTATGGTAGTACTGT
GCTTAATGGAGTTTGGTTAGGTGACACTGTTACTTGTCCTAGACATGTCATAGCACCATC
AACCACTGTTCTTATTGATTATGATCATGCATATAGTACTATGCGTTTGCATAATTTTTC
AGTGTCTCATAATGGTGTCTTCTTGGGAGTTGTCGGTGTTACAATGCATGGTTCTGTGTT
GCGTATTAAGGTTTCACAATCTAATGTACATACACCTAAACATGTTTTTAAAACGTTGAA
ACCTGGTGATTCTTTTAATATTTTAGCATGTTATGAAGGTATTGCATCTGGTGTTTTTGG
TGTTAATTTACGTACAAACTTTACTATTAAAGGTTCTTTTATAAATGGAGCTTGTGGTTC
TCCTGGTTATAATGTTAGAAATGATGGTACTGTTGAGTTTTGTTATTTACACCAAATTGA
GTTAGGTAGTGGTGCTCATGTTGGTTCTGATTTTACTGGTAGTGTTTATGGTAATTTGA
TGACCAACCTAGTTTGCAAGTTGAGAGTGCCAACCTTATGCTATCAGATAATGTTGTTGC
CTTTTTGTATGCTGCTTTGTTGAATGGTTGTAGGTGGTGGTTGTGTTCAACTAGAGTTAA
TGTTGATGGTTTTAATGAATGGGCTATGGCTAATGGTTATACAAGTGTTTCTAGTGTTGA
```

Fig. 19 cont'd

```
GTGCTATTCTATTTTGGCAGCAAAAACTGGTGTTAGTGTTGAACAATTGTTAGCTTCCAT
TCAACATCTTCATGAAGGTTTTGGTGGTAAAAACATACTTGGTTATTCTAGTTTATGTGA
TGAGTTCACACTAGCTGAAGTTGTGAAGCAGATGTATGGTGTTAACTTGCAAAGTGGTAA
GGTTATTTTTGGTTTAAAAACAATGTTTTTATTTAGCGTTTTCTTCACAATGTTTTGGGC
AGAACTCTTTATTTATACAAACACTATATGGATAAACCCTGTGATACTTACACCTATATT
TTGTCTACTTTTGTTTTTGTCATTAGTTTTAACTATGTTTCTTAAACATAAGTTTTTGTT
TTTGCAAGTATTTTTATTACCTACTGTTATTGCAACTGCTTTATATAATTGTGTTTTGGA
TTATTACATAGTAAAATTTTTGGCTGACCATTTTAACTATAATGTTTCAGTATTACAAAT
GGATGTTCAGGGTTTAGTTAATGTTTTGGTCTGTTTATTTGTTGTATTTTTACACACATG
GCGCTTTTCTAAAGAACGTTTTACACATTGGTTTACATATGTGTGTTCTCTTATAGCAGT
TGCTTACACTTATTTTTATAGTGGTGACTTTTTGAGTTTGCTTGTTATGTTTTTATGTGC
TATATCTAGTGATTGGTACATTGGTGCCATTGTTTTTAGGTTGTCACGTTTGATTGTATT
TTTTTCACCTGAAAGTGTATTTAGTGTTTTTGGTGATGTGAAACTTACTTTAGTTGTTTA
TTTAATTTGTGGTTATTTAGTTTGTACTTATTGGGGCATTTTGTATTGGTTCAATAGGTT
TTTTAAATGTACTATGGGTGTTTATGATTTTAAGGTGAGTGCTGCTGAATTTAAATACAT
GGTTGCTAATGGACTTCATGCACCACATGGACCTTTTGATGCACTTTGGTTATCATTCAA
ACTACTTGGTATTGGTGGTGACCGTTGTATAAAAATTTCAACTGTCCAATCCAAACTGAC
TGATTTGAAGTGTACTAATGTTGTGTTATTGGGTTGTTTGTCTAGTATGAACATTGCAGC
TAATTCTAGTGAATGGGCTTATTGTGTTGATTTACACAATAAGATTAATCTTTGTGATGA
CCCTGAAAAAGCTCAAAGTATGTTGTTAGCACTCCTTGCGTTCTTTCTAAGTAAACATAG
TGATTTTGGTCTTGATGGCCTTATTGATTCTTATTTTGATAATAGTAGCACCCTTCAGAG
TGTTGCTTCATCATTTGTTAGTATGCCATCATATATTGCTTATGAAAATGCTAGACAAGC
TTATGAGGATGCTATTCTAATGGATCTTCTTCTCAACTTATTAAACAATTGAAGCGTGC
CATGAATATCGCAAAGTCTGAATTTGATCATGAGATATCTGTTCAGAAGAAAATTAATAG
AATGGCTGAACAAGCTGCTACTCAGATGTATAAAGAAGCACGCTCTGTTAATAGAAAATC
TAAAGTTATTAGTGCTATGCACTCTTTACTTTTTGGAATGTTAAGACGTTTGGATATGTC
TAGTGTTGAAACTGTTTTGAATTTAGCACGTGATGGTGTTGTGCCATTGTCAGTTATACC
TGCAACTTCAGCTTCTAAACTAACTATTGTTAGTCCAGATCTTGAATCTTATTCTAAGAT
TGTTTGTGATGGTTCTGTTCATTATGCTGGAGTTGTTTGGACACTTAATGATGTTAAAGA
CAATGATGGTAGACCTGTTCATGTTAAAGAGATTACAAAGGAAAATGTTGAAACTTTGAC
ATGGCCTCTTATCCTTAATTGTGAACGTGTTGTTAAACTTCAAAATAATGAAATTATGCC
TGGTAAACTTAAGCAAAAACCTATGAAAGCTGAGGGTGATGGTGGTGTTTTAGGTGATGG
TAATGCCTTGTATAATACTGAGGGTGGTAAAACTTTTATGTACGCTTATATTTCTAATAA
AGCTGACCTTAAATTTGTTAAGTGGGAGTATGAGGGTGGTTGCAACACAATCGAGTTAGA
CTCTCCTTGTCGATTTATGGTCGAAACACCTAATGGTCCTCAAGTGAAGTATTTGTATTT
TGTTAAAAATTTAAATACCTTACGTAGAGGTGCCGTTCTTGGTTTTATAGGTGCCACAAT
TCGTCTACAAGCTGGTAAACAAACTGAATTGGCTGTTAATTCTGGACTTTTAACTGCTTG
TGCTTTTTCTGTTGATCCAGCAACTACTTACTTGGAAGCTGTTAAACATGGTGCAAAACC
TGTAAGTAATTGTATTAAGATGTTATCTAATGGTGCTGGTAATGGTCAAGCTATAACAAC
TAGTGTAGATGCTAACACCAATCAAGATTCTTATGGTGGAGCGTCTATTTGTTTGTATTG
TCGGGCCCACGTTCCTCACCCTAGTATGGATGGTTACTGTAAGTTTAAGGGTAAATGTGT
TCAGGTTCCTATTGGTTGTTTGGATCCTATTAGGTTTTGTTTAGAAAATAATGTGTGTAA
TGTTTGTGGTTGTTGGTTGGGACACGGGTGTGCTTGTGACCGTACAACTATTCAAAGTGT
TGACATTTCTTATTTAAACGAGCAAGGGGTTCTAGTGCAGCTCGACTAGAACCCTGCAAT
GGCACGGACATCGATAAGTGTGTTCGTGCTTTTGACATTTATAATAAAAATGTTTCATTC
TTGGGTAAGTGTTTGAAGATGAACTGTGTTCGTTTTAAAAATGCTGATCTTAAGGATGGT
TATTTTGTTATAAAGAGGTGTACTAAGTCGGTTATGGAACACGAGCAATCCATGTATAAC
CTACTTAACTTTTCTGGTGCTTTGGCTGAGCATGATTTCTTTACTTGGAAAGATGGCAGA
GTCATTTATGGTAATGTTAGTAGACATAATCTTACTAAATACTATGATGGACTTGGTC
TATGCTATGCGTAACTTTGATGAACAAAATTGTGATGTTCTAAAAGAAGTATTAGTTTTA
ACTGGTTGTTGTGACAATTCTTATTTTGATAGTAAGGGTTGGTATGACCCAGTTGAAAAT
GAAGATATACATAGAGTTTATGCATCTCTTGGCAAAATTGTAGCTAGAGCTATGCTTAAA
TGCGTTGCTCTATGCGATGCGATGGTTGCTAAAGGTGTTGTTGGTGTTTTAACATTAGAT
AACCAAGATCTTAATGGTAACTTTTATGATTTTGGTGATTTTGTTGTTAGCTTACCTAAT
ATGGGTGTTCCCTGTTGTACATCATATTATTCTTATATGATGCCTATTATGGGTTTAACT
AATTGTTTAGCTAGTGAGTGTTTTGTCAAGAGTGATATTTTTGGTAGTGATTTTAAAACT
```

Fig. 19 cont'd

```
TTTGATTTGCTTAAGTATGATTTCACTGAACATAAAGAAAATTTATTCAATAAGTACTTT
AAGCATTGGAGTTTTGATTATCATCCTAATTGTTGTGACTGTTATGATGATATGTGTGTT
ATACATTGTGCTAATTTTAATACACTATTTGCCACAACTATACCAGGTACTGCTTTTGGT
CCACTATGTCGTAAAGTTTTTATAGATGGTGTTCCACTTGTTACAACTGCTGGTTATCAT
TTTAAGCAATTAGGTTTGGTTTGGAATAAAGATGTTAACACACACTCAGTTAGGTTGACA
ATTACTGAACTTTTGCAATTTGTCACCGACCCTTCCTTGATAATAGCTTCTTCCCCAGCA
CTCGTTGATCAACGCACTATTTGTTTTTCTGTTGCAGCATTGAGTACTGGTTTGACAAAT
CAAGTTGTTAAGCCAGGTCATTTTAATGAAGAGTTTTATAACTTTCTTCGTTTAAGAGGT
TTCTTTGATGAAGGTTCTGAACTTACATTAAAACATTTCTTCTTCGCACAGAATGGTGAT
GCTGCTGTTAAAGATTTTGACTTTTACCGTTATAATAAGCCTACCATTTTAGATATTTGT
CAAGCTAGAGTTACATATAAGATAGTCTCTCGTTATTTTGACATTTATGAAGGTGGCTGT
ATTAAGGCATGTGAAGTTGTTGTAACAAATCTTAATAAGAGTGCTGGTTGGCCATTAAAT
AAGTTTGGTAAAGCTAGTTTGTATTATGAATCTATATCTTATGAAGAACAGGATGCTTTG
TTTGCTTTGACAAAGCGTAATGTCCTCCCTACTATGACACAGCTGAATCTTAAGTATGCT
ATTAGTGGTAAAGAACGTGCTAGAACTGTTGGTGGTGTTTCTCTGTTGTCTACAATGACC
ACAAGACAATACCATCAAAAACATCTTAAATCCATTGTTAATACACGCAATGCCACTGTT
GTTATTGGTACTACCAAATTTTATGGTGGTTGGAATAATATGTTGCGTACTTTAATTGAT
GGTGTTGAAAACCCTATGCTTATGGGTTGGGATTATCCCAAATGTGATAGAGCTTTGCCT
AACATGATACGTATGATTTCAGCCATGGTGTTGGGCTCTAAGCATGTTAATTGTTGTACT
GCAACAGATAGGTTTTATAGGCTTGGTAATGAGTTGGCACAAGTTTTAACAGAAGTTGTT
TATTCTAATGGTGGTTTTTATTTTAAGCCAGGTGGTACGACTTCTGGTGACGCTAGTACA
GCTTATGCTAATTCTATTTTTAACATTTTTCAAGCCGTGAGTTCTAACATTAACAGGTTG
CTTAGTGTCCCATCAGATTCATGTAATAATGTTAATGTTAGGGATCTACAACGACGTCTG
TATGATAATTGTTATAGGTTAACTAGTGTTGAAGAGTCATTCATTGAAGATTATTATGGT
TATCTTAGGAAACATTTTTCAATGATGATTCTCTCTGATGACGGTGTTGTCTGTTATAAC
AAGGATTATGCTGAGTTAGGTTATATAGCAGACATTAGTGCTTTTAAAGCCACTTTGTAT
TACCAGAATAATGTCTTTATGAGTACTTCTAAATGTTGGGTTGAAGAAGATTTAACTAAG
GGACCACATGAGTTTTGTTCCCAGCATACTATGCAAATAGTTGACAAAGATGGTACCTAT
TATTTGCCTTACCCAGATCCTAGTAGGATCTTGTCAGCTGGTGTTTTTGTTGATGATGTT
GTTAAGACAGATGCTGTTGTTTGTTAGAACGTTATGTGTCTTTAGCTATTGATGCATAC
CCTCTTTCAAAACACCCTAATTCCGAATATCGTAAGGTTTTTTACGTATTACTTGATTGG
GTTAAGCATCTTAACAAAAATTTGAATGAGGGTGTTCTTGAATCTTTTTCTGTTACACTT
CTTGATAATCAAGAACTAAGTTTTGGTGTGAAGATTTTTATGCTAGTATGATGAAAAT
TCTACAATATTGCAAGCTGCTGGTTTATGTGTTGTTTGTGGTTCACAAACTGTACTTCGT
TGTGGTGATTGTCTGCGTAAGCCTATGTTGTGCACTAAATGCGCATATGATCATGTATTT
GGTACCGACCACAAGTTTATTTTGGCTATAACACCGTATGTATGTAATGCATCAGGTTGT
GGTGTTAGTGATGTCAAAAAATTGTATCTTGGTGGTTTGAATTACTATTGTACAAATCAT
AAACCACAGTTGTCTTTTCCATTATGTTCAGCTGGTAATATATTTGGTTTATATAAAAAT
TCAGCAACTGGTTCCTTAGATGTTGAAGTTTTTAATAGGCTTGCAACGTCTGATTGGACT
GATGTTAGGGACTATAAACTTGCTAATGATGTTAAAGATACACTTAGACTCTTTGCGGCT
GAAACTATTAAAGCTAAAGAAGAGAGTGTTAAGTCTTCTTATGCTTTTGCAACTCTTAAA
GAGGTTGTTGGACCTAAAGAATTGCTTCTTAGTTGGGAAAGTGGTAAAGTTAAACCACCT
TTGAATCGTAATTCTGTTTTCACTTGTTTTCAAATAAGTAAGGACTCAAAATTCCAAATA
GGTGAGTTCATCTTTGAGAAGGTTGAATATGGTTCTGATACTGTTACGTATAAGTCTACT
GTAACTACTAAGTTAGTTCCTGGTATGATTTTTGTCTTAACATCTCACAATGTCCAACCT
TTACGTGCACCAACTATTGCAAACCAAGAGAAGTATTCTAGCATTTATAAATTGCACCCT
GCTTTTAATGTCAGTGATGCATATGCTAATTTGGTTCCATATTACCAACTTATTGGTAAA
CAAAAGATAACTACAATACAGGGTCCTCCTGGTAGTGGTAAGTCACATTGTTCCATTGGA
CTTGGATTGTACTACCCAGGTGCGCGTATTGTTTTTGTTGCTTGTGCCCATGCTGCTGTT
GATTCCTTATGTGCAAAAGCTATGACTGTTTATAGCATTGATAAGTGTACTAGGATTATA
CCTGCAAGAGCTCGGGTTGAGTGTTATAGTGGCTTTAAACCAAATAACACTAGTGCACAA
TACATATTTAGCACTGTTAACGCATTACCTGAGTGTAATGCTGATATCGTTGTTGTAGAT
GAAGTTTCAATGTGTACAAATTATGACCTTTCTGTTATTAACCAGCGTTTATCATATAAA
CATATTGTTTATGTTGGTGATCCACAACAACTTCCTGCACCTAGAGTAATGATTACTAAA
GGTGTTATGGAGCCTGTTGATTATAACGTTGTTACTCAACGTATGTGTGCTATAGGCCCT
GATGTTTTTCTTCATAAATGTTATAGATGTCCTGCTGAAATAGTAATACAGTTTCTGAAC
```

Fig. 19 cont'd

```
TTGTTTATGAGAACAAGTTTGTCCCTGTTAAACCTGCTAGTAAACAGTGTTTTAAAGTCT
TTTTTAAGGGTAATGTACAAGGTTGACAATGGTTCTAGTATTAACAGAAAGCAGCTTGAA
ATAGTTAAGCTGTTTTTAGTTAAAAATCCAAGTTGGAGTAAGGCTGTGTTTATTTCTCCT
TATAATAGTCAGAATTATGTTGCTAGTAGATTTTTAGGACTTCAAATTCAAACTGTTGAT
TCTTCTCAAGGTAGTGAGTATGATTATGTAATCTATGCACAAACTTCTGACACTGCACAT
GCTTGCAATGTAAACCGTTTTAATGTTGCTATAACACGTGCTAAGAAGGGTATATTTTGT
GTAATGTGTGATAAAACTTTGTTTGATTCACTTAAGTTTTTGAGATTAAACATGCAGAT
TTACACTCTAGCCAGGTTTGTGGCTTGTTTAAAAATTGTACACGCACTCCTCTTAATTTA
CCACCAACTCATGCACACACTTTCTTGTCGTTGTCAGATCAGTTTAAGACTACAGGTGAT
TTAGCTGTTCAAATAGGTTCAAATAACGTTTGTACTTATGAACATGTTATATCATTTATG
GGTTTTAGGTTTGATATTAGTATTCCTGGTAGTCATAGTTTGTTTTGTACACGTGACTTT
GCTATTCGTAATGTGCGTGGTTGGTTGGGTATGGATGTTGAAAGTGCTCATGTTTGTGGC
GATAACATAGGTACTAATGTTCCTTTACAGGTTGGTTTTTCAAATGGTGTTAATTTTGTT
GTGCAAACTGAAGGTTGTGTGTCTACCAATTTTGGTGATGTTATTAAACCTGTTTGTGCA
AAATCTCCACCAGGTGAACAATTTAGACACCTTATTCCTCTTTTACGTAAAGGACAACCT
TGGTTAATTGTTCGTAGACGCATTGTGCAAATGATATCTGATTATTTGTCCAATTTGTCT
GACATTCTTGTCTTTGTTTTGTGGGCAGGTAGTTTGGAATTAACTACAATGCGTTACTTT
GTAAAAATAGGGCCAATTAAATATTGTTATTGTGGTAATTTTGCCACTTGTTATAATTCA
GTTAGTAATGAATATTGTTGTTTTAAACATGCATTGGGTTGTGATTATGTTTACAATCCG
TATGCTTTTGATATACAACAGTGGGGTTATGTTGGTTCCTTGAGCCAAAACCACCACACA
TTCTGTAACATTCATAGAAACGAGCATGATGCCTCTGGTGATGCTGTTATGACACGTTGT
TTGGCAGTACATGATTGTTTTGTCAAAAATGTTGATTGGACTGTAACGTACCCCTTTATT
GCAAATGAGAAATTTATCAATGGCTGTGGGCGTAATGTCCAGGGACATGTTGTTCGTGCA
GCCTTGAAATTGTATAAACCTAGTGTTATTCATGACATTGGTAATCCTAAAGGTGTACGT
TGTGCTGTTACTGATGCCAAATGGTACTGTTATGACAAGCAACCTGTTAATAGTAATGTC
AAGTTGTTGGATTATGATTATGCAACCCATGGTCAACTTGATGGTCTTTGTTTATTCTGG
AATTGTAATGTTGATATGTATCCAGAATTTTCAATTGTGTGTCGTTTGACACACGTACT
CGTTCTGTTTTTAATTTAGAAGGTGTTAATGGTGGTTCTCTTTATGTTAACAAACATGCG
TTTCATACACCAGCATATGATAAACGTGCTTTTGTTAAATTAAAACCTATGCCCTTTTTT
TACTTTGATGACAGTGATTGTGATGTTGTGCAAGAACAAGTTAATTATGTACCCCTTCGC
GCTAGTAGTTGTGTTACTCGTTGTAATATAGGTGGTGCTGTTTGTTCAAAACATGCAAAT
TTGTATCAAAAATATGTTGAGGCATATAATACATTTACACAGGCAGGTTTTAACATTTGG
GTACCACATAGTTTTGATGTTTATAATTTGTGGCAAATTTTTATTGAAACTAATTTACAA
AGTCTTGAAAATATAGCATTTAATGTTGTAAAAAAAGGGTGTTTTACTGGTGTTGATGGT
GAGTTACCTGTTGCAGTTGTTAACGACAAAGTTTTTGTTCGCTATGGCGATGTTGACAAC
TTGGTTTTTACAAATAAAACAACATTGCCTACTAATGTTGCTTTTGAATTGTTTGCAAAA
CGAAAAATGGGTTTAACACCACCATTGTCTATTCTCAAAAATCTCGGTGTTGTTGTTACA
TATAAATTTGTTTTATGGGATTATGAAGCTGAAAGACCTTTTACCTCATATACTAAGAGT
GTATGTAAATACACTGATTTTAATGAGGATGTTTGTGTTTGTTTTTGACAATAGTATTCAG
GGTTCGTATGAGCGTTTTACGCTTACTACGAACGCTGTTTTATTTTCTACTGTTGTCATT
AAAAATTTAACACCTATAAAGTTGAATTTTGGTATGTTGAATGGTATGCCAGTTTCTTCT
ATTAAGGGTGATAAAGGTGTTGAAAAATTAGTTAATTGGTACATATATGTTCGTAAAAAT
GGTCAATTTCAAGATCACTATGATGGTTTTTACACTCAAGGTAGGAATTTATCAGACTTT
ACACCAAGAAGTGATATGGAGTATGATTTTCTTAACATGGATATGGGTGTTTTTATTAAT
AAATATGGTCTTGAGGATTTTAATTTTGAACATGTTGTATATGGTGATGTTTCAAAAACT
ACATTAGGAGGTCTTCATTTGTTGATATCACAGTTTAGGCTTAGTAAAATGGGTGTTTTG
AAAGCTGATGATTTTGTCACTGCTTCTGACACAACTTTGAGGTGCTGTACTGTTACTTAT
CTTAATGAACTTAGTTCAAAAGTTGTTTGTACTTATATGGATTTGTTGTTGGACGACTTT
GTTACTATACTAAAGAGTTTAGATCTTGGTGTAATATCTAAAGTTCATGAAGTTATTATA
GATAATAAACCTTATAGGTGGATGTTGTGGTGTAAAGATAACCACTTGTCCACTTTTTAT
CCACAGTTGCAGTCTGCTGAATGGAAGTGTGGTTATGCTATGCCACAAATTTATAAGCTT
CAACGTATGTGTTTGGAACCTTGTAATTTATATAATTATGGTGCTGGTATTAAGTTGCCT
AGTGGTATAATGTTAAATGTTGTTAAATACACTCAGCTTTGTCAATACCTAAATAGCACT
ACAATGTGCGTACCTCATAATATGCGTGTTTTGCACTATGGTGCTGGTTCTGACAAAGGT
GTGGCACCTGGTACAACTGTTTTAAAACGTTGGCTACCACCCGATGCAATAATCATTGAT
AATGATATCAATGATTATGTTAGTGATGCAGATTTTAGCATTACAGGTGATTGTGCTACT
```

Fig. 19 cont'd

```
GTTTATCTTGAAGATAAGTTTGACTTACTTATTTCTGATATGTATGATGGTAGAATTAAA
TTTTGTGATGGTGAAAATGTCTCTAAAGATGGGTTTTTTACTTATCTTAATGGTGTTATT
AGAGAAAAATTAGCTATTGGTGGTAGTGTTGCCATTAAGATTACAGAATATAGTTGGAAT
AAGTATCTTTATGAATTAATACAAAGATTTGCTTTTTGGACTTTGTTTTGCACGTCTGTT
AATACATCCTCTTCAGAAGCTTTTCTTATTGGTATTAATTATTTAGGTGACTTTATTCAA
GGTCCTTTTATAGCTGGTAACACTGTTCATGCTAATTATATATTTTGGCGTAATTCTACT
ATTATGTCTTTGTCATACAATTCAGTTTTAGATTTAAGTAAGTTTGAATGTAAACATAAA
GCCACTGTTGTTGTTACACTTAAAGATAGTGATGTAAATGATATGGTTTTGAGTTTGATT
AAGAGTGGTAGGTTGTTGTTACGCAATAATGGTCGTTTTGGTGGTTTTAGTAATCATTTA
GTCTCAACTAAATGAAACTTTTCTTGATTTTGCTTGTTTTGCCCCTGGCCTCTTGCTTTT
TCACATGTAATAGTAATGCTAATCTCTCTATGTTACAATTAGGTGTTCCTGACAATTCTT
CAACTATTGTTACGGGTTTATTGCCAACTCATTGGTTTTGTGCTAATCAGAGTACATCTG
TTTACTCAGCCAATGGTTTCTTTTATATTGATGTTGGTAATCACCGTAGTGCTTTTGCGC
TCCATACTGGTTATTATGATGCTAATCAGTATTATATTTATGTTACTAATGAAATAGGCT
TAAATGCTTCTGTTACTCTTAAGATTTGTAAGTTTAGTAGAAACACTACTTTTGATTTTT
TAAGTAATGCTTCTAGTTCTTTTGACTGTATAGTTAATTTGTTATTTACAGAACAGTTAG
GTGCGCCTTTGGGCATAACTATATCTGGTGAAACTGTGCGTCTGCATTTATATAATGTAA
CTCGTACTTTTATGTGCCAGCAGCTTATAAACTTACTAAACTTAGTGTTAAATGTTACT
TTAACTATTCCTGTGTTTTAGTGTTGTCAACGCCACCGTTACTGTGAATGTCACCACAC
ATAATGGCCGTGTAGTTAACTACACTGTTTGTGATGATTGTAATGGTTATACTGATAACA
TATTTTCTGTTCAACAGGATGGCCGCATTCCTAATGGTTTCCCTTTTAATAATTGGTTTT
TGTTAACTAATGGTTCCACACTAGTGGACGGGGTCTCTAGACTTTATCAACCACTCCGTT
TAACTTGTTTATGGCCTGTACCTGGTCTTAAATCTTCAACTGGTTTTGTTTATTTTAATG
CCACTGGTTCTGATGTTAATTGTAACGGCTATCAACATAATTCTGTTGTTGATGTTATGC
GTTACAATCTTAACTTCAGTGCTAATTCTTTGGACAATCTCAAGAGTGGTGTTATAGTTT
TTAAAACTTTACAGTACGATGTTTTGTTTTATTGTAGTAATTCTTCCTCAGGTGTTCTTG
ACACCACAATACCTTTTGGCCCGTCCTCTCAACCTTATTACTGTTTTATAAACAGCACTA
TCAACACTACTCATGTTAGCACTTTTGTGGGTATTTTACCACCCACTGTGCGTGAAATTG
TTGTTGCTAGAACTGGCCAGTTTTATATTAATGGTTTTAAGTATTTCGATTTGGGTTTCA
TAGAAGCTGTCAATTTTAATGTCACGACTGCTAGCGCCACAGATTTTTGGACGGTTGCAT
TTGCTACTTTTGTTGATGTTTTGGTTAATGTTAGTGCAACTAACATTCAAAACTTACTTT
ATTGCGATTCTCCATTTGAAAAGTTGCAGTGTGAGCACTTGCAGTTTGGATTGCAGGATG
GTTTTTATTCTGCAAATTTTCTTGATGATAATGTTTTGCCTGAGACTTATGTTGCACTCC
CCATTTATTATCAACACACGGACATAAATTTTACTGCAACTGCATCTTTTGGTGGTTCTT
GTTATGTTTGTAAACCACACCAGGTTAATATATCTCTTAATGGTAACACTTCAGTGTGTG
TTAGAACATCTCATTTTTCAATTAGGTATATTTATAACCGCGTTAAGAGTGGTTCACCAG
GTGACTCTTCATGGCACATTTATTTAAAGAGTGGCACTTGTCCATTTTCTTTTTCTAAGT
TAAATAATTTTCAAAAGTTCAAGACTATTTGTTTCTCAACCGTCGAAGTGCCTGGTAGTT
GTAATTTTCCGCTTGAAGCCACCTGGCATTACACTTCTTATACTATTGTTGGTGCTTTGT
ATGTTACTTGGTCTGAAGGTAATTCTATTACTGGTGTACCTTATCCTGTCTCTGGTATTC
GTGAGTTTAGTAATTTAGTTTTAAATAATTGTACCAAATATAATATTTATGATTATGTTG
GTACTGGAATTATACGTTCTTCAAACCAGTCACTTGCTGGTGGTATTACATATGTTTCTA
ACTCTGGTAATTTACTTGGTTTTAAAAATGTTTCCACTGGTAACATTTTTATTGTGACAC
CATGTAACCAACCAGACCAAGTAGCTGTTTATCAACAAAGCATTATTGGTGCCATGACCG
CTGTTAATGAGTCTAGATATGGCTTGCAAAACTTACTACAGTTACCTAACTTTTATTATG
TTAGTAATGGTGGTAACAATTGCACTACGGCCGTTATGACTTATTCTAATTTTGGTATTT
GTGCTGATGGTTCTTTGATTCCTGTTCGTCCGCGTAATTCTAGTGATAATGGTATTTCAG
CCATAATCACTGCTAATTTATCCATTCCTTCTAACTGGACTACTTCAGTTCAAGTTGAGT
ACCTCCAAATTACTAGTACTCCAATAGTTGTTGATTGTGCTACTTATGTGTGTAATGGTA
ACCCTCGCTGTAAGAATCTACTTAAGCAGTATACTTCTGCTTGTAAAACTATTGAAGATG
CCTTACGACTTAGTGCTCATTTGGAAACTAATGATGTTAGTAGTATGCTAACTTTCGATA
GCAATGCTTTTAGTTTGGCTAATGTTACTAGTTTTGGAGATTATAACCTTTCTAGTGTTT
TACCTCAGAGAAACATTCGTTCAAGCCGTATAGCAGGACGTAGTGCTTTGGAAGATTTGT
TGTTTAGCAAAGTTGTTACATCTGGTTTGGGTACTGTTGATGTTGACTATAAGTCTTGTA
CTAAAGGTCTTTCTATTGCTGACCTTGCTTGTGCTCAGTACTACAATGGCATAATGGTTT
TGCCAGGTGTTGCTGATGCTGAACGTATGGCCATGTACACAGGTTCTCTTATAGGTGGCA
```

Fig. 19 cont'd

```
TGGTGCTCGGAGGTCTTACATCAGCAGCCGCCATACCTTTTTCTTTGGCACTGCAAGCAC
GACTTAACTATGTTGCTTTACAAACTGATGTGCTTCAAGAAAATCAGAAAATTTTGGCTG
CATCATTTAATAAGGCTATTAATAATATTGTTGCTTCTTTTAGTAGCGTTAATGATGCTA
TTACACAAACTGCAGAGGCTATACATACTGTTACTATTGCACTTAATAAGATTCAGGATG
TTGTTAATCAACAGGGTAGTGCTCTTAACCATCTCACTTCACAATTGAGACATAATTTTC
AGGCCATTTCTAATTCAATTCAGGCTATTTATGACCGGCTTGATTCAATTCAAGCCGATC
AACAAGTTGACAGATTAATTACTGGACGGCTTGCAGCTTTGAATGCATTTGTTTCCCAAG
TTTTGAATAAATACTGAAGTTCGTGGTTCAAGACGCTTAGCACAGCAGAAGATTAATG
AATGTGTCAAGTCACAATCTAATAGATATGGTTTTTGTGGCAATGGCACTCACATCTTTT
CAATCGTCAACTCTGCTCCAGATGGTTTGCTTTTTCTTCATACTGTTTGCTGCCAACTG
ATTACAAGAATGTAAAGGCGTGGTCTGGTATCTGTGTTGATGGCATTTATGGCTATGTTC
TGCGTCAACCTAACTTGGTTCTTTATTCTGATAATGGTGTCTTTCGTGTAACTTCCAGGG
TCATGTTTCAACCTCGCTTACCTGTTTTGTCTGATTTTGTGCAAATATATAATTGTAATG
TTACTTTTGTTAACATATCTCGTGTTGAGTTACATACTGTCATACCTGACTACGTTGATG
TTAATAAAACATTACAAGAGTTTGCACAAAACTTACCAAAGTATGTTAAGCCTAATTTTG
ACTTGACTCCTTTTAATTTAACATATCTTAATTTGAGTTCTGAGTTGAAGCAACTCGAAG
CTAAAACTGCTAGTCTTTTTCAAACTACTGTTGAATTACAAGGTCTTATTGATCAGATTA
ACAGTACATATGTTGATTTGAAGTTGCTTAATAGGTTTGAAAATTATATCAAATGGCCTT
GGTGGGTTTGGCTCATTATTTCTGTTGTTTTGTTGTATTGTTGAGTCTTCTTGTGTTTT
GTTGTCTTTCTACAGGTTGTTGTGGTTGTTGCAATTGTTTAACTTCATCAATGCGAGGCT
GTTGTGATTGTGGTTCAACTAAACTTCCTTATTACGAATTTGAAAAGGTCCACGTTCAAT
AATGCCTTTTGGTGGCCTATTTCAACTTACTCTTGAAAGTACTATTAATAAGAGTGTGGC
TAATCTCAAATTACCACCTCATGATGTTACTGTCTTGCGTGACAATCTTAAACCTGTTAC
TACACTTAGTACTATTACTGCTTATTTGTTAGTTAGTTTGTTTGTCACTTACTTTGCTTT
ATTCAAACCTCTTACTGCTAGAGGTCGTGTTGCTTGTTTTGTTTTAAAACTATTGACACT
ATTTGTCTATGTGCCTTTATTGGTTCTTTTTGGTATGTATCTTGACAGTTTTATAATTTT
TTCTACGCTGTTGTTTCGATTCATACATGTTGGCTATTATGCCTATCTCTATAAAAATTT
TTCATTTGTTTTGTTCAATGTTACTAAACTATGCTTCGTTTCAGGCAAGTGTTGGTATCT
TGAACAATCATTTTATGAAAATCGTTTGCTGCTATTTATGGTGGTGACCACTATGTCGT
TTTAGGTGGTGAAACTATTACTTTTGTTTCTTTTGATGACCTTTATGTTGCTATTAGAGG
TTCTTGTGAAAAGAACCTACAACTTATGCGTAAGGTTGACTTGTATAATGGTGCTGTCAT
TTACATTTTTGCCGAAGAGCCTGTTGTTGGTATAGTCTACTCTTCTCAACTATACGAAGA
TGTTCCTTCGATTAATTGATGACAATGGTATTGTCCTCAATTCCATTTTATGGCTCCTTG
TTATGATATTTTTCTTTGTGTTGGCAATGACCTTTATTAAACTGATTCAATTGTGTTTA
CTTGTCATTATTTTTTAGTAGGACATTATATCAACCAGTTTATAAAATTTTTCTTGCTT
ACCAAGATTATATGCAAATAGCACCTGTTCCAGCTGAAGTACTAAATGTCTAAACTAAAC
GATGTCTAATAGTAGTGTGCCTCTTTTAGAGGTTTATGTCCATTTACGTAACTGGAACTT
TAGTTGGAATTTAATTCTAACGCTTTTTATAGTTGTGTTGCAGTATGGGCATTATAAGTA
TAGCAGACTTCTTTATGGTTTAAAGATGTCTGTTTTATGGTGTTTATGGCCACTTGTTCT
AGCTTTGTCTATTTTTGACTGTTTTGTCAATTTTAATGTGGACTGGGTCTTTTTTGGTTT
TAGTATTCTTATGTCTATTATTACACTTTGTTTATGGGTTATGTATTTTGTTAATAGTTT
CAGACTTTGGCGCCGTGTTAAAACTTTTTGGGCTTTTAATCCTGAAACTAATGCAATCAT
CTCTCTCCAGGTTTACGGACATAATTATTACTTACCGGTGATGGCTGCACCTACAGGTGT
TACATTAACACTTCTTAGTGGTGTACTTCTTGTTGATGGCCATAAGATTGCTACTCGTGT
TCAAGTGGGTCAGTTGCCTAAATATGTAATAGTTGCTACGCCTAGTACCACAATTGTTTG
TGACCGTGTTGGTCGCTCTGTTAATGAAACAAGCCAGACTGGTTGGGCATTCTACGTCCG
TGCTAAACATGGTGATTTTTCTGGTGTTGCCTCTCAGGAGGGTGTTTTGTCAGAAAGAGA
GAAGTTGCTTCATTTAATCTAAACTAAACAAAATGGCTAGTGTAAATTGGGCCGATGACA
GAGCTGCTAGGAAGAAATTTCCTCCTCCTTCATTTTACATGCCTCTTTTGGTTAGTTCTG
ATAAGGCACCATATAGGGTCATTCCCAGGAATCTTGTCCCTATTGGTAAGGGTAATAAAG
ATGAGCAGATTGGTTATTGGAATGTTCAAGAGCGTTGGCGTATGCGCAGGGGCAACGTG
TTGATTTGCCTCCTAAAGTTCATTTTTATTACCTAGGTACTGGACCTCATAAGGACCTTA
AATTCAGACAACGTTCTGATGGTGTTGTTTGGGTTGCTAAGGAAGGTGCTAAAACTGTTA
ATACCAGTCTTGGTAATCGCAAACGTAATCAGAAACCTTTGGAACCAAAGTTCTCTATTG
CTTTGCCTCCAGAGCTCTCTGTTGTTGAGTTTGAGGATCGCTCTAATAACTCATCTCGTG
CTAGCAGTCGTTCTTCAACTCGTAACAACTCACGAGACTCTTCTCGTAGCACTTCAAGAC
```

Fig. 19 cont'd

```
AACAGTCTCGCACTCGTTCTGATTCTAACCAGTCTTCTTCAGATCTTGTTGCTGCTGTTA
CTTTGGCCTTAAAGAACTTAGGTTTTGATAACCAGTCGAAGTCACCTAGTTCTTCTGGTA
CTTCCACTCCTAAGAAACCTAATAAGCCTCTTTCTCAACCCAGGGCTGATAAGCCTTCTC
AGTTGAAGAAACCTCGTTGGAAGCGTGTTCCTACCAGAGAGGAAAATGTTATTCAGTGCT
TTGGTCCTCGTGATTTTAATCACAATATGGGGATTCAGATCTTGTTCAGAATGGTGTTG
ATGCCAAAGGTTTTCCACAGCTTGCTGAATTGATTCCTAATCAGGCTGCGTTATTCTTTG
ATAGTGAGGTTAGCACTGATGAAGTGGGTGATAATGTTCAGATTACCTACACCTACAAAA
TGCTTGTAGCTAAGGATAATAAGAACCTTCCTAAGTTCATTGAGCAGATTAGTGCTTTTA
CTAAACCCAGTTCTATCAAAGAAATGCAGTCACAATCATCTCATGTTGCTCAGAACACAG
TACTTAATGCTTCTATTCCAGAATCTAAACCATTGGCTGATGATGATTCAGCCATTATAG
AAATTGTCAACGAGGTTTTGCATTAAATTGTTTTGTAATTCCAGTTGAATGTTTATTATT
ATTAGTTGCAACCCCATGCGTTTAGCGCATGATAAGGGTTTAGTCTTACACACAATGGTA
GGCCAGTGATAGTAAAGTGTAAGTAATTTGCTATCATATTAACATGTCTAGAGGAAAGTC
AGAACTTTTTCTGTTTGTGTTGTTGGAGTACTTAAAGATCGCATAGGCGCGCCAACAATG
GAAGAGCCAACAACATATCTAAAAATGTTTTGTCTGGTACTTGTTAATGATATTGTTTTT
GATATGGATACAC
```

Fig. 20

ORF 1a, replicase enzyme complex

MFYNQVTLAVASDSEISGFGFAIPSVAVRTYSEAAAQGFQACRFVAFGLQDCVTGINDDD
YVIALTGTNQLCAKILPFSDRPLNLRGWLIFSNSNYVLQDFDVVFGHGAGSVVFVDKYMC
GFDGKPVLPKNMWEFRDYFNNNTDSIVIGGVTYQLAWDVIRKDLSYEQQNVLAIESIHYL
GTTGHTLKSGCKLTNAKPPKYSSKVVLSGEWNAVYRAFGSPFITNGMSLLDIIVKPVFFN
AFVKCNCGSESWSVGAWDGYLSSCCGTPAKKLCVVPGNVVPGDVIITSTSAGCGVKYYAG
LVVKHITNITGVSLWRVTAVHSDGMFVASSSYDALLHRNSLDPFCFDVNTLLSNQLRLAF
LGASVTEDVKFAASTGVIDISAGMFGLYDDILTNNKPWFVRKASGLFDAIWDAFVAAIKL
VPTTTGVLVRFVKSIASTVLTVSNGVIIMCADVPDAFQSVYRTFTQAICAAFDFSLDVFK
IGDVKFKRLGDYVLTENALVRLTTEVVRGVRDARIKKAMFTKVVVGPTTEVKFSVIELAT
VNLRLVDCAPVVCPKGKIVVIAGQAFFYSGGFYRFMVDPTTVLNDPVFTGDLFYTIKFSG
FKLDGFNHQFVTASSATDAIIAVELLLLDFKTAVFVYTCVVDGCSVIVRRDATFATHVCF
KDCYNVWEQFCIDNCGEPWFLTDYNAILQSNNPQCAIVQASESKVLLERFLPKCPEILLS
IDDGHLWNLFVEKFNFVTDWLKTLKLTLTSNGLLGNCAKRFRRVLVKLLDVYNGFLETVC
SVAYTAGVCIKYYAVNVPYVVISGFVSRVIRRERCDMTFPCVSCVTFFYEFLDTCFGVSK
PNAIDVEHLELKETVFVEPKDGGQFFVSGDYLWYVVDDIYYPASCNGVLPVAFTKLAGGK
ISFSDDVIVHDVEPTHKVKLIFEFEDDVVTSLCKKSFGKSIIYTGDWEGLHEVLTSAMNV
IGQHIKLPQFYIYDEEGGYDVSKPVMISQWPISNDSNGCVVEASTDFHQLECIVDDSVRE
EVDIIEQPFEEVEHVLSIKQPFSFSFRDELGVRVLDQSDNNCWISTTLVQLQLTKLLDDS
IEMQLFKVGKVDSIVQKCYELSHLISGSLGDSGKLLSELLKEKYTCSITFEMSCDCGKKF
DDQVGCLFWIMPYTKLFQKGECCICHKMQTYKLVSMKGTGVFVQDPAPIDIDAFPVKPIC
SSVYLGVKGSGHYQTNLYSFNKAIDGFGVFDIKNSSVNTVCFVDVDFHSVEIEAGEVKPF
AVYKNVKFYLGDISHLVNCVSFDFVVNAANENLLHGGGVARAIDILTEGQLQSLSKDYIS
SNGPLKVGAGVMLECEKFNVFNVVGPRTGKHEHSLLVEAYNSILFENGIPLMPLLSCGIF
GVRIENSLKALFSCDINKPLQVFVYSSNEEQAVLKFLDGLDLTPVIDDVDVVKPFRVEGN
FSFFDCGVNALDGDIYLLFTNSILMLDKQGQLLDTKLNGILQQAALDYLATVKTVPAGNL
VKLFVESCTIYMCVVPSINDLSFDKNLGRCVRKLNRLKTCVIANVPAIDVLKKLLSSLTL
TVKFVVESNVMDVNDCFKNDNVVLKITEDGINVKDVVVESSKSLGKQLGVVSDGVDSFEG
VLPINTDTVLSVAPEVDWVAFYGFEKAALFASLDVKPYGYPNDFVGGFRVLGTTDNNCWV
NATCIILQYLKPTFKSKGLNVLWNKFVTGDVGPFVSFIYFITMSSKGQKGDAEEALSKLS
EYLISDSIVTLEQYSTCDICKSTVVEVKSAIVCASVLKDGCDVGFCPHRHKLRSRVKFVN
GRVVITNVGEPIISQPSKLLNGIAYTTFSGSFDNGHYVVVYDAANNAVYDGARLFSSDLST
LAVTAIVVVGGCVTSNVPTIVSEKISVMDKLDTGAQKFFQFGDFVMNNIVLFLTWLLSMF
SLLRTSIMKHDIKVIAKAPKRTGVILTRSFKYNIRSALFVIKQKWCVIVTLFKFLLLLYA
IYALVFMIVQFSPFNSLLCGDIVSGYEKSTFNKDIYCGNSMVCKMCLFSYQEFNDLDHTS
LVWKHIRDPILISLQPFVILVILLIFGNMYLRFGLLYFVAQFISTFGSFLGPHQKQWFLH
FVPFDVLCNEFLATFIVCKIVLFVRHIIVGCNNADCVACSKSARLKRVPLQTIINGMHKS
FYVNANGGTCFCNKHNFFCVNCDSFGPGNTFINGDIARELGNVVKTAVQPTAPAYVIIDK
VDFVNGFYRLYSGDTFWRYDFDITESKYSCKEVLKNCNVLENFIVYNNSGSNITQIKNAC
VYFSQLLCEPIKLVNSELLSTLSVDFNGVLHKAYVDVLCNSFFKELTANMSMAECKATLG
LTVSDDDFVSAVANAHRYDVLLSDLSFNNFFISYAKPEDKLSVYDIACCMRAGSKVVNHN
VLIKESIPIVWGVKDFNTLSQEGKKYLVKTTKAKGLTFLLTFNDNQAITQVPATSIVAKQ
GAGFKRTYNFLWYVCLFVVALFIGVSFIDYTTTVTSFHGYDFKYIENGQLKVFEAPLHCV
RNVFDNFNQWHEAKFGVVTTNSDKCPIVVGVSERINVVPGVPTNVYLVGKTLVFTLQAAF
GNTGVCYDFDGVTTSDKCIFNSACTRLEGLGGDNVYCYNTDLIEGSKPYSTLQPNAYYKY
DAKNYVRFPEILARGFGLRTIRTLATRYCRVGECRDSHKGVCFGFDKWYVNDGRVDDGYI
CGDGLIDLLVNVLSIFSSSFSVVAMSGHMLFNFLFAAFITFLCFLVTKFKRVFGDLSYGV
FTVVCATLINNISYVVTQNLFFMLLYAILYFVFTRTVRYAWIWHIAYIVAYFLLIPWWLL
TWFSFAAFLELLPNVFKLKISTQLFEGDKFIGTFESAAAGTFVLDMRSYERLINTISPEK
LKNYAASYNKYKYYSGSASEADYRCACYAHLAKAMLDYAKDHNDMLYSPPTISYNSTLQS
GLKKMAQPSGCVERCVVRVCYGSTVLNGVWLGDTVTCPRHVIAPSTTVLIDYDHAYSTMR
LHNFSVSHNGVFLGVVGVTMHGSVLRIKVSQSNVHTPKHVFKTLKPGDSFNILACYEGIA
SGVFGVNLRTNFTIKGSFINGACGSPGYNVRNDGTVEFCYLHQIELGSGAHVGSDFTGSV

Fig. 20 cont'd

```
YGNFDDQPSLQVESANLMLSDNVVAFLYAALLNGCRWWLCSTRVNVDGFNEWAMANGYTS
VSSVECYSILAAKTGVSVEQLLASIQHLHEGFGGKNILGYSSLCDEFTLAEVVKQMYGVN
LQSGKVIFGLKTMFLFSVFFTMFWAELFIYTNTIWINPVILTPIFCLLLFLSLVLTMFLK
HKFLFLQVFLLPTVIATALYNCVLDYYIVKFLADHFNYNVSVLQMDVQGLVNVLVCLFVV
FLHTWRFSKERFTHWFTYVCSLIAVAYTYFYSGDFLSLLVMFLCAISSDWYIGAIVFRLS
RLIVFFSPESVFSVFGDVKLTLVVYLICGYLVCTYWGILYWFNRFFKCTMGVYDFKVSAA
EFKYMVANGLHAPHGPFDALWLSFKLLGIGGDRCIKISTVQSKLTDLKCTNVVLLGCLSS
MNIAANSSEWAYCVDLHNKINLCDDPEKAQSMLLALLAFFLSKHSDFGLDGLIDSYFDNS
STLQSVASSFVSMPSYIAYENARQAYEDAIANGSSSQLIKQLKRAMNIAKSEFDHEISVQ
KKINRMAEQAATQMYKEARSVNRKSKVISAMHSLLFGMLRRLDMSSVETVLNLARDGVVP
LSVIPATSASKLTIVSPDLESYSKIVCDGSVHYAGVVWTLNDVKDNDGRPVHVKEITKEN
VETLTWPLILNCERVVKLQNNEIMPGKLKQKPMKAEGDGGVLGDGNALYNTEGGKTFMYA
YISNKADLKFVKWEYEGGCNTIELDSPCRFMVETPNGPQVKYLYFVKNLNTLRRGAVLGF
IGATIRLQAGKQTELAVNSGLLTACAFSVDPATTYLEAVKHGAKPVSNCIKMLSNGAGNG
QAITTSVDANTNQDSYGGASICLYCRAHVPHPSMDGYCKFKGKCVQVPIGCLDPIRFCLE
NNVCNVCGCWLGHGCACDRTTIQSVDISYLNEQGVLVQLD
```

Fig. 21

ORF 1ab replicase polyprotein

```
MFYNQVTLAVASDSEISGFGFAIPSVAVRTYSEAAAQGFQACRFVAFGLQDCVTGINDDD
YVIALTGTNQLCAKILPFSDRPLNLRGWLIFSNSNYVLQDFDVVFGHGAGSVVFVDKYMC
GFDGKPVLPKNMWEFRDYFNNNTDSIVIGGVTYQLAWDVIRKDLSYEQQNVLAIESIHYL
GTTGHTLKSGCKLTNAKPPKYSSKVVLSGEWNAVYRAFGSPFITNGMSLLDIIVKPVFFN
AFVKCNCGSESWSVGAWDGYLSSCCGTPAKKLCVVPGNVVPGDVIITSTSAGCGVKYYAG
LVVKHITNITGVSLWRVTAVHSDGMFVASSSYDALLHRNSLDPFCFDVNTLLSNQLRLAF
LGASVTEDVKFAASTGVIDISAGMFGLYDDILTNNKPWFVRKASGLFDAIWDAFVAAIKL
VPTTTGVLVRFVKSIASTVLTVSNGVIIMCADVPDAFQSVYRTFTQAICAAFDFSLDVFK
IGDVKFKRLGDYVLTENALVRLTTEVVRGVRDARIKKAMFTKVVVGPTTEVKFSVIELAT
VNLRLVDCAPVVCPKGKIVVIAGQAFFYSGGFYRFMVDPTTVLNDPVFTGDLFYTIKFSG
FKLDGFNHQFVTASSATDAIIAVELLLLDFKTAVFVYTCVVDGCSVIVRRDATFATHVCF
KDCYNVWEQFCIDNCGEPWFLTDYNAILQSNNPQCAIVQASESKVLLERFLPKCPEILLS
IDDGHLWNLFVEKFNFVTDWLKTLKLTLTSNGLLGNCAKRFRRVLVKLLDVYNGFLETVC
SVAYTAGVCIKYYAVNVPYVVISGFVSRVIRRERCDMTFPCVSCVTFFYEFLDTCFGVSK
PNAIDVEHLELKETVFVEPKDGGQFFVSGDYLWYVVDDIYYPASCNGVLPVAFTKLAGGK
ISFSDDVIVHDVEPTHKVKLIFEFEDDVVTSLCKKSFGKSIIYTGDWEGLHEVLTSAMNV
IGQHIKLPQFYIYDEEGGYDVSKPVMISQWPISNDSNGCVVEASTDFHQLECIVDDSVRE
EVDIIEQPFEEVEHVLSIKQPFSFSFRDELGVRVLDQSDNNCWISTTLVQLQLTKLLDDS
IEMQLFKVGKVDSIVQKCYELSHLISGSLGDSGKLLSELLKEKYTCSITFEMSCDCGKKF
DDQVGCLFWIMPYTKLFQKGECCICHKMQTYKLVSMKGTGVFVQDPAPIDIDAFPVKPIC
SSVYLGVKGSGHYQTNLYSFNKAIDGFGVFDIKNSSVNTVCFVDVDFHSVEIEAGEVKPF
AVYKNVKFYLGDISHLVNCVSFDFVVNAANENLLHGGGVARAIDILTEGQLQSLSKDYIS
SNGPLKVGAGVMLECEKFNVFNVVGPRTGKHEHSLLVEAYNSILFENGIPLMPLLSCGIF
GVRIENSLKALFSCDINKPLQVFVYSSNEEQAVLKFLDGLDLTPVIDDVDVVKPFRVEGN
FSFFDCGVNALDGDIYLLFTNSILMLDKQGQLLDTKLNGILQQAALDYLATVKTVPAGNL
VKLFVESCTIYMCVVPSINDLSFDKNLGRCVRKLNRLKTCVIANVPAIDVLKKLLSSLTL
TVKFVVESNVMDVNDCFKNDNVVLKITEDGINVKDVVVESSKSLGKQLGVVSDGVDSFEG
VLPINTDTVLSVAPEVDWVAFYGFEKAALFASLDVKPYGYPNDFVGGFRVLGTTDNNCWV
NATCIILQYLKPTFKSKGLNVLWNKFVTGDVGPFVSFIYFITMSSKGQKGDAEEALSKLS
EYLISDSIVTLEQYSTCDICKSTVVEVKSAIVCASVLKDGCDVGFCPHRHKLRSRVKFVN
GRVVITNVGEPIISQPSKLLNGIAYTTFSGSFDNGHYVVYDAANNAVYDGARLFSSDLST
LAVTAIVVVGGCVTSNVPTIVSEKISVMDKLDTGAQKFFQFGDFVMNNIVLFLTWLLSMF
SLLRTSIMKHDIKVIAKAPKRTGVILTRSFKYNIRSALFVIKQKWCVIVTLFKFLLLLYA
IYALVFMIVQFSPFNSLLCGDIVSGYEKSTFNKDIYCGNSMVCKMCLFSYQEFNDLDHTS
LVWKHIRDPILISLQPFVILVILLIFGNMYLRFGLLYFVAQFISTFGSFLGFHQKQWFLH
FVPFDVLCNEFLATFIVCKIVLFVRHIIVGCNNADCVACSKSARLKRVPLQTIINGMHKS
FYVNANGGTCFCNKHNFFCVNCDSFGPGNTFINGDIARELGNVVKTAVQPTAPAYVIIDK
VDFVNGFYRLYSGDTFWRYDFDITESKYSCKEVLKNCNVLENFIVYNNSGSNITQIKNAC
VYFSQLLCEPIKLVNSELLSTLSVDFNGVLHKAYVDVLCNSFFKELTANMSMAECKATLG
LTVSDDDFVSAVANAHRYDVLLSDLSFNNFFISYAKPEDKLSVYDIACCMRAGSKVVNHN
VLIKESIPIVWGVKDFNTLSQEGKKYLVKTTKAKGLTFLLTFNDNQAITQVPATSIVAKQ
GAGFKRTYNFLWYVCLFVVALFIGVSFIDYTTTVTSFHGYDFKYIENGQLKVFEAPLHCV
RNVFDNFNQWHEAKFGVVTTNSDKCPIVVGVSERINVVPGVPTNVYLVGKTLVFTLQAAF
GNTGVCYDFDGVTTSDKCIFNSACTRLEGLGGDNVYCYNTDLIEGSKPYSTLQPNAYYKY
DAKNYVRFPEILARGFGLRTIRTLATRYCRVGECRDSHKGVCFGFDKWYVNDGRVDDGYI
CGDGLIDLLVNVLSIFSSSFSVVAMSGHMLFNFLFAAFITFLCFLVTKFKRVFGDLSYGV
FTVVCATLINNISYVVTQNLFFMLLYAILYFVFTRTVRYAWIWHIAYIVAYFLLIPWWLL
TWFSFAAFLELLPNVFKLKISTQLFEGDKFIGTFESAAAGTFVLDMRSYERLINTISPEK
LKNYAASYNKYKYYSGSASEADYRCACYAHLAKAMLDYAKDHNDMLYSPPTISYNSTLQS
GLKKMAQPSGCVERCVVRVCYGSTVLNGVWLGDTVTCPRHVIAPSTTVLIDYDHAYSTMR
LHNFSVSHNGVFLGVVGVTMHGSVLRIKVSQSNVHTPKHVFKTLKPGDSFNILACYEGIA
SGVFGVNLRTNFTIKGSFINGACGSPGYNVRNDGTVEFCYLHQIELGSGAHVGSDFTGSV
```

Fig. 21 cont'd

```
YGNFDDQPSLQVESANLMLSDNVVAFLYAALLNGCRWWLCSTRVNVDGFNEWAMANGYTS
VSSVECYSILAAKTGVSVEQLLASIQHLHEGFGGKNILGYSSLCDEFTLAEVVKQMYGVN
LQSGKVIFGLKTMFLFSVFFTMFWAELFIYTNTIWINPVILTPIFCLLLFLSLVLTMFLK
HKFLFLQVFLLPTVIATALYNCVLDYYIVKFLADHFNYNVSVLQMDVQGLVNVLVCLFVV
FLHTWRFSKERFTHWFTYVCSLIAVAYTYFYSGDFLSLLVMFLCAISSDWYIGAIVFRLS
RLIVFFSPESVFSVFGDVKLTLVVYLICGYLVCTYWGILYWFNRFFKCTMGVYDFKVSAA
EFKYMVANGLHAPHGPFDALWLSFKLLGIGGDRCIKISTVQSKLTDLKCTNVVLLGCLSS
MNIAANSSEWAYCVDLHNKINLCDDPEKAQSMLLALLAFFLSKHSDFGLDGLIDSYFDNS
STLQSVASSFVSMPSYIAYENARQAYEDAIANGSSSQLIKQLKRAMNIAKSEFDHEISVQ
KKINRMAEQAATQMYKEARSVNRKSKVISAMHSLLFGMLRRLDMSSVETVLNLARDGVVP
LSVIPATSASKLTIVSPDLESYSKIVCDGSVHYAGVVWTLNDVKDNDGRPVHVKEITKEN
VETLTWPLILNCERVVKLQNNEIMPGKLKQKPMKAEGDGGVLGDGNALYNTEGGKTFMYA
YISNKADLKFVKWEYEGGCNTIELDSPCRFMVETPNGPQVKYLYFVKNLNTLRRGAVLGF
IGATIRLQAGKQTELAVNSGLLTACAFSVDPATTYLEAVKHGAKPVSNCIKMLSNGAGNG
QAITTSVDANTNQDSYGGASICLYCRAHVPHPSMDGYCKFKGKCVQVPIGCLDPIRFCLE
NNVCNVCGCWLGHGCACDRTTIQSVDISYLNEQGVLVQLDRARGSSAARLEPCNGTDIDK
CVRAFDIYNKNVSFLGKCLKMNCVRFKNADLKDGYFVIKRCTKSVMEHEQSMYNLLNFSG
ALAEHDFFTWKDGRVIYGNVSRHNLTKYTMMDLVYAMRNFDEQNCDVLKEVLVLTGCCDN
SYFDSKGWYDPVENEDIHRVYASLGKIVARAMLKCVALCDAMVAKGVVGVLTLDNQDLNG
NFYDFGDFVVSLPNMGVPCCTSYYSYMMPIMGLTNCLASECFVKSDIFGSDFKTFDLLKY
DFTEHKENLFNKYFKHWSFDYHPNCCDCYDDMCVIHCANFNTLFATTIPGTAFGPLCRKV
FIDGVPLVTTAGYHFKQLGLVWNKDVNTHSVRLTITELLQFVTDPSLIIASSPALVDQRT
ICFSVAALSTGLTNQVVKPGHFNEEFYNFLRLRGFFDEGSELTLKHFFFAQNGDAAVKDF
DFYRYNKPTILDICQARVTYKIVSRYFDIYEGGCIKACEVVVTNLNKSAGWPLNKFGKAS
LYYESISYEEQDALFALTKRNVLPTMQLNLKYAISGKERARTVGGVSLLSTMTTRQYHQ
KHLKSIVNTRNATVVIGTTKFYGGWNNMLRTLIDGVENPMLMGWDYPKCDRALPNMIRMI
SAMVLGSKHVNCCTATDRFYRLGNELAQVLTEVVYSNGGFYFKPGGTTSGDASTAYANSI
FNIFQAVSSNINRLLSVPSDSCNNVNVRDLQRRLYDNCYRLTSVEESFIEDYYGYLRKHF
SMMILSDDGVVCYNKDYAELGYIADISAFKATLYYQNNVFMSTSKCWVEEDLTKGPHEFC
SQHTMQIVDKDGTYYLPYPDPSRILSAGVFVDDVVKTDAVVLLERYVSLAIDAYPLSKHP
NSEYRKVFYVLLDWVKHLNKNLNEGVLESFSVTLLDNQEDKFWCEDFYASMYENSTILQA
AGLCVVCGSQTVLRCGDCLRKPMLCTKCAYDHVFGTDHKFILAITPYVCNASGCGVSDVK
KLYLGGLNYYCTNHKPQLSFPLCSAGNIFGLYKNSATGSLDVEVFNRLATSDWTDVRDYK
LANDVKDTLRLFAAETIKAKEESVKSSYAFATLKEVVGPKELLLSWESGKVKPPLNRNSV
FTCFQISKDSKFQIGEFIFEKVEYGSDTVTYKSTVTTKLVPGMIFVLTSHNVQPLRAPTI
ANQEKYSSIYKLHPAFNVSDAYANLVPYYQLIGKQKITTIQGPPGSGKSHCSIGLGLYYP
GARIVFVACAHAAVDSLCAKAMTVYSIDKCTRIIPARARVECYSGFKPNNTSAQYIFSTV
NALPECNADIVVVDEVSMCTNYDLSVINQRLSYKHIVYVGDPQQLPAPRVMITKGVMEPV
DYNVVTQRMCAIGPDVFLHKCYRCPAEIVIQFLNLFMRTSLSLLNLLVNSVLKSFLRVMY
KVDNGSSINRKQLEIVKLFLVKNPSWSKAVFISPYNSQNYVASRFLGLQIQTVDSSQGSE
YDYVIYAQTSDTAHACNVNRFNVAITRAKKGIFCVMCDKTLFDSLKFFEIKHADLHSSQV
CGLFKNCTRTPLNLPPTHAHTFLSLSDQFKTTGDLAVQIGSNNVCTYEHVISFMGFRFDI
SIPGSHSLFCTRDFAIRNVRGWLGMDVESAHVCGDNIGTNVPLQVGFSNGVNFVVQTEGC
VSTNFGDVIKPVCAKSPPGEQFRHLIPLLRKGQPWLIVRRRIVQMISDYLSNLSDILVFV
LWAGSLELTTMRYFVKIGPIKYCYCGNFATCYNSVSNEYCCFKHALGCDYVYNPYAFDIQ
QWGYVGSLSQNHHTFCNIHRNEHDASGDAVMTRCLAVHDCFVKNVDWTVTYPFIANEKFI
NGCGRNVQGHVVRAALKLYKPSVIHDIGNPKGVRCAVTDAKWYCYDKQPVNSNVKLLDYD
YATHGQLDGLCLFWNCNVDMYPEFSIVCRFDTRTRSVFNLEGVNGGSLYVNKHAFHTPAY
DKRAFVKLKPMPFFYFDDSDCDVVQEQVNYVPLRASSCVTRCNIGGAVCSKHANLYQKYV
EAYNTFTQAGFNIWVPHSFDVYNLWQIFIETNLQSLENIAFNVVKKGCFTGVDGELPVAV
VNDKVFVRYGDVDNLVFTNKTTLPTNVAFELFAKRKMGLTPPLSILKNLGVVATYKFVLW
DYEAERPFTSYTKSVCKYTDFNEDVCVCFDNSIQGSYERFTLTTNAVLFSTVVIKNLTPI
KLNFGMLNGMPVSSIKGDKGVEKLVNWYIYVRKNGQFQDHYDGFYTQGRNLSDFTPRSDM
EYDFLNMDMGVFINKYGLEDFNFEHVVYGDVSKTTLGGLHLLISQFRLSKMGVLKADDFV
TASDTTLRCCTVTYLNELSSKVVCTYMDLLLDDFVTILKSLDLGVISKVHEVIIDNKPYR
WMLWCKDNHLSTFYPQLQSAEWKCGYAMPQIYKLQRMCLEPCNLYNYGAGIKLPSGIMLN
```

Fig. 21 cont'd

```
VVKYTQLCQYLNSTTMCVPHNMRVLHYGAGSDKGVAPGTTVLKRWLPPDAIIIDNDINDY
VSDADFSITGDCATVYLEDKFDLLISDMYDGRIKFCDGENVSKDGFFTYLNGVIREKLAI
GGSVAIKITEYSWNKYLYELIQRFAFWTLFCTSVNTSSSEAFLIGINYLGDFIQGPFIAG
NTVHANYIFWRNSTIMSLSYNSVLDLSKFECKHKATVVVTLKDSDVNDMVLSLIKSGRLL
LRNNGRFGGFSNHLVSTK
```

Like the ORF 1a gene product, this polyprotein is proteolytically cleaved at sites corresponding to the consensus LQ?(S, G or A)[1] by action of the 3Cl$^{pro}$ protease. Potential proteolytic cleavage sites are indicated in bold print in grey background. The 3Cl$^{pro}$-encoding domain is boldly underlined and is also shown as separate protein below. The remaining proteolysis products perform functions in the replication and processing of the viral RNA. Normal blast searches are not sensitive enough to detect this kind of dispersed homology. However, using PFAM (Protein Family) domains tentative functions can be attributed to the proteolysis products.

```
MFYNQVTLAVASDSEISGFGFAIPSVAVRTYSEAAAQGFQACRFVAFGLQDCVTGINDDDYVIALTGT
NQLCAKILPFSDRPLNLRGWLIFSNSNYVLQDFDVVFGHGAGSVVFVDKYMCGFDGKPVLPKNMWEFR
DYFNNNTDSIVIGGVTYQLAWDVIRKDLSYEQQNVLAIESIHYLGTTGHTLKSGCKLTNAKPPKYSSK
VVLSGEWNAVYRAFGSPFITNGMSLLDIIVKPVFFNAFVKCNCGSESWSVGAWDGYLSSCCGTPAKKL
CVVPGNVVPGDVIITSTSAGCGVKYYAGLVVKHITNITGVSLWRVTAVHSDGMFVASSSYDALLHRNS
LDPFCFDVNTLLSNQLRLAFLGASVTEDVKFAASTGVIDISAGMFGLYDDILTNNKPWFVRKASGLFD
AIWDAFVAAIKLVPTTTGVLVRFVKSIASTVLTVSNGVIIMCADVPDAFQSVYRTFTQAICAAFDFSL
DVFKIGDVKFKRLGDYVLTENALVRLTTEVVRGVRDARIKKAMFTKVVVGPTTEVKFSVIELATVNLR
LVDCAPVVCPKGKIVVIAGQAFFYSGGFYRFMVDPTTVLNDPVFTGDLFYTIKFSGFKLDGFNHQFVT
ASSATDAIIAVELLLLDFKTAVFVYTCVVDGCSVIVRRDATFATHVCFKDCYNVWEQFCIDNCGEPWF
LTDYNAILQSNNPQCAIVQASESKVLLERFLPKCPEILLSIDDGHLWNLFVEKFNFVTDWLKTLKLTL
TSNGLLGNCAKRFRRVLVKLLDVYNGFLETVCSVAYTAGVCIKYYAVNVPYVVISGFVSRVIRRERCD
MTFPCVSCVTFFYEFLDTCFGVSKPNAIDVEHLELKETVFVEPKDGGQFFVSGDYLWYVVDDIYYPAS
CNGVLPVAFTKLAGGKISFSDDVIVHDVEPTHKVKLIFEFEDDVVTSLCKKSFGKSIIYTGDWEGLHE
VLTSAMNVIGQHIKLPQFYIYDEEGGYDVSKPVMISQWPISNDSNGCVVEASTDFHQLECIVDDSVRE
EVDIIEQPFEEVEHVLSIKQPFSFSFRDELGVRVLDQSDNNCWISTTLVQLQLTKLLDDSIEMQLFKV
GKVDSIVQKCYELSHLISGSLGDSGKLLSELLKEKYTCSITFEMSCDCGKKFDDQVGCLFWIMPYTKL
FQKGECCICHKMQTYKLVSMKGTGVFVQDPAPIDIDAFPVKPICSSVYLGVKGSGHYQTNLYSFNKAI
DGFGVFDIKNSSVNTVCFVDVDFHSVEIEAGEVKPFAVYKNVKFYLGDISHLVNCVSFDFVVNAANEN
LLHGGGVARAIDILTEGQLQSLSKDYISSNGPLKVGAGVMLECEKFNVFNVVGPRTGKHEHSLLVEAY
NSILFENGIPLMPLLSCGIFGVRIENSLKALFSCDINKPLQVFVYSSNEEQAVLKFLDGLDLTPVIDD
VDVVKPFRVEGNFSFFDCGVNALDGDIYLLFTNSILMLDKQGQLLDTKLNGILQQAALDYLATVKTVP
AGNLVKLFVESCTIYMCVVPSINDLSFDKNLGRCVRKLNRLKTCVIANVPAIDVLKKLLSSLTLTVKF
VVESNVMDVNDCFKNDNVVLKITEDGINVKDVVVESSKSLGKQLGVVSDGVDSFEGVLPINTDTVLSV
APEVDWVAFYGFEKAALFASLDVKPYGYPNDFVGGFRVLGTTDNNCWVNATCIILQYLKPTFKSKGLN
VLWNKFVTGDVGPFVSFIYFITMSSKGQKGDAEEALSKLSEYLISDSIVTLEQYSTCDICKSTVVEVK
SAIVCASVLKDGCDVGFCPHRHKLRSRVKFVNGRVVITNVGEPIISQPSKLLNGIAYTTFSGSFDNGH
YVVYDAANNAVYDGARLFSSDLSTLAVTAIVVVGGCVTSNVPTIVSEKISVMDKLDTGAQKFFQFGDF
VMNNIVLFLTWLLSMFSLLRTSIMKHDIKVIAKAPKRTGVILTRSFKYNIRSALFVIKQKWCVIVTLF
KFLLLLYAIYALVFMIVQFSPFNSLLCGDIVSGYEKSTFNKDIYCGNSMVCKMCLFSYQEFNDLDHTS
LVWKHIRDPILISLQPFVILVILLIFGNMYLRFGLLYFVAQFISTFGSFLGFHQKQWFLHFVPFDVLC
NEFLATFIVCKIVLFVRHIIVGCNNADCVACSKSARLKRVPLQTIINGMHKSFYVNANGGTCFCNKHN
FFCVNCDSFGPGNTFINGDIARELGNVVKTAVQPTAPAYVIIDKVDFVNGFYRLYSGDTFWRYDFDIT
ESKYSCKEVLKNCNVLENFIVYNNSGSNITQIKNACVYFSQLLCEPIKLVNSELLSTLSVDFNGVLHK
AYVDVLCNSFFKELTANMSMAECKATLGLTVSDDDFVSAVANAHRYDVLLSDLSFNNFFISYAKPEDK
LSVYDIACCMRAGSKVVNHNVLIKESIPIVWGVKDFNTLSQEGKKYLVKTTKAKGLTFLLTFNDNQAI
TQVPATSIVAKQGAGFKRTYNFLWYVCLFVVALFIGVSFIDYTTTVTSFHGYDFKYIENGQLKVFEAP
LHCVRNVFDNFNQWHEAKFGVVTTNSDKCPIVVGVSERINVVPGVPTNVYLVGKTLVFTLQAAFGNTG
VCYDFDGVTTSDKCIFNSACTRLEGLGGDNVYCYNTDLIEGSKPYSTLQPNAYYKYDAKNYVRFPEIL
ARGFGLRTIRTLATRYCRVGECRDSHKGVCFGFDKWYVNDGRVDDGYICGDGLIDLLVNVLSIFSSSF
SVVAMSGHMLFNFLFAAFITFLCFLVTKFKRVFGDLSYGVFTVVCATLINNISYVVTQNLFFMLLYAI
```

Fig. 21 cont'd

```
LYFVFTRTVRYAWIWHIAYIVAYFLLIPWWLLTWFSFAAFLELLPNVFKLKISTQLFEGDKFIGTFES
AAAGTFVLDMRSYERLINTISPEKLKNYAASYNKYKYYSGSASEADYRCACYAHLAKAMLDYAKDHND
MLYSPPTISYNSTLQSGLKKMAQPSGCVERCVVRVCYGSTVLNGVWLGDTVTCPRHVIAPSTTVLIDY
DHAYSTMRLHNFSVSHNGVFLGVVGVTMHGSVLRIKVSQSNVHTPKHVFKTLKPGDSFNILACYEGIA
SGVFGVNLRTNFTIKGSFINGACGSPGYNVRNDGTVEFCYLHQIELGSGAHVGSDFTGSVYGNFDDQP
SLQVESANLMLSDNVVAFLYAALLNGCRWWLCSTRVNVDGFNEWAMANGYTSVSSVECYSILAAKTGV
SVEQLLASIQHLHEGFGGKNILGYSSLCDEFTLAEVVKQMYGVNLQSGKVIFGLKTMFLFSVFFTMFW
AELFIYTNTIWINPVILTPIFCLLLFLSLVLTMFLKHKFLFLQVFLLPTVIATALYNCVLDYYIVKFL
ADHFNYNVSVLQMDVQGLVNVLVCLFVVFLHTWRFSKERFTHWFTYVCSLIAVAYTYFYSGDFLSLLV
MFLCAISSDWYIGAIVFRLSRLIVFFSPESVFSVFGDVKLTLVVYLICGYLVCTYWGILYWFNRFFKC
TMGVYDFKVSAAEFKYMVANGLHAPHGPFDALWLSFKLLGIGGDRCIKISTVQSKLTDLKCTNVVLLG
CLSSMNIAANSSEWAYCVDLHNKINLCDDPEKAQSMLLALLAFFLSKHSDFGLDGLIDSYFDNSSTLQ
SVASSFVSMPSYIAYENARQAYEDAIANGSSSQLIKQLKRAMNIAKSEFDHEISVQKKINRMAEQAAT
QMYKEARSVNRKSKVISAMHSLLFGMLRRLDMSSVETVLNLARDGVVPLSVIPATSASKLTIVSPDLE
SYSKIVCDGSVHYAGVVWTLNDVKDNDGRPVHVKEITKENVETLTWPLILNCERVVKLQNNEIMPGKL
KQKPMKAEGDGGVLGDGNALYNTEGGKTFMYAYISNKADLKFVKWEYEGGCNTIELDSPCRFMVETPN
GPQVKYLYFVKNLNTLRRGAVLGFIGATIRLQAGKQTELAVNSGLLTACAFSVDPATTYLEAVKHGAK
PVSNCIKMLSNGAGNGQAITTSVDANTNQDSYGGASICLYCRAHVPHPSMDGYCKFKGKCVQVPIGCL
DPIRFCLENNVCNVCGCWLGHGCACDRTTIQSVDISYLNEQGVLVQLDRARGSSAARLEPCNGTDIDK
CVRAFDIYNKNVSFLGKCLKMNCVRFKNADLKDGYFVIKRCTKSVMEHEQSMYNLLNFSGALAEHDFF
TWKDGRVIYGNVSRHNLTKYTMMDLVYAMRNFDEQNCDVLKEVLVLTGCCDNSYFDSKGWYDPVENED
IHRVYASLGKIVARAMLKCVALCDAMVAKGVVGVLTLDNQDLNGNFYDFGDFVVSLPNMGVPCCTSYY
SYMMPIMGLTNCLASECFVKSDIFGSDFKTFDLLKYDFTEHKENLFNKYFKHWSFDYHPNCCDCYDDM
CVIHCANFNTLFATTIPGTAFGPLCRKVFIDGVPLVTTAGYHFKQLGLVWNKDVNTHSVRLTITELLQ
FVTDPSLIIASSPALVDQRTICFSVAALSTGLTNQVVKPGHFNEEFYNFLRLRGFFDEGSELTLKHFF
FAQNGDAAVKDFDFYRYNKPTILDICQARVTYKIVSRYFDIYEGGCIKACEVVVTNLNKSAGWPLNKF
GKASLYYESISYEEQDALFALTKRNVLPTMTQLNLKYAISGKERARTVGGVSLLSTMTTRQYHQKHLK
SIVNTRNATVVIGTTKFYGGWNNMLRTLIDGVENPMLMGWDYPKCDRALPNMIRMISAMVLGSKHVNC
CTATDRFYRLGNELAQVLTEVVYSNGGFYFKPGGTTSGDASTAYANSIFNIFQAVSSNINRLLSVPSD
SCNNVNVRDLQRRLYDNCYRLTSVEESFIEDYYGYLRKHFSMMILSDDGVVCYNKDYAELGYIADISA
FKATLYYQNNVFMSTSKCWVEEDLTKGPHEFCSQHTMQIVDKDGTYYLPYPDPSRILSAGVFVDDVVK
TDAVVLLERYVSLAIDAYPLSKHPNSEYRKVFYVLLDWVKHLNKNLNEGVLESFSVTLLDNQEDKFWC
EDFYASMYENSTILQAAGLCVVCGSQTVLRCGDCLRKPMLCTKCAYDHVFGTDHKFILAITPYVCNAS
GCGVSDVKKLYLGGLNYYCTNHKPQLSFPLCSAGNIFGLYKNSATGSLDVEVFNRLATSDWTDVRDYK
LANDVKDTLRLFAAETIKAKEESVKSSYAFATLKEVVGPKELLLSWESGKVKPPLNRNSVFTCFQISK
DSKFQIGEFIFEKVEYGSDTVTYKSTVTTKLVPGMIFVLTSHNVQPLRAPTIANQEKYSSIYKLHPAF
NVSDAYANLVPYYQLIGKQKITTIQGPPGSGKSHCSIGLGLYYPGARIVFVACAHAAVDSLCAKAMTV
YSIDKCTRIIPARARVECYSGFKPNNTSAQYIFSTVNALPECNADIVVVDEVSMCTNYDLSVINQRLS
YKHIVYVGDPQQLPAPRVMITKGVMEPVDYNVVTQRMCAIGPDVFLHKCYRCPAEIVIQFLNLFMRTS
LSLLNLLVNSVLKSFLRVMYKVDNGSSINRKQLEIVKLFLVKNPSWSKAVFISPYNSQNYVASRFLGL
QIQTVDSSQGSEYDYVIYAQTSDTAHACNVNRFNVAITRAKKGIFCVMCDKTLFDSLKFFEIKHADLH
SSQVCGLFKNCTRTPLNLPPTHAHTFLSLSDQFKTTGDLAVQIGSNNVCTYEHVISFMGFRFDISIPG
SHSLFCTRDFAIRNVRGWLGMDVESAHVCGDNIGTNVPLQVGFSNGVNFVVQTEGCVSTNFGDVIKPV
CAKSPPGEQFRHLIPLLRKGQPWLIVRRRIVQMISDYLSNLSDILVFVLWAGSLELTTMRYFVKIGPI
KYCYCGNFATCYNSVSNEYCCFKHALGCDYVYNPYAFDIQQWGYVGSLSQNHHTFCNIHRNEHDASGD
AVMTRCLAVHDCFPKQPVNSNVKLLDYDYATHGQLDGLCLFWNCNVDMYPEFSIVCRFDTRTRSVFNLEGVN
GGSLYVNKHAFHTPAYDKRAFVKLKPMPFFYFDDSDCDVVQEQVNYVPLRASSCVTRCNIGGAVCSKH
ANLYQKYVEAYNTFTQAGFNIWVPHSFDVYNLWQIFIETNLQSLENIAFNVVKKGCFTGVDGELPVAV
VNDKVFVRYGDVDNLVFTNKTTLPTNVAFELFAKRKMGLTPPLSILKNLGVVATYKFVLWDYEAERPF
TSYTKSVCKYTDFNEDVCVCFDNSIQGSYERFTLTTNAVLFSTVVIKNLTPIKLNFGMLNGMPVSSIK
GDKGVEKLVNWYIYVRKNGQFQDHYDGFYTQGRNLSDFTPRSDMEYDFLNMDMGVFINKYGLEDFNFE
HVVYGDVSKTTLGGLHLLISQFRLSKMGVLKADDFVTASDTTLRCCTVTYLNELSSKVVCTYMDLLLD
DFVTILKSLDLGVISKVHEVIIDNKPYRWMLWCKDNHLSTFYPQLQSAEWKCGYAMPQIYKLQRMCLE
PCNLYNYGAGIKLPSGIMLNVVKYTQLCQYLNSTTMCVPHNMRVLHYGAGSDKGVAPGTTVLKRWLPP
DAIIIDNDINDYVSDADFSITGDCATVYLEDKFDLLISDMYDGRIKFCDGENVSKDGFFTYLNGVIRE
```

Fig. 21 cont'd

```
KLAIGGSVAIKITEYSWNKYLYELIQRFAFWTLFCTSVNTSSSEAFLIGINYLGDFIQGPFIAGNTVH
ANYIFWRNSTIMSLSYNSVLDLSKFECKHKATVVVTLKDSDVNDMVLSLIKSGRLLLRNNGRFGGFSN
HLVSTK
```

Fig. 21 cont'd

Annotated putative proteolytic cleavage products ORF 1ab

Adenosine diphosphate-ribose 1'- phosphatase
SNNPQCAIVQASESKVLLERFLPKCPEILLSIDDGHLWNLFVEKFNFVTDWLKTLKLTLTSNGLLGNC
AKRFRRVLVKLLDVYNGFLETVCSVAYTAGVCIKYYAVNVPYVVISGFVSRVIRRERCDMTFPCVSCV
TFFYEFLDTCFGVSKPNAIDVEHLELKETVFVEPKDGGQFFVSGDYLWYVVDDIYYPASCNGVLPVAF
TKLAGGKISFSDDVIVHDVEPTHKVKLIFEFEDDVVTSLCKKSFGKSIIYTGDWEGLHEVLTSAMNVI
GQHIKLPQFYIYDEEGGYDVSKPVMISQWPISNDSNGCVVEASTDFHQLECIVDDSVREEVDIIEQPF
EEVEHVLSIKQPFSFSFRDELGVRVLDQSDNNCWISTTLVQLQLTKLLDDSIEMQLFKVGKVDSIVQK
CYELSHLISGSLGDSGKLLSELLKEKYTCSITFEMSCDCGKKFDDQVGCLFWIMPYTKLFQKGECCIC
HKMQTYKLVSMKGTGVFVQDPAPIDIDAFPVKPICSSVYLGVKGSGHYQTNLYSFNKAIDGFGVFDIK
NSSVNTVCFVDVDFHSVEIEAGEVKPFAVYKNVKFYLGDISHLVNCVSFDFVVNAANENLLHGGGVAR
AIDILTEGQLQSLSKDYISSNGPLKVGAGVMLECEKFNVFNVVGPRTGKHEHSLLVEAYNSILFENGI
PLMPLLSCGIFGVRIENSLKALFSCDINKPLQVFVYSSNEEQAVLKFLDGLDLTPVIDDVDVVKPFRV
EGNFSFFDCGVNALDGDIYLLFTNSILMLDKQGQLLDTKLNGILQQAALDYLATVKTVPAGNLVKLFV
ESCTIYMCVVPSINDLSFDKNLGRCVRKLNRLKTCVIANVPAIDVLKKLLSSLTLTVKFVVESNVMDV
NDCFKNDNVVLKITEDGINVKDVVVESSKSLGKQLGVVSDGVDSFEGVLPINTDTVLSVAPEVDWVAF
YGFEKAALFASLDVKPYGYPNDFVGGFRVLGTTDNNCWVNATCIILQYLKPTFKSKGLNVLWNKFVTG
DVGPFVSFIYFITMSSKGQKGDAEEALSKLSEYLISDSIVTLEQYSTCDICKSTVVEVKSAIVCASVL
KDGCDVGFCPHRHKLRSRVKFVNGRVVITNVGEPIISQPSKLLNGIAYTTFSGSFDNGHYVVYDAANN
AVYDGARLFSSDLSTLAVTAIVVVGGCVTSNVPTIVSEKISVMDKLDTGAQKFFQFGDFVMNNIVLFL
TWLLSMFSLLRTSIMKHDIKVIAKAPKRTGVILTRSFKYNIRSALFVIKQKWCVIVTLFKFLLLLYAI
YALVFMIVQFSPFNSLLCGDIVSGYEKSTFNKDIYCGNSMVCKMCLFSYQEFNDLDHTSLVWKHIRDP
ILISLQPFVILVILLIFGNMYLRFGLLYFVAQFISTFGSFLGFHQKQWFLHFVPFDVLCNEFLATFIV
CKIVLFVRHIIVGCNNADCVACSKSARLKRVPLQTIINGMHKSFYVNANGGTCFCNKHNFFCVNCDSF
GPGNTFINGDIARELGNVVKTAVQPTAPAYVIIDKVDFVNGFYRLYSGDTFWRYDFDITESKYSCKEV
LKNCNVLENFIVYNNSGSNITQIKNACVYFSQLLCEPIKLVNSELLSTLSVDFNGVLHKAYVDVLCNS
FFKELTANMSMAECKATLGLTVSDDDFVSAVANAHRYDVLLSDLSFNNFFISYAKPEDKLSVYDIACC
MRAGSKVVNHNVLIKESIPIVWGVKDFNTLSQEGKKYLVKTTKAKGLTFLLTFNDNQAITQVPATSIV
AKQGAGFKRTYNFLWYVCLFVVALFIGVSFIDYTTTVTSFHGYDFKYIENGQLKVFEAPLHCVRNVFD
NFNQWHEAKFGVVTTNSDKCPIVVGVSERINVVPGVPTNVYLVGKTLVFTLQAAFGNTGVCYDFDGVT
TSDKCIFNSACTRLEGLGGDNVYCYNTDLIEGSKPYSTLQPNAYYKYDAKNYVRFPEILARGFGLRTI
RTLATRYCRVGECRDSHKGVCFGFDKWYVNDGRVDDGYICGDGLIDLLVNVLSIFSSSFSVVAMSGHM
LFNFLFAAFITFLCFLVTKFKRVFGDLSYGVFTVVCATLINNISYVVTQNLFFMLLYAILYFVFTRTV
RYAWIWHIAYIVAYFLLIPWWLLTWFSFAAFLELLPNVFKLKISTQLFEGDKFIGTFESAAAGTFVLD
MRSYERLINTISPEKLKNYAASYNKYKYYSGSASEADYRCACYAHLAKAMLDYAKDHNDMLYSPPTIS
YNSTLQ

3Cl^pro Coronavirus polyprotein processing endoprotease
SGLKKMAQPSGCVERCVVRVCYGSTVLNGVWLGDTVTCPRHVIAPSTTVLIDYDHAYSTMRLHNFSVS
HNGVFLGVVGVTMHGSVLRIKVSQSNVHTPKHVFKTLKPGDSFNILACYEGIASGVFGVNLRTNFTIK
GSFINGACGSPGYNVRNDGTVEFCYLHQIELGSGAHVGSDFTGSVYGNFDDQPSLQVESANLMLSDNV
VAFLYAALLNGCRWWLCSTRVNVDGFNEWAMANGYTSVSSVECYSILAAKTGVSVEQLLASIQHLHEG
FGGKNILGYSSLCDEFTLAEVVKQMYGVNLQ

RNA dependant RNA polymerase (pfam00680)
AGKQTELAVNSGLLTACAFSVDPATTYLEAVKHGAKPVSNCIKMLSNGAGNGQAITTSVDANTNQDSY
GGASICLYCRAHVPHPSMDGYCKFKGKCVQVPIGCLDPIRFCLENNVCNVCGCWLGHGCACDRTTIQS
VDISYLNEQGVLVQLDRARGSSAARLEPCNGTDIDKCVRAFDIYNKNVSFLGKCLKMNCVRFKNADLK
DGYFVIKRCTKSVMEHEQSMYNLLNFSGALAEHDFFTWKDGRVIYGNVSRHNLTKYTMMDLVYAMRNF
DEQNCDVLKEVLVLTGCCDNSYFDSKGWYDPVENEDIHRVYASLGKIVARAMLKCVALCDAMVAKGVV
GVLTLDNQDLNGNFYDFGDFVVSLPNMGVPCCTSYYSYMMPIMGLTNCLASECFVKSDIFGSDFKTFD
LLKYDFTEHKENLFNKYFKHWSFDYHPNCCDCYDDMCVIHCANFNTLFATTIPGTAFGPLCRKVFIDG
VPLVTTAGYHFKQLGLVWNKDVNTHSVRLTITELLQFVTDPSLIIASSPALVDQRTICFSVAALSTGL

Fig. 21 cont'd

```
TNQVVKPGHFNEEFYNFLRLRGFFDEGSELTLKHFFFAQNGDAAVKDFDFYRYNKPTILDICQARVTY
KIVSRYFDIYEGGCIKACEVVVTNLNKSAGWPLNKFGKASLYYESISYEEQDALFALTKRNVLPTMTQ
LNLKYAISGKERARTVGGVSLLSTMTTRQYHQKHLKSIVNTRNATVVIGTTKFYGGWNNMLRTLIDGV
ENPMLMGWDYPKCDRALPNMIRMISAMVLGSKHVNCCTATDRFYRLGNELAQVLTEVVYSNGGFYFKP
GGTTSGDASTAYANSIFNIFQAVSSNINRLLSVPSDSCNNVNVRDLQRRLYDNCYRLTSVEESFIEDY
YGYLRKHFSMMILSDDGVVCYNKDYAELGYIADISAFKATLYYQNNVFMSTSKCWVEEDLTKGPHEFC
SQHTMQIVDKDGTYYLPYPDPSRILSAGVFVDDVVKTDAVVLLERYVSLAIDAYPLSKHPNSEYRKVF
YVLLDWVKHLNKNLNEGVLESFSVTLLDNQEDKFWCEDFYASMYENSTILQ
```

ExoN 3'to 5' Exonuclease and helicase
The bold underlined amino acid residues are conserved in orthologous cellular and viral enzymes.

```
AAGLCVVCGSQTVLRCGDCLRKPMLCTKCAYDHVFGTDHKFILAITPYVCNASGCGVSDVKKLYLGGL
NYYCTNHKPQLSFPLCSAGNIFGLYKNSATGSLDVEVFNRLATSDWTDVRDYKLANDVKDTLRLFAAE
TIKAKEESVKSSYAFATLKEVVGPKELLLSWESGKVKPPLNRNSVFTCFQISKDSKFQIGEFIFEKVE
YGSDTVTYKSTVTTKLVPGMIFVLTSHNVQPLRAPTIANQEKYSSIYKLHPAFNVSDAYANLVPYYQL
IGKQKITTIQGPPGSGKSHCSIGLGLYYPGARIVFVACAHAAVDSLCAKAMTVYSIDKCTRIIPARAR
VECYSGFKPNNTSAQYIFSTVNALPECNADIVVVDEVSMCTNYDLSVINQRLSYKHIVYVGDPQQLPA
PRVMITKGVMEPVDYNVVTQRMCAIGPDVFLHKCYRCPAEIVIQFLNLFMRTSLSLLNLLVNSVLKSF
LRVMYKVDNGSSINRKQLEIVKLFLVKNPSWSKAVFISPYNSQNYVASRFLGLQIQTVDSSQGSEYDY
VIYAQTSDTAHACNVNRFNVAITRAKKGIFCVMCDKTLFDSLKFFEIKHADLHSSQVCGLFKNCTRTP
LNLPPTHAHTFLSLSDQFKTTGDLAVQIGSNNVCTYEHVISFMGFRFDISIPGSHSLFCTRDFAIRNV
RGWLGMDVESAHVCGDNIGTNVPLQVGFSNGVNFVVQTEGCVSTNFGDVIKPVCAKSPPGEQFRHLIP
LLRKGQPWLIVRRRIVQMISDYLSNLSDILVFVLWAGSLELTTMRYFVKIGPIKYCYCGNFATCYNSV
SNEYCCFKHALGCDYVYNPYAFDIQQWGYVGSLSQNHHTFCNIHRNEHDASGDAVMTRCLAVHDCFVK
NVDWTVTYPFIANEKFINGCGRNVQGHVVRAALKLYKPSVIHDIGNPKGVRCAVTDAKWYCYDKQPVN
SNVKLLDYDYATHGQLDGLCLFWNCNVDMYPEFSIVCRFDTRTRSVFNLEGVNGGSLYVNKHAFHTPA
YDKRAFVKLKPMPFFYFDDSDCDVVQEQVNYVPLRASSCVTRCNIGGAVCSKHANLYQKYVEAYNTFT
QAGFNIWVPHSFDVYNLWQIFIETNLQ
```

XendoU (homolog of) polyU-specific endoribonuclease

```
SLENIAFNVVKKGCFTGVDGELPVAVVNDKVFVRYGDVDNLVFTNKTTLPTNVAFELFAKRKMGLTPP
LSILKNLGVVATYKFVLWDYEAERPFTSYTKSVCKYTDFNEDVCVCFDNSIQGSYERFTLTTNAVLFS
TVVIKNLTPIKLNFGMLNGMPVSSIKGDKGVEKLVNWYIYVRKNGQFQDHYDGFYTQGRNLSDFTPRS
DMEYDFLNMDMGVFINKYGLEDFNFEHVVYGDVSKTTLGGLHLLISQFRLSKMGVLKADDFVTASDTT
LRCCTVTYLNELSSKVVCTYMDLLLDDFVTILKSLDLGVISKVHEVIIDNKPYRWMLWCKDNHLSTFY
PQLQ
```

2'-O-MT 2: S-adenosylmethionine-dependant ribose 2'-orthomethyltransferase
Plays a role in the methylation of cap structure (GpppNm) at the 5'end of the viral RNA. Antiviral compounds inhibiting this transfer of methyl groups to reaction (carboxylic adenosine analogs e.g. Neoplanocin A and 3-deazaneoplancin A) interfere with expression of viral proteins. Again the underlined residues in bold print are conserved

```
SAEWKCGYAMPQIYKLQRMCLEPCNLYNYGAGIKLPSGIMLNVVKYTQLCQYLNSTTMCVPHNMRVLH
YGAGSDKGVAPGTTVLKRWLPPDAIIIDNDINDYVSDADFSITGDCATVYLEDKFDLLISDMYDGRIK
FCDGENVSKDGFFTYLNGVIREKLAIGGSVAIKITEYSWNKYLYELIQRFAFWTLFCTSVNTSSSEAF
LIGINYLGDFIQGPFIAGNTVHANYIFWRNSTIMSLSYNSVLDLSKFECKHKATVVVTLKDSDVNDMV
LSLIKSGRLLLRNNGRFGGFSNHLVSTK
```

Fig. 22

ORF-2 Spike protein/S-gene (SEQ ID NO:63)

MKLFLILLVLPLASC

FFTCNSNANLSMLQLGVPDNSSTIVTGLLPTHWFCANQSTSVYSA
NGFFYIDVGNHRSAFALHTGYYDANQYYIYVTNEIGLNASVTLKICKFSRNTTFDFLSNA
SSSFDCIVNLLFTEQLGAPLGITISGETVRLHLYNVTRTFYVPAAYKLTKLSVKCYFNYS
CVFSVVNATVTVNVTTHNGRVVNYTVCDDCNGYTDNIFSVQQDGRIPNGFPFNNWFLLTN
GSTLVDGVSRLYQPLRLTCLWPVPGLKSSTGFVYFNATGSDVNCNGYQHNSVVDVMRYNL
NFSANSLDNLKSGVIVFKTLQYDVLFYCSNSSSGVLDTTIPFGPSSQPYYCFINSTINTT
HVSTFVGILPPTVREIVVARTGQFYINGFKYFDLGFIEAVNFNVTTASATDFWTVAFATF
VDVLVNVSATNIQNLLYCDSPFEKLQCEHLQFGLQDGFYSANFLDDNVLPETYVALPIYY
QHTDINFTATASFGGSCYVCKPHQVNISLNGNTSVCVRTSHFSIRYIYNRVKSGSPGDSS
WHIYLKSGTCPFSFSKLNNFQKFKTICFSTVEVPGSCNFPLEATWHYTSYTIVGALYVTW
SEGNSITGVPYPVSGIREFSNLVLNNCTKYNIYDYVGTGIIRSSNQSLAGGITYVSNSGN
LLGFKNVSTGNIFIVTPCNQPDQVAVYQQSIIGAMTAVNESRYGLQNLLQLPNFYYVSNG
GNNCTTAVMTYSNFGICADGSLIPVRPRNSSDNGISAIITANLSIPSNWTTSVQVEYLQI
TSTPIVVDCATYVCNGNPRCKNLLKQYTSACKTIEDALRLSAHLETNDVSSMLTFDSNAF
SLANVTSFGDYNLSSVLPQRNIRSSRIAGRSALEDLLFSKVVTSGLGTVDVDYKSCTKGL
SIADLACAQYYNGIMVLPGVADAERMAMYTGSLIGGMVLGGLTSAAAIPFSLALQARLNY
VALQTDVLQENQKILAASFNKAINNIVASFSSVNDAITQTAEAIHTVTIALNKIQDVVNQ
QGSALNHLTSQLRHNFQAISNSIQAIYDRLDSIQADQQVDRLITGRLAALNAFVSQVLNK
YTEVRGSRRLAQQKINECVKSQSNRYGFCGNGTHIFSIVNSAPDGLLFLHTVLLPTDYKN
VKAWSGICVDGIYGYVLRQPNLVLYSDNGVFRVTSRVMFQPRLPVLSDFVQIYNCNVTFV
NISRVELHTVIPDYVDVNKTLQEFAQNLPKYVKPNFDLTPFNLTYLNLSSELKQLEAKTA
SLFQTTVELQGLIDQINSTYVDLKLLNRFENYIKWPWWVWLIISVVFVVLLSLLVFCCLS
TGCCGCCNCLTSSMRGCCDCGSTKLPYYEFEKVHVQ

Fig. 23

ORF-4 Corona virus envelope protein/E-gene (SEQ ID NO:64)
MFLRLIDDNGIVLNSILWLLVMIFFFVLAMTFIKLIQLCFTCHYFFSRTLYQPVYKIFLA
YQDYMQIAPVPAEVLNV

ORF-5 pfam01635, Corona_M, Coronavirus M matrix/glycoprotein. (SEQ ID NO:65)
MSNSSVPLLEVYVHLRNWNFSWNLILTLFIVVLQYGHYKYSRLLYGLKMSVLWCLWPLVLA LSIFDCFVNFNVDWVFFGFSILMSIITLCLWVMYFVNSFRLWRRVKTFWAFNPETNAII
SLQVYGHNYYLPVMAAPTGVTLTLLSGVLLVDGHKIATRVQVGQLPKYVIVATPSTTIVC
DRVGRSVNETSQTGWAFYVRAKHGDFSGVASQEGVLSEREKLLHLI

ORF-6 Pfam 00937, Coronavirus nucleocapsid protein (SEQ ID NO:66)
MASVNWADDRAARKKFPPPSFYMPLLVSSDKAPYRVIPRNLVPIGKGNKDEQIGYWNVQE
RWRMRRGQRVDLPPKVHFYYLGTGPHKDLKFRQRSDGVVWVAKEGAKTVNTSLGNRKRNQ
KPLEPKFSIALPPELSVVEFEDRSNNSSRASSRSSTRNNSRDSSRSTSRQQSRTRSDSNQ
SSSDLVAAVTLALKNLGFDNQSKSPSSSGTSTPKKPNKPLSQPRADKPSQLKKPRWKRVP
TREENVIQCFGPRDFNHNMGDSDLVQNGVDAKGFPQLAELIPNQAALFFDSEVSTDEVGD
NVQITYTYKMLVAKDNKNLPKFIEQISAFTKPSSIKEMQSQSSHVAQNTVLNASIPESKP
LADDDSAIIEIVNEVLH

SEQUENCE LISTING

```
<160> NUMBER OF SEQ ID NOS: 67

<210> SEQ ID NO 1
<211> LENGTH: 6
<212> TYPE: PRT
<213> ORGANISM: Artificial Sequence
<220> FEATURE:
<223> OTHER INFORMATION: Synthetic sequence.  Hexapeptide

<400> SEQUENCE: 1

Val Asn Ser Thr Leu Gln
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic sequence.  Hexapeptide

<400> SEQUENCE: 2

Tyr Asn Ser Thr Leu Gln
1               5

<210> SEQ ID NO 3
<211> LENGTH: 17
<212> TYPE: DNA
<213> ORGANISM: Artificial Sequence
<220> FEATURE:
<223> OTHER INFORMATION: Synthetic sequence.  Top strand oligo for MSE
      adaptor
```

-continued

<400> SEQUENCE: 3
ctcgtagact gcgtacc                                                17

<210> SEQ ID NO 4
<211> LENGTH: 16
<212> TYPE: DNA
<213> ORGANISM: Artificial Sequence
<220> FEATURE:
<223> OTHER INFORMATION: Synthetic sequence.  Top strand oligo for HinP1
      adaptor

<400> SEQUENCE: 4
gacgatgagt cctgac                                                 16

<210> SEQ ID NO 5
<211> LENGTH: 13
<212> TYPE: DNA
<213> ORGANISM: Artificial Sequence
<220> FEATURE:
<223> OTHER INFORMATION: Synthetic sequence.  Bottom strand oligo for
      MSE adaptor

<400> SEQUENCE: 5
taggtacgca gtc                                                    13

<210> SEQ ID NO 6
<211> LENGTH: 14
<212> TYPE: DNA
<213> ORGANISM: Artificial Sequence
<220> FEATURE:
<223> OTHER INFORMATION: Synthetic sequence.  Bottom strand oligo for
      HinP1 adaptor

<400> SEQUENCE: 6
cggtcaggac tcat                                                   14

<210> SEQ ID NO 7
<211> LENGTH: 19
<212> TYPE: DNA
<213> ORGANISM: Artificial Sequence
<220> FEATURE:
<223> OTHER INFORMATION: Synthetic sequence.  HinP1 standard primer

<400> SEQUENCE: 7
gacgatgagt cctgaccgc                                              19

<210> SEQ ID NO 8
<211> LENGTH: 20
<212> TYPE: DNA
<213> ORGANISM: Artificial Sequence
<220> FEATURE:
<223> OTHER INFORMATION: Synthetic sequence.  MseI standard primer

<400> SEQUENCE: 8
ctcgtagact gcgtacctaa                                             20

<210> SEQ ID NO 9
<211> LENGTH: 10
<212> TYPE: DNA
<213> ORGANISM: Artificial Sequence
<220> FEATURE:
<223> OTHER INFORMATION: Synthetic sequence.  Primer repSZ-RT

<400> SEQUENCE: 9
ccactataac                                                        10

```
<210> SEQ ID NO 10
<211> LENGTH: 20
<212> TYPE: DNA
<213> ORGANISM: Artificial Sequence
<220> FEATURE:
<223> OTHER INFORMATION: Synthetic sequence.  Primer repSZ-1

<400> SEQUENCE: 10
gtgatgcata tgctaatttg                                                    20

<210> SEQ ID NO 11
<211> LENGTH: 20
<212> TYPE: DNA
<213> ORGANISM: Artificial Sequence
<220> FEATURE:
<223> OTHER INFORMATION: Synthetic sequence.  Primer repSZ-3

<400> SEQUENCE: 11
ctcttgcagg tataatccta                                                    20

<210> SEQ ID NO 12
<211> LENGTH: 20
<212> TYPE: DNA
<213> ORGANISM: Artificial Sequence
<220> FEATURE:
<223> OTHER INFORMATION: Synthetic sequence.  Primer repSZ-2

<400> SEQUENCE: 12
ttggtaaaca aaagataact                                                    20

<210> SEQ ID NO 13
<211> LENGTH: 20
<212> TYPE: DNA
<213> ORGANISM: Artificial Sequence
<220> FEATURE:
<223> OTHER INFORMATION: Synthetic sequence.  Primer repSZ-4

<400> SEQUENCE: 13
tcaatgctat aaacagtcat                                                    20

<210> SEQ ID NO 14
<211> LENGTH: 12
<212> TYPE: RNA
<213> ORGANISM: Artificial Sequence
<220> FEATURE:
<223> OTHER INFORMATION: Synthetic sequence.  Leader TRS

<400> SEQUENCE: 14
ucucaacuaa ac                                                            12

<210> SEQ ID NO 15
<211> LENGTH: 24
<212> TYPE: DNA
<213> ORGANISM: Artificial Sequence
<220> FEATURE:
<223> OTHER INFORMATION: Synthetic sequence.  Oligonucleotide JZH2R
<220> FEATURE:
<221> NAME/KEY: misc_feature
<222> LOCATION: (19)..(24)
<223> OTHER INFORMATION: "n" stands for any nucleic acid

<400> SEQUENCE: 15
gctatcatca caatggacnn nnng                                               24

<210> SEQ ID NO 16
```

<211> LENGTH: 129
<212> TYPE: DNA
<213> ORGANISM: Human Coronavirus 229E

<400> SEQUENCE: 16

```
gtattgtttt tgttgcttgt gcccatgctg ctgttgattc cttatgtgca aaagctatga      60
ctgtttatag cattgataag tgtactagga ttatacctgc aagagctcgg gttgagtgtt     120
atagtggct                                                             129
```

<210> SEQ ID NO 17
<211> LENGTH: 42
<212> TYPE: PRT
<213> ORGANISM: Human Coronavirus 229E

<400> SEQUENCE: 17

```
Ile Val Phe Val Ala Cys Ala His Ala Ala Val Asp Ser Leu Cys Ala
1               5                   10                  15

Lys Ala Met Thr Val Tyr Ser Ile Asp Lys Cys Thr Arg Ile Ile Pro
            20                  25                  30

Ala Arg Ala Arg Val Glu Cys Tyr Ser Gly
        35                  40
```

<210> SEQ ID NO 18
<211> LENGTH: 145
<212> TYPE: DNA
<213> ORGANISM: Human Coronavirus 229E

<400> SEQUENCE: 18

```
atgggtctag atatggcttg caaaacttac tacagttacc taactttat tatgttagta       60 atggtggtaa caattgcact acggccgtta tgacctattc taattttggt atttgtgctg     120
atggttcttt gattcctgtt cgtcc                                           145
```

<210> SEQ ID NO 19
<211> LENGTH: 47
<212> TYPE: PRT
<213> ORGANISM: Human Coronavirus 229E

<400> SEQUENCE: 19

```
Gly Ser Arg Tyr Gly Leu Gln Asn Leu Leu Gln Leu Pro Asn Phe Tyr
1               5                   10                  15

Tyr Val Ser Asn Gly Gly Asn Asn Cys Thr Thr Ala Val Met Thr Tyr
            20                  25                  30

Ser Asn Phe Gly Ile Cys Ala Asp Gly Ser Leu Ile Pro Val Arg
        35                  40                  45
```

<210> SEQ ID NO 20
<211> LENGTH: 71
<212> TYPE: DNA
<213> ORGANISM: Human Coronavirus 229E

<400> SEQUENCE: 20

```
atgataaggg tttagtctta cacacaatgg taggccagtg atagtaaagt gtaagtaatt      60
tgctatcata t                                                          71
```

<210> SEQ ID NO 21
<211> LENGTH: 134
<212> TYPE: DNA
<213> ORGANISM: Human Coronavirus 229E

<400> SEQUENCE: 21

```
atgtcagtga tgcatatgct aatttggttc catattacca acttattggt aaacaaaaga      60
taactacaat acagggtcct cctggtagtg gtaagtcaca ttgttccatt ggacttggat     120
tgtactaccc aggt                                                        134
```

<210> SEQ ID NO 22
<211> LENGTH: 44
<212> TYPE: PRT
<213> ORGANISM: Human Coronavirus 229E

<400> SEQUENCE: 22

```
Val Ser Asp Ala Tyr Ala Asn Leu Val Pro Tyr Tyr Gln Leu Ile Gly
1               5                  10                  15

Lys Gln Lys Ile Thr Thr Ile Gln Gly Pro Pro Gly Ser Gly Lys Ser
            20                  25                  30

His Cys Ser Ile Gly Leu Gly Leu Tyr Tyr Pro Gly
        35                  40
```

<210> SEQ ID NO 23
<211> LENGTH: 207
<212> TYPE: DNA
<213> ORGANISM: Human Coronavirus 229E

<400> SEQUENCE: 23

```
atctaaacta acaaaatgg ctagtgtaaa ttgggccgat gacagagctg ctaggaagaa       60
atttcctcct ccttcatttt acatgcctct tttggttagt tctgataagg caccatatag     120
ggtcattccc aggaatcttg tccctattgg taagggtaat aaagatgagc agattggtta     180
ttggaatgtt caagagcgtt ggcgtat                                         207
```

<210> SEQ ID NO 24
<211> LENGTH: 68
<212> TYPE: PRT
<213> ORGANISM: Human Coronavirus 229E

<400> SEQUENCE: 24

```
Ser Lys Leu Asn Lys Met Ala Ser Val Asn Trp Ala Asp Asp Arg Ala
1               5                  10                  15

Ala Arg Lys Lys Phe Pro Pro Pro Ser Phe Tyr Met Pro Leu Leu Val
            20                  25                  30

Ser Ser Asp Lys Ala Pro Tyr Arg Val Ile Pro Arg Asn Leu Val Pro
        35                  40                  45

Ile Gly Lys Gly Asn Lys Asp Glu Gln Ile Gly Tyr Trp Asn Val Gln
    50                  55                  60

Glu Arg Trp Arg
65
```

<210> SEQ ID NO 25
<211> LENGTH: 207
<212> TYPE: DNA
<213> ORGANISM: Human Coronavirus 229E

<400> SEQUENCE: 25

```
acaaaaattt gaatgagggt gttcttgaat cttttttctgt tacacttctt gataatcaag     60
aagataagtt ttggtgtgaa gatttttatg ctagtatgta tgaaaattct acaatattgc     120
aagctgctgg tttatgtgtt gtttgtggtt cacaaactgt acttcgttgt ggtgattgtc     180
tgcgtaagcc tatgttgtgc actaaat                                         207
```

-continued

```
<210> SEQ ID NO 26
<211> LENGTH: 68
<212> TYPE: PRT
<213> ORGANISM: Human Coronavirus 229E

<400> SEQUENCE: 26

Lys Asn Leu Asn Glu Gly Val Leu Glu Ser Phe Ser Val Thr Leu Leu
1               5                   10                  15

Asp Asn Gln Glu Asp Lys Phe Trp Cys Glu Asp Phe Tyr Ala Ser Met
            20                  25                  30

Tyr Glu Asn Ser Thr Ile Leu Gln Ala Ala Gly Leu Cys Val Val Cys
        35                  40                  45

Gly Ser Gln Thr Val Leu Arg Cys Gly Asp Cys Leu Arg Lys Pro Met
    50                  55                  60

Leu Cys Thr Lys
65

<210> SEQ ID NO 27
<211> LENGTH: 71
<212> TYPE: DNA
<213> ORGANISM: Human Coronavirus 229E

<400> SEQUENCE: 27 aggggggcaac gtgttgattt gcctcctaaa gttcattttt attacctagg tactggacct      60
cataaggacc t                                                            71

<210> SEQ ID NO 28
<211> LENGTH: 23
<212> TYPE: PRT
<213> ORGANISM: Human Coronavirus 229E

<400> SEQUENCE: 28

Arg Gly Gln Arg Val Asp Leu Pro Pro Lys Val His Phe Tyr Tyr Leu
1               5                   10                  15

Gly Thr Gly Pro His Lys Asp
            20

<210> SEQ ID NO 29
<211> LENGTH: 107
<212> TYPE: DNA
<213> ORGANISM: Human Coronavirus 229E

<400> SEQUENCE: 29
tagtagttgt gttactcgtt gtaatatagg tggtgctgtt tgttcaaaac atgcaaattt       60
gtatcaaaaa tacgttgagg catataatac atttacacag gcaggtt                   107

<210> SEQ ID NO 30
<211> LENGTH: 35
<212> TYPE: PRT
<213> ORGANISM: Human Coronavirus 229E

<400> SEQUENCE: 30

Ser Ser Cys Val Thr Arg Cys Asn Ile Gly Gly Ala Val Cys Ser Lys
1               5                   10                  15

His Ala Asn Leu Tyr Gln Lys Tyr Val Glu Ala Tyr Asn Thr Phe Thr
            20                  25                  30

Gln Ala Gly
        35
```

<210> SEQ ID NO 31
<211> LENGTH: 58
<212> TYPE: DNA
<213> ORGANISM: Artificial Sequence
<220> FEATURE:
<223> OTHER INFORMATION: Synthetic sequence. Primer S1

<400> SEQUENCE: 31
acaagtttgt acaaaaaagc aggcttcaaa cttttcttga ttttgcttgt tttgcccc       58

<210> SEQ ID NO 32
<211> LENGTH: 51
<212> TYPE: DNA
<213> ORGANISM: Artificial Sequence
<220> FEATURE:
<223> OTHER INFORMATION: Synthetic sequence. Primer S2

<400> SEQUENCE: 32
accactttgt acaagaaagc tgggtcttga acgtggacct tttcaaattc g              51

<210> SEQ ID NO 33
<211> LENGTH: 55
<212> TYPE: DNA
<213> ORGANISM: Artificial Sequence
<220> FEATURE:
<223> OTHER INFORMATION: Synthetic sequence. Primer M1

<400> SEQUENCE: 33
acaagtttgt acaaaaaagc aggcttctct aatagtagtg tgcctctttt agagg          55

<210> SEQ ID NO 34
<211> LENGTH: 47
<212> TYPE: DNA
<213> ORGANISM: Artificial Sequence
<220> FEATURE:
<223> OTHER INFORMATION: Synthetic sequence. Primer M2

<400> SEQUENCE: 34
accactttgt acaagaaagc tgggtcgatt aaatgaagca acttctc                   47

<210> SEQ ID NO 35
<211> LENGTH: 49
<212> TYPE: DNA
<213> ORGANISM: Artificial Sequence
<220> FEATURE:
<223> OTHER INFORMATION: Synthetic sequence. Primer N1

<400> SEQUENCE: 35
acaagtttgt acaaaaaagc aggcttcgct agtgtaaatt gggccgatg                 49

<210> SEQ ID NO 36
<211> LENGTH: 59
<212> TYPE: DNA
<213> ORGANISM: Artificial Sequence
<220> FEATURE:
<223> OTHER INFORMATION: Synthetic sequence. Primer N2

<400> SEQUENCE: 36
accactttgt acaagaaagc tgggtcatgc aaaacctcgt tgacaatttc tataatggc      59

<210> SEQ ID NO 37
<211> LENGTH: 8
<212> TYPE: DNA
<213> ORGANISM: Artificial Sequence
<220> FEATURE:
<223> OTHER INFORMATION: Synthetic sequence. Conserved sequence -continued

```
<400> SEQUENCE: 37
aattatgg 8

<210> SEQ ID NO 38
<211> LENGTH: 69
<212> TYPE: DNA
<213> ORGANISM: Artificial Sequence
<220> FEATURE:
<223> OTHER INFORMATION: Synthetic sequence. Recombination site NL63-229E
<400> SEQUENCE: 38
tcatcctaat tgttgtgact gttatgatga tatgtgtgtt atacattgtt caaattttaa 60
cacactctt 69

<210> SEQ ID NO 39
<211> LENGTH: 60
<212> TYPE: DNA
<213> ORGANISM: Artificial Sequence
<220> FEATURE:
<223> OTHER INFORMATION: Synthetic sequence. Recombination site NL63/OC43 hybrid
<400> SEQUENCE: 39
caacgtatgt gtttggaacc ttgtaattta tataattatg ggaagccagt tactttgcct 60

<210> SEQ ID NO 40
<211> LENGTH: 466
<212> TYPE: DNA
<213> ORGANISM: Artificial Sequence
<220> FEATURE:
<223> OTHER INFORMATION: Synthetic sequence. Sequence REF
<400> SEQUENCE: 40
taataatgct gtctatgatg gtgctcgttt attttcttca gatttgtcta ctttagctgt 60
tacagctatt gttgtagtag gtggttgtgt aacatctaat gttccaacaa ttgttagtga 120
gaaaatttct gttatggata aacttgatac tggtgcacaa aaatttttcc aatttggtga 180
ttttgttatg aataacattg ttctgttttt aacttggttg cttagtatgt ttagtctttt 240
acgtacttct attatgaagc atgatattaa agttattgcc aaggctccta aacgtacagg 300
tgttattttg acacgtagtt ttaagtataa cattagatct gctttgtttg ttataaagca 360
gaagtggtgt gttattgtta ctttgtttaa gttcttatta ttattatatg ctatttatgc 420
acttgttttt atgattgtgc aatttagtcc ttttaatagt ctttta 466

<210> SEQ ID NO 41
<211> LENGTH: 466
<212> TYPE: DNA
<213> ORGANISM: Artificial Sequence
<220> FEATURE:
<223> OTHER INFORMATION: Synthetic sequence. Sequence 223B
<400> SEQUENCE: 41
taataatgct gtctatgatg gtgctcgttt atctgcttca gatttgtcta ctttagctgt 60
tacagctatt gttgtagtag gtggttgtgt aacatctaat gttccaccaa ttgttagtga 120
gaaaatttct gttatggata aacttgatac tggtgcacaa aaatttttcc aatttggtga 180
ttttgttatg aataacattg ttctgttttt aacttggttg cttagtatgt ttagtctttt 240
acgtacttct attatgaagc atgatattaa agttattgcc aaggctccta aacgtacagg 300
tgttattttg acacgtagtt ttaagtataa cattagatct gctttgtttg ttgtaaagca 360
```

-continued

| | | |
|---|---|---|
| gaagtggtgt gttattgtta ctttgtttaa gttcttattg ttattatatg ctatttatgc | 420 | |
| acttgttttt atgattgtgc aatttagtcc ttttaatagt ctttta | 466 | |

<210> SEQ ID NO 42
<211> LENGTH: 466
<212> TYPE: DNA
<213> ORGANISM: Artificial Sequence
<220> FEATURE:
<223> OTHER INFORMATION: Synthetic sequence. Sequence 246B

<400> SEQUENCE: 42

| | |
|---|---|
| taataatgct gtctatgatg gtgctcgttt attttcttca gatttgtcta ctttagctgt | 60 |
| tacagctatt gttgtagtag gtggttgtgt aacatctaat gttccaccaa ttgttagtga | 120 |
| gaaaatttct gttatggata aacttgatac tggtgcacaa aaattttttcc aatttggtga | 180 |
| ttttgttatg aataacattg ttctgttttt aacttggttg cttagtatgt ttagtctttt | 240 |
| acgtacttct attatgaagc atgatattaa agttattgcc aaggctccta aacgtacagg | 300 |
| tgttattttg acacgtagtt ttaagtataa cattagatct gctttgtttg ttataaagca | 360 |
| gaagtggtgt gttattgtta ctttgtttaa gttcttattg ttattatatg ctatttatgc | 420 |
| acttgttttt atgattgtgc aatttagtcc ttttaatagt ctttta | 466 |

<210> SEQ ID NO 43
<211> LENGTH: 466
<212> TYPE: DNA
<213> ORGANISM: Artificial Sequence
<220> FEATURE:
<223> OTHER INFORMATION: Synthetic sequence. Sequence 248B

<400> SEQUENCE: 43

| | |
|---|---|
| taataatgct gtctatgatg gtgctcgttt atttgcttca gatttgtcta ctttagctgt | 60 |
| tacagctatt gttgtagtag gtggttgtgt aacatctaat gttccaccaa ttgttagtga | 120 |
| gaaaatttct gttatggata aacttgatac tggtgcacaa aaattttttcc aatttggtga | 180 |
| ttttgttatg aataacattg ttctgttttt aacttggttg cttagtatgt ttagtctttt | 240 |
| acgtacttct attatgaagc atgatattaa agttattgcc aaggctccta aacgtacagg | 300 |
| tgttattttg acacgtagtt ttaagtataa cattagatct gctttgtttg ttgtaaagca | 360 |
| gaagtggtgt gttattgtta ctttgtttaa gttcttattg ttattatatg ctatttatgc | 420 |
| acttgttttt atgattgtgc aatttagtcc ttttaatagt ctttta | 466 |

<210> SEQ ID NO 44
<211> LENGTH: 466
<212> TYPE: DNA
<213> ORGANISM: Artificial Sequence
<220> FEATURE:
<223> OTHER INFORMATION: Synthetic sequence. Sequence 251B

<400> SEQUENCE: 44

| | |
|---|---|
| taataatgct gtctatgatg gtgctcgttt attttcttca gatttgtcta ctttagctgt | 60 |
| tacagctatt gttgtagtag gtggttgtgt aacatctaat gttccaccaa ttgttagtga | 120 |
| gaaaatttct gttatggata aacttgatac tggtgcacaa aaattttttcc aatttggtga | 180 |
| ttttgttatg aataacattg ttctgttttt aacttggttg cttagtatgt ttagtctttt | 240 |
| acgtacttct attatgaagc atgatattaa agttattgcc aaggctccta aacgtacagg | 300 |
| tgttattttg acacgtagtt ttaagtataa cattagatct gctttgtttg ttataaagca | 360 |

```
gaagtggtgt gttattgtta ctttgtttaa gttcttatta ttattatatg ctatttatgc    420
acttgttttt atgattgtgc aatttagtcc ttttaatagt cttta                    466
```

<210> SEQ ID NO 45
<211> LENGTH: 466
<212> TYPE: DNA
<213> ORGANISM: Artificial Sequence
<220> FEATURE:
<223> OTHER INFORMATION: Synthetic sequence. Sequence 466B

<400> SEQUENCE: 45

```
taataatgct gtctatgatg gtgctcgttt attttcttca gatttgtcta ctttagctgt     60
tacagctatt gttgtagtag gtggttgtgt aacatctaat gttccaacaa ttgttagtga    120
gaaaatttct gttatggata aacttgatac tggtgcacaa aaattttttcc aatttggtga   180 ttttgttatg aataacattg ttctgttttt aacttggttg cttagtatgt ttagtctttt    240
acgtacttct attatgaagc atgatattaa agttattgcc aaggctccta acgtacagg     300 tgttattttg acacgtagtt ttaagtataa cattagatct gctttgtttg ttataaagca    360
gaagtggtgt gttattgtta ctttgtttaa gttcttatta ttattatatg ctatttatgc    420
acttgttttt atgattgtgc aatttagtcc ttttaatagt cttta                    466
```

<210> SEQ ID NO 46
<211> LENGTH: 466
<212> TYPE: DNA
<213> ORGANISM: Artificial Sequence
<220> FEATURE:
<223> OTHER INFORMATION: Synthetic sequence. Sequence 496B

<400> SEQUENCE: 46

```
taataatgct gtctatgatg gtgctcgttt atttgcttca gatttgtcta ctttagctgt     60
tacagctatt gttgtagtag gtggttgtgt aacatctaat gttccatcaa ttgttagtga    120
gaaaatttct gttatggata aacttgatac tggtgcacaa aaattttttcc aatttggtga   180 ttttgttatg aataacattg ttctgttttt aacttggttg cttagtatgt ttagtctttt    240
acgtacttct attatgaagc atgatattaa agttattgcc aaggctccta acgtacagg     300 tgttattttg acacgtagtt ttaagtataa cattagatct gctttgtttg ttataaagca    360
gaagtggtgt gttattgtta ctttgtttaa gttcttattg ttattatatg ctatttatgc    420
acttgttttt atgattgtgc aatttagtcc ttttaatagt cttta                    466
```

<210> SEQ ID NO 47
<211> LENGTH: 22
<212> TYPE: DNA
<213> ORGANISM: Artificial Sequence
<220> FEATURE:
<223> OTHER INFORMATION: Synthetic sequence. Oligo NL63NF1

<400> SEQUENCE: 47

```
gctagtgtaa attgggccga tg                                              22
```

<210> SEQ ID NO 48
<211> LENGTH: 24
<212> TYPE: DNA
<213> ORGANISM: Artificial Sequence
<220> FEATURE:
<223> OTHER INFORMATION: Synthetic sequence. Oligo NL63NR1

<400> SEQUENCE: 48

```
cttccaacga ggtttcttca actg                                            24
```

<210> SEQ ID NO 49
<211> LENGTH: 24
<212> TYPE: DNA
<213> ORGANISM: Artificial Sequence
<220> FEATURE:
<223> OTHER INFORMATION: Synthetic sequence. Oligo NL63NF2

<400> SEQUENCE: 49
tcctcctcct tcattttaca tgcc                                          24

<210> SEQ ID NO 50
<211> LENGTH: 25
<212> TYPE: DNA
<213> ORGANISM: Artificial Sequence
<220> FEATURE:
<223> OTHER INFORMATION: Synthetic sequence. Oligo NL63NR2

<400> SEQUENCE: 50
aactcaacaa cagagagctc tggag                                         25

<210> SEQ ID NO 51
<211> LENGTH: 26
<212> TYPE: DNA
<213> ORGANISM: Artificial Sequence
<220> FEATURE:
<223> OTHER INFORMATION: Synthetic sequence. Oligo COR1F
<220> FEATURE:
<221> NAME/KEY: misc_feature
<222> LOCATION: (18)..(18)
<223> OTHER INFORMATION: "n" stands for "i"

<400> SEQUENCE: 51
atgggwtggg aytatccnaa rtgtga                                        26

<210> SEQ ID NO 52
<211> LENGTH: 25
<212> TYPE: DNA
<213> ORGANISM: Artificial Sequence
<220> FEATURE:
<223> OTHER INFORMATION: Synthetic sequence. Oligo COR1R

<400> SEQUENCE: 52
gytgkgarca raaytcrtgw ggtcc                                         25

<210> SEQ ID NO 53
<211> LENGTH: 20
<212> TYPE: DNA
<213> ORGANISM: Artificial Sequence
<220> FEATURE:
<223> OTHER INFORMATION: Synthetic sequence. Oligo COR2F
<220> FEATURE:
<221> NAME/KEY: misc_feature
<222> LOCATION: (18)..(18)
<223> OTHER INFORMATION: "n" stands for "i"

<400> SEQUENCE: 53 tatktttaarc cwggtggnac                                              20

<210> SEQ ID NO 54
<211> LENGTH: 24
<212> TYPE: DNA
<213> ORGANISM: Artificial Sequence
<220> FEATURE:
<223> OTHER INFORMATION: Synthetic sequence. Oligo COR2R
<220> FEATURE:
<221> NAME/KEY: misc_feature
<222> LOCATION: (7)..(7)

<223> OTHER INFORMATION: "n" stands for unkown nucleic acid

<400> SEQUENCE: 54
catraanacr yyattytgrt aata                                              24

<210> SEQ ID NO 55
<211> LENGTH: 27553
<212> TYPE: DNA
<213> ORGANISM: Human coronavirus NL63

<400> SEQUENCE: 55
cttaaagaat ttttctatct atagatagag aattttctta tttagacttt gtgtctactc        60
ttctcaacta aacgaaattt ttctagtgct gtcatttgtt atggcagtcc tagtgtaatt       120
gaaatttcgt caagtttgta aactggttag caagtgttg tattttctgt gtctaagcac        180
tggtgattct gttcactagt gcatacattg atatttaagt ggtgttccgt cactgcttat       240 tgtgaagca acgttctgtc gttgtggaaa ccataactg ctaaccatgt tttacaatca         300
agtgacactt gctgttgcaa gtgattcgga aatttcaggt tttggttttg ccattccttc       360
tgtagccgtt cgcacctata gcgaagccgc tgcacaaggt tttcaggcat gccgttttgt       420
tgcttttggc ttacaggatt gtgtaaccgg tattaatgat gatgattatg tcattgcatt       480
gactggtact aatcagctct gtgccaaaat tttaccttt tctgatagac ccctaattt        540 gcgaggttgg ctcattttt ctaacagcaa ttatgttctt caggactttg atgttgtttt        600
tggccatggt gcaggaagtg tggttttgt ggataagtac atgtgtggtt ttgatggtaa        660
acctgtgtta cctaaaaaca tgtgggaatt tagggattac tttaataata atactgatag       720
tattgttatt ggtggtgtca cttatcaact agcatgggt gttatacgta aagaccttc         780 ttatgaacag caaaatgttt tagccattga gagcattcat taccttggta ctacaggtca       840
tactttgaag tctggttgca aacttactaa tgctaagccg cctaaatatt cttctaaggt        900
tgttttgagt ggtgaatgga atgctgtgta tagggcgttt ggttcaccat ttattacaaa       960
tggtatgtca ttgctagata taattgttaa accagtttc tttaatgctt ttgttaaatg      1020
caattgtggt tctgagagtt ggagtgttgg tgcatgggat ggttacttat cttcttgttg      1080
tggcacacct gctaagaaac tttgtgttgt tcctggtaat gtcgttcctg gtgatgtgat      1140
catcacctca actagtgctg gttgtggtgt taaatactat gctggcttag ttgttaaaca      1200
tattactaac attactggtg tgtctttat gcgtgttaca gctgttcatt ctgatggaat      1260
gtttgtggca tcatcttctt atgatgcact cttgcataga aattcattag acccttttg      1320 ctttgatgtt aacactttac tttctaatca attacgtcta gcttttcttg gtgcttctgt      1380
tacagaagat gttaaatttg ctgctagcac tggtgttatt gacattagtg ctggtatgtt      1440
tggtctttac gatgacatat tgacaaacaa taaaccttgg tttgtacgca aagcttctgg      1500 gcttttgat gcaatctggg atgcttttgt tgccgctatt aagcttgtac caactactac       1560
tggtgttttg gttaggtttg ttaagtctat tgcttcaact gttttaactg tctctaatgg      1620
tgttattatt atgtgtgcag atgttccaga tgcttttcaa tcagtttatc gcacatttac      1680
acaagctatt tgtgctgcat tgatttttc tttagatgta tttaaaattg gtgatgttaa      1740
atttaaacga cttggtgatt atgttcttac tgaaaacgct cttgttcgtt tgactactga      1800
agttgttcgt ggtgttcgtg atgctcgcat aaagaaagcc atgtttacta aagtagttgt      1860
aggtcctaca actgaagtta agtttttctgt tattgaactt gccactgtta atttgcgtct      1920
tgttgattgt gcacctgtag tttgccctaa aggtaagatt gttgttattg ctggacaagc      1980

```
tttttttctat agtggtggtt tttatcgttt tatggttgat cctacaactg tattaaatga    2040
tcctgttttt actggtgatt tattctacac tattaagttt agtggtttta agcttgatgg    2100
ttttaaccat cagtttgtta ctgctagttc tgctacagat gccattattg ctgttgagct    2160
gttgttattg gattttaaaa ctgcagtttt tgtgtacaca tgtgtggttg atggctgtag    2220
tgtcattgtt agacgtgatg ctacattcgc tacacatgtg tgttttaagg actgttataa    2280
tgtttgggag caattctgca ttgataattg tggtgagcca tggttttga ctgattataa    2340 tgctatcttg cagagtaata accctcaatg tgctattgtt caagcatcag agtctaaagt    2400
tttgcttgag aggttttac ctaagtgtcc tgaaatactg ttgagtattg atgatggcca    2460
tttatggaat cttttgttg aaaagtttaa ttttgttaca gattggttaa aaactcttaa    2520
gcttacactt acttctaatg gtcttttagg taattgtgcc aaacgtttta gacgtgtttt    2580
ggtaaaattg cttgatgtct ataatggttt tcttgaaact gtctgtagtg tcgcatacac    2640
tgctggtgtt tgcatcaaat attatgctgt taatgttcca tatgtagtta ttagtggttt    2700
tgtaagtcgt gtaattcgta gagaaaggtg tgacatgact tttccttgtg ttagttgtgt    2760
cacctttttc tatgaatttt tagacacttg ttttggtgtt agtaaaccta atgccattga    2820
tgttgaacat ttagagctta agaaactgt ttttgttgaa cctaaggatg gtggtcaatt    2880
ttttgtttct ggtgattatc tttggtatgt tgtagatgac atttattatc cagcttcatg    2940
taatggtgta ttgcctgttg ctttacaaa attagctggt ggtaaaatat cttttctga    3000 tgatgttata gttcatgatg ttgaacctac ccataagtc aagctcatat ttgagtttga    3060
agatgatgtt gttaccagtc tttgtaagaa gagttttggt aagtccatta tttatacagg    3120
tgattgggaa ggtctacatg aagttcttac atctgcaatg aatgtcattg gcaacatat    3180 taagttgcca caatttttata tttatgatga gagggtggt tatgatgttt ctaaaccagt    3240
tatgatttca caatgcccta ttagtaatga tagtaatggt tgtgttgttg aagcgagcac    3300 tgatttcat caattagaat gtattgttga tgactctgtt agagaagagg ttgatataat    3360
tgaacaacct tttgaagaag ttgaacatgt gctctcaatt aagcaacctt tttctttttc    3420
ttttagagat gaattgggtg ttcgtgttt agatcaatct gataataatt gttggattag    3480
taccacactt gtacagttgc aacttacaaa gcttttggat gattctattg agatgcaatt    3540
gtttaaagtt ggtaaagttg attcaattgt ccaaagtgt tatgagttgt ctcatttaat    3600
tagtggttca cttggtgata gtggtaaact tcttagtgaa cttcttaaag aaaaatatac    3660
atgttctata acttttgaga tgtcttgtga ttgtggtaaa aagtttgatg atcaggttgg    3720
ttgtttgttt tggattatgc cttacacaaa acttttcaa aaaggtgagt gttgtattg    3780 tcataaaatg cagacttata agcttgttag tatgaaaggt actggtgtgt tgtacagga    3840 tccagcacct attgacattg atgctttccc tgtgaaacct atatgttcat ctgtatattt    3900
aggtgttaag ggttctggtc attatcaaac aaatttatac agttttaaca agctattga    3960 tggttttggt gtcttttgaca ttaaaaatag tagtgttaat actgtttgtt ttgttgatgt    4020
tgattttcat agtgtagaaa tagaagctgg tgaagtaaaa cctttgctg tatataaaaa    4080 tgttaaattt tatttaggtg atattcaca ccttgtaaac tgtgtttctt ttgactttgt    4140
tgtcaatgct gctaatgaaa atctcttgca tggaggcggt gttgcacgtg ctattgatat    4200
tttgactgaa ggtcaacttc agtcactatc taaagattac attagtagta atggtccact    4260
taaggttgga gcaggtgtta tgttggagtg tgaaaaattc aacgtatta atgttgttgg    4320
```

-continued

```
tccgcgaact ggtaaacatg agcattcatt acttgttgaa gcttataatt ctattttatt    4380
tgaaaatggt attccactta tgcctcttct tagttgtgga ttttttggtg taaggattga    4440
aaattctctt aaagctttgt ttagttgtga cattaataaa ccattgcaag ttttttgttta   4500
ttcttcaaat gaagaacaag ctgttcttaa gtttttagat ggtttagatt taacaccagt    4560
cattgatgat gttgatgttg ttaaaccttt tagagttgaa ggtaattttt cattctttga    4620
ttgtggtgtc aatgccttgg atggtgatat ttacttatta tttactaact ctattttaat    4680
gttggataaa caaggacaat tattggacac aaaacttaat ggtattttgc aacaggcagc    4740
tcttgattat cttgctacag ttaaaactgt accagctggt aatttggtta aacttttttgt   4800
tgagagttgt accatttata tgtgtgttgt accatcgata atgatctttt cttttgataa    4860
aaatcttggt cgttgtgtgc gtaaacttaa tagattgaaa acttgtgtta ttgccaatgt    4920
tcctgctatt gatgttttga aaaagcttct ttcaagtttg actttaactg ttaaatttgt    4980
tgtagagagt aatgttatgg atgttaacga ctgtttttaag aatgataatg tagttttgaa    5040
aattactgaa gatggtatta atgttaaaga tgttgttgtt gagtcttcta agtcacttgg    5100
taaacaattg ggtgttgtga gtgatggtgt tgactctttt gaaggtgttt tacctattaa    5160
tactgatact gtcttatctg tagctccaga agttgactgg gttgcttttt acggttttga    5220
aaaggcagca cttttttgctt ctttggatgt aaagccatat ggttacccta atgattttgt    5280
tggtggtttt agagttcttg ggaccaccga caataattgt tgggttaatg caacttgtat    5340
aatttttacag tatcttaagc ctacttttaa atctaagggt ttaaatgttc tttggaacaa    5400
atttgttaca ggtgatgttg gacctttttgt tagttttatt tattttataa ctatgtcttc    5460
aaagggtcaa aagggtgatg ctgaagaggc attatctaaa ttgtcagagt atttgattag    5520
tgattctatt gttactcttg aacaatattc aacttgtgac atttgtaaaa gtactgtagt    5580
tgaagttaaa agtgctattg tctgtgctag tgtgctaaaa gatggttgtg atgttggttt    5640
ttgtccacac agacataaat tgcgttcacg tgttaagttt gttaatggac gtgttgttat    5700
taccaatgtt ggtgaaccta aatttcaca accttctaag ttgcttaatg gtattgctta    5760
tacaacattt tcaggttctt tgataacgg tcactatgta gtttatgatg ctgctaataa    5820
tgctgtctat gatggtgctc gtttatttttc ttcagatttg tctactttag ctgttacagc    5880
tattgttgta gtaggtggtt gtgtaacatc taatgttcca acaattgtta gtgagaaaat    5940
ttctgttatg gataaacttg atactggtgc acaaaaattt ttccaatttg gtgattttgt    6000
tatgaataac attgttctgt ttttaacttg gttgcttagt atgtttagtc ttttacgtac    6060
ttctattatg aagcatgata ttaaagttat tgccaaggct cctaaacgta caggtgttat    6120
tttgacacgt agttttaagt ataacattag atctgctttg tttgttataa agcagaagtg    6180
gtgtgttatt gttactttgt ttaagttctt attattatta tatgctattt atgcacttgt    6240
ttttatgatt gtgcaattta gtccttttaa tagtcttttta tgtggtgaca ttgtaagtgg    6300
ttatgaaaaa tccacttttta ataaggatat ttattgtggt aattctatgg tttgtaagat    6360
gtgtttgttc agttatcaag agtttaatga tttggatcat actagtcttg tttggaagca    6420
cattcgtgat cctatattaa tcagtttaca accatttgtt atacttgtta ttttgttaat    6480
ttttggtaat atgtatttgc gttttggact tttatttttt gttgcacaat ttattagtac    6540
ttttggttct ttcttaggct ttcatcagaa acagtggttt ttacattttg tgccgtttga    6600
tgtttatgt aatgagtttt tagctacatt tattgtctgc aaaatcgttt tatttgttag    6660
acatattatt gttggctgta ataatgctga ctgtgtagct tgttctaaaa gtgctagact    6720
```

```
taaacgtgta ccacttcaaa ctattattaa tggtatgcat aaatcattct atgttaatgc    6780
taatggtggt acttgtttct gtaataaaca taacttcttt tgtgttaatt gtgattcttt    6840
tgggcctggt aatacttta ttaatggtga tattgcaaga gagcttggta atgttgttaa     6900
aacagctgtt caacccacag ctcctgcata tgttattatt gataaggtag attttgttaa    6960
tggattttat cgtctttata gtggtgacac tttttggcgg tatgactttg acattactga    7020
atctaagtat agttgtaaag aggttctgaa gaattgtaat gttttagaaa attttattgt    7080
ttacaataat agtggtagta acattacaca gattaaaaat gcttgtgttt attttttctca    7140 attgttgtgt gaacctataa agttggtaaa ttcagagttg ttgtcaactt tatctgttga    7200
ttttaatggt gttttgcata aggcatatgt tgatgtttg tgtaatagtt ttttaagga      7260 gttaactgct aacatgtcca tggctgaatg taaagctaca cttggtttga ctgtttctga    7320
tgatgatttt gttcagctg ttgccaatgc acataggtat gacgttttgc tttcagattt     7380
gtcatttaat aattttttta tttcttatgc taaacctgaa gataagttgt ccgtttatga    7440
cattgcttgt tgtatgcgtg ccggttctaa ggttgttaac cataatgttt taattaaaga    7500
gtcaatacct attgtttggg gtgtcaagga ctttaatact ctttctcaag aaggtaagaa    7560
gtaccttgtt aaaacaacta aagcaaaggg tttgactttt ttattaactt ttaatgataa    7620
ccaagcaatt acacaagttc ctgctactag tatagttgca aaacagggtg ctggttttaa    7680
acgtacttat aattttctgt ggtatgtatg tttatttgtt gttgcattgt ttattggtgt    7740
ctcatttatt gattatacaa ccactgtaac tagctttcat ggttatgatt ttaagtacat    7800
tgagaatggt cagttgaagg tgtttgaagc acctttacac tgtgttcgta atgttttga    7860 taattttaat caatggcatg aggctaagtt tggtgttgtt actactaata gtgataaatg    7920
tcctatagtt gttggtgttt cagagcgtat taatgttgtt cctggtgttc aacaaatgt    7980 atatttggta ggaaagactc ttgtttttac attacaggct gcttttggaa acacaggtgt    8040
ttgttatgac tttgatggtg ttaccactag tgataagtgt attttaatt ctgcttgtac    8100 taggttggaa ggtttgggtg gtgacaatgt ttattgttac aacactgatc ttattgaagg    8160
ttctaaacct tatagtactt tacagcccaa tgcgtattat aagtatgatg ctaaaaatta    8220
tgtacgtttt ccagaaattt tagctagagg ttttggctta cgtactatta gaactttggc    8280
tacacgttat tgtagagttg gtgaatgccg tgactcacat aaaggtgttt gttttggttt    8340
tgataaatgg tatgttaatg atggacgtgt tgatgacggt tacatttgtg tgatggtct    8400 tatagacctt cttgttaatg tactctcaat ctttagttca tcttttagcg ttgtggctat    8460
gtctggacat atgttgttta attttctttt tgcagcattt attacatttt tgtgcttttt    8520
agttactaaa tttaaacgtg ttttttggtga tctttcttat ggtgttttta ctgttgtttg    8580
tgcaactttg attaataaca tttcttatgt tgttactcaa aatttatttt ttatgttgct    8640
ttatgctatt ttgtattttg tttttactag gacagtgcgt tatgcttgga tttggcatat    8700
tgcatacatt gttgcatact tcttgttaat accatggtgg cttctcacat ggtttagttt    8760
tgctgcattt ttagagcttt tacctaatgt ttttaagtta aaaatctcta ctcaattgtt    8820
tgaaggtgat aagtttatag gtactttga gagtgctgct gcaggtacat tgttcttga     8880 catgcgttct tatgaaaggc tgataaatac tatttcacct gagaaactta agaattatgc    8940
tgcaagttat aataaatata atatattag tggtagtgct agtgaggctg attatcgttg    9000
tgcttgttat gctcatttag ccaaggctat gttagattat gcaaaagatc ataatgacat    9060
```

```
gttatattct ccacctacta ttagctacaa ttccacctta caatctggtc ttaagaagat    9120
ggcacaacca tctggttgtg ttgagagatg tgtggttcgc gtctgttatg gtagtactgt    9180
gcttaatgga gtttggttag gtgacactgt tacttgtcct agacatgtca tagcaccatc    9240
aaccactgtt cttattgatt atgatcatgc atatagtact atgcgtttgc ataattttc     9300 agtgtctcat aatggtgtct tcttgggagt tgtcggtgtt acaatgcatg gttctgtgtt    9360
gcgtattaag gtttcacaat ctaatgtaca tacacctaaa catgttttta aaacgttgaa    9420
acctggtgat tcttttaata ttttagcatg ttatgaaggt attgcatctg tgttttttgg    9480
tgttaattta cgtacaaact ttactattaa aggttctttt ataaatggag cttgtggttc    9540
tcctggttat aatgttagaa atgatggtac tgttgagttt tgttatttac accaaattga    9600
gttaggtagt ggtgctcatg ttggttctga ttttactggt agtgtttatg gtaattttga    9660
tgaccaacct agtttgcaag ttgagagtgc caaccttatg ctatcagata atgttgttgc    9720 cttttttgtat gctgctttgt tgaatggttg taggtggtgg ttgtgttcaa ctagagttaa    9780
tgttgatggt tttaatgaat gggctatggc taatggttat acaagtgttt ctagtgttga    9840
gtgctattct attttggcag caaaaactgg tgttagtgtt gaacaattgt tagcttccat    9900
tcaacatctt catgaaggtt ttggtggtaa aaacatactt ggttattcta gtttatgtga    9960
tgagttcaca ctagctgaag ttgtgaagca gatgtatggt gttaacttgc aaagtggtaa   10020
ggttattttt ggttttaaaaa caatgttttt atttagcgtt ttcttcacaa tgtttttgggc  10080 agaactcttt atttatacaa acactatatg gataaaccct gtgatactta cacctatatt   10140
ttgtctactt ttgttttgt cattagttttt aactatgttt cttaaacata gttttgtt    10200 tttgcaagta tttttattac ctactgttat tgcaactgct ttatataatt gtgttttgga   10260
ttattacata gtaaaattt tggctgacca ttttaactat aatgtttcag tattacaaat    10320
ggatgttcag ggtttagtta atgttttggt ctgtttattt gttgtatttt tacacacatg   10380
gcgcttttct aaagaacgtt ttacacattg gtttacatat gtgtgttctc ttatagcagt   10440
tgcttacact tatttttata gtggtgactt tttgagtttg cttgttatgt ttttatgtgc   10500
tatatctagt gattggtaca ttggtgccat tgttttttagg ttgtcacgtt tgattgtatt   10560
tttttcacct gaaagtgtat ttagtgtttt tggtgatgtg aaacttactt tagttgtttta  10620 tttaatttgt ggttatttag tttgtacttta ttggggcatt ttgtattggt tcaataggtt   10680
ttttaaatgt actatgggtg tttatgattt taaggtgagt gctgctgaat ttaaatacat   10740
ggttgctaat ggacttcatg caccacatgg acctttgat gcactttggt tatcattcaa    10800
actacttggt attggtggtg accgttgtat aaaaatttca actgtccaat ccaaactgac   10860
tgatttgaag tgtactaatg ttgtgttatt gggttgtttg tctagtatga acattgcagc   10920
taattctagt gaatgggctt attgtgttga tttacacaat aagattaatc tttgtgatga  10980
ccctgaaaaa gctcaaagta tgttgttagc actccttgcg ttctttctaa gtaaacatag  11040
tgattttggt cttgatggcc ttattgattc ttatttgat aatagtagca cccttcagag    11100
tgttgcttca tcatttgtta gtatgccatc atatattgct tatgaaaatg ctagacaagc   11160
ttatgaggat gctattgcta atggatcttc ttctcaactt attaaacaat gaagcgtgc    11220 catgaatatc gcaaagtctg aatttgatca tgagatatct gttcagaaga aaattaatag   11280
aatggctgaa caagctgcta ctcagatgta taaagaagca cgctctgtta atagaaaatc   11340
taaagttatt agtgctatgc actctttact ttttggaatg ttaagacgtt tggatatgtc   11400
tagtgttgaa actgttttga atttagcacg tgatggtgtt gtgccattgt cagttatacc   11460
```

```
tgcaacttca gcttctaaac taactattgt tagtccagat cttgaatctt attctaagat    11520
tgtttgtgat ggttctgttc attatgctgg agttgtttgg acacttaatg atgttaaaga    11580
caatgatggt agacctgttc atgttaaaga gattacaaag gaaaatgttg aaactttgac    11640
atggcctctt atccttaatt gtgaacgtgt tgttaaactt caaaataatg aaattatgcc    11700
tggtaaactt aagcaaaaac ctatgaaagc tgagggtgat ggtggtgttt taggtgatgg    11760
taatgccttg tataatactg agggtggtaa aactttatg tacgcttata tttctaataa    11820 agctgaccttt aaatttgtta agtgggagta tgagggtggt tgcaacacaa tcgagttaga    11880
ctctccttgt cgatttatgg tcgaaacacc taatggtcct caagtgaagt atttgtatttt    11940 tgttaaaaat ttaaatacct tacgtagagg tgccgttctt ggttttatag gtgccacaat    12000
tcgtctacaa gctggtaaac aaactgaatt ggctgttaat tctggacttt taactgcttg    12060 tgcttttttct gttgatccag caactactta cttggaagct gttaaacatg gtgcaaaacc    12120
tgtaagtaat tgtattaaga tgttatctaa tggtgctggt aatggtcaag ctataacaac    12180
tagtgtagat gctaacacca atcaagattc ttatggtgga gcgtctattt gtttgtattg    12240
tcgggcccac gttcctcacc ctagtatgga tggttactgt aagtttaagg gtaaatgtgt    12300
tcaggttcct attggttgtt tggatcctat taggttttgt ttagaaaata atgtgtgtaa    12360
tgtttgtggt tgttggttgg gacacgggtg tgcttgtgac cgtacaacta ttcaaagtgt    12420 tgacattttct tatttaaacg agcaaggggt tctagtgcag ctcgactaga accctgcaat    12480
ggcacggaca tcgataagtg tgttcgtgct tttgacattt ataataaaaa tgtttcattc    12540
ttgggtaagt gtttgaagat gaactgtgtt cgttttaaaa atgctgatct taaggatggt    12600
tattttgtta taaagaggtg tactaagtcg gttatggaac acgagcaatc catgtataac    12660
ctacttaact tttctggtgc tttggctgag catgatttct ttacttggaa agatggcaga    12720
gtcatttatg gtaatgttag tagacataat cttactaaat atactatgat ggacttggtc    12780
tatgctatgc gtaactttga tgaacaaaat tgtgatgttc taaaagaagt attagtttta    12840
actggttgtt gtgacaattc ttattttgat agtaagggtt ggtatgaccc agttgaaaat    12900
gaagatatac atagagttta tgcatctctt ggcaaaattg tagctagagc tatgcttaaa    12960
tgcgttgctc tatgcgatgc gatggttgct aaaggtgttg ttggtgtttt aacattagat    13020
aaccaagatc ttaatggtaa ctttttatgat tttggtgatt tgttgttag cttacctaat    13080 atgggtgttc cctgttgtac atcatattat tcttatatga tgcctattat gggtttaact    13140
aattgtttag ctagtgagtg ttttgtcaag agtgatattt ttggtagtga ttttaaaact    13200
tttgatttgc ttaagtatga tttcactgaa cataaagaaa atttattcaa taagtacttt    13260
aagcattgga gttttgatta tcatcctaat tgttgtgact gttatgatga tatgtgtgtt    13320
atacattgtg ctaattttaa tacactattt gccacaacta taccaggtac tgcttttggt    13380
ccactatgtc gtaaagtttt tatagatggt gttccacttg ttacaactgc tggttatcat    13440
tttaagcaat taggtttggt ttggaataaa gatgttaaca cacactcagt taggttgaca    13500
attactgaac ttttgcaatt tgtcaccgac ccttccttga taatagcttc ttccccagca    13560
ctcgttgatc aacgcactat ttgttttttct gttgcagcat tgagtactgg tttgacaaat    13620
caagttgtta agccaggtca ttttaatgaa gagtttttata actttcttcg tttaagaggt    13680
ttctttgatg aaggtctga acttacatta aaacatttct tcttcgcaca gaatggtgat    13740
gctgctgtta aagattttga ctttttaccgt tataataagc ctaccatttt agatatttgt    13800
```

```
caagctagag ttacatataa gatagtctct cgttattttg acatttatga aggtggctgt   13860
attaaggcat gtgaagttgt tgtaacaaat cttaataaga gtgctggttg gccattaaat   13920
aagtttggta aagctagttt gtattatgaa tctatatctt atgaagaaca ggatgctttg   13980
tttgctttga caaagcgtaa tgtcctccct actatgacac agctgaatct aagtatgct   14040 attagtggta aagaacgtgc tagaactgtt ggtggtgttt ctctgttgtc tacaatgacc   14100
acaagacaat accatcaaaa acatcttaaa tccattgtta atacacgcaa tgccactgtt   14160
gttattggta ctaccaaatt ttatggtggt tggaataata tgttgcgtac tttaattgat   14220
ggtgttgaaa accctatgct tatgggttgg gattatccca aatgtgatag agctttgcct   14280
aacatgatac gtatgatttc agccatggtg ttgggctcta agcatgttaa ttgttgtact   14340
gcaacagata ggttttatag gcttggtaat gagttggcac aagttttaac agaagttgtt   14400
tattctaatg gtggttttta ttttaagcca ggtggtacga cttctggtga cgctagtaca   14460
gcttatgcta attctatttt taacattttt caagccgtga gttctaacat taacaggttg   14520
cttagtgtcc catcagattc atgtaataat gttaatgtta gggatctaca acgacgtctg   14580
tatgataatt gttataggtt aactagtgtt gaagagtcat tcattgaaga ttattatggt   14640
tatcttagga aacattttc aatgatgatt ctctctgatg acggtgttgt ctgttataac   14700
aaggattatg ctgagttagg ttatatagca gacattagtg ctttttaaagc cactttgtat   14760 taccagaata atgtctttat gagtacttct aaatgttggg ttgaagaaga tttaactaag   14820
ggaccacatg agttttgttc ccagcatact atgcaaatag ttgacaaaga tggtacctat   14880
tatttgcctt acccagatcc tagtaggatc ttgtcagctg gtgtttttgt tgatgatgtt   14940
gttaagacag atgctgttgt tttgttagaa cgttatgtgt ctttagctat tgatgcatac   15000 cctcttttcaa acacccctaa ttccgaatat cgtaaggttt tttacgtatt acttgattgg   15060
gttaagcatc ttaacaaaaa tttgaatgag ggtgttcttg aatcttttc tgttacactt   15120 cttgataatc aagaagataa gttttggtgt gaagattttt atgctagtat gtatgaaaat   15180
tctacaatat tgcaagctgc tggtttatgt gttgttgtg gttcacaaac tgtacttcgt   15240
tgtggtgatt gtctgcgtaa gcctatgttg tgcactaaat gcgcatatga tcatgtattt   15300
ggtaccgacc acaagtttat tttggctata acaccgtatg tatgtaatgc atcaggttgt   15360
ggtgttagtg atgtcaaaaa attgtatctt ggtggtttga attactattg tacaaatcat   15420
aaaccacagt tgtctttttcc attatgttca gctggtaata tatttggttt atataaaaat   15480
tcagcaactg gttccttaga tgttgaagtt tttaataggc ttgcaacgtc tgattggact   15540
gatgttaggg actataaact tgctaatgat gttaaagata cacttagact ctttgcggct   15600
gaaactatta agctaaaga agagagtgtt aagtcttctt atgcttttgc aactcttaaa   15660
gaggttgttg gacctaaaga attgcttctt agttgggaaa gtggtaaagt taaaccacct   15720
ttgaatcgta attctgtttt cacttgtttt caaataagta aggactcaaa attccaaata   15780
ggtgagttca tctttgagaa ggttgaatat ggttctgata ctgttacgta taagtctact   15840
gtaactacta agttagttcc tggtatgatt tttgtcttaa catctcacaa tgtccaacct   15900
ttacgtgcac caactattgc aaaccaagag aagtattcta gcatttataa attgcaccct   15960
gcttttaatg tcagtgatgc atatgctaat ttggttccat attccaact tattggtaaa   16020 caaaagataa ctacaataca gggtcctcct ggtagtggta agtcacattg ttccattgga   16080
cttggattgt actacccagg tgcgcgtatt gttttttgttg cttgtgccca tgctgctgtt   16140
gattccttat gtgcaaaagc tatgactgtt tatagcattg ataagtgtac taggattata   16200
```

```
cctgcaagag ctcgggttga gtgttatagt ggctttaaac caaataacac tagtgcacaa    16260
tacatattta gcactgttaa cgcattacct gagtgtaatg ctgatatcgt tgttgtagat    16320
gaagtttcaa tgtgtacaaa ttatgacctt tctgttatta accagcgttt atcatataaa    16380
catattgttt atgttggtga tccacaacaa cttcctgcac ctagagtaat gattactaaa    16440
ggtgttatgg agcctgttga ttataacgtt gttactcaac gtatgtgtgc tataggccct    16500
gatgtttttc ttcataaatg ttatagatgt cctgctgaaa tagtaataca gtttctgaac    16560
ttgtttatga gaacaagttt gtccctgtta aacctgctag taaacagtgt tttaaagtct    16620
tttttaaggg taatgtacaa ggttgacaat ggttctagta ttaacagaaa gcagcttgaa    16680
atagttaagc tgttttagt taaaaatcca agttggagta aggctgtgtt tatttctcct    16740
tataatagtc agaattatgt tgctagtaga tttttaggac ttcaaattca aactgttgat    16800
tcttctcaag gtagtgagta tgattatgta atctatgcac aaacttctga cactgcacat    16860
gcttgcaatg taaaccgttt taatgttgct ataacacgtg ctaagaaggg tatattttgt    16920
gtaatgtgtg ataaaacttt gtttgattca cttaagtttt ttgagattaa acatgcagat    16980
ttacactcta gccaggtttg tggcttgttt aaaaattgta cacgcactcc tcttaattta    17040
ccaccaactc atgcacacac tttcttgtcg ttgtcagatc agtttaagac tacaggtgat    17100
ttagctgttc aaataggttc aaataacgtt tgtacttatg aacatgttat atcatttatg    17160
ggttttaggt ttgatattag tattcctggt agtcatagtt tgttttgtac acgtgacttt    17220
gctattcgta atgtgcgtgg ttggttgggt atggatgttg aaagtgctca tgtttgtggc    17280
gataacatag gtactaatgt tcctttacag gttggttttt caaatggtgt taattttgtt    17340
gtgcaaactg aaggttgtgt gtctaccaat tttggtgatg ttattaaacc tgtttgtgca    17400
aaatctccac caggtgaaca atttagacac cttattcctc ttttacgtaa aggacaacct    17460
tggttaattg ttcgtagacg cattgtgcaa atgatatctg attatttgtc caatttgtct    17520
gacattcttg tctttgtttt gtgggcaggt agtttggaat taactacaat gcgttacttt    17580
gtaaaaatag ggccaattaa atattgttat tgtggtaatt ttgccacttg ttataattca    17640
gttagtaatg aatattgttg ttttaaacat gcattgggtt gtgattatgt ttacaatccg    17700
tatgcttttg atatacaaca gtggggttat gttggttcct tgagccaaaa ccaccacaca    17760
ttctgtaaca ttcatagaaa cgagcatgat gcctctggtg atgctgttat gacacgttgt    17820
ttggcagtac atgattgttt tgtcaaaaat gttgattgga ctgtaacgta cccctttatt    17880
gcaaatgaga aatttatcaa tggctgtggg cgtaatgtcc agggacatgt tgttcgtgca    17940
gccttgaaat tgtataaacc tagtgttatt catgacattg gtaatcctaa aggtgtacgt    18000
tgtgctgtta ctgatgccaa atggtactgt tatgacaagc aacctgttaa tagtaatgtc    18060
aagttgttgg attatgatta tgcaacccat ggtcaacttg atggtctttg tttattctgg    18120
aattgtaatg ttgatatgta tccagaattt tcaattgtgt gtcgttttga cacacgtact    18180
cgttctgttt ttaatttaga aggtgttaat ggtggttctc tttatgttaa caaacatgcg    18240
tttcatacac cagcatatga taacgtgct tttgttaaat taaaacctat gccctttttt    18300
tactttgatg acagtgattg tgatgttgtg caagaacaag ttaattatgt acccccttcgc    18360 gctagtagtt gtgttactcg ttgtaatata ggtggtgctg tttgttcaaa acatgcaaat    18420
ttgtatcaaa aatatgttga ggcatataat acatttacac aggcaggttt taacattgg    18480 gtaccacata gttttgatgt ttataatttg tggcaaattt ttattgaaac taatttcaa    18540
```

-continued

```
agtcttgaaa atatagcatt taatgttgta aaaaaagggt gttttactgg tgttgatggt     18600
gagttacctg ttgcagttgt taacgacaaa gttttttgttc gctatggcga tgttgacaac    18660
ttggttttta caaataaaac aacattgcct actaatgttg cttttgaatt gtttgcaaaa     18720
cgaaaaatgg gtttaacacc accattgtct attctcaaaa atctcggtgt tgttgctaca    18780
tataaatttg ttttatggga ttatgaagct gaaagacctt ttacctcata tactaagagt     18840
gtatgtaaat acactgattt taatgaggat gtttgtgttt gttttgacaa tagtattcag    18900
ggttcgtatg agcgttttac gcttactacg aacgctgttt tattttctac tgttgtcatt    18960
aaaaatttaa cacctataaa gttgaatttt ggtatgttga atggtatgcc agtttcttct    19020
attaagggtg ataaaggtgt tgaaaaatta gttaattggt acatatatgt tcgtaaaaat    19080
ggtcaatttc aagatcacta tgatggtttt tacactcaag gtaggaattt atcagacttt    19140
acaccaagaa gtgatatgga gtatgatttt cttaacatgg atatgggtgt ttttattaat    19200
aaatatggtc ttgaggattt taattttgaa catgttgtat atggtgatgt ttcaaaaact    19260
acattaggag gtcttcattt gttgatatca cagtttaggc ttagtaaaat gggtgttttg    19320
aaagctgatg attttgtcac tgcttctgac acaactttga ggtgctgtac tgttacttat    19380
cttaatgaac ttagttcaaa agttgtttgt acttatatgg atttgttgtt ggacgacttt    19440
gttactatac taaagagttt agatcttggt gtaatatcta agttcatga agttattata    19500
gataataaac cttataggtg gatgttgtgg tgtaaagata accacttgtc cacttttat    19560
ccacagttgc agtctgctga atggaagtgt ggttatgcta tgccacaaat ttataagctt    19620
caacgtatgt gtttggaacc ttgtaattta tataattatg gtgctggtat taagttgcct    19680
agtggtataa tgttaaatgt tgttaaatac actcagcttt gtcaataccct aaatagcact   19740
acaatgtgcg tacctcataa tatgcgtgtt ttgcactatg gtgctggttc tgacaaaggt    19800
gtggcacctg gtacaactgt tttaaaaacgt tggctaccac ccgatgcaat aatcattgat    19860
aatgatatca atgattatgt tagtgatgca gattttagca ttacaggtga ttgtgctact    19920
gtttatcttg aagataagtt tgacttactt atttctgata tgtatgatgg tagaattaaa    19980
ttttgtgatg gtgaaaatgt ctctaaagat gggtttttta cttatcttaa tggtgttatt    20040
agagaaaaat tagctattgg tggtagtgtt gccattaaga ttacagaata tagttggaat    20100
aagtatcttt atgaattaat acaaagattt gcttttttga ctttgttttg cacgtctgtt    20160
aatacatcct cttcagaagc ttttcttatt ggtattaatt atttaggtga ctttattcaa    20220
ggtccttta tagctggtaa cactgttcat gctaattata tattttggcg taattctact     20280
attatgtctt tgtcatacaa ttcagtttta gatttaagta agtttgaatg taaacataaa    20340
gccactgttg ttgttacact taaagatagt gatgtaaatg atatggttttt gagtttgatt   20400
aagagtggta ggttgttgtt acgcaataat ggtcgttttg gtggttttag taatcattta    20460
gtctcaacta aatgaaactt ttcttgattt tgcttgtttt gcccctggcc tcttgctttt    20520
tcacatgtaa tagtaatgct aatctctcta tgttacaatt aggtgttcct gacaattctt    20580
caactattgt tacggggttta ttgccaactc attggttttg tgctaatcag agtacatctg    20640
tttactcagc caatggtttc ttttatattg atgttggtaa tcaccgtagt gcttttgcgc    20700
tccatactgg ttattatgat gctaatcagt attatttta tgttactaat gaaataggct    20760
taaatgcttc tgttactctt aagatttgta agtttagtag aaacactact tttgattttt    20820
taagtaatgc ttctagttct tttgactgta tagttaattt gttatttaca gaacagttag    20880
gtgcgccttt gggcataact atatctggtg aaactgtgcg tctgcattta tataatgtaa    20940
```

```
ctcgtacttt ttatgtgcca gcagcttata aacttactaa acttagtgtt aaatgttact    21000
ttaactattc ctgtgttttt agtgttgtca acgccaccgt tactgtgaat gtcaccacac    21060
ataatggccg tgtagttaac tacactgttt gtgatgattg taatggttat actgataaca    21120
tattttctgt tcaacaggat ggccgcattc ctaatggttt ccctttttaat aattggtttt   21180
tgttaactaa tggttccaca ctagtggacg gggtctctag actttatcaa ccactccgtt    21240
taacttgttt atggcctgta cctggtctta aatcttcaac tggttttgtt tattttaatg    21300
ccactggttc tgatgttaat tgtaacggct atcaacataa ttctgttgtt gatgttatgc    21360
gttacaatct taacttcagt gctaattctt ggacaatct caagagtggt gttatagttt     21420
ttaaaacttt acagtacgat gttttgtttt attgtagtaa ttcttcctca ggtgttcttg    21480
acaccacaat accttttggc ccgtcctctc aaccttatta ctgttttata aacagcacta    21540
tcaacactac tcatgttagc acttttgtgg gtattttacc acccactgtg cgtgaaattg    21600
ttgttgctag aactggccag ttttatatta atggttttaa gtatttcgat ttgggtttca    21660
tagaagctgt caatttttaat gtcacgactg ctagcgccac agattttggg acggttgcat   21720
ttgctacttt tgttgatgtt ttggttaatg ttagtgcaac taacattcaa aacttactttt  21780
attgcgattc tccatttgaa aagttgcagt gtgagcactt gcagtttgga ttgcaggatg    21840
gttttattc tgcaaatttt cttgatgata atgttttgcc tgagacttat gttgcactcc    21900
ccatttatta tcaacacacg gacataaatt ttactgcaac tgcatctttt ggtggttctt    21960
gttatgtttg taaaccacac caggttaata tatctcttaa tggtaacact tcagtgtgtg   22020
ttagaacatc tcattttttca attaggtata tttataaccg cgttaagagt ggttcaccag   22080
gtgactcttc atggcacatt tatttaaaga gtggcacttg tccatttttct ttttctaagt   22140
taaataattt tcaaaagttc aagactattt gtttctcaac cgtcgaagtg cctggtagtt    22200
gtaattttcc gcttgaagcc acctggcatt acacttctta tactattgtt ggtgctttgt    22260
atgttacttg gtctgaaggt aattctatta ctggtgtacc ttatcctgtc tctggtattc    22320
gtgagtttag taatttagtt ttaaataatt gtaccaaata taatatttat gattatgttg    22380
gtactggaat tatacgttct tcaaaccagt cacttgctgg tggtattaca tatgtttcta   22440
actctggtaa tttacttggt tttaaaaatg tttccactgg taacatttttt attgtgacac   22500
catgtaacca accagaccaa gtagctgttt atcaacaaag cattattggt gccatgaccg   22560
ctgttaatga gtctagatat ggcttgcaaa acttactaca gttacctaac ttttattatg    22620
ttagtaatgg tggtaacaat tgcactacgg ccgttatgac ttattctaat tttggtattt    22680
gtgctgatgg ttcttttgatt cctgttcgtc cgcgtaattc tagtgataat ggtatttcag   22740
ccataatcac tgctaattta ccattccttc taactggac tacttcagtt caagttgagt    22800
acctccaaat tactagtact ccaatagttg ttgattgtgc tacttatgtg tgtaatggta    22860
accctcgctg taagaatcta cttaagcagt atacttctgc ttgtaaaact attgaagatg    22920
ccttacgact tagtgctcat ttggaaacta atgatgttag tagtatgcta actttcgata   22980
gcaatgcttt tagtttggct aatgttacta gttttggaga ttataacctt tctagtgttt    23040
tacctcagag aaacattcgt tcaagccgta tagcaggacg tagtgctttg gaagatttgt    23100
tgtttagcaa agttgttaca tctggtttgg gtactgttga tgttgactat aagtcttgta   23160
ctaaaggtct ttctattgct gaccttgctt gtgctcagta ctacaatggc ataatggttt    23220
tgccaggtgt tgctgatgct gaacgtatgg ccatgtacac aggttctctt ataggtggca    23280
```

```
tggtgctcgg aggtcttaca tcagcagccg ccatacctttt tctttggca ctgcaagcac    23340
gacttaacta tgttgcttta caaactgatg tgcttcaaga aaatcagaaa attttggctg    23400
catcatttaa taaggctatt aataatattg ttgcttctttt tagtagcgtt aatgatgcta    23460
ttacacaaac tgcagaggct atacatactg ttactattgc acttaataag attcaggatg    23520
ttgttaatca acagggtagt gctcttaacc atctcacttc acaattgaga cataattttc    23580
aggccatttc taattcaatt caggctattt atgaccggct tgattcaatt caagccgatc    23640
aacaagttga cagattaatt actggacggc ttgcagcttt gaatgcattt gtttcccaag    23700
ttttgaataa atatactgaa gttcgtggtt caagacgctt agcacagcag aagattaatg    23760
aatgtgtcaa gtcacaatct aatagatatg ttttttgtgg caatggcact cacatctttt    23820
caatcgtcaa ctctgctcca gatggttttgc ttttcttca tactgttttg ctgccaactg    23880
attacaagaa tgtaaaggcg tggtctggta tctgtgttga tggcatttat ggctatgttc    23940
tgcgtcaacc taacttggtt ctttattctg ataatggtgt ctttcgtgta acttccaggg    24000
tcatgtttca acctcgctta cctgttttgt ctgattttgt gcaaatatat aattgtaatg    24060
ttacttttgt taacatatct cgtgttgagt tacatactgt catacctgac tacgttgatg    24120
ttaataaaac attacaagag tttgcacaaa acttaccaaa gtatgttaag cctaattttg    24180
acttgactcc ttttaattta acatatctta atttgagttc tgagttgaag caactcgaag    24240
ctaaaactgc tagtctttttt caaactactg ttgaattaca aggtcttatt gatcagatta    24300
acagtacata tgttgatttg aagttgctta ataggtttga aaattatatc aaatggcctt    24360
ggtgggtttg gctcattatt tctgttgttt ttgttgtatt gttgagtctt cttgtgtttt    24420
gttgtctttc tacaggttgt tgtggttgtt gcaattgttt aacttcatca atgcgaggct    24480
gttgtgattg tggttcaact aaacttcctt attacgaatt tgaaaaggtc cacgttcaat    24540
aatgcctttt ggtggcctat ttcaacttac tcttgaaagt actattaata agagtgtggc    24600
taatctcaaa ttaccacctc atgatgttac tgtcttgcgt gacaatctta aacctgttac    24660
tacacttagt actattactg cttatttgtt agttagtttg tttgtcactt actttgcttt    24720
attcaaacct cttactgcta gaggtcgtgt tgcttgtttt gttttaaaac tattgacact    24780
atttgtctat gtgcctttat tggttctttt tggtatgtat cttgacagtt ttataatttt    24840
ttctacgctg ttgtttcgat tcatacatgt tggctattat gcctatctct ataaaaatttt    24900
ttcatttgtt ttgttcaatg ttactaaaact atgcttcgtt tcaggcaagt gttggtatct    24960
tgaacaatca ttttatgaaa atcgttttgc tgctatttat ggtggtgacc actatgtcgt    25020
tttaggtggt gaaactatta cttttgtttc ttttgatgac ctttatgttg ctattagagg    25080
ttcttgtgaa aagaacctac aacttatgcg taaggttgac ttgtataatg gtgctgtcat    25140
ttacattttt gccgaagagc ctgttgttgg tatagtctac tcttctcaac tatacgaaga    25200
tgttccttcg attaattgat gacaatggta ttgtcctcaa ttccattttta ggctccttg    25260
ttatgatatt tttctttgtg ttggcaatga cctttattaa actgattcaa ttgtgttttta    25320
cttgtcatta tttttttagt aggacattat atcaaccagt ttataaaatt ttcttgcttt    25380
accaagatta tatgcaaata gcacctgttc cagctgaagt actaaatgtc taaactaaac    25440
gatgtctaat agtagtgtgc ctctttttaga ggttatgtc catttacgta actggaactt    25500
tagttggaat ttaattctaa cgcttttttat agttgtgttg cagtatgggc attataagta    25560
tagcagactc ctttatggtt taaagatgtc tgttttatgg tgtttatggc cacttgttct    25620
agctttgtct atttttgact gttttgtcaa ttttaatgtg gactgggtct ttttttggttt    25680
```

```
tagtattctt atgtctatta ttacactttg tttatgggtt atgtattttg ttaatagttt    25740
cagactttgg cgccgtgtta aaacttttgg gcttttaat cctgaaacta atgcaatcat     25800
ctctctccag gtttacggac ataattatta cttaccggtg atggctgcac ctacaggtgt    25860
tacattaaca cttcttagtg gtgtacttct tgttgatggc cataagattg ctactcgtgt    25920
tcaagtgggt cagttgccta aatatgtaat agttgctacg cctagtacca caattgtttg    25980
tgaccgtgtt ggtcgctctg ttaatgaaac aagccagact ggttgggcat tctacgtccg    26040
tgctaaacat ggtgattttt ctggtgttgc ctctcaggag ggtgttttgt cagaaagaga    26100
gaagttgctt catttaatct aaactaaaca aaatggctag tgtaaattgg gccgatgaca    26160
gagctgctag gaagaaattt cctcctcctt cattttacat gcctcttttg gttagttctg    26220
ataaggcacc atatagggtc attcccagga atcttgtccc tattggtaag ggtaataaag    26280
atgagcagat tggttattgg aatgttcaag agcgttggcg tatgcgcagg gggcaacgtg    26340
ttgatttgcc tcctaaagtt catttttatt acctaggtac tggacctcat aaggacctta    26400
aattcagaca acgttctgat ggtgttgttt gggttgctaa ggaaggtgct aaaactgtta    26460
ataccagtct tggtaatcgc aaacgtaatc agaaaccttt ggaaccaaag ttctctattg    26520
ctttgcctcc agagctctct gttgttgagt tgaggatcg ctctaataac tcatctcgtg     26580
ctagcagtcg ttcttcaact cgtaacaact cacgagactc ttctcgtagc acttcaagac    26640
aacagtctcg cactcgttct gattctaacc agtcttcttc agatcttgtt gctgctgtta    26700
ctttggcctt aaagaactta ggttttgata accagtcgaa gtcacctagt tcttctggta    26760
cttccactcc taagaaacct aataagcctc tttctcaacc cagggctgat aagccttctc    26820
agttgaagaa acctcgttgg aagcgtgttc ctaccagaga ggaaaatgtt attcagtgct    26880
ttggtcctcg tgattttaat cacaatatgg gggattcaga tcttgttcag aatggtgttg    26940
atgccaaagg ttttccacag cttgctgaat tgattcctaa tcaggctgcg ttattctttg    27000
atagtgaggt tagcactgat gaagtgggtg ataatgttca gattacctac acctacaaaa    27060
tgcttgtagc taaggataat aagaaccttc ctaagttcat tgagcagatt agtgctttta    27120
ctaaacccag ttctatcaaa gaatgcagt cacaatcatc tcatgttgct cagaacacag     27180
tacttaatgc ttctattcca gaatctaaac cattggctga tgatgattca gccattatag    27240
aaattgtcaa cgaggttttg cattaaattg ttttgtaatt ccagttgaat gtttattatt    27300
attagttgca accccatgcg tttagcgcat gataagggtt tagtcttaca cacaatggta    27360
ggccagtgat agtaaagtgt aagtaatttg ctatcatatt aacatgtcta gaggaaagtc    27420 agaactttt ctgtttgtgt tgttggagta cttaaagatc gcataggcgc gccaacaatg     27480
gaagagccaa caacatatct aaaaatgttt tgtctggtac ttgttaatga tattgttttt    27540
gatatggata cac                                                      27553
```

<210> SEQ ID NO 56
<211> LENGTH: 4060
<212> TYPE: PRT
<213> ORGANISM: Human coronavirus
<220> FEATURE:
<221> NAME/KEY: MISC_FEATURE
<222> LOCATION: (1)..(4060)
<223> OTHER INFORMATION: ORF 1a, replicase enzyme complex

<400> SEQUENCE: 56

```
Met Phe Tyr Asn Gln Val Thr Leu Ala Val Ala Ser Asp Ser Glu Ile
1               5                   10                  15
```

```
Ser Gly Phe Gly Phe Ala Ile Pro Ser Val Ala Val Arg Thr Tyr Ser
             20                  25                  30

Glu Ala Ala Ala Gln Gly Phe Gln Ala Cys Arg Phe Val Ala Phe Gly
             35                  40                  45

Leu Gln Asp Cys Val Thr Gly Ile Asn Asp Asp Tyr Val Ile Ala
             50                  55                  60

Leu Thr Gly Thr Asn Gln Leu Cys Ala Lys Ile Leu Pro Phe Ser Asp
 65                  70                  75                  80

Arg Pro Leu Asn Leu Arg Gly Trp Leu Ile Phe Ser Asn Ser Asn Tyr
                 85                  90                  95

Val Leu Gln Asp Phe Asp Val Val Phe Gly His Gly Ala Gly Ser Val
            100                 105                 110

Val Phe Val Asp Lys Tyr Met Cys Gly Phe Asp Gly Lys Pro Val Leu
            115                 120                 125

Pro Lys Asn Met Trp Glu Phe Arg Asp Tyr Phe Asn Asn Asn Thr Asp
            130                 135                 140

Ser Ile Val Ile Gly Gly Val Thr Tyr Gln Leu Ala Trp Asp Val Ile
145                 150                 155                 160

Arg Lys Asp Leu Ser Tyr Glu Gln Gln Asn Val Leu Ala Ile Glu Ser
                165                 170                 175

Ile His Tyr Leu Gly Thr Thr Gly His Thr Leu Lys Ser Gly Cys Lys
            180                 185                 190

Leu Thr Asn Ala Lys Pro Pro Lys Tyr Ser Ser Lys Val Val Leu Ser
            195                 200                 205

Gly Glu Trp Asn Ala Val Tyr Arg Ala Phe Gly Ser Pro Phe Ile Thr
            210                 215                 220

Asn Gly Met Ser Leu Leu Asp Ile Ile Val Lys Pro Val Phe Phe Asn
225                 230                 235                 240

Ala Phe Val Lys Cys Asn Cys Gly Ser Glu Ser Trp Ser Val Gly Ala
                245                 250                 255

Trp Asp Gly Tyr Leu Ser Ser Cys Cys Gly Thr Pro Ala Lys Lys Leu
            260                 265                 270

Cys Val Val Pro Gly Asn Val Val Pro Gly Asp Val Ile Ile Thr Ser
            275                 280                 285

Thr Ser Ala Gly Cys Gly Val Lys Tyr Tyr Ala Gly Leu Val Val Lys
            290                 295                 300

His Ile Thr Asn Ile Thr Gly Val Ser Leu Trp Arg Val Thr Ala Val
305                 310                 315                 320

His Ser Asp Gly Met Phe Val Ala Ser Ser Tyr Asp Ala Leu Leu
                325                 330                 335

His Arg Asn Ser Leu Asp Pro Phe Cys Phe Asp Val Asn Thr Leu Leu
            340                 345                 350

Ser Asn Gln Leu Arg Leu Ala Phe Leu Gly Ala Ser Val Thr Glu Asp
            355                 360                 365

Val Lys Phe Ala Ala Ser Thr Gly Val Ile Asp Ile Ser Ala Gly Met
            370                 375                 380

Phe Gly Leu Tyr Asp Asp Ile Leu Thr Asn Asn Lys Pro Trp Phe Val
385                 390                 395                 400

Arg Lys Ala Ser Gly Leu Phe Asp Ala Ile Trp Asp Ala Phe Val Ala
                405                 410                 415

Ala Ile Lys Leu Val Pro Thr Thr Thr Gly Val Leu Val Arg Phe Val
            420                 425                 430
```

-continued

```
Lys Ser Ile Ala Ser Thr Val Leu Thr Val Ser Asn Gly Val Ile Ile
            435                 440                 445

Met Cys Ala Asp Val Pro Asp Ala Phe Gln Ser Val Tyr Arg Thr Phe
450                 455                 460

Thr Gln Ala Ile Cys Ala Ala Phe Asp Phe Ser Leu Asp Val Phe Lys
465                 470                 475                 480

Ile Gly Asp Val Lys Phe Lys Arg Leu Gly Asp Tyr Val Leu Thr Glu
                485                 490                 495

Asn Ala Leu Val Arg Leu Thr Thr Glu Val Val Arg Gly Val Arg Asp
                500                 505                 510

Ala Arg Ile Lys Lys Ala Met Phe Thr Lys Val Val Gly Pro Thr
            515                 520                 525

Thr Glu Val Lys Phe Ser Val Ile Glu Leu Ala Thr Val Asn Leu Arg
530                 535                 540

Leu Val Asp Cys Ala Pro Val Val Cys Pro Lys Gly Lys Ile Val Val
545                 550                 555                 560

Ile Ala Gly Gln Ala Phe Phe Tyr Ser Gly Phe Tyr Arg Phe Met
                565                 570                 575

Val Asp Pro Thr Thr Val Leu Asn Asp Pro Val Phe Thr Gly Asp Leu
                580                 585                 590

Phe Tyr Thr Ile Lys Phe Ser Gly Phe Lys Leu Asp Gly Phe Asn His
                595                 600                 605

Gln Phe Val Thr Ala Ser Ser Ala Thr Asp Ala Ile Ile Ala Val Glu
                610                 615                 620

Leu Leu Leu Leu Asp Phe Lys Thr Ala Val Phe Val Tyr Thr Cys Val
625                 630                 635                 640

Val Asp Gly Cys Ser Val Ile Val Arg Arg Asp Ala Thr Phe Ala Thr
                645                 650                 655

His Val Cys Phe Lys Asp Cys Tyr Asn Val Trp Glu Gln Phe Cys Ile
                660                 665                 670

Asp Asn Cys Gly Glu Pro Trp Phe Leu Thr Asp Tyr Asn Ala Ile Leu
            675                 680                 685

Gln Ser Asn Asn Pro Gln Cys Ala Ile Val Gln Ala Ser Glu Ser Lys
            690                 695                 700

Val Leu Leu Glu Arg Phe Leu Pro Lys Cys Pro Glu Ile Leu Leu Ser
705                 710                 715                 720

Ile Asp Asp Gly His Leu Trp Asn Leu Phe Val Glu Lys Phe Asn Phe
                725                 730                 735

Val Thr Asp Trp Leu Lys Thr Leu Lys Leu Thr Leu Thr Ser Asn Gly
            740                 745                 750

Leu Leu Gly Asn Cys Ala Lys Arg Phe Arg Val Leu Val Lys Leu
            755                 760                 765

Leu Asp Val Tyr Asn Gly Phe Leu Glu Thr Val Cys Ser Val Ala Tyr
770                 775                 780

Thr Ala Gly Val Cys Ile Lys Tyr Tyr Ala Val Asn Val Pro Tyr Val
785                 790                 795                 800

Val Ile Ser Gly Phe Val Ser Arg Val Ile Arg Arg Glu Arg Cys Asp
                805                 810                 815

Met Thr Phe Pro Cys Val Ser Cys Val Thr Phe Phe Tyr Glu Phe Leu
            820                 825                 830

Asp Thr Cys Phe Gly Val Ser Lys Pro Asn Ala Ile Asp Val Glu His
            835                 840                 845

Leu Glu Leu Lys Glu Thr Val Phe Val Glu Pro Lys Asp Gly Gly Gln
```

-continued

```
                850                 855                 860
Phe Phe Val Ser Gly Asp Tyr Leu Trp Tyr Val Asp Asp Ile Tyr
865                 870                 875                 880

Tyr Pro Ala Ser Cys Asn Gly Val Leu Pro Val Ala Phe Thr Lys Leu
                885                 890                 895

Ala Gly Gly Lys Ile Ser Phe Ser Asp Asp Val Ile Val His Asp Val
                900                 905                 910

Glu Pro Thr His Lys Val Lys Leu Ile Phe Glu Phe Asp Asp Val
                915                 920                 925

Val Thr Ser Leu Cys Lys Lys Ser Phe Gly Lys Ser Ile Ile Tyr Thr
930                 935                 940

Gly Asp Trp Glu Gly Leu His Glu Val Leu Thr Ser Ala Met Asn Val
945                 950                 955                 960

Ile Gly Gln His Ile Lys Leu Pro Gln Phe Tyr Ile Tyr Asp Glu Glu
                965                 970                 975

Gly Gly Tyr Asp Val Ser Lys Pro Val Met Ile Ser Gln Trp Pro Ile
                980                 985                 990

Ser Asn Asp Ser Asn Gly Cys Val  Val Glu Ala Ser Thr  Asp Phe His
                995                 1000                 1005

Gln Leu  Glu Cys Ile Val Asp  Asp Ser Val Arg Glu  Glu Val Asp
     1010                 1015                 1020

Ile Ile  Glu Gln Pro Phe Glu  Glu Val Glu His Val  Leu Ser Ile
     1025                 1030                 1035

Lys Gln  Pro Phe Ser Phe Ser  Phe Arg Asp Glu Leu  Gly Val Arg
     1040                 1045                 1050

Val Leu  Asp Gln Ser Asp Asn  Asn Cys Trp Ile Ser  Thr Thr Leu
     1055                 1060                 1065

Val Gln  Leu Gln Leu Thr Lys  Leu Leu Asp Asp Ser  Ile Glu Met
     1070                 1075                 1080

Gln Leu  Phe Lys Val Gly Lys  Val Asp Ser Ile Val  Gln Lys Cys
     1085                 1090                 1095

Tyr Glu  Leu Ser His Leu Ile  Ser Gly Ser Leu Gly  Asp Ser Gly
     1100                 1105                 1110

Lys Leu  Leu Ser Glu Leu Leu  Lys Glu Lys Tyr Thr  Cys Ser Ile
     1115                 1120                 1125

Thr Phe  Glu Met Ser Cys Asp  Cys Gly Lys Lys Phe  Asp Asp Gln
     1130                 1135                 1140

Val Gly  Cys Leu Phe Trp Ile  Met Pro Tyr Thr Lys  Leu Phe Gln
     1145                 1150                 1155

Lys Gly  Glu Cys Cys Ile Cys  His Lys Met Gln Thr  Tyr Lys Leu
     1160                 1165                 1170

Val Ser  Met Lys Gly Thr Gly  Val Phe Val Gln Asp  Pro Ala Pro
     1175                 1180                 1185

Ile Asp  Ile Asp Ala Phe Pro  Val Lys Pro Ile Cys  Ser Ser Val
     1190                 1195                 1200

Tyr Leu  Gly Val Lys Gly Ser  Gly His Tyr Gln Thr  Asn Leu Tyr
     1205                 1210                 1215

Ser Phe  Asn Lys Ala Ile Asp  Gly Phe Gly Val Phe  Asp Ile Lys
     1220                 1225                 1230

Asn Ser  Ser Val Asn Thr Val  Cys Phe Val Asp Val  Asp Phe His
     1235                 1240                 1245

Ser Val  Glu Ile Glu Ala Gly  Glu Val Lys Pro Phe  Ala Val Tyr
     1250                 1255                 1260
```

-continued

```
Lys Asn Val Lys Phe Tyr Leu Gly Asp Ile Ser His Leu Val Asn
    1265                1270                1275
Cys Val Ser Phe Asp Phe Val Asn Ala Ala Asn Glu Asn Leu
    1280                1285                1290
Leu His Gly Gly Gly Val Ala Arg Ala Ile Asp Ile Leu Thr Glu
    1295                1300                1305
Gly Gln Leu Gln Ser Leu Ser Lys Asp Tyr Ile Ser Ser Asn Gly
    1310                1315                1320
Pro Leu Lys Val Gly Ala Val Met Leu Glu Cys Glu Lys Phe
    1325                1330                1335
Asn Val Phe Asn Val Val Gly Pro Arg Thr Gly Lys His Glu His
    1340                1345                1350
Ser Leu Leu Val Glu Ala Tyr Asn Ser Ile Leu Phe Glu Asn Gly
    1355                1360                1365
Ile Pro Leu Met Pro Leu Leu Ser Cys Gly Ile Phe Gly Val Arg
    1370                1375                1380
Ile Glu Asn Ser Leu Lys Ala Leu Phe Ser Cys Asp Ile Asn Lys
    1385                1390                1395
Pro Leu Gln Val Phe Val Tyr Ser Ser Asn Glu Glu Gln Ala Val
    1400                1405                1410
Leu Lys Phe Leu Asp Gly Leu Asp Leu Thr Pro Val Ile Asp Asp
    1415                1420                1425
Val Asp Val Val Lys Pro Phe Arg Val Glu Gly Asn Phe Ser Phe
    1430                1435                1440
Phe Asp Cys Gly Val Asn Ala Leu Asp Gly Asp Ile Tyr Leu Leu
    1445                1450                1455
Phe Thr Asn Ser Ile Leu Met Leu Asp Lys Gln Gly Gln Leu Leu
    1460                1465                1470
Asp Thr Lys Leu Asn Gly Ile Leu Gln Gln Ala Ala Leu Asp Tyr
    1475                1480                1485
Leu Ala Thr Val Lys Thr Val Pro Ala Gly Asn Leu Val Lys Leu
    1490                1495                1500
Phe Val Glu Ser Cys Thr Ile Tyr Met Cys Val Val Pro Ser Ile
    1505                1510                1515
Asn Asp Leu Ser Phe Asp Lys Asn Leu Gly Arg Cys Val Arg Lys
    1520                1525                1530
Leu Asn Arg Leu Lys Thr Cys Val Ile Ala Asn Val Pro Ala Ile
    1535                1540                1545
Asp Val Leu Lys Lys Leu Leu Ser Ser Leu Thr Leu Thr Val Lys
    1550                1555                1560
Phe Val Val Glu Ser Asn Val Met Asp Val Asn Asp Cys Phe Lys
    1565                1570                1575
Asn Asp Asn Val Val Leu Lys Ile Thr Glu Asp Gly Ile Asn Val
    1580                1585                1590
Lys Asp Val Val Val Glu Ser Lys Ser Leu Gly Lys Gln Leu
    1595                1600                1605
Gly Val Val Ser Asp Gly Val Asp Ser Phe Glu Gly Val Leu Pro
    1610                1615                1620
Ile Asn Thr Asp Thr Val Leu Ser Val Ala Pro Glu Val Asp Trp
    1625                1630                1635
Val Ala Phe Tyr Gly Phe Glu Lys Ala Ala Leu Phe Ala Ser Leu
    1640                1645                1650
```

-continued

Asp Val Lys Pro Tyr Gly Tyr Pro Asn Asp Phe Val Gly Gly Phe
1655                1660                1665

Arg Val Leu Gly Thr Thr Asp Asn Asn Cys Trp Val Asn Ala Thr
1670                1675                1680

Cys Ile Ile Leu Gln Tyr Leu Lys Pro Thr Phe Lys Ser Lys Gly
1685                1690                1695

Leu Asn Val Leu Trp Asn Lys Phe Val Thr Gly Asp Val Gly Pro
1700                1705                1710

Phe Val Ser Phe Ile Tyr Phe Ile Thr Met Ser Ser Lys Gly Gln
1715                1720                1725

Lys Gly Asp Ala Glu Glu Ala Leu Ser Lys Leu Ser Glu Tyr Leu
1730                1735                1740

Ile Ser Asp Ser Ile Val Thr Leu Glu Gln Tyr Ser Thr Cys Asp
1745                1750                1755

Ile Cys Lys Ser Thr Val Val Glu Val Lys Ser Ala Ile Val Cys
1760                1765                1770

Ala Ser Val Leu Lys Asp Gly Cys Asp Val Gly Phe Cys Pro His
1775                1780                1785

Arg His Lys Leu Arg Ser Arg Val Lys Phe Val Asn Gly Arg Val
1790                1795                1800

Val Ile Thr Asn Val Gly Glu Pro Ile Ile Ser Gln Pro Ser Lys
1805                1810                1815

Leu Leu Asn Gly Ile Ala Tyr Thr Thr Phe Ser Gly Ser Phe Asp
1820                1825                1830

Asn Gly His Tyr Val Val Tyr Asp Ala Ala Asn Asn Ala Val Tyr
1835                1840                1845

Asp Gly Ala Arg Leu Phe Ser Ser Asp Leu Ser Thr Leu Ala Val
1850                1855                1860

Thr Ala Ile Val Val Gly Gly Cys Val Thr Ser Asn Val Pro
1865                1870                1875

Thr Ile Val Ser Glu Lys Ile Ser Val Met Asp Lys Leu Asp Thr
1880                1885                1890

Gly Ala Gln Lys Phe Phe Gln Phe Gly Asp Phe Val Met Asn Asn
1895                1900                1905

Ile Val Leu Phe Leu Thr Trp Leu Leu Ser Met Phe Ser Leu Leu
1910                1915                1920

Arg Thr Ser Ile Met Lys His Asp Ile Lys Val Ile Ala Lys Ala
1925                1930                1935

Pro Lys Arg Thr Gly Val Ile Leu Thr Arg Ser Phe Lys Tyr Asn
1940                1945                1950

Ile Arg Ser Ala Leu Phe Val Ile Lys Gln Lys Trp Cys Val Ile
1955                1960                1965

Val Thr Leu Phe Lys Phe Leu Leu Leu Tyr Ala Ile Tyr Ala
1970                1975                1980

Leu Val Phe Met Ile Val Gln Phe Ser Pro Phe Asn Ser Leu Leu
1985                1990                1995

Cys Gly Asp Ile Val Ser Gly Tyr Glu Lys Ser Thr Phe Asn Lys
2000                2005                2010

Asp Ile Tyr Cys Gly Asn Ser Met Val Cys Lys Met Cys Leu Phe
2015                2020                2025

Ser Tyr Gln Glu Phe Asn Asp Leu Asp His Thr Ser Leu Val Trp
2030                2035                2040

Lys His Ile Arg Asp Pro Ile Leu Ile Ser Leu Gln Pro Phe Val

-continued

```
                2045                2050                2055
Ile Leu Val Ile Leu Leu Ile Phe Gly Asn Met Tyr Leu Arg Phe
        2060                2065                2070
Gly Leu Leu Tyr Phe Val Ala Gln Phe Ile Ser Thr Phe Gly Ser
        2075                2080                2085
Phe Leu Gly Phe His Gln Lys Gln Trp Phe Leu His Phe Val Pro
        2090                2095                2100
Phe Asp Val Leu Cys Asn Glu Phe Leu Ala Thr Phe Ile Val Cys
        2105                2110                2115
Lys Ile Val Leu Phe Val Arg His Ile Ile Val Gly Cys Asn Asn
        2120                2125                2130
Ala Asp Cys Val Ala Cys Ser Lys Ser Ala Arg Leu Lys Arg Val
        2135                2140                2145
Pro Leu Gln Thr Ile Ile Asn Gly Met His Lys Ser Phe Tyr Val
        2150                2155                2160
Asn Ala Asn Gly Gly Thr Cys Phe Cys Asn Lys His Asn Phe Phe
        2165                2170                2175
Cys Val Asn Cys Asp Ser Phe Gly Pro Gly Asn Thr Phe Ile Asn
        2180                2185                2190
Gly Asp Ile Ala Arg Glu Leu Gly Asn Val Val Lys Thr Ala Val
        2195                2200                2205
Gln Pro Thr Ala Pro Ala Tyr Val Ile Ile Asp Lys Val Asp Phe
        2210                2215                2220
Val Asn Gly Phe Tyr Arg Leu Tyr Ser Gly Asp Thr Phe Trp Arg
        2225                2230                2235
Tyr Asp Phe Asp Ile Thr Glu Ser Lys Tyr Ser Cys Lys Glu Val
        2240                2245                2250
Leu Lys Asn Cys Asn Val Leu Glu Asn Phe Ile Val Tyr Asn Asn
        2255                2260                2265
Ser Gly Ser Asn Ile Thr Gln Ile Lys Asn Ala Cys Val Tyr Phe
        2270                2275                2280
Ser Gln Leu Leu Cys Glu Pro Ile Lys Leu Val Asn Ser Glu Leu
        2285                2290                2295
Leu Ser Thr Leu Ser Val Asp Phe Asn Gly Val Leu His Lys Ala
        2300                2305                2310
Tyr Val Asp Val Leu Cys Asn Ser Phe Phe Lys Glu Leu Thr Ala
        2315                2320                2325
Asn Met Ser Met Ala Glu Cys Lys Ala Thr Leu Gly Leu Thr Val
        2330                2335                2340
Ser Asp Asp Phe Val Ser Ala Val Ala Asn Ala His Arg Tyr
        2345                2350                2355
Asp Val Leu Leu Ser Asp Leu Ser Phe Asn Asn Phe Phe Ile Ser
        2360                2365                2370
Tyr Ala Lys Pro Glu Asp Lys Leu Ser Val Tyr Asp Ile Ala Cys
        2375                2380                2385
Cys Met Arg Ala Gly Ser Lys Val Val Asn His Asn Val Leu Ile
        2390                2395                2400
Lys Glu Ser Ile Pro Ile Val Trp Gly Val Lys Asp Phe Asn Thr
        2405                2410                2415
Leu Ser Gln Glu Gly Lys Lys Tyr Leu Val Lys Thr Thr Lys Ala
        2420                2425                2430
Lys Gly Leu Thr Phe Leu Leu Thr Phe Asn Asp Asn Gln Ala Ile
        2435                2440                2445
```

-continued

```
Thr Gln Val Pro Ala Thr Ser Ile Val Ala Lys Gln Gly Ala Gly
    2450                2455                2460

Phe Lys Arg Thr Tyr Asn Phe Leu Trp Tyr Val Cys Leu Phe Val
    2465                2470                2475

Val Ala Leu Phe Ile Gly Val Ser Phe Ile Asp Tyr Thr Thr Thr
    2480                2485                2490

Val Thr Ser Phe His Gly Tyr Asp Phe Lys Tyr Ile Glu Asn Gly
    2495                2500                2505

Gln Leu Lys Val Phe Glu Ala Pro Leu His Cys Val Arg Asn Val
    2510                2515                2520

Phe Asp Asn Phe Asn Gln Trp His Glu Ala Lys Phe Gly Val Val
    2525                2530                2535

Thr Thr Asn Ser Asp Lys Cys Pro Ile Val Val Gly Val Ser Glu
    2540                2545                2550

Arg Ile Asn Val Val Pro Gly Val Pro Thr Asn Val Tyr Leu Val
    2555                2560                2565

Gly Lys Thr Leu Val Phe Thr Leu Gln Ala Ala Phe Gly Asn Thr
    2570                2575                2580

Gly Val Cys Tyr Asp Phe Asp Gly Val Thr Thr Ser Asp Lys Cys
    2585                2590                2595

Ile Phe Asn Ser Ala Cys Thr Arg Leu Glu Gly Leu Gly Gly Asp
    2600                2605                2610

Asn Val Tyr Cys Tyr Asn Thr Asp Leu Ile Glu Gly Ser Lys Pro
    2615                2620                2625

Tyr Ser Thr Leu Gln Pro Asn Ala Tyr Tyr Lys Tyr Asp Ala Lys
    2630                2635                2640

Asn Tyr Val Arg Phe Pro Glu Ile Leu Ala Arg Gly Phe Gly Leu
    2645                2650                2655

Arg Thr Ile Arg Thr Leu Ala Thr Arg Tyr Cys Arg Val Gly Glu
    2660                2665                2670

Cys Arg Asp Ser His Lys Gly Val Cys Phe Gly Phe Asp Lys Trp
    2675                2680                2685

Tyr Val Asn Asp Gly Arg Val Asp Asp Gly Tyr Ile Cys Gly Asp
    2690                2695                2700

Gly Leu Ile Asp Leu Leu Val Asn Val Leu Ser Ile Phe Ser Ser
    2705                2710                2715

Ser Phe Ser Val Val Ala Met Ser Gly His Met Leu Phe Asn Phe
    2720                2725                2730

Leu Phe Ala Ala Phe Ile Thr Phe Leu Cys Phe Leu Val Thr Lys
    2735                2740                2745

Phe Lys Arg Val Phe Gly Asp Leu Ser Tyr Gly Val Phe Thr Val
    2750                2755                2760

Val Cys Ala Thr Leu Ile Asn Asn Ile Ser Tyr Val Val Thr Gln
    2765                2770                2775

Asn Leu Phe Phe Met Leu Leu Tyr Ala Ile Leu Tyr Phe Val Phe
    2780                2785                2790

Thr Arg Thr Val Arg Tyr Ala Trp Ile Trp His Ile Ala Tyr Ile
    2795                2800                2805

Val Ala Tyr Phe Leu Leu Ile Pro Trp Trp Leu Leu Thr Trp Phe
    2810                2815                2820

Ser Phe Ala Ala Phe Leu Glu Leu Leu Pro Asn Val Phe Lys Leu
    2825                2830                2835
```

-continued

```
Lys Ile Ser Thr Gln Leu Phe Glu Gly Asp Lys Phe Ile Gly Thr
2840                 2845                 2850

Phe Glu Ser Ala Ala Ala Gly Thr Phe Val Leu Asp Met Arg Ser
2855                 2860                 2865

Tyr Glu Arg Leu Ile Asn Thr Ile Ser Pro Glu Lys Leu Lys Asn
2870                 2875                 2880

Tyr Ala Ala Ser Tyr Asn Lys Tyr Lys Tyr Tyr Ser Gly Ser Ala
2885                 2890                 2895

Ser Glu Ala Asp Tyr Arg Cys Ala Cys Tyr Ala His Leu Ala Lys
2900                 2905                 2910

Ala Met Leu Asp Tyr Ala Lys Asp His Asn Asp Met Leu Tyr Ser
2915                 2920                 2925

Pro Pro Thr Ile Ser Tyr Asn Ser Thr Leu Gln Ser Gly Leu Lys
2930                 2935                 2940

Lys Met Ala Gln Pro Ser Gly Cys Val Glu Arg Cys Val Val Arg
2945                 2950                 2955

Val Cys Tyr Gly Ser Thr Val Leu Asn Gly Val Trp Leu Gly Asp
2960                 2965                 2970

Thr Val Thr Cys Pro Arg His Val Ile Ala Pro Ser Thr Thr Val
2975                 2980                 2985

Leu Ile Asp Tyr Asp His Ala Tyr Ser Thr Met Arg Leu His Asn
2990                 2995                 3000

Phe Ser Val Ser His Asn Gly Val Phe Leu Gly Val Val Gly Val
3005                 3010                 3015

Thr Met His Gly Ser Val Leu Arg Ile Lys Val Ser Gln Ser Asn
3020                 3025                 3030

Val His Thr Pro Lys His Val Phe Lys Thr Leu Lys Pro Gly Asp
3035                 3040                 3045

Ser Phe Asn Ile Leu Ala Cys Tyr Glu Gly Ile Ala Ser Gly Val
3050                 3055                 3060

Phe Gly Val Asn Leu Arg Thr Asn Phe Thr Ile Lys Gly Ser Phe
3065                 3070                 3075

Ile Asn Gly Ala Cys Gly Ser Pro Gly Tyr Asn Val Arg Asn Asp
3080                 3085                 3090

Gly Thr Val Glu Phe Cys Tyr Leu His Gln Ile Glu Leu Gly Ser
3095                 3100                 3105

Gly Ala His Val Gly Ser Asp Phe Thr Gly Ser Val Tyr Gly Asn
3110                 3115                 3120

Phe Asp Asp Gln Pro Ser Leu Gln Val Glu Ser Ala Asn Leu Met
3125                 3130                 3135

Leu Ser Asp Asn Val Val Ala Phe Leu Tyr Ala Ala Leu Leu Asn
3140                 3145                 3150

Gly Cys Arg Trp Trp Leu Cys Ser Thr Arg Val Asn Val Asp Gly
3155                 3160                 3165

Phe Asn Glu Trp Ala Met Ala Asn Gly Tyr Thr Ser Val Ser Ser
3170                 3175                 3180

Val Glu Cys Tyr Ser Ile Leu Ala Ala Lys Thr Gly Val Ser Val
3185                 3190                 3195

Glu Gln Leu Leu Ala Ser Ile Gln His Leu His Glu Gly Phe Gly
3200                 3205                 3210

Gly Lys Asn Ile Leu Gly Tyr Ser Ser Leu Cys Asp Glu Phe Thr
3215                 3220                 3225

Leu Ala Glu Val Val Lys Gln Met Tyr Gly Val Asn Leu Gln Ser
```

-continued

```
            3230              3235              3240
Gly Lys Val Ile Phe Gly Leu Lys Thr Met Phe Leu Phe Ser Val
            3245              3250              3255
Phe Phe Thr Met Phe Trp Ala Glu Leu Phe Ile Tyr Thr Asn Thr
            3260              3265              3270
Ile Trp Ile Asn Pro Val Ile Leu Thr Pro Ile Phe Cys Leu Leu
            3275              3280              3285
Leu Phe Leu Ser Leu Val Leu Thr Met Phe Leu Lys His Lys Phe
            3290              3295              3300
Leu Phe Leu Gln Val Phe Leu Leu Pro Thr Val Ile Ala Thr Ala
            3305              3310              3315
Leu Tyr Asn Cys Val Leu Asp Tyr Tyr Ile Val Lys Phe Leu Ala
            3320              3325              3330
Asp His Phe Asn Tyr Asn Val Ser Val Leu Gln Met Asp Val Gln
            3335              3340              3345
Gly Leu Val Asn Val Leu Val Cys Leu Phe Val Val Phe Leu His
            3350              3355              3360
Thr Trp Arg Phe Ser Lys Glu Arg Phe Thr His Trp Phe Thr Tyr
            3365              3370              3375
Val Cys Ser Leu Ile Ala Val Ala Tyr Thr Tyr Phe Tyr Ser Gly
            3380              3385              3390
Asp Phe Leu Ser Leu Leu Val Met Phe Leu Cys Ala Ile Ser Ser
            3395              3400              3405
Asp Trp Tyr Ile Gly Ala Ile Val Phe Arg Leu Ser Arg Leu Ile
            3410              3415              3420
Val Phe Phe Ser Pro Glu Ser Val Phe Ser Val Phe Gly Asp Val
            3425              3430              3435
Lys Leu Thr Leu Val Val Tyr Leu Ile Cys Gly Tyr Leu Val Cys
            3440              3445              3450
Thr Tyr Trp Gly Ile Leu Tyr Trp Phe Asn Arg Phe Phe Lys Cys
            3455              3460              3465
Thr Met Gly Val Tyr Asp Phe Lys Val Ser Ala Ala Glu Phe Lys
            3470              3475              3480
Tyr Met Val Ala Asn Gly Leu His Ala Pro His Gly Pro Phe Asp
            3485              3490              3495
Ala Leu Trp Leu Ser Phe Lys Leu Leu Gly Ile Gly Gly Asp Arg
            3500              3505              3510
Cys Ile Lys Ile Ser Thr Val Gln Ser Lys Leu Thr Asp Leu Lys
            3515              3520              3525
Cys Thr Asn Val Val Leu Leu Gly Cys Leu Ser Ser Met Asn Ile
            3530              3535              3540
Ala Ala Asn Ser Ser Glu Trp Ala Tyr Cys Val Asp Leu His Asn
            3545              3550              3555
Lys Ile Asn Leu Cys Asp Asp Pro Glu Lys Ala Gln Ser Met Leu
            3560              3565              3570
Leu Ala Leu Leu Ala Phe Phe Leu Ser Lys His Ser Asp Phe Gly
            3575              3580              3585
Leu Asp Gly Leu Ile Asp Ser Tyr Phe Asp Asn Ser Ser Thr Leu
            3590              3595              3600
Gln Ser Val Ala Ser Ser Phe Val Ser Met Pro Ser Tyr Ile Ala
            3605              3610              3615
Tyr Glu Asn Ala Arg Gln Ala Tyr Glu Asp Ala Ile Ala Asn Gly
            3620              3625              3630
```

-continued

```
Ser Ser Ser Gln Leu Ile Lys Gln Leu Lys Arg Ala Met Asn Ile
    3635                3640                3645

Ala Lys Ser Glu Phe Asp His Glu Ile Ser Val Gln Lys Lys Ile
    3650                3655                3660

Asn Arg Met Ala Glu Gln Ala Thr Gln Met Tyr Lys Glu Ala
    3665                3670                3675

Arg Ser Val Asn Arg Lys Ser Lys Val Ile Ser Ala Met His Ser
    3680                3685                3690

Leu Leu Phe Gly Met Leu Arg Arg Leu Asp Met Ser Ser Val Glu
    3695                3700                3705

Thr Val Leu Asn Leu Ala Arg Asp Gly Val Val Pro Leu Ser Val
    3710                3715                3720

Ile Pro Ala Thr Ser Ala Ser Lys Leu Thr Ile Val Ser Pro Asp
    3725                3730                3735

Leu Glu Ser Tyr Ser Lys Ile Val Cys Asp Gly Ser Val His Tyr
    3740                3745                3750

Ala Gly Val Val Trp Thr Leu Asn Asp Val Lys Asp Asn Asp Gly
    3755                3760                3765

Arg Pro Val His Val Lys Glu Ile Thr Lys Glu Asn Val Glu Thr
    3770                3775                3780

Leu Thr Trp Pro Leu Ile Leu Asn Cys Glu Arg Val Val Lys Leu
    3785                3790                3795

Gln Asn Asn Glu Ile Met Pro Gly Lys Leu Lys Gln Lys Pro Met
    3800                3805                3810

Lys Ala Glu Gly Asp Gly Gly Val Leu Gly Asp Gly Asn Ala Leu
    3815                3820                3825

Tyr Asn Thr Glu Gly Gly Lys Thr Phe Met Tyr Ala Tyr Ile Ser
    3830                3835                3840

Asn Lys Ala Asp Leu Lys Phe Val Lys Trp Glu Tyr Glu Gly Gly
    3845                3850                3855

Cys Asn Thr Ile Glu Leu Asp Ser Pro Cys Arg Phe Met Val Glu
    3860                3865                3870

Thr Pro Asn Gly Pro Gln Val Lys Tyr Leu Tyr Phe Val Lys Asn
    3875                3880                3885

Leu Asn Thr Leu Arg Arg Gly Ala Val Leu Gly Phe Ile Gly Ala
    3890                3895                3900

Thr Ile Arg Leu Gln Ala Gly Lys Gln Thr Glu Leu Ala Val Asn
    3905                3910                3915

Ser Gly Leu Leu Thr Ala Cys Ala Phe Ser Val Asp Pro Ala Thr
    3920                3925                3930

Thr Tyr Leu Glu Ala Val Lys His Gly Ala Lys Pro Val Ser Asn
    3935                3940                3945

Cys Ile Lys Met Leu Ser Asn Gly Ala Gly Asn Gly Gln Ala Ile
    3950                3955                3960

Thr Thr Ser Val Asp Ala Asn Thr Asn Gln Asp Ser Tyr Gly Gly
    3965                3970                3975

Ala Ser Ile Cys Leu Tyr Cys Arg Ala His Val Pro His Pro Ser
    3980                3985                3990

Met Asp Gly Tyr Cys Lys Phe Lys Gly Lys Cys Val Gln Val Pro
    3995                4000                4005

Ile Gly Cys Leu Asp Pro Ile Arg Phe Cys Leu Glu Asn Asn Val
    4010                4015                4020
```

-continued

Cys Asn Val Cys Gly Cys Trp Leu Gly His Gly Cys Ala Cys Asp
        4025                4030                4035

Arg Thr Thr Ile Gln Ser Val Asp Ile Ser Tyr Leu Asn Glu Gln
    4040                4045                4050

Gly Val Leu Val Gln Leu Asp
    4055            4060

<210> SEQ ID NO 57
<211> LENGTH: 6738
<212> TYPE: PRT
<213> ORGANISM: Human coronavirus
<220> FEATURE:
<221> NAME/KEY: MISC_FEATURE
<222> LOCATION: (1)..(6738)
<223> OTHER INFORMATION: ORF 1ab replicase polyprotein

<400> SEQUENCE: 57

Met Phe Tyr Asn Gln Val Thr Leu Ala Val Ala Ser Asp Ser Glu Ile
1               5                   10                  15

Ser Gly Phe Gly Phe Ala Ile Pro Ser Val Ala Val Arg Thr Tyr Ser
            20                  25                  30

Glu Ala Ala Ala Gln Gly Phe Gln Ala Cys Arg Phe Val Ala Phe Gly
        35                  40                  45

Leu Gln Asp Cys Val Thr Gly Ile Asn Asp Asp Tyr Val Ile Ala
    50                  55                  60

Leu Thr Gly Thr Asn Gln Leu Cys Ala Lys Ile Leu Pro Phe Ser Asp
65                  70                  75                  80

Arg Pro Leu Asn Leu Arg Gly Trp Leu Ile Phe Ser Asn Ser Asn Tyr
                85                  90                  95

Val Leu Gln Asp Phe Asp Val Val Phe Gly His Gly Ala Gly Ser Val
            100                 105                 110

Val Phe Val Asp Lys Tyr Met Cys Gly Phe Asp Gly Lys Pro Val Leu
        115                 120                 125

Pro Lys Asn Met Trp Glu Phe Arg Asp Tyr Phe Asn Asn Thr Asp
    130                 135                 140

Ser Ile Val Ile Gly Gly Val Thr Tyr Gln Leu Ala Trp Asp Val Ile
145                 150                 155                 160

Arg Lys Asp Leu Ser Tyr Glu Gln Gln Asn Val Leu Ala Ile Glu Ser
                165                 170                 175

Ile His Tyr Leu Gly Thr Thr Gly His Thr Leu Lys Ser Gly Cys Lys
            180                 185                 190

Leu Thr Asn Ala Lys Pro Pro Lys Tyr Ser Ser Lys Val Val Leu Ser
        195                 200                 205

Gly Glu Trp Asn Ala Val Tyr Arg Ala Phe Gly Ser Pro Phe Ile Thr
    210                 215                 220

Asn Gly Met Ser Leu Leu Asp Ile Ile Val Lys Pro Val Phe Phe Asn
225                 230                 235                 240

Ala Phe Val Lys Cys Asn Cys Gly Ser Glu Ser Trp Ser Val Gly Ala
                245                 250                 255

Trp Asp Gly Tyr Leu Ser Ser Cys Cys Gly Thr Pro Ala Lys Leu
            260                 265                 270

Cys Val Val Pro Gly Asn Val Val Pro Gly Asp Val Ile Ile Thr Ser
        275                 280                 285

Thr Ser Ala Gly Cys Gly Val Lys Tyr Tyr Ala Gly Leu Val Val Lys
    290                 295                 300

His Ile Thr Asn Ile Thr Gly Val Ser Leu Trp Arg Val Thr Ala Val

```
            305                 310                 315                 320
His Ser Asp Gly Met Phe Val Ala Ser Ser Tyr Asp Ala Leu Leu
                325                 330                 335

His Arg Asn Ser Leu Asp Pro Phe Cys Phe Asp Val Asn Thr Leu Leu
                340                 345                 350

Ser Asn Gln Leu Arg Leu Ala Phe Leu Gly Ala Ser Val Thr Glu Asp
                355                 360                 365

Val Lys Phe Ala Ala Ser Thr Gly Val Ile Asp Ile Ser Ala Gly Met
                370                 375                 380

Phe Gly Leu Tyr Asp Asp Ile Leu Thr Asn Asn Lys Pro Trp Phe Val
385                 390                 395                 400

Arg Lys Ala Ser Gly Leu Phe Asp Ala Ile Trp Asp Ala Phe Val Ala
                405                 410                 415

Ala Ile Lys Leu Val Pro Thr Thr Thr Gly Val Leu Val Arg Phe Val
                420                 425                 430

Lys Ser Ile Ala Ser Thr Val Leu Thr Val Ser Asn Gly Val Ile Ile
                435                 440                 445

Met Cys Ala Asp Val Pro Asp Ala Phe Gln Ser Val Tyr Arg Thr Phe
    450                 455                 460

Thr Gln Ala Ile Cys Ala Ala Phe Asp Phe Ser Leu Asp Val Phe Lys
465                 470                 475                 480

Ile Gly Asp Val Lys Phe Lys Arg Leu Gly Asp Tyr Val Leu Thr Glu
                485                 490                 495

Asn Ala Leu Val Arg Leu Thr Thr Glu Val Val Arg Gly Val Arg Asp
                500                 505                 510

Ala Arg Ile Lys Lys Ala Met Phe Thr Lys Val Val Gly Pro Thr
                515                 520                 525

Thr Glu Val Lys Phe Ser Val Ile Glu Leu Ala Thr Val Asn Leu Arg
    530                 535                 540

Leu Val Asp Cys Ala Pro Val Val Cys Pro Lys Gly Lys Ile Val Val
545                 550                 555                 560

Ile Ala Gly Gln Ala Phe Phe Tyr Ser Gly Gly Phe Tyr Arg Phe Met
                565                 570                 575

Val Asp Pro Thr Thr Val Leu Asn Asp Pro Val Phe Thr Gly Asp Leu
                580                 585                 590

Phe Tyr Thr Ile Lys Phe Ser Gly Phe Lys Leu Asp Gly Phe Asn His
                595                 600                 605

Gln Phe Val Thr Ala Ser Ser Ala Thr Asp Ala Ile Ile Ala Val Glu
    610                 615                 620

Leu Leu Leu Leu Asp Phe Lys Thr Ala Val Phe Val Tyr Thr Cys Val
625                 630                 635                 640

Val Asp Gly Cys Ser Val Ile Val Arg Arg Asp Ala Thr Phe Ala Thr
                645                 650                 655

His Val Cys Phe Lys Asp Cys Tyr Asn Val Trp Glu Gln Phe Cys Ile
                660                 665                 670

Asp Asn Cys Gly Glu Pro Trp Phe Leu Thr Asp Tyr Asn Ala Ile Leu
                675                 680                 685

Gln Ser Asn Asn Pro Gln Cys Ala Ile Val Gln Ala Ser Glu Ser Lys
                690                 695                 700

Val Leu Leu Glu Arg Phe Leu Pro Lys Cys Pro Glu Ile Leu Leu Ser
705                 710                 715                 720

Ile Asp Asp Gly His Leu Trp Asn Leu Phe Val Glu Lys Phe Asn Phe
                725                 730                 735
```

```
Val Thr Asp Trp Leu Lys Thr Leu Lys Leu Thr Leu Thr Ser Asn Gly
            740                 745                 750

Leu Leu Gly Asn Cys Ala Lys Arg Phe Arg Arg Val Leu Val Lys Leu
            755                 760                 765

Leu Asp Val Tyr Asn Gly Phe Leu Glu Thr Val Cys Ser Val Ala Tyr
            770                 775                 780

Thr Ala Gly Val Cys Ile Lys Tyr Tyr Ala Val Asn Val Pro Tyr Val
785                 790                 795                 800

Val Ile Ser Gly Phe Val Ser Arg Val Ile Arg Arg Glu Arg Cys Asp
                805                 810                 815

Met Thr Phe Pro Cys Val Ser Cys Val Thr Phe Phe Tyr Glu Phe Leu
            820                 825                 830

Asp Thr Cys Phe Gly Val Ser Lys Pro Asn Ala Ile Asp Val Glu His
            835                 840                 845

Leu Glu Leu Lys Glu Thr Val Phe Val Glu Pro Lys Asp Gly Gly Gln
            850                 855                 860

Phe Phe Val Ser Gly Asp Tyr Leu Trp Tyr Val Val Asp Asp Ile Tyr
865                 870                 875                 880

Tyr Pro Ala Ser Cys Asn Gly Val Leu Pro Val Ala Phe Thr Lys Leu
                885                 890                 895

Ala Gly Gly Lys Ile Ser Phe Ser Asp Asp Val Ile Val His Asp Val
            900                 905                 910

Glu Pro Thr His Lys Val Lys Leu Ile Phe Glu Phe Glu Asp Asp Val
            915                 920                 925

Val Thr Ser Leu Cys Lys Lys Ser Phe Gly Lys Ser Ile Ile Tyr Thr
930                 935                 940

Gly Asp Trp Glu Gly Leu His Glu Val Leu Thr Ser Ala Met Asn Val
945                 950                 955                 960

Ile Gly Gln His Ile Lys Leu Pro Gln Phe Tyr Ile Tyr Asp Glu Glu
                965                 970                 975

Gly Gly Tyr Asp Val Ser Lys Pro Val Met Ile Ser Gln Trp Pro Ile
            980                 985                 990

Ser Asn Asp Ser Asn Gly Cys Val  Val Glu Ala Ser Thr  Asp Phe His
            995                 1000                1005

Gln Leu  Glu Cys Ile Val Asp  Asp Ser Val Arg Glu  Glu Val Asp
    1010                1015                1020

Ile Ile  Glu Gln Pro Phe Glu  Glu Val Glu His Val  Leu Ser Ile
    1025                1030                1035

Lys Gln  Pro Phe Ser Phe Ser  Phe Arg Asp Glu Leu  Gly Val Arg
    1040                1045                1050

Val Leu  Asp Gln Ser Asp Asn  Asn Cys Trp Ile Ser  Thr Thr Leu
    1055                1060                1065

Val Gln  Leu Gln Leu Thr Lys  Leu Leu Asp Asp Ser  Ile Glu Met
    1070                1075                1080

Gln Leu  Phe Lys Val Gly Lys  Val Asp Ser Ile Val  Gln Lys Cys
    1085                1090                1095

Tyr Glu  Leu Ser His Leu Ile  Ser Gly Ser Leu Gly  Asp Ser Gly
    1100                1105                1110

Lys Leu  Leu Ser Glu Leu Leu  Lys Glu Lys Tyr Thr  Cys Ser Ile
    1115                1120                1125

Thr Phe  Glu Met Ser Cys Asp  Cys Gly Lys Lys Phe  Asp Asp Gln
    1130                1135                1140
```

-continued

```
Val Gly Cys Leu Phe Trp Ile Met Pro Tyr Thr Lys Leu Phe Gln
1145                1150                1155

Lys Gly Glu Cys Cys Ile Cys His Lys Met Gln Thr Tyr Lys Leu
1160                1165                1170

Val Ser Met Lys Gly Thr Gly Val Phe Val Gln Asp Pro Ala Pro
1175                1180                1185

Ile Asp Ile Asp Ala Phe Pro Val Lys Pro Ile Cys Ser Ser Val
1190                1195                1200

Tyr Leu Gly Val Lys Gly Ser Gly His Tyr Gln Thr Asn Leu Tyr
1205                1210                1215

Ser Phe Asn Lys Ala Ile Asp Gly Phe Gly Val Phe Asp Ile Lys
1220                1225                1230

Asn Ser Ser Val Asn Thr Val Cys Phe Val Asp Val Asp Phe His
1235                1240                1245

Ser Val Glu Ile Glu Ala Gly Glu Val Lys Pro Phe Ala Val Tyr
1250                1255                1260

Lys Asn Val Lys Phe Tyr Leu Gly Asp Ile Ser His Leu Val Asn
1265                1270                1275

Cys Val Ser Phe Asp Phe Val Val Asn Ala Ala Asn Glu Asn Leu
1280                1285                1290

Leu His Gly Gly Gly Val Ala Arg Ala Ile Asp Ile Leu Thr Glu
1295                1300                1305

Gly Gln Leu Gln Ser Leu Ser Lys Asp Tyr Ile Ser Ser Asn Gly
1310                1315                1320

Pro Leu Lys Val Gly Ala Gly Val Met Leu Glu Cys Glu Lys Phe
1325                1330                1335

Asn Val Phe Asn Val Val Gly Pro Arg Thr Gly Lys His Glu His
1340                1345                1350

Ser Leu Leu Val Glu Ala Tyr Asn Ser Ile Leu Phe Glu Asn Gly
1355                1360                1365

Ile Pro Leu Met Pro Leu Leu Ser Cys Gly Ile Phe Gly Val Arg
1370                1375                1380

Ile Glu Asn Ser Leu Lys Ala Leu Phe Ser Cys Asp Ile Asn Lys
1385                1390                1395

Pro Leu Gln Val Phe Val Tyr Ser Ser Asn Glu Glu Gln Ala Val
1400                1405                1410

Leu Lys Phe Leu Asp Gly Leu Asp Leu Thr Pro Val Ile Asp Asp
1415                1420                1425

Val Asp Val Val Lys Pro Phe Arg Val Glu Gly Asn Phe Ser Phe
1430                1435                1440

Phe Asp Cys Gly Val Asn Ala Leu Asp Gly Asp Ile Tyr Leu Leu
1445                1450                1455

Phe Thr Asn Ser Ile Leu Met Leu Asp Lys Gln Gly Gln Leu Leu
1460                1465                1470

Asp Thr Lys Leu Asn Gly Ile Leu Gln Gln Ala Ala Leu Asp Tyr
1475                1480                1485

Leu Ala Thr Val Lys Thr Val Pro Ala Gly Asn Leu Val Lys Leu
1490                1495                1500

Phe Val Glu Ser Cys Thr Ile Tyr Met Cys Val Val Pro Ser Ile
1505                1510                1515

Asn Asp Leu Ser Phe Asp Lys Asn Leu Gly Arg Cys Val Arg Lys
1520                1525                1530

Leu Asn Arg Leu Lys Thr Cys Val Ile Ala Asn Val Pro Ala Ile
```

-continued

```
            1535                1540                1545

Asp Val Leu Lys Lys Leu Leu Ser Ser Leu Thr Leu Thr Val Lys
    1550                1555                1560

Phe Val Val Glu Ser Asn Val Met Asp Val Asn Asp Cys Phe Lys
    1565                1570                1575

Asn Asp Asn Val Val Leu Lys Ile Thr Glu Asp Gly Ile Asn Val
    1580                1585                1590

Lys Asp Val Val Val Glu Ser Ser Lys Ser Leu Gly Lys Gln Leu
    1595                1600                1605

Gly Val Val Ser Asp Gly Val Asp Ser Phe Glu Gly Val Leu Pro
    1610                1615                1620

Ile Asn Thr Asp Thr Val Leu Ser Val Ala Pro Glu Val Asp Trp
    1625                1630                1635

Val Ala Phe Tyr Gly Phe Glu Lys Ala Ala Leu Phe Ala Ser Leu
    1640                1645                1650

Asp Val Lys Pro Tyr Gly Tyr Pro Asn Asp Phe Val Gly Gly Phe
    1655                1660                1665

Arg Val Leu Gly Thr Thr Asp Asn Asn Cys Trp Val Asn Ala Thr
    1670                1675                1680

Cys Ile Ile Leu Gln Tyr Leu Lys Pro Thr Phe Lys Ser Lys Gly
    1685                1690                1695

Leu Asn Val Leu Trp Asn Lys Phe Val Thr Gly Asp Val Gly Pro
    1700                1705                1710

Phe Val Ser Phe Ile Tyr Phe Ile Thr Met Ser Ser Lys Gly Gln
    1715                1720                1725

Lys Gly Asp Ala Glu Glu Ala Leu Ser Lys Leu Ser Glu Tyr Leu
    1730                1735                1740

Ile Ser Asp Ser Ile Val Thr Leu Glu Gln Tyr Ser Thr Cys Asp
    1745                1750                1755

Ile Cys Lys Ser Thr Val Val Glu Val Lys Ser Ala Ile Val Cys
    1760                1765                1770

Ala Ser Val Leu Lys Asp Gly Cys Asp Val Gly Phe Cys Pro His
    1775                1780                1785

Arg His Lys Leu Arg Ser Arg Val Lys Phe Val Asn Gly Arg Val
    1790                1795                1800

Val Ile Thr Asn Val Gly Glu Pro Ile Ile Ser Gln Pro Ser Lys
    1805                1810                1815

Leu Leu Asn Gly Ile Ala Tyr Thr Thr Phe Ser Gly Ser Phe Asp
    1820                1825                1830

Asn Gly His Tyr Val Val Tyr Asp Ala Ala Asn Asn Ala Val Tyr
    1835                1840                1845

Asp Gly Ala Arg Leu Phe Ser Ser Asp Leu Ser Thr Leu Ala Val
    1850                1855                1860

Thr Ala Ile Val Val Val Gly Gly Cys Val Thr Ser Asn Val Pro
    1865                1870                1875

Thr Ile Val Ser Glu Lys Ile Ser Val Met Asp Lys Leu Asp Thr
    1880                1885                1890

Gly Ala Gln Lys Phe Phe Gln Phe Gly Asp Phe Val Met Asn Asn
    1895                1900                1905

Ile Val Leu Phe Leu Thr Trp Leu Leu Ser Met Phe Ser Leu Leu
    1910                1915                1920

Arg Thr Ser Ile Met Lys His Asp Ile Lys Val Ile Ala Lys Ala
    1925                1930                1935
```

```
Pro Lys Arg Thr Gly Val Ile Leu Thr Arg Ser Phe Lys Tyr Asn
    1940                1945                1950

Ile Arg Ser Ala Leu Phe Val Ile Lys Gln Lys Trp Cys Val Ile
    1955                1960                1965

Val Thr Leu Phe Lys Phe Leu Leu Leu Tyr Ala Ile Tyr Ala
    1970                1975                1980

Leu Val Phe Met Ile Val Gln Phe Ser Pro Phe Asn Ser Leu Leu
    1985                1990                1995

Cys Gly Asp Ile Val Ser Gly Tyr Glu Lys Ser Thr Phe Asn Lys
    2000                2005                2010

Asp Ile Tyr Cys Gly Asn Ser Met Val Cys Lys Met Cys Leu Phe
    2015                2020                2025

Ser Tyr Gln Glu Phe Asn Asp Leu Asp His Thr Ser Leu Val Trp
    2030                2035                2040

Lys His Ile Arg Asp Pro Ile Leu Ile Ser Leu Gln Pro Phe Val
    2045                2050                2055

Ile Leu Val Ile Leu Leu Ile Phe Gly Asn Met Tyr Leu Arg Phe
    2060                2065                2070

Gly Leu Leu Tyr Phe Val Ala Gln Phe Ile Ser Thr Phe Gly Ser
    2075                2080                2085

Phe Leu Gly Phe His Gln Lys Gln Trp Phe Leu His Phe Val Pro
    2090                2095                2100

Phe Asp Val Leu Cys Asn Glu Phe Leu Ala Thr Phe Ile Val Cys
    2105                2110                2115

Lys Ile Val Leu Phe Val Arg His Ile Ile Val Gly Cys Asn Asn
    2120                2125                2130

Ala Asp Cys Val Ala Cys Ser Lys Ser Ala Arg Leu Lys Arg Val
    2135                2140                2145

Pro Leu Gln Thr Ile Ile Asn Gly Met His Lys Ser Phe Tyr Val
    2150                2155                2160

Asn Ala Asn Gly Gly Thr Cys Phe Cys Asn Lys His Asn Phe Phe
    2165                2170                2175

Cys Val Asn Cys Asp Ser Phe Gly Pro Gly Asn Thr Phe Ile Asn
    2180                2185                2190

Gly Asp Ile Ala Arg Glu Leu Gly Asn Val Val Lys Thr Ala Val
    2195                2200                2205

Gln Pro Thr Ala Pro Ala Tyr Val Ile Ile Asp Lys Val Asp Phe
    2210                2215                2220

Val Asn Gly Phe Tyr Arg Leu Tyr Ser Gly Asp Thr Phe Trp Arg
    2225                2230                2235

Tyr Asp Phe Asp Ile Thr Glu Ser Lys Tyr Ser Cys Lys Glu Val
    2240                2245                2250

Leu Lys Asn Cys Asn Val Leu Glu Asn Phe Ile Val Tyr Asn Asn
    2255                2260                2265

Ser Gly Ser Asn Ile Thr Gln Ile Lys Asn Ala Cys Val Tyr Phe
    2270                2275                2280

Ser Gln Leu Leu Cys Glu Pro Ile Lys Leu Val Asn Ser Glu Leu
    2285                2290                2295

Leu Ser Thr Leu Ser Val Asp Phe Asn Gly Val Leu His Lys Ala
    2300                2305                2310

Tyr Val Asp Val Leu Cys Asn Ser Phe Phe Lys Glu Leu Thr Ala
    2315                2320                2325
```

-continued

```
Asn Met Ser Met Ala Glu Cys Lys Ala Thr Leu Gly Leu Thr Val
2330                 2335                 2340

Ser Asp Asp Asp Phe Val Ser Ala Val Ala Asn Ala His Arg Tyr
2345                 2350                 2355

Asp Val Leu Leu Ser Asp Leu Ser Phe Asn Asn Phe Phe Ile Ser
2360                 2365                 2370

Tyr Ala Lys Pro Glu Asp Lys Leu Ser Val Tyr Asp Ile Ala Cys
2375                 2380                 2385

Cys Met Arg Ala Gly Ser Lys Val Val Asn His Asn Val Leu Ile
2390                 2395                 2400

Lys Glu Ser Ile Pro Ile Val Trp Gly Val Lys Asp Phe Asn Thr
2405                 2410                 2415

Leu Ser Gln Glu Gly Lys Lys Tyr Leu Val Lys Thr Thr Lys Ala
2420                 2425                 2430

Lys Gly Leu Thr Phe Leu Leu Thr Phe Asn Asp Asn Gln Ala Ile
2435                 2440                 2445

Thr Gln Val Pro Ala Thr Ser Ile Val Ala Lys Gln Gly Ala Gly
2450                 2455                 2460

Phe Lys Arg Thr Tyr Asn Phe Leu Trp Tyr Val Cys Leu Phe Val
2465                 2470                 2475

Val Ala Leu Phe Ile Gly Val Ser Phe Ile Asp Tyr Thr Thr Thr
2480                 2485                 2490

Val Thr Ser Phe His Gly Tyr Asp Phe Lys Tyr Ile Glu Asn Gly
2495                 2500                 2505

Gln Leu Lys Val Phe Glu Ala Pro Leu His Cys Val Arg Asn Val
2510                 2515                 2520

Phe Asp Asn Phe Asn Gln Trp His Glu Ala Lys Phe Gly Val Val
2525                 2530                 2535

Thr Thr Asn Ser Asp Lys Cys Pro Ile Val Val Gly Val Ser Glu
2540                 2545                 2550

Arg Ile Asn Val Val Pro Gly Val Pro Thr Asn Val Tyr Leu Val
2555                 2560                 2565

Gly Lys Thr Leu Val Phe Thr Leu Gln Ala Ala Phe Gly Asn Thr
2570                 2575                 2580

Gly Val Cys Tyr Asp Phe Asp Gly Val Thr Thr Ser Asp Lys Cys
2585                 2590                 2595

Ile Phe Asn Ser Ala Cys Thr Arg Leu Glu Gly Leu Gly Gly Asp
2600                 2605                 2610

Asn Val Tyr Cys Tyr Asn Thr Asp Leu Ile Glu Gly Ser Lys Pro
2615                 2620                 2625

Tyr Ser Thr Leu Gln Pro Asn Ala Tyr Tyr Lys Tyr Asp Ala Lys
2630                 2635                 2640

Asn Tyr Val Arg Phe Pro Glu Ile Leu Ala Arg Gly Phe Gly Leu
2645                 2650                 2655

Arg Thr Ile Arg Thr Leu Ala Thr Arg Tyr Cys Arg Val Gly Glu
2660                 2665                 2670

Cys Arg Asp Ser His Lys Gly Val Cys Phe Gly Phe Asp Lys Trp
2675                 2680                 2685

Tyr Val Asn Asp Gly Arg Val Asp Asp Gly Tyr Ile Cys Gly Asp
2690                 2695                 2700

Gly Leu Ile Asp Leu Leu Val Asn Val Leu Ser Ile Phe Ser Ser
2705                 2710                 2715

Ser Phe Ser Val Val Ala Met Ser Gly His Met Leu Phe Asn Phe
```

```
            2720                2725                2730

Leu Phe Ala Ala Phe Ile Thr Phe Leu Cys Phe Leu Val Thr Lys
    2735                2740                2745

Phe Lys Arg Val Phe Gly Asp Leu Ser Tyr Gly Val Phe Thr Val
    2750                2755                2760

Val Cys Ala Thr Leu Ile Asn Asn Ile Ser Tyr Val Val Thr Gln
    2765                2770                2775

Asn Leu Phe Phe Met Leu Leu Tyr Ala Ile Leu Tyr Phe Val Phe
    2780                2785                2790

Thr Arg Thr Val Arg Tyr Ala Trp Ile Trp His Ile Ala Tyr Ile
    2795                2800                2805

Val Ala Tyr Phe Leu Leu Ile Pro Trp Trp Leu Leu Thr Trp Phe
    2810                2815                2820

Ser Phe Ala Ala Phe Leu Glu Leu Leu Pro Asn Val Phe Lys Leu
    2825                2830                2835

Lys Ile Ser Thr Gln Leu Phe Glu Gly Asp Lys Phe Ile Gly Thr
    2840                2845                2850

Phe Glu Ser Ala Ala Ala Gly Thr Phe Val Leu Asp Met Arg Ser
    2855                2860                2865

Tyr Glu Arg Leu Ile Asn Thr Ile Ser Pro Glu Lys Leu Lys Asn
    2870                2875                2880

Tyr Ala Ala Ser Tyr Asn Lys Tyr Lys Tyr Tyr Ser Gly Ser Ala
    2885                2890                2895

Ser Glu Ala Asp Tyr Arg Cys Ala Cys Tyr Ala His Leu Ala Lys
    2900                2905                2910

Ala Met Leu Asp Tyr Ala Lys Asp His Asn Asp Met Leu Tyr Ser
    2915                2920                2925

Pro Pro Thr Ile Ser Tyr Asn Ser Thr Leu Gln Ser Gly Leu Lys
    2930                2935                2940

Lys Met Ala Gln Pro Ser Gly Cys Val Glu Arg Cys Val Val Arg
    2945                2950                2955

Val Cys Tyr Gly Ser Thr Val Leu Asn Gly Val Trp Leu Gly Asp
    2960                2965                2970

Thr Val Thr Cys Pro Arg His Val Ile Ala Pro Ser Thr Thr Val
    2975                2980                2985

Leu Ile Asp Tyr Asp His Ala Tyr Ser Thr Met Arg Leu His Asn
    2990                2995                3000

Phe Ser Val Ser His Asn Gly Val Phe Leu Gly Val Val Gly Val
    3005                3010                3015

Thr Met His Gly Ser Val Leu Arg Ile Lys Val Ser Gln Ser Asn
    3020                3025                3030

Val His Thr Pro Lys His Val Phe Lys Thr Leu Lys Pro Gly Asp
    3035                3040                3045

Ser Phe Asn Ile Leu Ala Cys Tyr Glu Gly Ile Ala Ser Gly Val
    3050                3055                3060

Phe Gly Val Asn Leu Arg Thr Asn Phe Thr Ile Lys Gly Ser Phe
    3065                3070                3075

Ile Asn Gly Ala Cys Gly Ser Pro Gly Tyr Asn Val Arg Asn Asp
    3080                3085                3090

Gly Thr Val Glu Phe Cys Tyr Leu His Gln Ile Glu Leu Gly Ser
    3095                3100                3105

Gly Ala His Val Gly Ser Asp Phe Thr Gly Ser Val Tyr Gly Asn
    3110                3115                3120
```

```
Phe Asp Asp Gln Pro Ser Leu Gln Val Glu Ser Ala Asn Leu Met
3125                3130                3135

Leu Ser Asp Asn Val Val Ala Phe Leu Tyr Ala Ala Leu Leu Asn
3140                3145                3150

Gly Cys Arg Trp Trp Leu Cys Ser Thr Arg Val Asn Val Asp Gly
3155                3160                3165

Phe Asn Glu Trp Ala Met Ala Asn Gly Tyr Thr Ser Val Ser Ser
3170                3175                3180

Val Glu Cys Tyr Ser Ile Leu Ala Ala Lys Thr Gly Val Ser Val
3185                3190                3195

Glu Gln Leu Leu Ala Ser Ile Gln His Leu His Glu Gly Phe Gly
3200                3205                3210

Gly Lys Asn Ile Leu Gly Tyr Ser Ser Leu Cys Asp Glu Phe Thr
3215                3220                3225

Leu Ala Glu Val Val Lys Gln Met Tyr Gly Val Asn Leu Gln Ser
3230                3235                3240

Gly Lys Val Ile Phe Gly Leu Lys Thr Met Phe Leu Phe Ser Val
3245                3250                3255

Phe Phe Thr Met Phe Trp Ala Glu Leu Phe Ile Tyr Thr Asn Thr
3260                3265                3270

Ile Trp Ile Asn Pro Val Ile Leu Thr Pro Ile Phe Cys Leu Leu
3275                3280                3285

Leu Phe Leu Ser Leu Val Leu Thr Met Phe Leu Lys His Lys Phe
3290                3295                3300

Leu Phe Leu Gln Val Phe Leu Leu Pro Thr Val Ile Ala Thr Ala
3305                3310                3315

Leu Tyr Asn Cys Val Leu Asp Tyr Tyr Ile Val Lys Phe Leu Ala
3320                3325                3330

Asp His Phe Asn Tyr Asn Val Ser Val Leu Gln Met Asp Val Gln
3335                3340                3345

Gly Leu Val Asn Val Leu Val Cys Leu Phe Val Val Phe Leu His
3350                3355                3360

Thr Trp Arg Phe Ser Lys Glu Arg Phe Thr His Trp Phe Thr Tyr
3365                3370                3375

Val Cys Ser Leu Ile Ala Val Ala Tyr Thr Tyr Phe Tyr Ser Gly
3380                3385                3390

Asp Phe Leu Ser Leu Leu Val Met Phe Leu Cys Ala Ile Ser Ser
3395                3400                3405

Asp Trp Tyr Ile Gly Ala Ile Val Phe Arg Leu Ser Arg Leu Ile
3410                3415                3420

Val Phe Phe Ser Pro Glu Ser Val Phe Ser Val Phe Gly Asp Val
3425                3430                3435

Lys Leu Thr Leu Val Val Tyr Leu Ile Cys Gly Tyr Leu Val Cys
3440                3445                3450

Thr Tyr Trp Gly Ile Leu Tyr Trp Phe Asn Arg Phe Phe Lys Cys
3455                3460                3465

Thr Met Gly Val Tyr Asp Phe Lys Val Ser Ala Ala Glu Phe Lys
3470                3475                3480

Tyr Met Val Ala Asn Gly Leu His Ala Pro His Gly Pro Phe Asp
3485                3490                3495

Ala Leu Trp Leu Ser Phe Lys Leu Leu Gly Ile Gly Gly Asp Arg
3500                3505                3510
```

-continued

Cys Ile Lys Ile Ser Thr Val Gln Ser Lys Leu Thr Asp Leu Lys
3515                3520                3525

Cys Thr Asn Val Val Leu Leu Gly Cys Leu Ser Ser Met Asn Ile
3530                3535                3540

Ala Ala Asn Ser Ser Glu Trp Ala Tyr Cys Val Asp Leu His Asn
3545                3550                3555

Lys Ile Asn Leu Cys Asp Asp Pro Glu Lys Ala Gln Ser Met Leu
3560                3565                3570

Leu Ala Leu Leu Ala Phe Phe Leu Ser Lys His Ser Asp Phe Gly
3575                3580                3585

Leu Asp Gly Leu Ile Asp Ser Tyr Phe Asp Asn Ser Ser Thr Leu
3590                3595                3600

Gln Ser Val Ala Ser Ser Phe Val Ser Met Pro Ser Tyr Ile Ala
3605                3610                3615

Tyr Glu Asn Ala Arg Gln Ala Tyr Glu Asp Ala Ile Ala Asn Gly
3620                3625                3630

Ser Ser Ser Gln Leu Ile Lys Gln Leu Lys Arg Ala Met Asn Ile
3635                3640                3645

Ala Lys Ser Glu Phe Asp His Glu Ile Ser Val Gln Lys Lys Ile
3650                3655                3660

Asn Arg Met Ala Glu Gln Ala Ala Thr Gln Met Tyr Lys Glu Ala
3665                3670                3675

Arg Ser Val Asn Arg Lys Ser Lys Val Ile Ser Ala Met His Ser
3680                3685                3690

Leu Leu Phe Gly Met Leu Arg Arg Leu Asp Met Ser Ser Val Glu
3695                3700                3705

Thr Val Leu Asn Leu Ala Arg Asp Gly Val Val Pro Leu Ser Val
3710                3715                3720

Ile Pro Ala Thr Ser Ala Ser Lys Leu Thr Ile Val Ser Pro Asp
3725                3730                3735

Leu Glu Ser Tyr Ser Lys Ile Val Cys Asp Gly Ser Val His Tyr
3740                3745                3750

Ala Gly Val Val Trp Thr Leu Asn Asp Val Lys Asp Asn Asp Gly
3755                3760                3765

Arg Pro Val His Val Lys Glu Ile Thr Lys Glu Asn Val Glu Thr
3770                3775                3780

Leu Thr Trp Pro Leu Ile Leu Asn Cys Glu Arg Val Val Lys Leu
3785                3790                3795

Gln Asn Asn Glu Ile Met Pro Gly Lys Leu Lys Gln Lys Pro Met
3800                3805                3810

Lys Ala Glu Gly Asp Gly Gly Val Leu Gly Asp Gly Asn Ala Leu
3815                3820                3825

Tyr Asn Thr Glu Gly Gly Lys Thr Phe Met Tyr Ala Tyr Ile Ser
3830                3835                3840

Asn Lys Ala Asp Leu Lys Phe Val Lys Trp Glu Tyr Glu Gly Gly
3845                3850                3855

Cys Asn Thr Ile Glu Leu Asp Ser Pro Cys Arg Phe Met Val Glu
3860                3865                3870

Thr Pro Asn Gly Pro Gln Val Lys Tyr Leu Tyr Phe Val Lys Asn
3875                3880                3885

Leu Asn Thr Leu Arg Arg Gly Ala Val Leu Gly Phe Ile Gly Ala
3890                3895                3900

Thr Ile Arg Leu Gln Ala Gly Lys Gln Thr Glu Leu Ala Val Asn

-continued

```
                 3905                 3910                 3915
Ser Gly Leu Leu Thr Ala Cys Ala Phe Ser Val Asp Pro Ala Thr
    3920                3925                3930

Thr Tyr Leu Glu Ala Val Lys His Gly Ala Lys Pro Val Ser Asn
    3935                3940                3945

Cys Ile Lys Met Leu Ser Asn Gly Ala Gly Asn Gly Gln Ala Ile
    3950                3955                3960

Thr Thr Ser Val Asp Ala Asn Thr Asn Gln Asp Ser Tyr Gly Gly
    3965                3970                3975

Ala Ser Ile Cys Leu Tyr Cys Arg Ala His Val Pro His Pro Ser
    3980                3985                3990

Met Asp Gly Tyr Cys Lys Phe Lys Gly Lys Cys Val Gln Val Pro
    3995                4000                4005

Ile Gly Cys Leu Asp Pro Ile Arg Phe Cys Leu Glu Asn Asn Val
    4010                4015                4020

Cys Asn Val Cys Gly Cys Trp Leu Gly His Gly Cys Ala Cys Asp
    4025                4030                4035

Arg Thr Thr Ile Gln Ser Val Asp Ile Ser Tyr Leu Asn Glu Gln
    4040                4045                4050

Gly Val Leu Val Gln Leu Asp Arg Ala Arg Gly Ser Ser Ala Ala
    4055                4060                4065

Arg Leu Glu Pro Cys Asn Gly Thr Asp Ile Asp Lys Cys Val Arg
    4070                4075                4080

Ala Phe Asp Ile Tyr Asn Lys Asn Val Ser Phe Leu Gly Lys Cys
    4085                4090                4095

Leu Lys Met Asn Cys Val Arg Phe Lys Asn Ala Asp Leu Lys Asp
    4100                4105                4110

Gly Tyr Phe Val Ile Lys Arg Cys Thr Lys Ser Val Met Glu His
    4115                4120                4125

Glu Gln Ser Met Tyr Asn Leu Leu Asn Phe Ser Gly Ala Leu Ala
    4130                4135                4140

Glu His Asp Phe Phe Thr Trp Lys Asp Gly Arg Val Ile Tyr Gly
    4145                4150                4155

Asn Val Ser Arg His Asn Leu Thr Lys Tyr Thr Met Met Asp Leu
    4160                4165                4170

Val Tyr Ala Met Arg Asn Phe Asp Glu Gln Asn Cys Asp Val Leu
    4175                4180                4185

Lys Glu Val Leu Val Leu Thr Gly Cys Cys Asp Asn Ser Tyr Phe
    4190                4195                4200

Asp Ser Lys Gly Trp Tyr Asp Pro Val Glu Asn Glu Asp Ile His
    4205                4210                4215

Arg Val Tyr Ala Ser Leu Gly Lys Ile Val Ala Arg Ala Met Leu
    4220                4225                4230

Lys Cys Val Ala Leu Cys Asp Ala Met Val Ala Lys Gly Val Val
    4235                4240                4245

Gly Val Leu Thr Leu Asp Asn Gln Asp Leu Asn Gly Asn Phe Tyr
    4250                4255                4260

Asp Phe Gly Asp Phe Val Val Ser Leu Pro Asn Met Gly Val Pro
    4265                4270                4275

Cys Cys Thr Ser Tyr Tyr Ser Tyr Met Met Pro Ile Met Gly Leu
    4280                4285                4290

Thr Asn Cys Leu Ala Ser Glu Cys Phe Val Lys Ser Asp Ile Phe
    4295                4300                4305
```

-continued

```
Gly Ser Asp Phe Lys Thr Phe Asp Leu Leu Lys Tyr Asp Phe Thr
    4310            4315                4320
Glu His Lys Glu Asn Leu Phe Asn Lys Tyr Phe Lys His Trp Ser
    4325            4330                4335
Phe Asp Tyr His Pro Asn Cys Cys Asp Cys Tyr Asp Asp Met Cys
    4340            4345                4350
Val Ile His Cys Ala Asn Phe Asn Thr Leu Phe Ala Thr Thr Ile
    4355            4360                4365
Pro Gly Thr Ala Phe Gly Pro Leu Cys Arg Lys Val Phe Ile Asp
    4370            4375                4380
Gly Val Pro Leu Val Thr Thr Ala Gly Tyr His Phe Lys Gln Leu
    4385            4390                4395
Gly Leu Val Trp Asn Lys Asp Val Asn Thr His Ser Val Arg Leu
    4400            4405                4410
Thr Ile Thr Glu Leu Leu Gln Phe Val Thr Asp Pro Ser Leu Ile
    4415            4420                4425
Ile Ala Ser Ser Pro Ala Leu Val Asp Gln Arg Thr Ile Cys Phe
    4430            4435                4440
Ser Val Ala Ala Leu Ser Thr Gly Leu Thr Asn Gln Val Val Lys
    4445            4450                4455
Pro Gly His Phe Asn Glu Glu Phe Tyr Asn Phe Leu Arg Leu Arg
    4460            4465                4470
Gly Phe Phe Asp Glu Gly Ser Glu Leu Thr Leu Lys His Phe Phe
    4475            4480                4485
Phe Ala Gln Asn Gly Asp Ala Ala Val Lys Asp Phe Asp Phe Tyr
    4490            4495                4500
Arg Tyr Asn Lys Pro Thr Ile Leu Asp Ile Cys Gln Ala Arg Val
    4505            4510                4515
Thr Tyr Lys Ile Val Ser Arg Tyr Phe Asp Ile Tyr Glu Gly Gly
    4520            4525                4530
Cys Ile Lys Ala Cys Glu Val Val Val Thr Asn Leu Asn Lys Ser
    4535            4540                4545
Ala Gly Trp Pro Leu Asn Lys Phe Gly Lys Ala Ser Leu Tyr Tyr
    4550            4555                4560
Glu Ser Ile Ser Tyr Glu Glu Gln Asp Ala Leu Phe Ala Leu Thr
    4565            4570                4575
Lys Arg Asn Val Leu Pro Thr Met Thr Gln Leu Asn Leu Lys Tyr
    4580            4585                4590
Ala Ile Ser Gly Lys Glu Arg Ala Arg Thr Val Gly Gly Val Ser
    4595            4600                4605
Leu Leu Ser Thr Met Thr Thr Arg Gln Tyr His Gln Lys His Leu
    4610            4615                4620
Lys Ser Ile Val Asn Thr Arg Asn Ala Thr Val Val Ile Gly Thr
    4625            4630                4635
Thr Lys Phe Tyr Gly Gly Trp Asn Asn Met Leu Arg Thr Leu Ile
    4640            4645                4650
Asp Gly Val Glu Asn Pro Met Leu Met Gly Trp Asp Tyr Pro Lys
    4655            4660                4665
Cys Asp Arg Ala Leu Pro Asn Met Ile Arg Met Ile Ser Ala Met
    4670            4675                4680
Val Leu Gly Ser Lys His Val Asn Cys Cys Thr Ala Thr Asp Arg
    4685            4690                4695
```

-continued

Phe Tyr Arg Leu Gly Asn Glu Leu Ala Gln Val Leu Thr Glu Val
4700                4705                4710

Val Tyr Ser Asn Gly Gly Phe Tyr Phe Lys Pro Gly Gly Thr Thr
4715                4720                4725

Ser Gly Asp Ala Ser Thr Ala Tyr Ala Asn Ser Ile Phe Asn Ile
4730                4735                4740

Phe Gln Ala Val Ser Ser Asn Ile Asn Arg Leu Leu Ser Val Pro
4745                4750                4755

Ser Asp Ser Cys Asn Asn Val Asn Val Arg Asp Leu Gln Arg Arg
4760                4765                4770

Leu Tyr Asp Asn Cys Tyr Arg Leu Thr Ser Val Glu Glu Ser Phe
4775                4780                4785

Ile Glu Asp Tyr Tyr Gly Tyr Leu Arg Lys His Phe Ser Met Met
4790                4795                4800

Ile Leu Ser Asp Asp Gly Val Val Cys Tyr Asn Lys Asp Tyr Ala
4805                4810                4815

Glu Leu Gly Tyr Ile Ala Asp Ile Ser Ala Phe Lys Ala Thr Leu
4820                4825                4830

Tyr Tyr Gln Asn Asn Val Phe Met Ser Thr Ser Lys Cys Trp Val
4835                4840                4845

Glu Glu Asp Leu Thr Lys Gly Pro His Glu Phe Cys Ser Gln His
4850                4855                4860

Thr Met Gln Ile Val Asp Lys Asp Gly Thr Tyr Tyr Leu Pro Tyr
4865                4870                4875

Pro Asp Pro Ser Arg Ile Leu Ser Ala Gly Val Phe Val Asp Asp
4880                4885                4890

Val Val Lys Thr Asp Ala Val Val Leu Leu Glu Arg Tyr Val Ser
4895                4900                4905

Leu Ala Ile Asp Ala Tyr Pro Leu Ser Lys His Pro Asn Ser Glu
4910                4915                4920

Tyr Arg Lys Val Phe Tyr Val Leu Leu Asp Trp Val Lys His Leu
4925                4930                4935

Asn Lys Asn Leu Asn Glu Gly Val Leu Glu Ser Phe Ser Val Thr
4940                4945                4950

Leu Leu Asp Asn Gln Glu Asp Lys Phe Trp Cys Glu Asp Phe Tyr
4955                4960                4965

Ala Ser Met Tyr Glu Asn Ser Thr Ile Leu Gln Ala Ala Gly Leu
4970                4975                4980

Cys Val Val Cys Gly Ser Gln Thr Val Leu Arg Cys Gly Asp Cys
4985                4990                4995

Leu Arg Lys Pro Met Leu Cys Thr Lys Cys Ala Tyr Asp His Val
5000                5005                5010

Phe Gly Thr Asp His Lys Phe Ile Leu Ala Ile Thr Pro Tyr Val
5015                5020                5025

Cys Asn Ala Ser Gly Cys Gly Val Ser Asp Val Lys Lys Leu Tyr
5030                5035                5040

Leu Gly Gly Leu Asn Tyr Tyr Cys Thr Asn His Lys Pro Gln Leu
5045                5050                5055

Ser Phe Pro Leu Cys Ser Ala Gly Asn Ile Phe Gly Leu Tyr Lys
5060                5065                5070

Asn Ser Ala Thr Gly Ser Leu Asp Val Glu Val Phe Asn Arg Leu
5075                5080                5085

Ala Thr Ser Asp Trp Thr Asp Val Arg Asp Tyr Lys Leu Ala Asn

```
                    5090              5095             5100
Asp Val Lys Asp Thr Leu Arg Leu Phe Ala Ala Glu Thr Ile Lys
        5105            5110            5115
Ala Lys Glu Glu Ser Val Lys Ser Ser Tyr Ala Phe Ala Thr Leu
        5120            5125            5130
Lys Glu Val Val Gly Pro Lys Glu Leu Leu Ser Trp Glu Ser
        5135            5140            5145
Gly Lys Val Lys Pro Pro Leu Asn Arg Asn Ser Val Phe Thr Cys
        5150            5155            5160
Phe Gln Ile Ser Lys Asp Ser Lys Phe Gln Ile Gly Glu Phe Ile
        5165            5170            5175
Phe Glu Lys Val Glu Tyr Gly Ser Asp Thr Val Thr Tyr Lys Ser
        5180            5185            5190
Thr Val Thr Thr Lys Leu Val Pro Gly Met Ile Phe Val Leu Thr
        5195            5200            5205
Ser His Asn Val Gln Pro Leu Arg Ala Pro Thr Ile Ala Asn Gln
        5210            5215            5220
Glu Lys Tyr Ser Ser Ile Tyr Lys Leu His Pro Ala Phe Asn Val
        5225            5230            5235
Ser Asp Ala Tyr Ala Asn Leu Val Pro Tyr Tyr Gln Leu Ile Gly
        5240            5245            5250
Lys Gln Lys Ile Thr Thr Ile Gln Gly Pro Pro Gly Ser Gly Lys
        5255            5260            5265
Ser His Cys Ser Ile Gly Leu Gly Leu Tyr Tyr Pro Gly Ala Arg
        5270            5275            5280
Ile Val Phe Val Ala Cys Ala His Ala Ala Val Asp Ser Leu Cys
        5285            5290            5295
Ala Lys Ala Met Thr Val Tyr Ser Ile Asp Lys Cys Thr Arg Ile
        5300            5305            5310
Ile Pro Ala Arg Ala Arg Val Glu Cys Tyr Ser Gly Phe Lys Pro
        5315            5320            5325
Asn Asn Thr Ser Ala Gln Tyr Ile Phe Ser Thr Val Asn Ala Leu
        5330            5335            5340
Pro Glu Cys Asn Ala Asp Ile Val Val Val Asp Glu Val Ser Met
        5345            5350            5355
Cys Thr Asn Tyr Asp Leu Ser Val Ile Asn Gln Arg Leu Ser Tyr
        5360            5365            5370
Lys His Ile Val Tyr Val Gly Asp Pro Gln Gln Leu Pro Ala Pro
        5375            5380            5385
Arg Val Met Ile Thr Lys Gly Val Met Glu Pro Val Asp Tyr Asn
        5390            5395            5400
Val Val Thr Gln Arg Met Cys Ala Ile Gly Pro Asp Val Phe Leu
        5405            5410            5415
His Lys Cys Tyr Arg Cys Pro Ala Glu Ile Val Ile Gln Phe Leu
        5420            5425            5430
Asn Leu Phe Met Arg Thr Ser Leu Ser Leu Leu Asn Leu Leu Val
        5435            5440            5445
Asn Ser Val Leu Lys Ser Phe Leu Arg Val Met Tyr Lys Val Asp
        5450            5455            5460
Asn Gly Ser Ser Ile Asn Arg Lys Gln Leu Glu Ile Val Lys Leu
        5465            5470            5475
Phe Leu Val Lys Asn Pro Ser Trp Ser Lys Ala Val Phe Ile Ser
        5480            5485            5490
```

-continued

```
Pro Tyr Asn Ser Gln Asn Tyr Val Ala Ser Arg Phe Leu Gly Leu
    5495            5500                5505
Gln Ile Gln Thr Val Asp Ser Ser Gln Gly Ser Glu Tyr Asp Tyr
    5510            5515                5520
Val Ile Tyr Ala Gln Thr Ser Asp Thr Ala His Ala Cys Asn Val
    5525            5530                5535
Asn Arg Phe Asn Val Ala Ile Thr Arg Ala Lys Lys Gly Ile Phe
    5540            5545                5550
Cys Val Met Cys Asp Lys Thr Leu Phe Asp Ser Leu Lys Phe Phe
    5555            5560                5565
Glu Ile Lys His Ala Asp Leu His Ser Ser Gln Val Cys Gly Leu
    5570            5575                5580
Phe Lys Asn Cys Thr Arg Thr Pro Leu Asn Leu Pro Pro Thr His
    5585            5590                5595
Ala His Thr Phe Leu Ser Leu Ser Asp Gln Phe Lys Thr Thr Gly
    5600            5605                5610
Asp Leu Ala Val Gln Ile Gly Ser Asn Asn Val Cys Thr Tyr Glu
    5615            5620                5625
His Val Ile Ser Phe Met Gly Phe Arg Phe Asp Ile Ser Ile Pro
    5630            5635                5640
Gly Ser His Ser Leu Phe Cys Thr Arg Asp Phe Ala Ile Arg Asn
    5645            5650                5655
Val Arg Gly Trp Leu Gly Met Asp Val Glu Ser Ala His Val Cys
    5660            5665                5670
Gly Asp Asn Ile Gly Thr Asn Val Pro Leu Gln Val Gly Phe Ser
    5675            5680                5685
Asn Gly Val Asn Phe Val Val Gln Thr Glu Gly Cys Val Ser Thr
    5690            5695                5700
Asn Phe Gly Asp Val Ile Lys Pro Val Cys Ala Lys Ser Pro Pro
    5705            5710                5715
Gly Glu Gln Phe Arg His Leu Ile Pro Leu Leu Arg Lys Gly Gln
    5720            5725                5730
Pro Trp Leu Ile Val Arg Arg Ile Val Gln Met Ile Ser Asp
    5735            5740                5745
Tyr Leu Ser Asn Leu Ser Asp Ile Leu Val Phe Val Leu Trp Ala
    5750            5755                5760
Gly Ser Leu Glu Leu Thr Thr Met Arg Tyr Phe Val Lys Ile Gly
    5765            5770                5775
Pro Ile Lys Tyr Cys Tyr Cys Gly Asn Phe Ala Thr Cys Tyr Asn
    5780            5785                5790
Ser Val Ser Asn Glu Tyr Cys Cys Phe Lys His Ala Leu Gly Cys
    5795            5800                5805
Asp Tyr Val Tyr Asn Pro Tyr Ala Phe Asp Ile Gln Gln Trp Gly
    5810            5815                5820
Tyr Val Gly Ser Leu Ser Gln Asn His His Thr Phe Cys Asn Ile
    5825            5830                5835
His Arg Asn Glu His Asp Ala Ser Gly Asp Ala Val Met Thr Arg
    5840            5845                5850
Cys Leu Ala Val His Asp Cys Phe Val Lys Asn Val Asp Trp Thr
    5855            5860                5865
Val Thr Tyr Pro Phe Ile Ala Asn Glu Lys Phe Ile Asn Gly Cys
    5870            5875                5880
```

-continued

```
Gly Arg Asn Val Gln Gly His Val Val Arg Ala Ala Leu Lys Leu
5885                5890                5895

Tyr Lys Pro Ser Val Ile His Asp Ile Gly Asn Pro Lys Gly Val
5900                5905                5910

Arg Cys Ala Val Thr Asp Ala Lys Trp Tyr Cys Tyr Asp Lys Gln
5915                5920                5925

Pro Val Asn Ser Asn Val Lys Leu Leu Asp Tyr Asp Tyr Ala Thr
5930                5935                5940

His Gly Gln Leu Asp Gly Leu Cys Leu Phe Trp Asn Cys Asn Val
5945                5950                5955

Asp Met Tyr Pro Glu Phe Ser Ile Val Cys Arg Phe Asp Thr Arg
5960                5965                5970

Thr Arg Ser Val Phe Asn Leu Glu Gly Val Asn Gly Gly Ser Leu
5975                5980                5985

Tyr Val Asn Lys His Ala Phe His Thr Pro Ala Tyr Asp Lys Arg
5990                5995                6000

Ala Phe Val Lys Leu Lys Pro Met Pro Phe Phe Tyr Phe Asp Asp
6005                6010                6015

Ser Asp Cys Asp Val Val Gln Glu Gln Val Asn Tyr Val Pro Leu
6020                6025                6030

Arg Ala Ser Ser Cys Val Thr Arg Cys Asn Ile Gly Gly Ala Val
6035                6040                6045

Cys Ser Lys His Ala Asn Leu Tyr Gln Lys Tyr Val Glu Ala Tyr
6050                6055                6060

Asn Thr Phe Thr Gln Ala Gly Phe Asn Ile Trp Val Pro His Ser
6065                6070                6075

Phe Asp Val Tyr Asn Leu Trp Gln Ile Phe Ile Glu Thr Asn Leu
6080                6085                6090

Gln Ser Leu Glu Asn Ile Ala Phe Asn Val Val Lys Lys Gly Cys
6095                6100                6105

Phe Thr Gly Val Asp Gly Glu Leu Pro Val Ala Val Val Asn Asp
6110                6115                6120

Lys Val Phe Val Arg Tyr Gly Asp Val Asp Asn Leu Val Phe Thr
6125                6130                6135

Asn Lys Thr Thr Leu Pro Thr Asn Val Ala Phe Glu Leu Phe Ala
6140                6145                6150

Lys Arg Lys Met Gly Leu Thr Pro Pro Leu Ser Ile Leu Lys Asn
6155                6160                6165

Leu Gly Val Val Ala Thr Tyr Lys Phe Val Leu Trp Asp Tyr Glu
6170                6175                6180

Ala Glu Arg Pro Phe Thr Ser Tyr Thr Lys Ser Val Cys Lys Tyr
6185                6190                6195

Thr Asp Phe Asn Glu Asp Val Cys Val Cys Phe Asp Asn Ser Ile
6200                6205                6210

Gln Gly Ser Tyr Glu Arg Phe Thr Leu Thr Thr Asn Ala Val Leu
6215                6220                6225

Phe Ser Thr Val Val Ile Lys Asn Leu Thr Pro Ile Lys Leu Asn
6230                6235                6240

Phe Gly Met Leu Asn Gly Met Pro Val Ser Ser Ile Lys Gly Asp
6245                6250                6255

Lys Gly Val Glu Lys Leu Val Asn Trp Tyr Ile Tyr Val Arg Lys
6260                6265                6270

Asn Gly Gln Phe Gln Asp His Tyr Asp Gly Phe Tyr Thr Gln Gly
```

```
                    6275                6280                6285
Arg Asn Leu Ser Asp Phe Thr Pro Arg Ser Asp Met Glu Tyr Asp
                    6290                6295                6300

Phe Leu Asn Met Asp Met Gly Val Phe Ile Asn Lys Tyr Gly Leu
                    6305                6310                6315

Glu Asp Phe Asn Phe Glu His Val Val Tyr Gly Asp Val Ser Lys
                    6320                6325                6330

Thr Thr Leu Gly Gly Leu His Leu Leu Ile Ser Gln Phe Arg Leu
                    6335                6340                6345

Ser Lys Met Gly Val Leu Lys Ala Asp Asp Phe Val Thr Ala Ser
                    6350                6355                6360

Asp Thr Thr Leu Arg Cys Cys Thr Val Thr Tyr Leu Asn Glu Leu
                    6365                6370                6375

Ser Ser Lys Val Val Cys Thr Tyr Met Asp Leu Leu Leu Asp Asp
                    6380                6385                6390

Phe Val Thr Ile Leu Lys Ser Leu Asp Leu Gly Val Ile Ser Lys
                    6395                6400                6405

Val His Glu Val Ile Ile Asp Asn Lys Pro Tyr Arg Trp Met Leu
                    6410                6415                6420

Trp Cys Lys Asp Asn His Leu Ser Thr Phe Tyr Pro Gln Leu Gln
                    6425                6430                6435

Ser Ala Glu Trp Lys Cys Gly Tyr Ala Met Pro Gln Ile Tyr Lys
                    6440                6445                6450

Leu Gln Arg Met Cys Leu Glu Pro Cys Asn Leu Tyr Asn Tyr Gly
                    6455                6460                6465

Ala Gly Ile Lys Leu Pro Ser Gly Ile Met Leu Asn Val Val Lys
                    6470                6475                6480

Tyr Thr Gln Leu Cys Gln Tyr Leu Asn Ser Thr Thr Met Cys Val
                    6485                6490                6495

Pro His Asn Met Arg Val Leu His Tyr Gly Ala Gly Ser Asp Lys
                    6500                6505                6510

Gly Val Ala Pro Gly Thr Thr Val Leu Lys Arg Trp Leu Pro Pro
                    6515                6520                6525

Asp Ala Ile Ile Ile Asp Asn Asp Ile Asn Asp Tyr Val Ser Asp
                    6530                6535                6540

Ala Asp Phe Ser Ile Thr Gly Asp Cys Ala Thr Val Tyr Leu Glu
                    6545                6550                6555

Asp Lys Phe Asp Leu Leu Ile Ser Asp Met Tyr Asp Gly Arg Ile
                    6560                6565                6570

Lys Phe Cys Asp Gly Glu Asn Val Ser Lys Asp Gly Phe Phe Thr
                    6575                6580                6585

Tyr Leu Asn Gly Val Ile Arg Glu Lys Leu Ala Ile Gly Gly Ser
                    6590                6595                6600

Val Ala Ile Lys Ile Thr Glu Tyr Ser Trp Asn Lys Tyr Leu Tyr
                    6605                6610                6615

Glu Leu Ile Gln Arg Phe Ala Phe Trp Thr Leu Phe Cys Thr Ser
                    6620                6625                6630

Val Asn Thr Ser Ser Ser Glu Ala Phe Leu Ile Gly Ile Asn Tyr
                    6635                6640                6645

Leu Gly Asp Phe Ile Gln Gly Pro Phe Ile Ala Gly Asn Thr Val
                    6650                6655                6660

His Ala Asn Tyr Ile Phe Trp Arg Asn Ser Thr Ile Met Ser Leu
                    6665                6670                6675
```

```
Ser Tyr Asn Ser Val Leu Asp Leu Ser Lys Phe Glu Cys Lys His
            6680                6685                6690

Lys Ala Thr Val Val Val Thr Leu Lys Asp Ser Asp Val Asn Asp
    6695                6700                6705

Met Val Leu Ser Leu Ile Lys Ser Gly Arg Leu Leu Leu Arg Asn
        6710                6715                6720

Asn Gly Arg Phe Gly Gly Phe Ser Asn His Leu Val Ser Thr Lys
    6725                6730                6735

<210> SEQ ID NO 58
<211> LENGTH: 2250
<212> TYPE: PRT
<213> ORGANISM: Human coronavirus
<220> FEATURE:
<221> NAME/KEY: MISC_FEATURE
<222> LOCATION: (1)..(2250)
<223> OTHER INFORMATION: Adenosine diphosphate-ribose 1'-phosphatase

<400> SEQUENCE: 58

Ser Asn Asn Pro Gln Cys Ala Ile Val Gln Ala Ser Glu Ser Lys Val
1               5                   10                  15

Leu Leu Glu Arg Phe Leu Pro Lys Cys Pro Glu Ile Leu Leu Ser Ile
                20                  25                  30

Asp Asp Gly His Leu Trp Asn Leu Phe Glu Lys Phe Asn Phe Val
            35                  40                  45

Thr Asp Trp Leu Lys Thr Leu Lys Leu Thr Leu Thr Ser Asn Gly Leu
    50                  55                  60

Leu Gly Asn Cys Ala Lys Arg Phe Arg Arg Val Leu Val Lys Leu Leu
65                  70                  75                  80

Asp Val Tyr Asn Gly Phe Leu Glu Thr Val Cys Ser Val Ala Tyr Thr
                85                  90                  95

Ala Gly Val Cys Ile Lys Tyr Tyr Ala Val Asn Val Pro Tyr Val Val
                100                 105                 110

Ile Ser Gly Phe Val Ser Arg Val Ile Arg Arg Glu Arg Cys Asp Met
            115                 120                 125

Thr Phe Pro Cys Val Ser Cys Val Thr Phe Phe Tyr Glu Phe Leu Asp
    130                 135                 140

Thr Cys Phe Gly Val Ser Lys Pro Asn Ala Ile Asp Val Glu His Leu
145                 150                 155                 160

Glu Leu Lys Glu Thr Val Phe Val Glu Pro Lys Asp Gly Gly Gln Phe
                165                 170                 175

Phe Val Ser Gly Asp Tyr Leu Trp Tyr Val Val Asp Asp Ile Tyr Tyr
            180                 185                 190

Pro Ala Ser Cys Asn Gly Val Leu Pro Val Ala Phe Thr Lys Leu Ala
    195                 200                 205

Gly Gly Lys Ile Ser Phe Ser Asp Asp Val Ile His Asp Val Glu
210                 215                 220

Pro Thr His Lys Val Lys Leu Ile Phe Glu Phe Glu Asp Asp Val Val
225                 230                 235                 240

Thr Ser Leu Cys Lys Lys Ser Phe Gly Lys Ser Ile Ile Tyr Thr Gly
                245                 250                 255

Asp Trp Glu Gly Leu His Glu Val Leu Thr Ser Ala Met Asn Val Ile
            260                 265                 270

Gly Gln His Ile Lys Leu Pro Gln Phe Tyr Ile Tyr Asp Glu Glu Gly
    275                 280                 285
```

```
Gly Tyr Asp Val Ser Lys Pro Val Met Ile Ser Gln Trp Pro Ile Ser
    290                 295                 300

Asn Asp Ser Asn Gly Cys Val Val Glu Ala Ser Thr Asp Phe His Gln
305                 310                 315                 320

Leu Glu Cys Ile Val Asp Asp Ser Val Arg Glu Val Asp Ile Ile
            325                 330                 335

Glu Gln Pro Phe Glu Val Glu His Val Leu Ser Ile Lys Gln Pro
            340                 345                 350

Phe Ser Phe Ser Phe Arg Asp Glu Leu Gly Val Arg Val Leu Asp Gln
                355                 360                 365

Ser Asp Asn Asn Cys Trp Ile Ser Thr Thr Leu Val Gln Leu Gln Leu
    370                 375                 380

Thr Lys Leu Leu Asp Asp Ser Ile Glu Met Gln Leu Phe Lys Val Gly
385                 390                 395                 400

Lys Val Asp Ser Ile Val Gln Lys Cys Tyr Glu Leu Ser His Leu Ile
                405                 410                 415

Ser Gly Ser Leu Gly Asp Ser Gly Lys Leu Leu Ser Glu Leu Leu Lys
            420                 425                 430

Glu Lys Tyr Thr Cys Ser Ile Thr Phe Glu Met Ser Cys Asp Cys Gly
        435                 440                 445

Lys Lys Phe Asp Asp Gln Val Gly Cys Leu Phe Trp Ile Met Pro Tyr
450                 455                 460

Thr Lys Leu Phe Gln Lys Gly Glu Cys Ile Cys His Lys Met Gln
465                 470                 475                 480

Thr Tyr Lys Leu Val Ser Met Lys Gly Thr Gly Val Phe Val Gln Asp
                485                 490                 495

Pro Ala Pro Ile Asp Ile Asp Ala Phe Pro Val Lys Pro Ile Cys Ser
            500                 505                 510

Ser Val Tyr Leu Gly Val Lys Gly Ser Gly His Tyr Gln Thr Asn Leu
        515                 520                 525

Tyr Ser Phe Asn Lys Ala Ile Asp Gly Phe Gly Val Phe Asp Ile Lys
    530                 535                 540

Asn Ser Ser Val Asn Thr Val Cys Phe Val Asp Val Asp Phe His Ser
545                 550                 555                 560

Val Glu Ile Glu Ala Gly Glu Val Lys Pro Phe Ala Val Tyr Lys Asn
                565                 570                 575

Val Lys Phe Tyr Leu Gly Asp Ile Ser His Leu Val Asn Cys Val Ser
            580                 585                 590

Phe Asp Phe Val Val Asn Ala Ala Asn Glu Asn Leu Leu His Gly Gly
        595                 600                 605

Gly Val Ala Arg Ala Ile Asp Ile Leu Thr Glu Gly Gln Leu Gln Ser
    610                 615                 620

Leu Ser Lys Asp Tyr Ile Ser Ser Asn Gly Pro Leu Lys Val Gly Ala
625                 630                 635                 640

Gly Val Met Leu Glu Cys Glu Lys Phe Asn Val Phe Asn Val Val Gly
                645                 650                 655

Pro Arg Thr Gly Lys His Glu His Ser Leu Leu Val Glu Ala Tyr Asn
            660                 665                 670

Ser Ile Leu Phe Glu Asn Gly Ile Pro Leu Met Pro Leu Leu Ser Cys
        675                 680                 685

Gly Ile Phe Gly Val Arg Ile Glu Asn Ser Leu Lys Ala Leu Phe Ser
    690                 695                 700

Cys Asp Ile Asn Lys Pro Leu Gln Val Phe Val Tyr Ser Ser Asn Glu
```

-continued

```
            705                 710                 715                 720
Glu Gln Ala Val Leu Lys Phe Leu Asp Gly Leu Asp Leu Thr Pro Val
                725                 730                 735
Ile Asp Val Asp Val Val Lys Pro Phe Arg Val Glu Gly Asn Phe
            740                 745                 750
Ser Phe Phe Asp Cys Gly Val Asn Ala Leu Asp Gly Asp Ile Tyr Leu
                755                 760                 765
Leu Phe Thr Asn Ser Ile Leu Met Leu Asp Lys Gln Gly Gln Leu Leu
            770                 775                 780
Asp Thr Lys Leu Asn Gly Ile Leu Gln Gln Ala Ala Leu Asp Tyr Leu
785                 790                 795                 800
Ala Thr Val Lys Thr Val Pro Ala Gly Asn Leu Val Lys Leu Phe Val
                805                 810                 815
Glu Ser Cys Thr Ile Tyr Met Cys Val Val Pro Ser Ile Asn Asp Leu
                820                 825                 830
Ser Phe Asp Lys Asn Leu Gly Arg Cys Val Arg Lys Leu Asn Arg Leu
            835                 840                 845
Lys Thr Cys Val Ile Ala Asn Val Pro Ala Ile Asp Val Leu Lys Lys
850                 855                 860
Leu Leu Ser Ser Leu Thr Leu Thr Val Lys Phe Val Glu Ser Asn
865                 870                 875                 880
Val Met Asp Val Asn Asp Cys Phe Lys Asn Asp Val Val Leu Lys
                885                 890                 895
Ile Thr Glu Asp Gly Ile Asn Val Lys Asp Val Val Glu Ser Ser
                900                 905                 910
Lys Ser Leu Gly Lys Gln Leu Gly Val Ser Asp Gly Val Asp Ser
            915                 920                 925
Phe Glu Gly Val Leu Pro Ile Asn Thr Asp Thr Val Leu Ser Val Ala
    930                 935                 940
Pro Glu Val Asp Trp Val Ala Phe Tyr Gly Phe Glu Lys Ala Ala Leu
945                 950                 955                 960
Phe Ala Ser Leu Asp Val Lys Pro Tyr Gly Tyr Pro Asn Asp Phe Val
                965                 970                 975
Gly Gly Phe Arg Val Leu Gly Thr Thr Asp Asn Asn Cys Trp Val Asn
                980                 985                 990
Ala Thr Cys Ile Ile Leu Gln Tyr  Leu Lys Pro Thr Phe  Lys Ser Lys
            995                 1000                1005
Gly Leu  Asn Val Leu Trp Asn  Lys Phe Val Thr Gly  Asp Val Gly
    1010                1015                1020
Pro Phe  Val Ser Phe Ile Tyr  Phe Ile Thr Met Ser  Ser Lys Gly
    1025                1030                1035
Gln Lys  Gly Asp Ala Glu Glu  Ala Leu Ser Lys Leu  Ser Glu Tyr
    1040                1045                1050
Leu Ile  Ser Asp Ser Ile Val  Thr Leu Glu Gln Tyr  Ser Thr Cys
    1055                1060                1065
Asp Ile  Cys Lys Ser Thr Val  Val Glu Val Lys Ser  Ala Ile Val
    1070                1075                1080
Cys Ala  Ser Val Leu Lys Asp  Gly Cys Asp Val Gly  Phe Cys Pro
    1085                1090                1095
His Arg  His Lys Leu Arg Ser  Arg Val Lys Phe Val  Asn Gly Arg
    1100                1105                1110
Val Val  Ile Thr Asn Val Gly  Glu Pro Ile Ile Ser  Gln Pro Ser
    1115                1120                1125
```

-continued

```
Lys Leu Leu Asn Gly Ile Ala Tyr Thr Thr Phe Ser Gly Ser Phe
    1130                1135                1140

Asp Asn Gly His Tyr Val Val Tyr Asp Ala Ala Asn Asn Ala Val
    1145                1150                1155

Tyr Asp Gly Ala Arg Leu Phe Ser Ser Asp Leu Ser Thr Leu Ala
    1160                1165                1170

Val Thr Ala Ile Val Val Gly Gly Cys Val Thr Ser Asn Val
    1175                1180                1185

Pro Thr Ile Val Ser Glu Lys Ile Ser Val Met Asp Lys Leu Asp
    1190                1195                1200

Thr Gly Ala Gln Lys Phe Phe Gln Phe Gly Asp Phe Val Met Asn
    1205                1210                1215

Asn Ile Val Leu Phe Leu Thr Trp Leu Ser Met Phe Ser Leu
    1220                1225                1230

Leu Arg Thr Ser Ile Met Lys His Asp Ile Lys Val Ile Ala Lys
    1235                1240                1245

Ala Pro Lys Arg Thr Gly Val Ile Leu Thr Arg Ser Phe Lys Tyr
    1250                1255                1260

Asn Ile Arg Ser Ala Leu Phe Val Ile Lys Gln Lys Trp Cys Val
    1265                1270                1275

Ile Val Thr Leu Phe Lys Phe Leu Leu Leu Leu Tyr Ala Ile Tyr
    1280                1285                1290

Ala Leu Val Phe Met Ile Val Gln Phe Ser Pro Phe Asn Ser Leu
    1295                1300                1305

Leu Cys Gly Asp Ile Val Ser Gly Tyr Glu Lys Ser Thr Phe Asn
    1310                1315                1320

Lys Asp Ile Tyr Cys Gly Asn Ser Met Val Cys Lys Met Cys Leu
    1325                1330                1335

Phe Ser Tyr Gln Glu Phe Asn Asp Leu Asp His Thr Ser Leu Val
    1340                1345                1350

Trp Lys His Ile Arg Asp Pro Ile Leu Ile Ser Leu Gln Pro Phe
    1355                1360                1365

Val Ile Leu Val Ile Leu Leu Ile Phe Gly Asn Met Tyr Leu Arg
    1370                1375                1380

Phe Gly Leu Leu Tyr Phe Val Ala Gln Phe Ile Ser Thr Phe Gly
    1385                1390                1395

Ser Phe Leu Gly Phe His Gln Lys Gln Trp Phe Leu His Phe Val
    1400                1405                1410

Pro Phe Asp Val Leu Cys Asn Glu Phe Leu Ala Thr Phe Ile Val
    1415                1420                1425

Cys Lys Ile Val Leu Phe Val Arg His Ile Ile Val Gly Cys Asn
    1430                1435                1440

Asn Ala Asp Cys Val Ala Cys Ser Lys Ser Ala Arg Leu Lys Arg
    1445                1450                1455

Val Pro Leu Gln Thr Ile Ile Asn Gly Met His Lys Ser Phe Tyr
    1460                1465                1470

Val Asn Ala Asn Gly Gly Thr Cys Phe Cys Asn Lys His Asn Phe
    1475                1480                1485

Phe Cys Val Asn Cys Asp Ser Phe Gly Pro Gly Asn Thr Phe Ile
    1490                1495                1500

Asn Gly Asp Ile Ala Arg Glu Leu Gly Asn Val Val Lys Thr Ala
    1505                1510                1515
```

-continued

```
Val Gln Pro Thr Ala Pro Ala Tyr Val Ile Ile Asp Lys Val Asp
1520                1525                1530

Phe Val Asn Gly Phe Tyr Arg Leu Tyr Ser Gly Asp Thr Phe Trp
1535                1540                1545

Arg Tyr Asp Phe Asp Ile Thr Glu Ser Lys Tyr Ser Cys Lys Glu
1550                1555                1560

Val Leu Lys Asn Cys Asn Val Leu Glu Asn Phe Ile Val Tyr Asn
1565                1570                1575

Asn Ser Gly Ser Asn Ile Thr Gln Ile Lys Asn Ala Cys Val Tyr
1580                1585                1590

Phe Ser Gln Leu Leu Cys Glu Pro Ile Lys Leu Val Asn Ser Glu
1595                1600                1605

Leu Leu Ser Thr Leu Ser Val Asp Phe Asn Gly Val Leu His Lys
1610                1615                1620

Ala Tyr Val Asp Val Leu Cys Asn Ser Phe Phe Lys Glu Leu Thr
1625                1630                1635

Ala Asn Met Ser Met Ala Glu Cys Lys Ala Thr Leu Gly Leu Thr
1640                1645                1650

Val Ser Asp Asp Phe Val Ser Ala Val Ala Asn Ala His Arg
1655                1660                1665

Tyr Asp Val Leu Leu Ser Asp Leu Ser Phe Asn Asn Phe Phe Ile
1670                1675                1680

Ser Tyr Ala Lys Pro Glu Asp Lys Leu Ser Val Tyr Asp Ile Ala
1685                1690                1695

Cys Cys Met Arg Ala Gly Ser Lys Val Val Asn His Asn Val Leu
1700                1705                1710

Ile Lys Glu Ser Ile Pro Ile Val Trp Gly Val Lys Asp Phe Asn
1715                1720                1725

Thr Leu Ser Gln Glu Gly Lys Lys Tyr Leu Val Lys Thr Thr Lys
1730                1735                1740

Ala Lys Gly Leu Thr Phe Leu Leu Thr Phe Asn Asp Asn Gln Ala
1745                1750                1755

Ile Thr Gln Val Pro Ala Thr Ser Ile Val Ala Lys Gln Gly Ala
1760                1765                1770

Gly Phe Lys Arg Thr Tyr Asn Phe Leu Trp Tyr Val Cys Leu Phe
1775                1780                1785

Val Val Ala Leu Phe Ile Gly Val Ser Phe Ile Asp Tyr Thr Thr
1790                1795                1800

Thr Val Thr Ser Phe His Gly Tyr Asp Phe Lys Tyr Ile Glu Asn
1805                1810                1815

Gly Gln Leu Lys Val Phe Glu Ala Pro Leu His Cys Val Arg Asn
1820                1825                1830

Val Phe Asp Asn Phe Asn Gln Trp His Glu Ala Lys Phe Gly Val
1835                1840                1845

Val Thr Thr Asn Ser Asp Lys Cys Pro Ile Val Val Gly Val Ser
1850                1855                1860

Glu Arg Ile Asn Val Val Pro Gly Val Pro Thr Asn Val Tyr Leu
1865                1870                1875

Val Gly Lys Thr Leu Val Phe Thr Leu Gln Ala Ala Phe Gly Asn
1880                1885                1890

Thr Gly Val Cys Tyr Asp Phe Asp Gly Val Thr Thr Ser Asp Lys
1895                1900                1905

Cys Ile Phe Asn Ser Ala Cys Thr Arg Leu Glu Gly Leu Gly Gly
```

-continued

```
            1910               1915                1920

Asp Asn Val Tyr Cys Tyr Asn Thr Asp Leu Ile Glu Gly Ser Lys
    1925                1930                1935

Pro Tyr Ser Thr Leu Gln Pro Asn Ala Tyr Tyr Lys Tyr Asp Ala
    1940                1945                1950

Lys Asn Tyr Val Arg Phe Pro Glu Ile Leu Ala Arg Gly Phe Gly
    1955                1960                1965

Leu Arg Thr Ile Arg Thr Leu Ala Thr Arg Tyr Cys Arg Val Gly
    1970                1975                1980

Glu Cys Arg Asp Ser His Lys Gly Val Cys Phe Gly Phe Asp Lys
    1985                1990                1995

Trp Tyr Val Asn Asp Gly Arg Val Asp Asp Gly Tyr Ile Cys Gly
    2000                2005                2010

Asp Gly Leu Ile Asp Leu Leu Val Asn Val Leu Ser Ile Phe Ser
    2015                2020                2025

Ser Ser Phe Ser Val Val Ala Met Ser Gly His Met Leu Phe Asn
    2030                2035                2040

Phe Leu Phe Ala Ala Phe Ile Thr Phe Leu Cys Phe Leu Val Thr
    2045                2050                2055

Lys Phe Lys Arg Val Phe Gly Asp Leu Ser Tyr Gly Val Phe Thr
    2060                2065                2070

Val Val Cys Ala Thr Leu Ile Asn Asn Ile Ser Tyr Val Val Thr
    2075                2080                2085

Gln Asn Leu Phe Phe Met Leu Leu Tyr Ala Ile Leu Tyr Phe Val
    2090                2095                2100

Phe Thr Arg Thr Val Arg Tyr Ala Trp Ile Trp His Ile Ala Tyr
    2105                2110                2115

Ile Val Ala Tyr Phe Leu Leu Ile Pro Trp Trp Leu Leu Thr Trp
    2120                2125                2130

Phe Ser Phe Ala Ala Phe Leu Glu Leu Leu Pro Asn Val Phe Lys
    2135                2140                2145

Leu Lys Ile Ser Thr Gln Leu Phe Glu Gly Asp Lys Phe Ile Gly
    2150                2155                2160

Thr Phe Glu Ser Ala Ala Ala Gly Thr Phe Val Leu Asp Met Arg
    2165                2170                2175

Ser Tyr Glu Arg Leu Ile Asn Thr Ile Ser Pro Glu Lys Leu Lys
    2180                2185                2190

Asn Tyr Ala Ala Ser Tyr Asn Lys Tyr Lys Tyr Tyr Ser Gly Ser
    2195                2200                2205

Ala Ser Glu Ala Asp Tyr Arg Cys Ala Cys Tyr Ala His Leu Ala
    2210                2215                2220

Lys Ala Met Leu Asp Tyr Ala Lys Asp His Asn Asp Met Leu Tyr
    2225                2230                2235

Ser Pro Pro Thr Ile Ser Tyr Asn Ser Thr Leu Gln
    2240                2245                2250

<210> SEQ ID NO 59
<211> LENGTH: 361
<212> TYPE: PRT
<213> ORGANISM: Human coronavirus
<220> FEATURE:
<221> NAME/KEY: MISC_FEATURE
<222> LOCATION: (1)..(361)
<223> OTHER INFORMATION: 3CI pro Coronavirus polyprotein processing
      endoprotease
```

-continued

```
<400> SEQUENCE: 59

Ser Gly Leu Lys Lys Met Ala Gln Pro Ser Gly Cys Val Glu Arg Cys
1               5                   10                  15

Val Val Arg Val Cys Tyr Gly Ser Thr Val Leu Asn Gly Val Trp Leu
            20                  25                  30

Gly Asp Thr Val Thr Cys Pro Arg His Val Ile Ala Pro Ser Thr Thr
        35                  40                  45

Val Leu Ile Asp Tyr Asp His Ala Tyr Ser Thr Met Arg Leu His Asn
    50                  55                  60

Phe Ser Val Ser His Asn Gly Val Phe Leu Gly Val Val Gly Val Thr
65                  70                  75                  80

Met His Gly Ser Val Leu Arg Ile Lys Val Ser Gln Ser Asn Val His
                85                  90                  95

Thr Pro Lys His Val Phe Lys Thr Leu Lys Pro Gly Asp Ser Phe Asn
            100                 105                 110

Ile Leu Ala Cys Tyr Glu Gly Ile Ala Ser Gly Val Phe Gly Val Asn
        115                 120                 125

Leu Arg Thr Asn Phe Thr Ile Lys Gly Ser Phe Ile Asn Gly Ala Cys
130                 135                 140

Gly Ser Pro Gly Tyr Asn Val Arg Asn Asp Gly Thr Val Glu Phe Cys
145                 150                 155                 160

Tyr Leu His Gln Ile Glu Leu Gly Ser Gly Ala His Val Gly Ser Asp
                165                 170                 175

Phe Thr Gly Ser Val Tyr Gly Asn Phe Asp Asp Gln Pro Ser Leu Gln
            180                 185                 190

Val Glu Ser Ala Asn Leu Met Leu Ser Asp Asn Val Val Ala Phe Leu
        195                 200                 205

Tyr Ala Ala Leu Leu Asn Gly Cys Arg Trp Trp Leu Cys Ser Thr Arg
    210                 215                 220

Val Asn Val Asp Gly Phe Asn Glu Trp Ala Met Ala Asn Gly Tyr Thr
225                 230                 235                 240

Ser Val Ser Ser Val Glu Cys Tyr Ser Ile Leu Ala Ala Lys Thr Gly
                245                 250                 255

Val Ser Val Glu Gln Leu Leu Ala Ser Ile Gln His Leu His Glu Gly
            260                 265                 270

Phe Gly Gly Lys Asn Ile Leu Gly Tyr Ser Ser Leu Cys Asp Glu Phe
        275                 280                 285

Thr Leu Ala Glu Val Val Lys Gln Met Tyr Gly Val Asn Leu Gln Ser
    290                 295                 300

Gly Lys Val Ile Phe Gly Leu Lys Thr Met Phe Leu Phe Ser Val Phe
305                 310                 315                 320

Phe Thr Met Phe Trp Ala Glu Leu Phe Ile Tyr Thr Asn Thr Ile Trp
                325                 330                 335

Ile Asn Pro Val Ile Leu Thr Pro Ile Phe Cys Leu Leu Leu Phe Leu
            340                 345                 350

Ser Leu Val Leu Thr Met Phe Leu Lys
        355                 360

<210> SEQ ID NO 60
<211> LENGTH: 1071
<212> TYPE: PRT
<213> ORGANISM: Human coronavirus
<220> FEATURE:
<221> NAME/KEY: MISC_FEATURE
<222> LOCATION: (1)..(1071)
```

<223> OTHER INFORMATION: RNA dependant RNA polymerase (pfam00680)

<400> SEQUENCE: 60

```
Ala Gly Lys Gln Thr Glu Leu Ala Val Asn Ser Gly Leu Leu Thr Ala
1               5                   10                  15

Cys Ala Phe Ser Val Asp Pro Ala Thr Thr Tyr Leu Glu Ala Val Lys
            20                  25                  30

His Gly Ala Lys Pro Val Ser Asn Cys Ile Lys Met Leu Ser Asn Gly
        35                  40                  45

Ala Gly Asn Gly Gln Ala Ile Thr Thr Ser Val Asp Ala Asn Thr Asn
    50                  55                  60

Gln Asp Ser Tyr Gly Gly Ala Ser Ile Cys Leu Tyr Cys Arg Ala His
65                  70                  75                  80

Val Pro His Pro Ser Met Asp Gly Tyr Cys Lys Phe Lys Gly Lys Cys
                85                  90                  95

Val Gln Val Pro Ile Gly Cys Leu Asp Pro Ile Arg Phe Cys Leu Glu
            100                 105                 110

Asn Asn Val Cys Asn Val Cys Gly Cys Trp Leu Gly His Gly Cys Ala
        115                 120                 125

Cys Asp Arg Thr Thr Ile Gln Ser Val Asp Ile Ser Tyr Leu Asn Glu
    130                 135                 140

Gln Gly Val Leu Val Gln Leu Asp Arg Ala Arg Gly Ser Ser Ala Ala
145                 150                 155                 160

Arg Leu Glu Pro Cys Asn Gly Thr Asp Ile Asp Lys Cys Val Arg Ala
                165                 170                 175

Phe Asp Ile Tyr Asn Lys Asn Val Ser Phe Leu Gly Lys Cys Leu Lys
            180                 185                 190

Met Asn Cys Val Arg Phe Lys Asn Ala Asp Leu Lys Asp Gly Tyr Phe
        195                 200                 205

Val Ile Lys Arg Cys Thr Lys Ser Val Met Glu His Glu Gln Ser Met
    210                 215                 220

Tyr Asn Leu Leu Asn Phe Ser Gly Ala Leu Ala Glu His Asp Phe Phe
225                 230                 235                 240

Thr Trp Lys Asp Gly Arg Val Ile Tyr Gly Asn Val Ser Arg His Asn
                245                 250                 255

Leu Thr Lys Tyr Thr Met Met Asp Leu Val Tyr Ala Met Arg Asn Phe
            260                 265                 270

Asp Glu Gln Asn Cys Asp Val Leu Lys Glu Val Leu Val Leu Thr Gly
        275                 280                 285

Cys Cys Asp Asn Ser Tyr Phe Asp Ser Lys Gly Trp Tyr Asp Pro Val
    290                 295                 300

Glu Asn Glu Asp Ile His Arg Val Tyr Ala Ser Leu Gly Lys Ile Val
305                 310                 315                 320

Ala Arg Ala Met Leu Lys Cys Val Ala Leu Cys Asp Ala Met Val Ala
                325                 330                 335

Lys Gly Val Val Gly Val Leu Thr Leu Asp Asn Gln Asp Leu Asn Gly
            340                 345                 350

Asn Phe Tyr Asp Phe Gly Asp Phe Val Val Ser Leu Pro Asn Met Gly
        355                 360                 365

Val Pro Cys Cys Thr Ser Tyr Tyr Ser Tyr Met Met Pro Ile Met Gly
    370                 375                 380

Leu Thr Asn Cys Leu Ala Ser Glu Cys Phe Val Lys Ser Asp Ile Phe
385                 390                 395                 400
```

-continued

Gly Ser Asp Phe Lys Thr Phe Asp Leu Leu Lys Tyr Asp Phe Thr Glu
            405                 410                 415

His Lys Glu Asn Leu Phe Asn Lys Tyr Phe Lys His Trp Ser Phe Asp
            420                 425                 430

Tyr His Pro Asn Cys Cys Asp Cys Tyr Asp Asp Met Cys Val Ile His
            435                 440                 445

Cys Ala Asn Phe Asn Thr Leu Phe Ala Thr Thr Ile Pro Gly Thr Ala
    450                 455                 460

Phe Gly Pro Leu Cys Arg Lys Val Phe Ile Asp Gly Val Pro Leu Val
465                 470                 475                 480

Thr Thr Ala Gly Tyr His Phe Lys Gln Leu Gly Leu Val Trp Asn Lys
                485                 490                 495

Asp Val Asn Thr His Ser Val Arg Leu Thr Ile Thr Glu Leu Leu Gln
            500                 505                 510

Phe Val Thr Asp Pro Ser Leu Ile Ile Ala Ser Ser Pro Ala Leu Val
            515                 520                 525

Asp Gln Arg Thr Ile Cys Phe Ser Val Ala Ala Leu Ser Thr Gly Leu
            530                 535                 540

Thr Asn Gln Val Val Lys Pro Gly His Phe Asn Glu Glu Phe Tyr Asn
545                 550                 555                 560

Phe Leu Arg Leu Arg Gly Phe Phe Asp Glu Gly Ser Glu Leu Thr Leu
                565                 570                 575

Lys His Phe Phe Phe Ala Gln Asn Gly Asp Ala Ala Val Lys Asp Phe
            580                 585                 590

Asp Phe Tyr Arg Tyr Asn Lys Pro Thr Ile Leu Asp Ile Cys Gln Ala
            595                 600                 605

Arg Val Thr Tyr Lys Ile Val Ser Arg Tyr Phe Asp Ile Tyr Glu Gly
            610                 615                 620

Gly Cys Ile Lys Ala Cys Glu Val Val Thr Asn Leu Asn Lys Ser
625                 630                 635                 640

Ala Gly Trp Pro Leu Asn Lys Phe Gly Lys Ala Ser Leu Tyr Tyr Glu
                645                 650                 655

Ser Ile Ser Tyr Glu Glu Gln Asp Ala Leu Phe Ala Leu Thr Lys Arg
            660                 665                 670

Asn Val Leu Pro Thr Met Thr Gln Leu Asn Leu Lys Tyr Ala Ile Ser
            675                 680                 685

Gly Lys Glu Arg Ala Arg Thr Val Gly Gly Val Ser Leu Leu Ser Thr
        690                 695                 700

Met Thr Thr Arg Gln Tyr His Gln Lys His Leu Lys Ser Ile Val Asn
705                 710                 715                 720

Thr Arg Asn Ala Thr Val Val Ile Gly Thr Thr Lys Phe Tyr Gly Gly
                725                 730                 735

Trp Asn Asn Met Leu Arg Thr Leu Ile Asp Gly Val Glu Asn Pro Met
            740                 745                 750

Leu Met Gly Trp Asp Tyr Pro Lys Cys Asp Arg Ala Leu Pro Asn Met
            755                 760                 765

Ile Arg Met Ile Ser Ala Met Val Leu Gly Ser Lys His Val Asn Cys
            770                 775                 780

Cys Thr Ala Thr Asp Arg Phe Tyr Arg Leu Gly Asn Glu Leu Ala Gln
785                 790                 795                 800

Val Leu Thr Glu Val Val Tyr Ser Asn Gly Gly Phe Tyr Phe Lys Pro
                805                 810                 815

Gly Gly Thr Thr Ser Gly Asp Ala Ser Thr Ala Tyr Ala Asn Ser Ile

-continued

```
                        820                 825                 830
Phe Asn Ile Phe Gln Ala Val Ser Ser Asn Ile Asn Arg Leu Leu Ser
    835                 840                 845

Val Pro Ser Asp Ser Cys Asn Asn Val Asn Val Arg Asp Leu Gln Arg
850                 855                 860

Arg Leu Tyr Asp Asn Cys Tyr Arg Leu Thr Ser Val Glu Glu Ser Phe
865                 870                 875                 880

Ile Glu Asp Tyr Tyr Gly Tyr Leu Arg Lys His Phe Ser Met Met Ile
                885                 890                 895

Leu Ser Asp Asp Gly Val Val Cys Tyr Asn Lys Asp Tyr Ala Glu Leu
            900                 905                 910

Gly Tyr Ile Ala Asp Ile Ser Ala Phe Lys Ala Thr Leu Tyr Tyr Gln
        915                 920                 925

Asn Asn Val Phe Met Ser Thr Ser Lys Cys Trp Val Glu Glu Asp Leu
    930                 935                 940

Thr Lys Gly Pro His Glu Phe Cys Ser Gln His Thr Met Gln Ile Val
945                 950                 955                 960

Asp Lys Asp Gly Thr Tyr Tyr Leu Pro Tyr Pro Asp Pro Ser Arg Ile
                965                 970                 975

Leu Ser Ala Gly Val Phe Val Asp Asp Val Val Lys Thr Asp Ala Val
            980                 985                 990

Val Leu Leu Glu Arg Tyr Val Ser  Leu Ala Ile Asp Ala  Tyr Pro Leu
        995                 1000                1005

Ser Lys  His Pro Asn Ser Glu  Tyr Arg Lys Val Phe  Tyr Val Leu
    1010                1015                1020

Leu Asp  Trp Val Lys His Leu  Asn Lys Asn Leu Asn  Glu Gly Val
    1025                1030                1035

Leu Glu  Ser Phe Ser Val Thr  Leu Leu Asp Asn Gln  Glu Asp Lys
    1040                1045                1050

Phe Trp  Cys Glu Asp Phe Tyr  Ala Ser Met Tyr Glu  Asn Ser Thr
    1055                1060                1065

Ile Leu  Gln
    1070

<210> SEQ ID NO 61
<211> LENGTH: 1115
<212> TYPE: PRT
<213> ORGANISM: Human coronavirus
<220> FEATURE:
<221> NAME/KEY: MISC_FEATURE
<222> LOCATION: (1)..(1115)
<223> OTHER INFORMATION: ExoN 3' to 5' Exonuclease and helicase

<400> SEQUENCE: 61

Ala Ala Gly Leu Cys Val Val Cys Gly Ser Gln Thr Val Leu Arg Cys
1               5                   10                  15

Gly Asp Cys Leu Arg Lys Pro Met Leu Cys Thr Lys Cys Ala Tyr Asp
            20                  25                  30

His Val Phe Gly Thr Asp His Lys Phe Ile Leu Ala Ile Thr Pro Tyr
        35                  40                  45

Val Cys Asn Ala Ser Gly Cys Gly Val Ser Asp Val Lys Lys Leu Tyr
    50                  55                  60

Leu Gly Gly Leu Asn Tyr Tyr Cys Thr Asn His Lys Pro Gln Leu Ser
65                  70                  75                  80

Phe Pro Leu Cys Ser Ala Gly Asn Ile Phe Gly Leu Tyr Lys Asn Ser
                85                  90                  95
```

```
Ala Thr Gly Ser Leu Asp Val Glu Val Phe Asn Arg Leu Ala Thr Ser
            100                 105                 110
Asp Trp Thr Asp Val Arg Asp Tyr Lys Leu Ala Asn Asp Val Lys Asp
            115                 120                 125
Thr Leu Arg Leu Phe Ala Ala Glu Thr Ile Lys Ala Lys Glu Glu Ser
            130                 135                 140
Val Lys Ser Ser Tyr Ala Phe Ala Thr Leu Lys Glu Val Val Gly Pro
145                 150                 155                 160
Lys Glu Leu Leu Leu Ser Trp Glu Ser Gly Lys Val Lys Pro Pro Leu
                165                 170                 175
Asn Arg Asn Ser Val Phe Thr Cys Phe Gln Ile Ser Lys Asp Ser Lys
            180                 185                 190
Phe Gln Ile Gly Glu Phe Ile Phe Glu Lys Val Glu Tyr Gly Ser Asp
            195                 200                 205
Thr Val Thr Tyr Lys Ser Thr Val Thr Lys Leu Val Pro Gly Met
            210                 215                 220
Ile Phe Val Leu Thr Ser His Asn Val Gln Pro Leu Arg Ala Pro Thr
225                 230                 235                 240
Ile Ala Asn Gln Glu Lys Tyr Ser Ser Ile Tyr Lys Leu His Pro Ala
                245                 250                 255
Phe Asn Val Ser Asp Ala Tyr Ala Asn Leu Val Pro Tyr Tyr Gln Leu
            260                 265                 270
Ile Gly Lys Gln Lys Ile Thr Thr Ile Gln Gly Pro Pro Gly Ser Gly
            275                 280                 285
Lys Ser His Cys Ser Ile Gly Leu Gly Leu Tyr Tyr Pro Gly Ala Arg
290                 295                 300
Ile Val Phe Val Ala Cys Ala His Ala Ala Val Asp Ser Leu Cys Ala
305                 310                 315                 320
Lys Ala Met Thr Val Tyr Ser Ile Asp Lys Cys Thr Arg Ile Ile Pro
            325                 330                 335
Ala Arg Ala Arg Val Glu Cys Tyr Ser Gly Phe Lys Pro Asn Asn Thr
            340                 345                 350
Ser Ala Gln Tyr Ile Phe Ser Thr Val Asn Ala Leu Pro Glu Cys Asn
            355                 360                 365
Ala Asp Ile Val Val Asp Glu Val Ser Met Cys Thr Asn Tyr Asp
            370                 375                 380
Leu Ser Val Ile Asn Gln Arg Leu Ser Tyr Lys His Ile Val Tyr Val
385                 390                 395                 400
Gly Asp Pro Gln Gln Leu Pro Ala Pro Arg Val Met Ile Thr Lys Gly
            405                 410                 415
Val Met Glu Pro Val Asp Tyr Asn Val Val Thr Gln Arg Met Cys Ala
            420                 425                 430
Ile Gly Pro Asp Val Phe Leu His Lys Cys Tyr Arg Cys Pro Ala Glu
            435                 440                 445
Ile Val Ile Gln Phe Leu Asn Leu Phe Met Arg Thr Ser Leu Ser Leu
            450                 455                 460
Leu Asn Leu Leu Val Asn Ser Val Leu Lys Ser Phe Leu Arg Val Met
465                 470                 475                 480
Tyr Lys Val Asp Asn Gly Ser Ser Ile Asn Arg Lys Gln Leu Glu Ile
                485                 490                 495
Val Lys Leu Phe Leu Val Lys Asn Pro Ser Trp Ser Lys Ala Val Phe
            500                 505                 510
```

```
Ile Ser Pro Tyr Asn Ser Gln Asn Tyr Val Ala Ser Arg Phe Leu Gly
        515                 520                 525

Leu Gln Ile Gln Thr Val Asp Ser Ser Gln Gly Ser Glu Tyr Asp Tyr
        530                 535                 540

Val Ile Tyr Ala Gln Thr Ser Asp Thr Ala His Ala Cys Asn Val Asn
545                 550                 555                 560

Arg Phe Asn Val Ala Ile Thr Arg Ala Lys Lys Gly Ile Phe Cys Val
                565                 570                 575

Met Cys Asp Lys Thr Leu Phe Asp Ser Leu Lys Phe Phe Glu Ile Lys
            580                 585                 590

His Ala Asp Leu His Ser Ser Gln Val Cys Gly Leu Phe Lys Asn Cys
        595                 600                 605

Thr Arg Thr Pro Leu Asn Leu Pro Pro Thr His Ala His Thr Phe Leu
    610                 615                 620

Ser Leu Ser Asp Gln Phe Lys Thr Thr Gly Asp Leu Ala Val Gln Ile
625                 630                 635                 640

Gly Ser Asn Asn Val Cys Thr Tyr Glu His Val Ile Ser Phe Met Gly
                645                 650                 655

Phe Arg Phe Asp Ile Ser Ile Pro Gly Ser His Ser Leu Phe Cys Thr
            660                 665                 670

Arg Asp Phe Ala Ile Arg Asn Val Arg Gly Trp Leu Gly Met Asp Val
        675                 680                 685

Glu Ser Ala His Val Cys Gly Asp Asn Ile Gly Thr Asn Val Pro Leu
    690                 695                 700

Gln Val Gly Phe Ser Asn Gly Val Asn Phe Val Gln Thr Glu Gly
705                 710                 715                 720

Cys Val Ser Thr Asn Phe Gly Asp Val Ile Lys Pro Val Cys Ala Lys
                725                 730                 735

Ser Pro Pro Gly Glu Gln Phe Arg His Leu Ile Pro Leu Leu Arg Lys
            740                 745                 750

Gly Gln Pro Trp Leu Ile Val Arg Arg Ile Val Gln Met Ile Ser
        755                 760                 765

Asp Tyr Leu Ser Asn Leu Ser Asp Ile Leu Val Phe Val Leu Trp Ala
    770                 775                 780

Gly Ser Leu Glu Leu Thr Thr Met Arg Tyr Phe Val Lys Ile Gly Pro
785                 790                 795                 800

Ile Lys Tyr Cys Tyr Cys Gly Asn Phe Ala Thr Cys Tyr Asn Ser Val
                805                 810                 815

Ser Asn Glu Tyr Cys Cys Phe Lys His Ala Leu Gly Cys Asp Tyr Val
            820                 825                 830

Tyr Asn Pro Tyr Ala Phe Asp Ile Gln Gln Trp Gly Tyr Val Gly Ser
        835                 840                 845

Leu Ser Gln Asn His His Thr Phe Cys Asn Ile His Arg Asn Glu His
    850                 855                 860

Asp Ala Ser Gly Asp Ala Val Met Thr Arg Cys Leu Ala Val His Asp
865                 870                 875                 880

Cys Phe Val Lys Asn Val Asp Trp Thr Val Thr Tyr Pro Phe Ile Ala
                885                 890                 895

Asn Glu Lys Phe Ile Asn Gly Cys Gly Arg Asn Val Gln Gly His Val
            900                 905                 910

Val Arg Ala Ala Leu Lys Leu Tyr Lys Pro Ser Val Ile His Asp Ile
        915                 920                 925

Gly Asn Pro Lys Gly Val Arg Cys Ala Val Thr Asp Ala Lys Trp Tyr
```

```
                    930               935               940
Cys Tyr Asp Lys Gln Pro Val Asn Ser Asn Val Lys Leu Leu Asp Tyr
945                 950               955                   960

Asp Tyr Ala Thr His Gly Gln Leu Asp Gly Leu Cys Leu Phe Trp Asn
                965               970                   975

Cys Asn Val Asp Met Tyr Pro Glu Phe Ser Ile Val Cys Arg Phe Asp
                980               985                   990

Thr Arg Thr Arg Ser Val Phe Asn Leu Glu Gly Val Asn Gly Gly Ser
                995              1000              1005

Leu Tyr Val Asn Lys His Ala Phe His Thr Pro Ala Tyr Asp Lys
    1010              1015              1020

Arg Ala Phe Val Lys Leu Lys Pro Met Pro Phe Phe Tyr Phe Asp
    1025              1030              1035

Asp Ser Asp Cys Asp Val Val Gln Glu Gln Val Asn Tyr Val Pro
    1040              1045              1050

Leu Arg Ala Ser Ser Cys Val Thr Arg Cys Asn Ile Gly Gly Ala
    1055              1060              1065

Val Cys Ser Lys His Ala Asn Leu Tyr Gln Lys Tyr Val Glu Ala
    1070              1075              1080

Tyr Asn Thr Phe Thr Gln Ala Gly Phe Asn Ile Trp Val Pro His
    1085              1090              1095

Ser Phe Asp Val Tyr Asn Leu Trp Gln Ile Phe Ile Glu Thr Asn
    1100              1105              1110

Leu Gln
    1115

<210> SEQ ID NO 62
<211> LENGTH: 344
<212> TYPE: PRT
<213> ORGANISM: Human coronavirus
<220> FEATURE:
<221> NAME/KEY: MISC_FEATURE
<222> LOCATION: (1)..(344)
<223> OTHER INFORMATION: XendoU (homolog of) polyU-specific
      endoribonuclease

<400> SEQUENCE: 62

Ser Leu Glu Asn Ile Ala Phe Asn Val Val Lys Lys Gly Cys Phe Thr
1               5                   10                  15

Gly Val Asp Gly Glu Leu Pro Val Ala Val Asn Asp Lys Val Phe
            20                  25                  30

Val Arg Tyr Gly Asp Val Asp Asn Leu Val Phe Thr Asn Lys Thr Thr
            35                  40                  45

Leu Pro Thr Asn Val Ala Phe Glu Leu Phe Ala Lys Arg Lys Met Gly
    50                  55                  60

Leu Thr Pro Pro Leu Ser Ile Leu Lys Asn Leu Gly Val Val Ala Thr
65                  70                  75                  80

Tyr Lys Phe Val Leu Trp Asp Tyr Glu Ala Glu Arg Pro Phe Thr Ser
                85                  90                  95

Tyr Thr Lys Ser Val Cys Lys Tyr Thr Asp Phe Asn Glu Asp Val Cys
            100                 105                 110

Val Cys Phe Asp Asn Ser Ile Gln Gly Ser Tyr Glu Arg Phe Thr Leu
            115                 120                 125

Thr Thr Asn Ala Val Leu Phe Ser Thr Val Ile Lys Asn Leu Thr
    130                 135                 140

Pro Ile Lys Leu Asn Phe Gly Met Leu Asn Gly Met Pro Val Ser Ser
```

```
                145                 150                 155                 160
Ile Lys Gly Asp Lys Gly Val Glu Lys Leu Val Asn Trp Tyr Ile Tyr
                165                 170                 175

Val Arg Lys Asn Gly Gln Phe Gln Asp His Tyr Asp Gly Phe Tyr Thr
            180                 185                 190

Gln Gly Arg Asn Leu Ser Asp Phe Thr Pro Arg Ser Asp Met Glu Tyr
            195                 200                 205

Asp Phe Leu Asn Met Asp Met Gly Val Phe Ile Asn Lys Tyr Gly Leu
        210                 215                 220

Glu Asp Phe Asn Phe Glu His Val Val Tyr Gly Asp Val Ser Lys Thr
225                 230                 235                 240

Thr Leu Gly Gly Leu His Leu Leu Ile Ser Gln Phe Arg Leu Ser Lys
                245                 250                 255

Met Gly Val Leu Lys Ala Asp Asp Phe Val Thr Ala Ser Asp Thr Thr
            260                 265                 270

Leu Arg Cys Cys Thr Val Thr Tyr Leu Asn Glu Leu Ser Ser Lys Val
            275                 280                 285

Val Cys Thr Tyr Met Asp Leu Leu Asp Asp Phe Val Thr Ile Leu
        290                 295                 300

Lys Ser Leu Asp Leu Gly Val Ile Ser Lys Val His Glu Val Ile Ile
305                 310                 315                 320

Asp Asn Lys Pro Tyr Arg Trp Met Leu Trp Cys Lys Asp Asn His Leu
                325                 330                 335

Ser Thr Phe Tyr Pro Gln Leu Gln
            340

<210> SEQ ID NO 63
<211> LENGTH: 300
<212> TYPE: PRT
<213> ORGANISM: Human coronavirus
<220> FEATURE:
<221> NAME/KEY: MISC_FEATURE
<222> LOCATION: (1)..(300)
<223> OTHER INFORMATION: 2'-O-MT 2: S-adenosylmethionine-dependant
      ribose 2'-orthomethyltransferase

<400> SEQUENCE: 63

Ser Ala Glu Trp Lys Cys Gly Tyr Ala Met Pro Gln Ile Tyr Lys Leu
1               5                   10                  15

Gln Arg Met Cys Leu Glu Pro Cys Asn Leu Tyr Asn Tyr Gly Ala Gly
            20                  25                  30

Ile Lys Leu Pro Ser Gly Ile Met Leu Asn Val Val Lys Tyr Thr Gln
        35                  40                  45

Leu Cys Gln Tyr Leu Asn Ser Thr Thr Met Cys Val Pro His Asn Met
    50                  55                  60

Arg Val Leu His Tyr Gly Ala Gly Ser Asp Lys Gly Val Ala Pro Gly
65                  70                  75                  80

Thr Thr Val Leu Lys Arg Trp Leu Pro Pro Asp Ala Ile Ile Ile Asp
                85                  90                  95

Asn Asp Ile Asn Asp Tyr Val Ser Asp Ala Asp Phe Ser Ile Thr Gly
            100                 105                 110

Asp Cys Ala Thr Val Tyr Leu Glu Asp Lys Phe Asp Leu Leu Ile Ser
        115                 120                 125

Asp Met Tyr Asp Gly Arg Ile Lys Phe Cys Asp Gly Glu Asn Val Ser
    130                 135                 140

Lys Asp Gly Phe Phe Thr Tyr Leu Asn Gly Val Ile Arg Glu Lys Leu
```

```
                    145                 150                 155                 160
Ala Ile Gly Gly Ser Val Ala Ile Lys Ile Thr Glu Tyr Ser Trp Asn
                165                 170                 175

Lys Tyr Leu Tyr Glu Leu Ile Gln Arg Phe Ala Phe Trp Thr Leu Phe
            180                 185                 190

Cys Thr Ser Val Asn Thr Ser Ser Glu Ala Phe Leu Ile Gly Ile
            195                 200                 205

Asn Tyr Leu Gly Asp Phe Ile Gln Gly Pro Phe Ile Ala Gly Asn Thr
            210                 215                 220

Val His Ala Asn Tyr Ile Phe Trp Arg Asn Ser Thr Ile Met Ser Leu
225                 230                 235                 240

Ser Tyr Asn Ser Val Leu Asp Leu Ser Lys Phe Glu Cys Lys His Lys
                245                 250                 255

Ala Thr Val Val Val Thr Leu Lys Asp Ser Asp Val Asn Asp Met Val
            260                 265                 270

Leu Ser Leu Ile Lys Ser Gly Arg Leu Leu Arg Asn Asn Gly Arg
            275                 280                 285

Phe Gly Gly Phe Ser Asn His Leu Val Ser Thr Lys
    290                 295                 300

<210> SEQ ID NO 64
<211> LENGTH: 1356
<212> TYPE: PRT
<213> ORGANISM: Human coronavirus
<220> FEATURE:
<221> NAME/KEY: MISC_FEATURE
<222> LOCATION: (1)..(1356)
<223> OTHER INFORMATION: ORF-2 Spike protein/S-gene

<400> SEQUENCE: 64

Met Lys Leu Phe Leu Ile Leu Val Leu Pro Leu Ala Ser Cys Phe
1               5                   10                  15

Phe Thr Cys Asn Ser Asn Ala Asn Leu Ser Met Leu Gln Leu Gly Val
                20                  25                  30

Pro Asp Asn Ser Ser Thr Ile Val Thr Gly Leu Leu Pro Thr His Trp
            35                  40                  45

Phe Cys Ala Asn Gln Ser Thr Ser Val Tyr Ser Ala Asn Gly Phe Phe
        50                  55                  60

Tyr Ile Asp Val Gly Asn His Arg Ser Ala Phe Ala Leu His Thr Gly
65                  70                  75                  80

Tyr Tyr Asp Ala Asn Gln Tyr Tyr Ile Tyr Val Thr Asn Glu Ile Gly
                85                  90                  95

Leu Asn Ala Ser Val Thr Leu Lys Ile Cys Lys Phe Ser Arg Asn Thr
            100                 105                 110

Thr Phe Asp Phe Leu Ser Asn Ala Ser Ser Ser Phe Asp Cys Ile Val
        115                 120                 125

Asn Leu Leu Phe Thr Glu Gln Leu Gly Ala Pro Leu Gly Ile Thr Ile
    130                 135                 140

Ser Gly Glu Thr Val Arg Leu His Leu Tyr Asn Val Thr Arg Thr Phe
145                 150                 155                 160

Tyr Val Pro Ala Ala Tyr Lys Leu Thr Lys Leu Ser Val Lys Cys Tyr
                165                 170                 175

Phe Asn Tyr Ser Cys Val Phe Ser Val Val Asn Ala Thr Val Thr Val
            180                 185                 190

Asn Val Thr Thr His Asn Gly Arg Val Val Asn Tyr Thr Val Cys Asp
        195                 200                 205
```

-continued

```
Asp Cys Asn Gly Tyr Thr Asp Asn Ile Phe Ser Val Gln Gln Asp Gly
210                 215                 220

Arg Ile Pro Asn Gly Phe Pro Phe Asn Asn Trp Phe Leu Leu Thr Asn
225                 230                 235                 240

Gly Ser Thr Leu Val Asp Gly Val Ser Arg Leu Tyr Gln Pro Leu Arg
                245                 250                 255

Leu Thr Cys Leu Trp Pro Val Pro Gly Leu Lys Ser Ser Thr Gly Phe
            260                 265                 270

Val Tyr Phe Asn Ala Thr Gly Ser Asp Val Asn Cys Asn Gly Tyr Gln
        275                 280                 285

His Asn Ser Val Val Asp Val Met Arg Tyr Asn Leu Asn Phe Ser Ala
    290                 295                 300

Asn Ser Leu Asp Asn Leu Lys Ser Gly Val Ile Val Phe Lys Thr Leu
305                 310                 315                 320

Gln Tyr Asp Val Leu Phe Tyr Cys Ser Asn Ser Ser Ser Gly Val Leu
                325                 330                 335

Asp Thr Thr Ile Pro Phe Gly Pro Ser Ser Gln Pro Tyr Tyr Cys Phe
            340                 345                 350

Ile Asn Ser Thr Ile Asn Thr Thr His Val Ser Thr Phe Val Gly Ile
        355                 360                 365

Leu Pro Pro Thr Val Arg Glu Ile Val Val Ala Arg Thr Gly Gln Phe
    370                 375                 380

Tyr Ile Asn Gly Phe Lys Tyr Phe Asp Leu Gly Phe Ile Glu Ala Val
385                 390                 395                 400

Asn Phe Asn Val Thr Thr Ala Ser Ala Thr Asp Phe Trp Thr Val Ala
                405                 410                 415

Phe Ala Thr Phe Val Asp Val Leu Val Asn Val Ser Ala Thr Asn Ile
            420                 425                 430

Gln Asn Leu Leu Tyr Cys Asp Ser Pro Phe Glu Lys Leu Gln Cys Glu
        435                 440                 445

His Leu Gln Phe Gly Leu Gln Asp Gly Phe Tyr Ser Ala Asn Phe Leu
    450                 455                 460

Asp Asp Asn Val Leu Pro Glu Thr Tyr Val Ala Leu Pro Ile Tyr Tyr
465                 470                 475                 480

Gln His Thr Asp Ile Asn Phe Thr Ala Thr Ala Ser Phe Gly Gly Ser
                485                 490                 495

Cys Tyr Val Cys Lys Pro His Gln Val Asn Ile Ser Leu Asn Gly Asn
            500                 505                 510

Thr Ser Val Cys Val Arg Thr Ser His Phe Ser Ile Arg Tyr Ile Tyr
        515                 520                 525

Asn Arg Val Lys Ser Gly Ser Pro Gly Asp Ser Ser Trp His Ile Tyr
    530                 535                 540

Leu Lys Ser Gly Thr Cys Pro Phe Ser Phe Ser Lys Leu Asn Asn Phe
545                 550                 555                 560

Gln Lys Phe Lys Thr Ile Cys Phe Ser Thr Val Glu Val Pro Gly Ser
                565                 570                 575

Cys Asn Phe Pro Leu Glu Ala Thr Trp His Tyr Thr Ser Tyr Thr Ile
            580                 585                 590

Val Gly Ala Leu Tyr Val Thr Trp Ser Glu Gly Asn Ser Ile Thr Gly
        595                 600                 605

Val Pro Tyr Pro Val Ser Gly Ile Arg Glu Phe Ser Asn Leu Val Leu
    610                 615                 620
```

```
Asn Asn Cys Thr Lys Tyr Asn Ile Tyr Asp Tyr Val Gly Thr Gly Ile
625                 630                 635                 640

Ile Arg Ser Ser Asn Gln Ser Leu Ala Gly Gly Ile Thr Tyr Val Ser
            645                 650                 655

Asn Ser Gly Asn Leu Leu Gly Phe Lys Asn Val Ser Thr Gly Asn Ile
        660                 665                 670

Phe Ile Val Thr Pro Cys Asn Gln Pro Asp Gln Val Ala Val Tyr Gln
    675                 680                 685

Gln Ser Ile Ile Gly Ala Met Thr Ala Val Asn Glu Ser Arg Tyr Gly
690                 695                 700

Leu Gln Asn Leu Leu Gln Leu Pro Asn Phe Tyr Val Ser Asn Gly
705                 710                 715                 720

Gly Asn Asn Cys Thr Thr Ala Val Met Thr Tyr Ser Asn Phe Gly Ile
            725                 730                 735

Cys Ala Asp Gly Ser Leu Ile Pro Val Arg Pro Arg Asn Ser Ser Asp
        740                 745                 750

Asn Gly Ile Ser Ala Ile Ile Thr Ala Asn Leu Ser Ile Pro Ser Asn
    755                 760                 765

Trp Thr Thr Ser Val Gln Val Glu Tyr Leu Gln Ile Thr Ser Thr Pro
770                 775                 780

Ile Val Val Asp Cys Ala Thr Tyr Val Cys Asn Gly Asn Pro Arg Cys
785                 790                 795                 800

Lys Asn Leu Leu Lys Gln Tyr Thr Ser Ala Cys Lys Thr Ile Glu Asp
            805                 810                 815

Ala Leu Arg Leu Ser Ala His Leu Glu Thr Asn Asp Val Ser Ser Met
        820                 825                 830

Leu Thr Phe Asp Ser Asn Ala Phe Ser Leu Ala Asn Val Thr Ser Phe
    835                 840                 845

Gly Asp Tyr Asn Leu Ser Ser Val Leu Pro Gln Arg Asn Ile Arg Ser
850                 855                 860

Ser Arg Ile Ala Gly Arg Ser Ala Leu Glu Asp Leu Leu Phe Ser Lys
865                 870                 875                 880

Val Val Thr Ser Gly Leu Gly Thr Val Asp Val Asp Tyr Lys Ser Cys
            885                 890                 895

Thr Lys Gly Leu Ser Ile Ala Asp Leu Ala Cys Ala Gln Tyr Tyr Asn
        900                 905                 910

Gly Ile Met Val Leu Pro Gly Val Ala Asp Ala Glu Arg Met Ala Met
    915                 920                 925

Tyr Thr Gly Ser Leu Ile Gly Gly Met Val Leu Gly Gly Leu Thr Ser
930                 935                 940

Ala Ala Ala Ile Pro Phe Ser Leu Ala Leu Gln Ala Arg Leu Asn Tyr
945                 950                 955                 960

Val Ala Leu Gln Thr Asp Val Leu Gln Glu Asn Gln Lys Ile Leu Ala
            965                 970                 975

Ala Ser Phe Asn Lys Ala Ile Asn Asn Ile Val Ala Ser Phe Ser Ser
        980                 985                 990

Val Asn Asp Ala Ile Thr Gln Thr  Ala Glu Ala Ile His  Thr Val Thr
    995                 1000                 1005

Ile Ala  Leu Asn Lys Ile Gln  Asp Val Val Asn Gln  Gln Gly Ser
    1010                 1015                 1020

Ala Leu  Asn His Leu Thr Ser  Gln Leu Arg His Asn  Phe Gln Ala
    1025                 1030                 1035

Ile Ser  Asn Ser Ile Gln Ala  Ile Tyr Asp Arg Leu  Asp Ser Ile
```

```
              1040                1045                1050

Gln Ala Asp Gln Gln Val Asp Arg Leu Ile Thr Gly Arg Leu Ala
        1055                1060                1065

Ala Leu Asn Ala Phe Val Ser Gln Val Leu Asn Lys Tyr Thr Glu
        1070                1075                1080

Val Arg Gly Ser Arg Leu Ala Gln Gln Lys Ile Asn Glu Cys
        1085                1090                1095

Val Lys Ser Gln Ser Asn Arg Tyr Gly Phe Cys Gly Asn Gly Thr
        1100                1105                1110

His Ile Phe Ser Ile Val Asn Ser Ala Pro Asp Gly Leu Leu Phe
        1115                1120                1125

Leu His Thr Val Leu Leu Pro Thr Asp Tyr Lys Asn Val Lys Ala
        1130                1135                1140

Trp Ser Gly Ile Cys Val Asp Gly Ile Tyr Gly Tyr Val Leu Arg
        1145                1150                1155

Gln Pro Asn Leu Val Leu Tyr Ser Asp Asn Gly Val Phe Arg Val
        1160                1165                1170

Thr Ser Arg Val Met Phe Gln Pro Arg Leu Pro Val Leu Ser Asp
        1175                1180                1185

Phe Val Gln Ile Tyr Asn Cys Asn Val Thr Phe Val Asn Ile Ser
        1190                1195                1200

Arg Val Glu Leu His Thr Val Ile Pro Asp Tyr Val Asp Val Asn
        1205                1210                1215

Lys Thr Leu Gln Glu Phe Ala Gln Asn Leu Pro Lys Tyr Val Lys
        1220                1225                1230

Pro Asn Phe Asp Leu Thr Pro Phe Asn Leu Thr Tyr Leu Asn Leu
        1235                1240                1245

Ser Ser Glu Leu Lys Gln Leu Glu Ala Lys Thr Ala Ser Leu Phe
        1250                1255                1260

Gln Thr Thr Val Glu Leu Gln Gly Leu Ile Asp Gln Ile Asn Ser
        1265                1270                1275

Thr Tyr Val Asp Leu Lys Leu Leu Asn Arg Phe Glu Asn Tyr Ile
        1280                1285                1290

Lys Trp Pro Trp Trp Val Trp Leu Ile Ile Ser Val Val Phe Val
        1295                1300                1305

Val Leu Leu Ser Leu Leu Val Phe Cys Cys Leu Ser Thr Gly Cys
        1310                1315                1320

Cys Gly Cys Cys Asn Cys Leu Thr Ser Ser Met Arg Gly Cys Cys
        1325                1330                1335

Asp Cys Gly Ser Thr Lys Leu Pro Tyr Tyr Glu Phe Glu Lys Val
        1340                1345                1350

His Val Gln
        1355

<210> SEQ ID NO 65
<211> LENGTH: 77
<212> TYPE: PRT
<213> ORGANISM: Human coronavirus
<220> FEATURE:
<221> NAME/KEY: MISC_FEATURE
<222> LOCATION: (1)..(77)
<223> OTHER INFORMATION: ORF-4 Corona virus envelope protein/E-gene

<400> SEQUENCE: 65

Met Phe Leu Arg Leu Ile Asp Asp Asn Gly Ile Val Leu Asn Ser Ile
1               5                   10                  15
```

```
Leu Trp Leu Leu Val Met Ile Phe Phe Phe Val Leu Ala Met Thr Phe
            20                  25                  30

Ile Lys Leu Ile Gln Leu Cys Phe Thr Cys His Tyr Phe Phe Ser Arg
            35                  40                  45

Thr Leu Tyr Gln Pro Val Tyr Lys Ile Phe Leu Ala Tyr Gln Asp Tyr
        50                  55                  60

Met Gln Ile Ala Pro Val Pro Ala Glu Val Leu Asn Val
65                  70                  75

<210> SEQ ID NO 66
<211> LENGTH: 226
<212> TYPE: PRT
<213> ORGANISM: Human coronavirus
<220> FEATURE:
<221> NAME/KEY: MISC_FEATURE
<222> LOCATION: (1)..(226)
<223> OTHER INFORMATION: ORF-5 pfam01635, Corona_M, Coronavirus M
      matrix/glycoprotein

<400> SEQUENCE: 66

Met Ser Asn Ser Ser Val Pro Leu Leu Glu Val Tyr Val His Leu Arg
1               5                   10                  15

Asn Trp Asn Phe Ser Trp Asn Leu Ile Leu Thr Leu Phe Ile Val Val
            20                  25                  30

Leu Gln Tyr Gly His Tyr Lys Tyr Ser Arg Leu Leu Tyr Gly Leu Lys
            35                  40                  45

Met Ser Val Leu Trp Cys Leu Trp Pro Leu Val Leu Ala Leu Ser Ile
        50                  55                  60

Phe Asp Cys Phe Val Asn Phe Asn Val Asp Trp Val Phe Phe Gly Phe
65                  70                  75                  80

Ser Ile Leu Met Ser Ile Ile Thr Leu Cys Leu Trp Val Met Tyr Phe
                85                  90                  95

Val Asn Ser Phe Arg Leu Trp Arg Arg Val Lys Thr Phe Trp Ala Phe
            100                 105                 110

Asn Pro Glu Thr Asn Ala Ile Ile Ser Leu Gln Val Tyr Gly His Asn
            115                 120                 125

Tyr Tyr Leu Pro Val Met Ala Ala Pro Thr Gly Val Thr Leu Thr Leu
        130                 135                 140

Leu Ser Gly Val Leu Leu Val Asp Gly His Lys Ile Ala Thr Arg Val
145                 150                 155                 160

Gln Val Gly Gln Leu Pro Lys Tyr Val Ile Val Ala Thr Pro Ser Thr
                165                 170                 175

Thr Ile Val Cys Asp Arg Val Gly Arg Ser Val Asn Glu Thr Ser Gln
            180                 185                 190

Thr Gly Trp Ala Phe Tyr Val Arg Ala Lys His Gly Asp Phe Ser Gly
        195                 200                 205

Val Ala Ser Gln Glu Gly Val Leu Ser Glu Arg Glu Lys Leu Leu His
    210                 215                 220

Leu Ile
225

<210> SEQ ID NO 67
<211> LENGTH: 377
<212> TYPE: PRT
<213> ORGANISM: Human coronavirus
<220> FEATURE:
<221> NAME/KEY: MISC_FEATURE
<222> LOCATION: (1)..(377)
```

-continued

```
<223> OTHER INFORMATION: ORF-6 Pfam 00937, Coronavirus nucleocapsid
      protein

<400> SEQUENCE: 67

Met Ala Ser Val Asn Trp Ala Asp Asp Arg Ala Ala Arg Lys Lys Phe
1               5                   10                  15

Pro Pro Pro Ser Phe Tyr Met Pro Leu Leu Val Ser Ser Asp Lys Ala
            20                  25                  30

Pro Tyr Arg Val Ile Pro Arg Asn Leu Val Pro Ile Gly Lys Gly Asn
        35                  40                  45

Lys Asp Glu Gln Ile Gly Tyr Trp Asn Val Gln Glu Arg Trp Arg Met
    50                  55                  60

Arg Arg Gly Gln Arg Val Asp Leu Pro Pro Lys Val His Phe Tyr Tyr
65                  70                  75                  80

Leu Gly Thr Gly Pro His Lys Asp Leu Lys Phe Arg Gln Arg Ser Asp
                85                  90                  95

Gly Val Val Trp Val Ala Lys Glu Gly Ala Lys Thr Val Asn Thr Ser
            100                 105                 110

Leu Gly Asn Arg Lys Arg Asn Gln Lys Pro Leu Glu Pro Lys Phe Ser
        115                 120                 125

Ile Ala Leu Pro Pro Glu Leu Ser Val Val Glu Phe Glu Asp Arg Ser
    130                 135                 140

Asn Asn Ser Ser Arg Ala Ser Ser Arg Ser Ser Thr Arg Asn Asn Ser
145                 150                 155                 160

Arg Asp Ser Ser Arg Ser Thr Ser Arg Gln Gln Ser Arg Thr Arg Ser
                165                 170                 175

Asp Ser Asn Gln Ser Ser Ser Asp Leu Val Ala Ala Val Thr Leu Ala
            180                 185                 190

Leu Lys Asn Leu Gly Phe Asp Asn Gln Ser Lys Ser Pro Ser Ser Ser
        195                 200                 205

Gly Thr Ser Thr Pro Lys Lys Pro Asn Lys Pro Leu Ser Gln Pro Arg
    210                 215                 220

Ala Asp Lys Pro Ser Gln Leu Lys Lys Pro Arg Trp Lys Arg Val Pro
225                 230                 235                 240

Thr Arg Glu Glu Asn Val Ile Gln Cys Phe Gly Pro Arg Asp Phe Asn
                245                 250                 255

His Asn Met Gly Asp Ser Asp Leu Val Gln Asn Gly Val Asp Ala Lys
            260                 265                 270

Gly Phe Pro Gln Leu Ala Glu Leu Ile Pro Asn Gln Ala Ala Leu Phe
        275                 280                 285

Phe Asp Ser Glu Val Ser Thr Asp Glu Val Gly Asp Asn Val Gln Ile
    290                 295                 300

Thr Tyr Thr Tyr Lys Met Leu Val Ala Lys Asp Asn Lys Asn Leu Pro
305                 310                 315                 320

Lys Phe Ile Glu Gln Ile Ser Ala Phe Thr Lys Pro Ser Ser Ile Lys
                325                 330                 335

Glu Met Gln Ser Gln Ser Ser His Val Ala Gln Asn Thr Val Leu Asn
            340                 345                 350

Ala Ser Ile Pro Glu Ser Lys Pro Leu Ala Asp Asp Asp Ser Ala Ile
        355                 360                 365

Ile Glu Ile Val Asn Glu Val Leu His
    370                 375
```

CORONAVIRUS, NUCLEIC ACID, PROTEIN, AND METHODS FOR THE GENERATION OF VACCINE, MEDICAMENTS AND DIAGNOSTICS

CROSS-REFERENCE TO RELATED APPLICATION

This patent application claims the benefit, under the provisions of 35 U.S.C. §119(3), of U.S. Provisional Patent Application 60/535,002, filed Jan. 7, 2004, the contents of the entirety of which is incorporated herein by this reference.

TECHNICAL FIELD

The invention relates generally to biotechnology, especially to virology and medicine. More particularly, the invention relates to the identification of a new coronavirus and to means and methods associated with a virus such as means and methods for typing the virus in various samples and diagnosing of disease and means and methods for developing vaccines and medicaments for the treatment of infected subjects or of subjects at risk thereof.

BACKGROUND

Coronaviruses, a genus in the family of Coronaviridae, are large, enveloped plus strand RNA viruses. The genomic RNA is 27 to 32 kb in size, capped and polyadenylated. Three serologically distinct groups of coronaviruses have been identified. Within each group, viruses are identified by hosts range and genome sequence. Coronaviruses have been identified in mice, rats, chickens, turkeys, swine, dogs; cats, rabbits, horses, cattle and humans (39, 40). Most coronaviruses infect only one host species, and can cause severe disease including gastroenteritis, and respiratory tract diseases. In humans, 3 coronaviruses have been studied in detail. HCoV-229E and HCo\7-0C43 have been identified in the mid sixties and are known to cause common cold (13-17 19, 41, 42). Besides common cold it has been suggested that the HCoV may cause a more serious disease in infants as HCoV-229E virus has been isolated from infants suffering from lower respiratory tract disease (28). The third and most recently identified coronavirus: SARS-CoV, is, with its ability to cause a life threatening pneumonia (43), the most pathogenic human coronavirus identified thus far. It has been suggested that SARS-CoV is the first member of a fourth group of coronaviruses, or that the virus is an outlier of the group 2 coronaviruses (27, 44).

The coronavirus genome encodes four structural proteins: the spike protein, the membrane protein, the envelope protein and the nucleocapsid protein. Several non-structural proteins are involved in replication and transcription, which are encoded by two long overlapping open reading frames (ORFs) at the 5'end of the genome (1A and 1B). These 2 ORFs are connected via a ribosomal frame shift. The polypeptides encoded by ORF 1A and 1B are post-translationally processed by viral encoded proteases. Furthermore, additional non-structural proteins are encoded between the S and E gene, or between the M and N gene or downstream of the N gene. Some of these "accessory non-structural protein genes" have been found to be not essential for virus reproduction (45, 46). The coronavirus gene products of 1A and 1B are translated from the genomic RNA but the remaining viral proteins are translated from subgenomic mRNAs (sg mRNA), each with a 5'end derived from the 5' part of the genome. The sg mRNA are derived via a discontinuous transcription process that most probably occurs during negative strand synthesis (47). Discontinuous transcription requires base-pairing between cis-acting elements, the transcription associated sequences (TRSs), one located at the 5' part of the genome (the leader TRS) and others located upstream of the OCRFs (the body TRSs) (48)).

The novel coronavirus that we present here was isolated from a child suffering from bronchiolitis. Infection by this virus was not an isolated case since we found 7 more persons suffering from respiratory tract disease carrying the virus. In addition, we show here the complete genome sequence providing critical information concerning the genome structure of the new coronavirus.

To date there is a range of human diseases with unknown etiology. For many of these a viral origin has been suggested, emphasizing the importance of a continuous search for new viruses[22, 23, 24]. Major difficulties are encountered when searching for new viruses. First, some viruses do not replicate in vitro, at least not in the cells that are commonly used in viral diagnostics. Second, for those viruses that do replicate in vitro and that cause a cytopathic effect (CPE), the subsequent virus-identification methods may fail. Antibodies raised against known viruses may not recognize the cultured virus and virus specific PCR methods may not amplify the new viral genome. We have developed a method for virus discovery based on the cDNA amplified restriction fragment length polymorphism technique (cDNA-AFLP). With this technique, RNA or DNA is reproducibly amplified. There is no need to have prior knowledge of the sequence of the target gene[1]. Generally the cDNA-AFLP method is used to monitor differential gene expression, however, we modified this method such that it can amplify viral sequences either directly from patient blood-plasma/serum samples or indirectly from CPE-positive virus culture (FIG. 1). In the modified Virus-Discovery-cDNA-AFLP (VIDISCA) method the mRNA isolation step prior to amplification is replaced by a treatment to selectively enrich for viral nucleic acid. Of relevance to the purification is a centrifugation step to remove residual cells and mitochondria. In addition, a DNAse treatment can be used to remove interfering chromosomal and mitochondrial DNA from degraded cells whereas viral nucleic acid is protected within the viral particle. Finally, by choosing frequently cutting restriction enzymes, the method can be fine-tuned such that most viruses will be amplified.

In January 2003 a 7-month-old child appeared in the hospital with coryza, conjunctivitis and fever. Chest radiography showed typical features of bronchiolitis and a nasopharyngeal aspirate specimen was collected (sample nr: NL63) five days after the onset of disease. All diagnostic tests on this sample for respiratory syncytial virus (RSV), adenovirus, influenza A and B virus, parainfluenza virus type 1, 2 and 3, rhinovirus, enterovirus, HCoV-229E and HCoV-OC43 were negative. Immunofluorescent assays to detect RSV, adenovirus, influenza A and B virus, and parainfluenza virus type 1, 2 and 3 in cultures of the virus remained negative. Acid lability and chloroform sensitivity tests demonstrated that the virus was most likely enveloped and not a member of the Picornavirus group. In fact it was a new coronavirus.

In the present invention we present a detailed description of a novel human coronavirus. Coronaviruses are characterized by a very long non-segmented, single-stranded, (+) sense RNA of approximately 27-31 kb. This is the longest genome of any known RNA virus. The genome has a 5' methylated cap and 3' poly-A and functions directly as mRNA. Thus far only 3 human coronaviruses have been characterized, therefore sorting out the characteristics of a fourth human coronavirus supplies attractive information on the variation among the human coronaviruses. The novel virus is a member of the group 1 coronaviruses and is most related to HCoV-229B, yet the differences are prominent. The similarity is not larger than 85% at the nucleotide level, at the position of the 4A and 4B gene of HCoV-229E only one ORF is present in HCoV-NL63 (ORF 3), and the 5' region of the S gene of HCoV-NL63 contains a unique in frame insertion of 537 nucleotides. Since binding of the receptor has been mapped to the N-terminal part of the protein, the 179 amino acids encoded by the insertion are most likely involved in receptor binding. This unique part at the N-terminus of the spike protein might explain the expanded host range of the virus in cell culture. Where HCoV-229E is fastidious in cell culture with a narrow host range, HCoV-NL63 replicates efficiently in monkey kidney cells. Besides HCoV-NL63 also SARS-CoV is able to replicate in monkey kidney cells (Vero-E6 cells and NCI-H292 cells for SARS-CoV (21)). Yet, comparing the predicted Spike genes did not identify a protein region that is shared by both viruses to clarify the common host range of the viruses in vitro. Also the insertion in the S gene of HCoV-NL63 was not present in the SARS S gene. Alternatively, other viral proteins may be involved in the cell tropism of a virus, however we did not identify any gene of HCoV-NL63 that had more similarity at the protein level to the SARS-CoV than to the similarity to HCoV-229E.

The 2 major differences between HCoV-229E and HCoV-NL63: the insertion in the S gene and the altered non-structural accessory proteins genes, are comparably to the differences that are noted between the porcine coronaviruses PRCoV and TGEV. Although these 2 porcine viruses are antigenically and genetically related their pathogenicity is very different. TGEV causes severe diarrhea with a high mortality in neonatal swine. It replicates and destroys the enterocytes in the small intestine whereas PRCoV has a selective tropism for respiratory tissue with very little to no replication in intestinal tissue. The genome differences in the S, 3A and 3B genes between TGEV and PRCoV are comparable with the differences between HCoV-NL63 and HCoV-229E. Alike HCoV-NL63, TGEV has a unique in frame insertion at the 5' part of the S gene ranging from 672 to 681 nt (53). Furthermore, the accessory protein genes 3A and 3B that are intact in TGEV, are often mutated or inactive in the PRCoV. Extrapolating these data to the human coronaviruses one can speculate that HCoV-NL63 might be a more pathogenic human virus in comparison with HCoV-229E. However there are no epidemiological data supporting this. Based on our data it seems likely that HCoV-NL63 and HCoV-229E share the same pathogenicity. The common cold virus HCoV-229E can cause a more serious disease in infants (28), comparable to our data that suggest that HCoV-NL63 is causing a respiratory disease only in infants and immuno-compromised patients.

To date, a viral pathogen cannot be identified in a substantial portion of respiratory disease cases in humans (on average 20%[59]), our data indicate that in a part of these cases HCoV-NL63 is involved. The frequency with which HCoV-NL63 was detected in patients suffering from respiratory disease was up to 5% in January 2003. The virus was not detected in any of the samples collected in the spring or summer of 2003, which is in harmony with the epidemiology of human coronaviruses that have a tendency to spread predominantly in the winter season (15). The primers for our diagnostic PCR were located in the 1B gene and the genomic RNA can be used as template. Using primers that anneal in the nucleocapsid gene or 3'UTR supplies more template in the PCR because besides the genomic RNA also all sg mRNA in infected cells are template for amplification. It might be that the number of persons that we found positive for HCoV-NL63 is an underestimation of the correct number of persons carrying HCoV-NL63.

The newly found coronavirus, (designated HCoV-NL63) was characterized and sequenced. A sequence of a prototype HCoV-NL63 is provided in FIG. 19 and parts thereof in table 3. In one aspect the invention therefore provides an isolated and/or recombinant nucleic acid comprising a sequence as depicted in FIG. 19 and/or table 3, or a functional part, derivative and/or analogue thereof. The virus HCoV-NL63 is characterized by the prototype, however, many natural variants exist as for instance shown in FIG. 16 for polymorphisms in the ORF 1a region. The existence of such natural variants is normal for RNA viruses that undergo frequent mutation through for instance the introduction of mistakes by the polymerases that copy the genome. HCoV-NL63 viruses that have a slightly divergent nucleic acid sequence are thus also provided by the present invention. Such viruses are considered to be a derivative of the nucleic acid having the prototype nucleic acid sequence. The variant does not necessarily have to be a natural variant. It is very well possible to generate variants through recombinant means. For instance many parts of the virus can be altered through nucleotide substitution to make use of the redundancy in the triplet genetic code for particular amino acids. Thus without altering the amino acid sequence of the encoded proteins. However, even amino acid alterations can typically be introduced without affecting the replicating and coding potential of the viruses. For instance conservative amino acid substitutions are often tolerated. Alterations in the prototype virus may be up to 70% of the nucleic acid sequence without altering the replicating potential of the virus. Thus in one embodiment the invention provides an isolated and/or recombinant nucleic acid that is at least 70% homologous to a nucleic acid of the prototype RCoV-NL63. Most of the viable variants however are at least 95% homologous and more preferably at least 99% to a nucleic acid according to the prototype HCoV-NL63. The homology between different coronaviruses in the UTR regions is typically high, for this reason the homology in this application is measured in a region outside the UTR regions, preferably in a protein coding region. Thus the invention provides a derivative of HCoV-NL63 virus comprising at least 95% homology and preferably at least 99% homology (on the nucleic acid level) in at least one protein coding region depicted FIG. 20, 21, 22, 23, or table 3. The nucleic acid of the virus or parts thereof can be cloned and used as a probe to detect the virus in samples. Thus the present invention further provides an isolated and/or recombinant nucleic acid comprising a stretch of 100 consecutive nucleotides of a nucleic acid of the prototype virus, or a region that is at least 95% and preferably at least 99% homologous to said 100 consecutive nucleotides(when measured on the nucleic acid level outside a UTR region). A stretch of 100 consecutive nucleotides is considered to be a functional part of the virus of the present invention. Further provided is a bacterial vector comprising a nucleic acid of HCoV-NL63 or a functional part, derivative and/or analogue thereof. Further provided is a bacterium comprising said bacterial vector. The sequence of HCoV-NL63 or a part thereof can be used to generate a primer that is specific for HCoV-NL63 and thus capable of specifically replicating HCoV-NL63 nucleic acid. Similarly, a probe can be generated that specifically hybridizes to HCoV-NL63 nucleic acid under stringent conditions. Thus the invention further provides a primer and/or probe, capable of specifically hybridizing to a nucleic acid of a HCoV-NL63 virus or functional part, derivative or analogue thereof. Preferably, said primer or probe is capable of hybridizing to said nucleic acid under stringent conditions. In a particularly preferred embodiment said primer and/or probe comprises a sequence as depicted in table 3, table 7, table 10 or FIGS. 16 to 18. The nucleic acid of the prototype virus encodes various proteins and poly-proteins. These proteins are expressed for instance in cells producing the virus or transformed with a nucleic acid encoding the (poly)protein. The invention thus further provides an isolated and/or recombinant proteinaceous molecule comprising a sequence as depicted in FIG. 20, 21, 22, 23 or table 8, or a functional part, derivative and/or analogue thereof. Many different variants of the proteins having the same function in kind, not necessarily in amount are, as mentioned above, present in nature and can be generated artificially, thus the invention further provides an isolated and/or recombinant proteinaceous molecule that is at least 70% homologues to a proteinaceous molecule mentioned above. Such homologous proteins are considered derivatives of a protein encoded by the prototype. Preferably, a derivative protein comprises at least 95% and more preferably at least 99% homology with a protein encoded by the prototype HCoV-NL63. Fragments and parts of a proteinaceous molecule encoded by the prototype virus can be generated, such parts are therefore also provided by the present invention. In a preferred embodiment is provided an isolated and/or recombinant proteinaceous molecule comprising a stretch of at least 30 consecutive amino acids of a proteinaceous molecule encoded by the prototype virus. A protein encoded by the prototype virus can be encoded through a variety of different nucleic acid sequences using the redundancy of the genetic code. Thus the invention further provides a nucleic acid encoding a protein depicted in FIG. 20, 21, 22, 28 or table 3. The HCoV-NL63 virus can be replicated using in vitro growing cell lines. The virus can be harvested from such cultures and used in a variety of different application including but not limited to the generation of an immune response in a subject. The invention thus further provides an isolated or recombinant virus comprising a HCoV-NL63 nucleic acid sequence or a functional part, derivative and/or analogue thereof. Also provided is an isolated or recombinant virus comprising a proteinaceous molecule as depicted in FIG. 20, 21, 22, 23 or table 8, or a functional part, derivative and/or analogue thereof. Subjects that have become infected with HCoV-NL63 can display a number of different clinical and/or sub-clinical symptoms. Thus further provided is an isolated or recombinant virus or a functional part, derivative or analogue thereof capable of inducing a HCoV-N63-related disease. The virus comprises substances that can be used to generate specific binding partners that are able to specifically bind the substance of the virus. Binding partners can be generated by means of injection of the virus into in an immuno-competent subject. As a result of the immunization the serum obtained from the subject will typically contain a number of different antibodies specific for the virus or an immunogenic part, derivative and/or analogue thereof. Specific binding partners can of course be generated through a large variety of different technologies. For instance phage display technologies. The method of producing the specific binding partner is not limited herein. The binding is typically specific for a proteinaceous part of the virus. But can of course also be specific for a virus specific post translation modification of a protein contained in the virus. Thus the present invention further provides an isolated binding molecule capable of specifically binding a proteinaceous molecule of a HCoV-NL63 virus preferably against encoded by a nucleic acid of the prototype HCoV-NL63. Preferably, a proteinaceous molecule as depicted in FIG. 20, 21, 22, 23 or table 3, or a functional part, derivative and/or analogue thereof. The binding molecule can be capable of specifically binding a nucleic acid sequence of a HCoV-NL63, preferably of FIG. 19 or table 3. The binding molecule is preferably a proteinaceous molecule. However, other binding molecules are also within the scope of the present invention. For instance, it is possible to generate protein mimetics or analogues having the same binding quality as a protein in kind not necessarily in amount. Provided is further a method for producing a binding molecule according to the invention comprising producing molecules capable of binding a HCoV-NL63 virus or functional part, derivative or analogue thereof or an isolated and/or recombinant proteinaceous molecule encoded by a prototype nucleic acid of HCoV-NL63, and selecting a proteinaceous binding molecule that is specific for said virus and/or said proteinaceous molecule.

The overall homology of HCoV-NL63 virus with other human coronaviruses is not very high. Thus many different binding molecules capable of specifically binding to HCoV-NL63 virus can be generated. Such binding molecules can be used to detect HCoV-NL63 virus in a sample. The invention thus further provides an isolated or recombinant virus which is immunoreactive with a binding molecule capable of specifically binding HCoV-NL63 virus. Similarly, the invention provides the use of an isolated and/or recombinant proteinaceous molecule as depicted in FIG. 20, 21, 22, 23 or table 3, or a functional part, derivative and/or analogue thereof, for detecting a binding molecule capable of specifically binding HCoV-NL63 virus, or functional part, derivative and/or analogue of said virus in a sample Vise versa, HCoV-NL63 virus can be used to detect a molecule capable of specifically binding said virus in a sample. Binding of HCoV-NL63 virus to a susceptible target cell occurs via a specific receptor. This receptor can be used as a binding molecule of the invention. Preferably, the binding molecule comprises an antibody or functional equivalent thereof. The detection methods can be used to diagnose HCoV-NL63 related disease in a subject. Thus provided is a method for detecting a HCoV-NL63 virus or functional part, derivative or analogue thereof in a sample, comprising hybridizing and/or amplifying a nucleic acid of said virus or functional part, derivative or analogue with a HCoV-NL63 specific primer and/or probe and detecting hybridized and/or amplified product. Further provided is a kit, preferably a diagnostic kit comprising a HCoV-NL63 virus or functional part, derivative or analogue thereof a binding molecule according to the invention, and/or a HCoV-NL63 virus specific primer/probe according to invention.

In a particular preferred embodiment is provided the use of a primer or probe capable of specifically hybridizing to a nucleic acid of a HCoV-NL63 virus or functional part, derivative or analogue thereof or a binding molecule capable of specifically binding a proteinaceous molecule depicted in FIG. 20, 21, 22, 23 or table 3 or an HCoV-NL63 virus and/or a nucleic acid or functional part, derivative or analogue of a prototype HCoV-NL63 for detecting and/or identifying a HCoV-NL63 coronavirus in a sample. Preferably said nucleic acid comprises a sequence as depicted in table 3.

The invention further provides a vaccine comprising HCoV-NL63 virus or functional part, derivative or analogue thereof. Further provided is a vaccine comprising a proteinaceous molecule depicted in FIG. 20, 21, 22, 23 or table 3 or functional part, derivative and/or analogue of such a proteinaceous molecule. A proteinaceous molecule of the invention may be provided as a vaccine by itself or as a part of the protein or as derivatives or analogues thereof. A suitable analogue is a nucleic acid encoding a HCoV-NL63 virus proteinaceous molecule or a functional part or derivative thereof. The nucleic acid may be used in a DNA vaccine approach which is also provided in the present invention. As carrier for the DNA vaccine it is often suitable to incorporate an expressible HCoV-NL63 virus nucleic acid in a viral replicon allowing replication of the HCoV-NL63 virus nucleic acid in the target cell and thereby allowing boosting of the provided immune response. A HCoV-NL63 virus encoded protein that is suited for such a DNA vaccine approach is the S protein depicted in FIG. 22 or a functional part, derivative and/or analogue thereof. A part of an S protein preferably comprises an immunogenic part of the 537 in frame insertion as compared with HCoV-229E virus. Preferably said part comprises essentially said 537 insertion. With the 537 insertion is meant a sequence corresponding to sequences 20472 to 21009 of FIG. 19. Other suitable candidates are the M and or the N protein or a functional part, derivative and/or analogue thereof. Typically a vaccine includes an appropriate adjuvant. Apart from the use in a vaccine the mentioned virus and/or proteinaceous molecules can also be used to generate and/or boost a HCoV-NL63 virus specific immune response in a subject. The immune response can be both cellular or humoral. Thus further provided is an isolated T-cell comprising a T-cell receptor that is specific for HCoV-NL63 virus or a proteinaceous molecule encoded by a prototype HCoV-NL63 virus. Further provided is an isolated B-cell producing an antibody specific for HCoV-NL63 virus or a proteinaceous molecule encoded by a HCoV-NL63 virus. The antibody or T-cell receptor can be cloned whereupon a cell line can be provided with an expression cassette comprising the cloned receptor or antibody. Thus the invention further provides a cell producing such a receptor or antibody. Such a cell is preferably a cell that is suitable for large scale production of the mentioned proteins such as CHO cells.

It is also possible to provide a subject with passive immunity to HCoV-NL63 virus. To this end the subject can be provided with a HCoV-NL63 specific binding molecule of the invention. Such immunity can be used to provide a barrier for (further) infection with HCoV-NL63 virus in the subject, thus further provided is a vaccine comprising a HCoV-NL63 virus specific binding molecule according to the invention. In a preferred embodiment, passive immunity is provided by a human or humanized antibody capable of specifically binding a HCoV-NL63 virus of the invention. The barrier does not have to be perfect. The presence of a binding molecule at least reduces the spread of the virus to other target cells in the subject. The passive immunity may be administered to a subject as prophylactic to at least reduce the spread of HCoV-NL63 virus in the subject when exposed to the virus. Alternatively, the passive immunity may be provided to a subject already infected with the virus. In the latter case one or more HCoV-NL63 virus specific binding molecules of the invention are used as a medicament to at least reduce the spread of the virus in the subject and thereby at least in part combat the virus infection. The invention thus further provides a medicament comprising a HCoV-NL63 virus specific binding molecule according to the invention. Further provided is the use of a virus of the invention or functional part, derivative or analogue thereof or a proteinaceous molecule of the invention or a HCoV-NL63 virus specific binding molecule of the invention, for the preparation of a vaccine against a coronaviral genus related disease. Further provided is a method for treating an individual suffering from, or at risk of suffering from, an HCoV-NL63 related disease, comprising administering to said individual a vaccine or medicament according to the invention. In yet another embodiment is provided a method for determining whether an individual suffers from an HCoV-NL63 related disease, comprising obtaining a sample from said individual and detecting a HCoV-NL63 virus or functional part, derivative or analogue thereof in said sample.

In yet another embodiment is provided an isolated cell, or recombinant or cell line comprising HCoV-NL63 virus, or a functional part, derivative and/or analogue thereof. Preferably said cell is a primate cell, preferably a monkey cell. In a preferred embodiment, said cell is a cell that replicates the HCoV-NL63 virus of the invention. In a particular embodiment the cell is a kidney cell. The cell can be used to produce the HCoV-NL63 virus of the invention or to attenuate HCoV-NL63 such that it becomes less pathogenic. Virus attenuation is spontaneous upon continued culture of the virus on the mentioned preferred cell lines. Attenuated HCoV-NL63 virus can be used as a vaccine.

HCoV-NL63 virus encodes an endoprotease. A sequence for the protease in the prototype HCoV-NL63 virus is depicted in FIG. (21). The protease is important for the processing of the polyproteins encoded by HCoV-NL63. The action of the protease is at least in part inhibited by a viral protease inhibitor as further described herein. Thus the invention further provides a compound for at least in part inhibiting HCoV-NL63 virus replication. Preferred compounds are inhibitors of inosine monophosphate dehydrogenase (55) (e.g. Ribavirin(54) and mycophenolic acid), orotidine-5'-phosphate decarboxylase inhibitors (e.g. 6-azauridine and pyrazofurin), 3CL-protease inhibitors(56) (e.g. the VNSTLQ (SEQ. ID. NO: 1)-AG7088 ester, see below), cap-methylase inhibitors(58) (carboxylic adenosine analogs e.g. Neoplanocin A and 3-deazaneoplancin A), nitrous oxide synthase inducing compounds (e.g. glycyrrhizin) and Interferons (57). Of these the protease inhibitors are particularly preferred. The sequence VNSTLQ (SEQ. ID. NO: 1) is the N-terminal proteolytic processing site of SARS-3CLpro that is used in the 3Clpro inhibitor VNSTLQ (SEQ. ID. NO: 1)-AG7088 (56). In this compound the hexapeptide VNSTLQ (SEQ. ID. NO: 1) is C-terminally linked to the vinylogous ethyl ester (AG7088, see structural formula 1 depicted below,) that inhibits SARS 3CLpro activity.

Structure of formula I

P2 = p-fluoro-benzyl: AG7088

The hexapeptide VNSTLQ (SEQ. ID. NO: 1) corresponds to YNSTLQ (SEQ. ID. NO: 2)in HCoV-NL63. Therefore YNSTLQ (SEQ. ID. NO: 2)- AG7088 inhibits the HCoV-NL63 3CLpro orthologs. Thus in a preferred embodiment the protease inhibitor comprises the amino acid sequence VNSTLQ (SEQ. ID. NO: 1) more preferably YNSTLQ (SEQ. ID. NO: 2). Analogues of such protease inhibitors that comprise the same activity in kind not necessarily in amount are also provided by the present invention. Such analogues include, compounds comprising a peptide with the preferred sequence, wherein the peptide comprises a modification. Other analogues include compounds having protein mimetic activity that mimic the preferred amino-acid sequence. S-adenosylmethionine-dependant ribose 2'-orthomethyltransferase Plays a role in the methylation of cap structure (GppPNm) at the 5'end of the viral RNA. Antiviral compounds inhibiting this transfer of methyl groups to reaction (carboxylic adenosine analogs e.g. Neoplanocin A and 3-deazaneoplancin A) interfere with expression of viral proteins.

The invention further provides a proteinaceous molecule encoded by HCoV-NL63 nucleic acid, wherein said proteinaceous molecule is a 3CL protease or a functional equivalent thereof. Functional equivalents include an proteolytically active part and/or derivative having one or more conservative amino acid substitutions. There are many methods known in the art to determine whether a compound has anticoronaviral activity, preferably antiproteolytic activity of a coronavirus. The invention thus further provides a method for determining whether a compound comprises anticoronavirus replication activity characterized in that said method utilizes HCoV-NL63-virus or a HCoV-NL63 protein involved in replication of HCoV-NL63 or a functional part, derivative and/or analogue thereof. Preferably, the invention provides a method for determining whether a compound is capable of at least in part inhibiting a viral protease characterized in that said protease is a 3CL protease of HCoV-NL63 or a functional part, derivative and/or analogue thereof. Preferred compounds that can be tested for 3CL inhibiting quality are hexapeptides located N-terminally of 3Clpro cleavage sites. Compounds effective in at least in part inhibiting 3Cl proteolytic activity can be used for the preparation of a medicament for the treatment of an individual suffering or at risk of suffering from a HCoV-NL63 virus infection.

One or more of the preferred anticoronaviral replication compounds can be used as a medicament for the treatment of a subject suffering from or at risk of suffering from a HCoV-NL63 virus infection. The invention thus further provides a medicament for the treatment of an individual suffering from an coronavirus infection or an individual at risk of suffering there from comprising wherein said coronavirus comprises a nucleic acid sequence of a HCoV-NL63 prototype virus or a functional part, derivative and/or analogue thereof.

In the present invention several different recombinant viruses are produced using HCoV-NL63 virus nucleic acid as a backbone. Such replication competent or replication defective recombinant virus can be used for instance as gene delivery vehicles. On the other hand parts of a HCoV-NL63 virus can be used in gene delivery vehicles that are based on other means for delivering genetic material to a cell. Thus the invention further provides a gene delivery vehicle comprising at least part of a HCoV-NL63 virus nucleic acid. Preferably of the prototype virus. Preferably comprising a nucleic acid encoding a protein of HCoV-NL63 virus or a functional part, derivative and/or analogue thereof. The invention also shows chimearic coronaviruses comprising nucleic acid derived from at least two coronaviruses wherein at least one of said parts is derived from a HCoV-NL63 virus. Said HCoV-NL63 virus derived part comprises preferably at least 50 nucleotides of a protein coding domain. More preferably said HCoV-NL63 derived part comprises at least 500 and more preferably at least 1000 nucleotides of the sequence as depicted in FIG. 19 or a functional derivative thereof. In a preferred embodiment the invention provides a chimearic coronavirus comprising at least 1000 nucleotides of a sequence as depicted in FIG. 19 and at least 1000 nucleotides of another coronavirus wherein said latter 1000 nucleotides comprise a sequence that is more than 5% sequence divergent with a sequence as depicted in FIG. 19. The sequences of a number of HCoV-NL63 virus fragments are depicted in table 3. The location of the fragments in the large genomic RNA is depicted in FIG. 5. The invention therefore, in one aspect, provides an isolated or recombinant virus comprising a nucleic acid sequence as depicted in table 3, or a functional part, derivative or analogue of said virus. With the aid of the identifying prototype fragments it is possible to further sequence the genome. One way of doing this by primer walking on the genome. A primer is directed to a region of which the sequence is known and this primer is used to sequence a flaking region that is as yet unknown. A subsequent primer can be generated against the newly identified sequence and a further region can be sequenced. This procedure can be repeated until the entire sequence of the virus is elucidated. As a source of the virus one may turn to Dr. C. van der Hoek, Department of Human Retrovirology, Academic Medical Center, University of Amsterdam, Amsterdam, The Netherlands.

Alignments of the determined nucleic acid sequences revealed the reading frame used in the sequences found, accordingly the invention further provides an isolated or recombinant virus comprising an amino acid sequence as depicted in (table 3). or a functional part, derivative or analogue of said virus. A particular amino acid sequence can be produced from a variety of nucleic acids depending on the codons used. Thus the invention further provides a nucleic acid encoding an amino acid sequence as depicted in (table 3). Further provided is an isolated or recombinant virus comprising a nucleic acid sequence encoding an amino acid sequence as depicted in (table 3 ), or a functional part, derivative or analogue of said virus.

Coronaviruses as many other types of viruses acquire a plurality of spontaneous and selected mutations upon spreading of the virus through the subject population and/or during culturing ex vivo. Moreover, artificial mutations having no recognized counterpart in nature can be introduced into the sequence of the prototype virus or a derivative thereof, without altering the viral- and/or disease causing properties of the virus. Having characterized the prototype of the newly discovered subtype gives access to this group of viruses belonging to the same subtype. Thus the invention further provides an isolated or recombinant virus comprising a nucleic acid sequence that is approximately 80% homologous to a sequence as depicted in table 3, or 80% homologous to an amino acid sequence depicted in Table 3 (. Preferably the homology is at least 90%, more preferably at least 95% and even more preferably at least 99%.

The respective prototype fragments were compared with a database of viral sequences and hits having a particularly high homology are mentioned in the tables 5 and 6. It may be noted that the compared fragments do not share extensive homology with any of the currently known Coronaviruses. The invention thus provides an isolated and/or recombinant virus comprising an amino acid sequence which is more than 89% homologous to 163-2 amino acid sequence as depicted in Table 3. Preferably said homology is at least 90%, more preferably at least 95% and even more preferably at least 99%. Further provided is an isolated or recombinant virus comprising an amino acid sequence which is more than 60% homologous to 163-4 amino acid sequence as depicted in Table 3. Preferably said homology is at least 90%, more preferably at least 95% and even more preferably at least 99%. Further provided is an isolated or recombinant virus comprising a nucleic acid sequence which is more than 85% homologous to 163-9 nucleic acid sequence as depicted in Table 3. Preferably said homology is at least 90%, more preferably at least 95% and even more preferably at least 99%. Further provided is an isolated or recombinant virus comprising an amino acid sequence which is more than 94% homologous to 163-10 amino acid sequence as depicted in Table 3. Preferably said homology is at least 90%, more preferably at least 95% and even more preferably at least 99%. Further provided is an isolated or recombinant virus comprising an amino acid sequence which is more than 50% homologous to 163-11 amino acid sequence as depicted in Table 3. Preferably said homology is at least 90%, more preferably at least 95% and even more preferably at least 99%.

Further provided is an isolated or recombinant virus comprising an amino acid sequence which is more than 87% homologous to 163-14 amino acid sequence as depicted in Table 3. Preferably said homology is at least 90%, more preferably at least 95% and even more preferably at least 99%. Further provided is an isolated or recombinant virus comprising an amino acid sequence which is more than 88% homologous to 163-15 amino acid sequence as depicted in Table 3. Preferably said homology is at least 90%, more preferably at least 95% and even more preferably at least 99%. Further provided is an isolated or recombinant virus comprising an amino acid sequence which is more than 78% homologous to 163-18 amino acid sequence as depicted in Table 3. Preferably said homology is at least 90%, more preferably at least 95% and even more preferably at least 99%. Further provided is an isolated or recombinant virus comprising a nucleic acid sequence which is at least 50% homologous to a nucleic acid sequence as depicted in Table 3. Preferably said homology is at least 80%, more preferably at least 90%, more preferably at least 95% and even more preferably at least 99%.

The invention also provides a functional part, derivative and/or analogue of an isolated and/or recombinant HCoV-NL63 virus. A part of a virus can be a membrane containing part, a nucleocapsid containing part, a proteinaceous fragment and/or a nucleic acid containing part. The functionality of the part varies with the application chosen for the part, for instance, part of the virus may be used for immunization purposes. In this embodiment the functionality comprises similar immunogenic properties in kind as the entire virus not necessarily in amount. Another use of the virus is the infectivity of the virus, for instance, for in vitro (or in vivo) culture, in this embodiment the functionality comprises a similar infectivity in kind not necessarily in amount. Many other functionalities may be defined, as there are many different uses for viruses, non-limiting examples are the generation of chimeric viruses, (i.e. with one or more other (corona) viruses, and the generation of viral vectors for vaccination and/or gene therapeutic purposes. Such viruses and/or vectors also contain a functional part of HCoV-NL63 and are thus also encompassed in the present invention. A functional derivative of a virus of the invention is defined as a virus that has been altered such that the properties of said compound are essentially the same in kind, not necessarily in amount. A derivative can be provided in many ways, for instance through nucleotide substitution (preferably "wobble" based), through (conservative) amino acid substitution, subsequent modification, etcetera.

Analogous compounds of a virus can also be generated using methods in the art. For instance, a chimeric virus can be produced, or an HCoV-NL63 virus having a chimeric protein. For instance, HCoV-NL63 can be rendered more immunogenic by generating a cell surface associated fusion protein comprising at least part of an HCoV-NL63 surface protein and a non-HCoV-NL63 immunogenic part. HCoV-NL63 virus comprising such chimeric protein can be used for inducing an enhanced immune response in a host, for instance for vaccination purposes.

As used herein, the term "a virus of the invention" is meant to also comprise a functional part, derivative and/or analogue of said virus.

The three groups of coronaviruses are associated with a variety of diseases of humans and domestic animals, including gastroenteritis and upper and lower respiratory tract disease. The human coronaviruses HCoV-229E and HCoV-OC43 are associated with mild disease (the common cold) but more severe disease is observed in children[16], albeit at a very low incidence. Several coronaviruses cause a severe disease in animals and SARS-CoV is the first example of a coronavirus that causes severe disease in humans. However, it should be emphasized that a substantial part of respiratory disease cases in humans remains undiagnosed. For instance, a recent survey of respiratory viruses in hospitalized children with bronchiolitis in Canada could not reveal a viral pathogen in about 20% of the patients[17]. The fact that we identified the new coronavirus in a child with bronchiolitis shows that HCoV-NL63 is a pathogenic respiratory virus. When considering that the HCoV-NL63 is a pathogenic respiratory virus able to cause bronchiolitis in infected children, the interesting question remains why HCoV-NL63 was not recognized previously by cell culture. We found that the virus can be cultured in monkey kidney cells (tMK or LLC-MK2 cells), cells that are often used in a routine diagnostic setting and one might therefore speculate that HCoV-NL63, like SARS-CoV, was newly introduced from an animal reservoir into the human population or that this is a human virus that recently broadened its host cell range. Clearly it is of importance to study the prevalence of HCoV-NL63 infection, and screening specimens from patients with respiratory tract disease using the HCoV-NL63 diagnostic RT-PCR will shed light on this issue. It is remarkable that the new human coronavirus was harvested from tMK cells and LLC-MK2 cells since coronaviruses are typically fastidious in cell culture with a narrow host range. However, both SARS-CoV and HCoV-NL63 seem to replicate efficiently in monkey kidney cells (Vero-E6 cells and NCI-H292 cells for SARS-CoV). The recently described genome of SARS-CoV has several exclusive features, including some unique open reading frames that are probably of biological significance[15, 18]. We will therefore analyze the complete genome sequence of HCoV-NL63 to screen for similarities and differences with SARS-CoV that may determine the expanded host cell range and enhanced pathogenicity of these viruses.

HCoV-NL63 is associated with a particular phenotype in infected subjects. The phenotype can encompass bronchiolitis, coryza, conjunctivitis and fever and may further encompass other respiratory problems and diarrhea. In one embodiment the invention thus further provides an isolated and or recombinant virus of the invention (having one or more of the above mentioned homology) wherein said virus or functional part, derivative and/or analogue further comprises the capability to induce an HCoV-NL63 related disease or symptom in a subject. In another embodiment the invention provides an isolated and/or recombinant virus of the invention further comprising the property to cause CPE in tertiary monkey kidney cells (tMK; Cynomolgus monkey[37]) and/or upon passage onto the monkey cell line LLC-MK2 (ECCAC 85062804, ATCC CCL-7). In a preferred embodiment said virus does not produce CPE in Vero-cells (ATCC CRL-1586)[34].

The invention further provides a nucleic acid as depicted in table 3, and an amino acid sequence as depicted in Table 3, or a functional part and/or equivalent of such a nucleic acid and/or amino acid sequence. A functional equivalent of said nucleic acid comprises the same hybridization properties in kind, not necessarily in amount, as said nucleic acid (or part thereof). A functional equivalent of an amino acid sequence of the invention comprises the same immunogenic properties in kind, not necessarily in amount, as said amino acid sequence (or part thereof). A part of a nucleic acid of the invention comprises at least 15 nucleotides, preferably at least 20, more preferably at least 30 nucleotides. A part of an amino acid sequence comprises at least 5 amino acids in peptidic linkage with each other, more preferably at least 8, and more preferably at least 12, more preferably at least 16 amino acids. In a preferred embodiment said nucleotides and/or amino acids are at least semi-consecutive, more preferably, said nucleotides and/or amino acids are consecutive. An equivalent of a nucleic acid and/or amino acid sequence of the invention or part thereof comprises at least 80% homology to a nucleic acid and/or amino acid sequence of the invention, preferably at least 90% homology, more preferably at least 95% and even more preferably at least 99% homology to a nucleic acid and/or amino acid sequence of the invention or a part thereof.

The invention further provides a primer and/or probe, capable of specifically hybridizing to a nucleic acid of a virus or functional part, derivative or analogue according to the invention, preferably a primer and/or probe, capable of specifically hybridizing to a nucleic acid sequence as depicted in Table 3. More preferably, a primer and/or probe, which is capable of hybridizing to said nucleic acid under stringent conditions. In a particular preferred embodiment is provided a primer and/or probe, comprising a sequence as depicted in Table 7.

The art knows many ways in which a specific binding member can be generated against an identified nucleic acid, lipid and/or amino acid sequence. Such specific binding members may be of any nature but are typically of a nucleic acid and/or proteinaceous nature. The invention thus further provides an isolated molecule capable of specifically binding a virus, nucleic acid and/or amino acid or functional part, derivative or analogue thereof according to the invention. Said isolated molecule is also referred to as specific binding member. Preferably said specific binding member is capable of specifically binding at least part of a nucleic acid sequence as depicted in table 8 and/or at least part of an amino acid sequence as depicted in Table 3. In a preferred embodiment said binding member is a proteinaceous molecule. Preferably an antibody or a functional part, derivative and/or analogue thereof. A specific binding member preferably comprises a significantly better binding property for the HCoV-NL63 virus compared to unrelated control. However, for instance for antibodies, it is possible that the epitope specifically recognized in HCoV-NL63 is also present in a limited number of other molecules. Thus though the binding of the binding member may be specific, it may recognize also other molecules than those present in HCoV-NL63. This cross-reactivity is to be separated from a-specific binding and is a general property of antibodies. Cross-reactivity does not usually hinder the selection of suitable specific binding members for particular purposes. For instance a specific binding member that also recognized a protein in liver cells can be used in many applications even in the presence of liver cells, where additional information such as location in the cell can often be used to discriminate.

One source of an antibody of the invention is the blood of the infected subjects screened for the virus of the present invention. One may further characterize B-cells obtained from said subject, A suitable B-cell may be cultured and the antibody collected. Alternatively, the antibody may be sequenced from this B-cell and generated artificially. Another source of an antibody of the invention can be generated by immunisation of test animals or using artificial libraries to screen a purified fraction of virus. A functional part of an antibody has essentially the same properties of said antibody in kind, not necessarily in amount. Said functional part is preferably capable of specifically binding an antigen of HCoV-NL63. However, said functional part may bind such antigen to a different extend as compared to said whole antibody. A functional part or derivative of an antibody for instance comprises a FAB fragment or a single chain antibody. An analogue of an antibody for instance comprises a chimeric antibody. As used herein, the term "antibody" is also meant to comprise a functional part, derivative and/or analogue of said antibody.

Once antibody of the invention is obtained, a desired property, such as its binding capacity, can be improved. This can for instance be done by an Ala-scan and/or replacement net mapping method. With these methods, many different proteinaceous molecules are generated, based on an original amino acid sequence but each molecule containing a substitution of at least one amino acid residue. Said amino acid residue may either be replaced by Alanine (Ala-scan) or by any other amino acid residue (replacement net mapping). Each variant is subsequently screened for said desired property. Generated data are used to design an improved proteinaceous molecule.

There are many different ways in which a specific binding member can be generated. In a preferred embodiment the invention provides a method for producing a specific proteinaceous binding member comprising producing proteinaceous molecules capable of binding a virus according to the invention or to a functional part, derivative or analogue, and selecting a proteinaceous molecule that is specific for said virus. If need be, the method may be used to generate a collection of proteinaceous molecules capable of binding to said virus or functional part, derivative and/or analogue thereof and selecting from said collection one or more binding members capable of specifically binding said virus or functional part, derivative and/or analogue thereof.

Any specific binding member is characteristic for the HCoV-NL63 virus of the invention. Thus a virus that is specifically reactive with such binding member is an HCoV-NL63 virus and thus provided by the invention. Thus the invention provides an isolated and/or recombinant virus that is immunoreactive with specific binding member of the invention, preferably a proteinaceous binding member. The invention further provides a composition of matter comprising isolated HCoV-NL63 virus, and/or a virus essentially corresponding to HCoV-NL63. The term, a virus "essentially corresponding to HCoV-NL63" refers to HCoV-NL63 viruses which are either identical to the HCoV-NL63 strain described hereinabove, or which comprises one or more mutations compared to the said HCoV-NL63strain. These mutations may include natural mutations or artificial mutations. Said mutations of course should allow detection with a specific binding member of HCoV-NL63, not necessarily with all of the specific binding members). Said mutations should allow the detection of the variants using common detection methods such as antibody interaction, amplification and/or hybridization.

Considering that specific binding members are important molecules for instance for diagnostic purposes, the invention further provides the use of a virus of the invention or functional part, derivative and/or analogue thereof, for detecting a molecule capable of specifically binding said virus in a sample. Further provided is the use of a nucleic acid and/or amino acid sequence of a virus or functional part, derivative or analogue as defined by the invention, or detecting a molecule capable of specifically binding said virus or functional part, derivative and/or analogue in a sample. Preferably said nucleic acid and/or amino acid sequence comprises a sequence as depicted in table 3 or Table 3 or a functional part, derivative or analogue thereof. Preferably said part is at least 30 nucleotides and/or amino acids long wherein said part preferably comprises more than 95% sequence identity, preferably more than 99%. In a preferred aspect said specific binding member comprises a specific ligand and/or antibody of said virus.

Further provided is a primer and/or probe according to the invention, a specific binding member of the invention, and/or a nucleic acid of a virus or functional part, derivative or analogue according to the invention, for detecting and/or identifying a HCoV-NL63 coronavirus or part thereof in a sample. Preferably, said nucleic acid comprises a sequence as depicted in table 3.

HCoV-NL63 virus may be used to generate an immune response in a subject. This can be useful for instance in vaccination strategies. Thus the invention further HCoV-NL63 provides HCoV-NL63 virus or functional part, derivative or analogue thereof for use as a vaccine or medicament. The medicament use is typically when the subject is already infected with the virus and the immunogen is used to augment the immune response against the virus. The invention further provides a specific binding member of the invention for use as a vaccine or medicament This use is particularly favorable for when the specific binding member comprises a proteinaceous molecule, preferably an antibody or functional part, derivative and/or analogue thereof. Such an antibody can provide passive immunity but may also have active components such as proteases attached to it. The medicament use may again be the case wherein a subject infected with an HCoV-NL63 virus is treated with the specific binding member.

Vaccines may be generated in a variety of ways. One way is to culture the HCoV-NL63 virus for example on the mentioned monkey cell line(s) and to use inactivated virus harvested from the culture. Alternatively, attenuated virus may be used either inactivated or as a live vaccine. Methods for the generation of coronavirus vaccines may be adapted to produce vaccines for the HCoV-NL63 of the invention. The invention thus further provides the use of an HCoV-NL63 virus or functional part, derivative or analogue thereof for the preparation of a vaccine against a coronaviral genus related disease. The invention further provides the use of a specific binding member of the invention for the preparation of a vaccine or medicament against a coronaviral genus related disease. Further provided is the use of an HCoV-NL63 virus or functional part, derivative or analogue thereof, a specific binding member of the invention, a nucleic acid of the invention or a primer and/or probe of the invention for diagnosis of a coronaviral genus related disease. Preferably said coronaviral genus related disease comprises a HCoV-NL63 coronavirus related disease.

Further provided is a vaccine comprising an HCoV-NL63 virus or functional part, derivative or analogue thereof and/or a specific binding member of the invention. Also provided is a medicament comprising an HCoV-NL63 virus or functional part, derivative or analogue thereof and/or a specific binding member of the invention. Preferably said vaccine or medicament is used for at least in part preventing and/or treating a HCoV-NL63 related disease.

An important use of the present invention is the generation of a diagnostic tool for determining whether a subject is suffering from an HCoV-NL63 virus infection or has been exposed to an HCoV-NL63 virus infection. Many diffrent diagnostic applications can be envisioned. They typically contain an identifying component allowing the typing of the virus that is or was present in the subject. One diagnostic tool for HCoV-NL63 makes use of the particular proliferation characteristics of the virus in various cell lines. It replicates in the mentioned preferred monkey cell lines but does not replicate in Vero-cells. This property can be used to discriminate HCoV-NL63 from other known coronaviruses. Thus in one aspect the invention provides a diagnostic kit comprising at least one of the preferred monkey cell lines, preferably the tertiary monkey kidney cells (tMK; Cynomolgus monkey or the monkey cell line LLC-MK2.

Many modern diagnostic kits comprise a specific binding member (to detect the virus or virus infected cells) and/or an HCoV-NL63 virus or a functional part, derivative and/or analogue thereof and/or ammo acid of the invention or a functional part, derivative and/or analogue thereof (for detecting antibodies in blood components of the diagnosed subject). Many other current diagnostic kits rely on identification of HCoV-NL63 virus specific nucleic acid in a sample. There are various ways in which such an assay may be implemented one is a method for detecting an HCoV-NL63 virus or functional part, derivative or analogue thereof in a sample, comprising hybridizing and/or amplifying a nucleic acid of said virus or functional part, derivative or analogue with a primer and/or probe according to the invention and detecting hybridized and/or amplified product. The invention thus also provides a diagnostic kit comprising an HCoV-NL63 virus or functional part, derivative or analogue thereof, a specific binding member according to the invention and/or a primer/probe according to the invention.

Further provided is a method for treating an individual suffering from, or at risk of suffering from, a HCoV-NL63 related disease, comprising administering to said individual a vaccine or medicament according to the invention. Also provided is a method for determining whether an individual suffers from a HCoV-NL63 related disease, comprising obtaining a sample from said individual and detecting a HCoV-NL63 virus or functional part, derivative or analogue thereof in said sample with a method and/or diagnostic kit of the invention.

Further provided is an isolated or recombinant nucleic acid encoding a virus or functional part, derivative and/or analogue according to the invention and a nucleic acid according to the invention, comprising at least a functional part of a sequence as depicted in Table 3. Further provided is an amino acid sequence encoded by a nucleic acid according to the invention, and an amino acid sequence according to the invention, comprising at least a functional part of a sequence as depicted in Table 3. Further provided is a proteinaceous molecule capable of specifically binding HCoV-NL63, obtainable by a method according to the invention and, the use of such a proteinaceous molecule in a vaccine or a diagnostic method for the detection of HCoV-NL63.

EXAMPLES

Example 1 cDNA-AFLP for Virus Discovery

We modified the cDNA-AFLP technique such that it can amplify viral sequences from blood-plasma/serum samples or from CPE-positive culture supernatants (FIG. 1). In the adjusted method the mRNA isolation step prior to amplification is replaced by a treatment to purify viral nucleic acid. Of importance to the purification is a centrifugation step to remove residual cells and mitochondria. In addition, a single DNAse treatment is sufficient to get rid of interfering chromosomal DNA and mitochondrial DNA from broken down cells and finally, by choosing frequent cutting restriction enzymes, the method is fine-tuned such that the majority of viruses will be amplified. With this so-called Virus Discovery cDNA-AFLP (VIDISCA) we were able to amplify viral nucleic acids from EDTA-plasma of a person with hepatitis B virus infection and a person with an acute Parvo B19 infection (results not shown). The technique can also detect HIV-1 in a positive culture supernatant demonstrating its capacity to identify both RNA and DNA viruses (results not shown).

To eliminate residual cells, 110 µl of virus culture supernatant was spun down for 10 min at maximum speed in an Eppendorf microcentrifuge (13500 rpm). One hundred µl was transferred to a fresh tube and DNAse treated for 45 minutes at 37° C. using 15 µl of DNAse buffer and 20 Units of DNAse I (Ambion). The DNAse treatment was included to get rid of chromosomal DNA from broken down cells. After this 900 µl of L6 lysis buffer and 40 µl of silica suspension was added and nucleic acids were extracted as described by Boom[4]. The viral nucleic acids were eluted in 40 µl $H_2O$. With 20 µl eluate the reverse transcription was performed using 2.5 µg random hexamers (Amersham Bioscience), 200 U MMLV-RT (InVitrogen) in a buffer containing 10 mM Tris-HCl pH 8.3, 50 mM KCl, 0.1% Triton X-100, 4.8 mM MgCl2, and 0.4 mM of each dNTP. The sample was incubated at 37° C. for 90 minutes. Subsequently the second strand DNA synthesis was performed using 26 U Sequenase II (Amersham Bioscience), 7.5 U RNAse H (Amersham Bioscience) in 0.25 mM dNTPs each, 17.5 mM MgCl2 and 35 mM Tris-HCl pH 7.5. After the incubation at 37° C. for 90 minutes a phenol/chloroform extraction was performed followed by an ethanol precipitation. The pellet was dissolved in 30 µl of $H_2O$. The cDNA-AFLP was performed essentially as described by Bachem[1] with some modifications. The dsDNA was digested with the HinP I and MseI restriction enzymes (New England Biolabs) according to the manufacturers protocol. After the digestion, MseI adaptor and HinP I adaptor (see below) are added together with 5U ligase enzyme (InVitrogen) and ligase buffer, followed by an additional incubation of 2 hrs at 37° C. The MseI adaptor and HinP I adaptor were prepared previously by mixing a top strand oligo for the MSE and the HinPI adaptors (Table 1) with a bottom strand oligo for the MSE adaptor and for the HinPI adaptor, incubate at 65° C. followed by cooling down to room temperature in the presence of a 1:40 dilution of ligase buffer.

The first PCR was performed with 10 µl of ligation mixture as input, 2.5 U of AmpliTaq polymerase (Perkin-Elmer), 100 ng of HinPI standard primer and 100 ng of MseI standard primer. The PCR reaction was performed according to the profile 5 min 95C; 20 cycles of: 1 min 95° C.–1 min 55° C.–2 min 72° C.; 10 min 72° C. Five µl of first PCR product was used as input in the second "selective" amplification step containing 100 ng of HinPI-N primer and 100 ng MseI-N (sequence of the standard primers extended with one nucleotide) and 2 U AmpliTaq polymerase. The selective PCRs were amplified according to the profile of the "touch down PCR": 10 cycles of 60 sec 94° C.–30 sec 65° C.–1 min 72° C. over which the annealing temperature was reduced from 65° C. with 1° C. with each cycle, followed by 23 cycles: 30 sec 94° C.–30 sec 56° C.–1 min 72° C. Finally the sample was incubated for 10 min at 72° C. The PCR products were evaluated on 4% Metaphor® gels (Cambrex, Rockland, USA). If the bands on the gel were very faint the PCR products were concentrated by vacuum drying using 60 µl of the PCR product. The PCR fragments of interest were cut out of gel and DNA was eluted from the gel using the Qiagen gel purification kit according to the manufacturer's protocol. The PCR products were cloned using pCR® 2.1-TOPO plasmid (InVitrogen) and chemically competent One Shot *E. coli* (InVitrogen). A PCR on the colony was performed and this PCR product was input for sequencing the insert using Big Dye terminator chemistry (Applied Biosystems). The reverse transcription step was excluded, only HinP I digestion and adaptor ligation was performed, the first PCR was performed with 35 cycles instead of 20 and those first PCR fragments were visualized on agarose gel electrophoresis.

DNA Sequencing and Analysis

Coronavirus-PCR product containing plasmids were sequenced with the BigDyeTM Terminator Cycle Sequencing Kit (Applied Biosystems, Foster City, Calif.), using the –21 M13RP and T7 primers. Electrophoresis of sequencing reaction mixtures was performed with an Applied Biosystems 377 automated sequencer, following the manufacturer's protocols. The Sequence Navigator (version 1.01) and Auto Assembler (version 2.1) software packages (ABI, Calif., USA) were used to analyze all sequencing data. Sequences were compared to all sequences in the Genbank database using the BLAST tool of the NCBI web page: http://www.ncbi.nlm.nih.gov/blast. For phylogenetic analysis the sequences were aligned using the ClustalX software package[34] with the following settings: Gap opening penalties: 10.00; Gap extension penalty 0.20, Delay divergent sequences switch at 30% and transition weight 0.59. Phylogenetic analysis was carried out using the neighbor-joining method of the MEGA program (9). The nucleotide distance matrix was generated either by Kimura's 2-parameter estimation or by the p-distance estimation (5), Bootstrap resampling (500 replications) was employed to place approximate confidence limits on individual branches.

Determining the Nucleotide Sequence of the Complete HCoV-NL63 Genome

Using a combination of specific primers, located in the already sequenced domains of the HCoV-NL63 genome, and the proprietary PALM-method (WO 0151661) we are in the process of cloning and determining the full-length genomic sequence for this new coronavirus. Using a combination of 5'-oligonucleotides located in the analyzed part of the HCoV-NL63 genome and a 3' tagged random primer (JZH2R) additional fragments were amplified using a nested RT-PCR protocol similar to the one mentioned previously.

Isolation of SZ 163

In January 2008 a 7-month-old child appeared in hospital with coryza, conjunctivitis and fever. Chest radiography showed typical features of bronchiolitis and four days after the onset of disease a nasopharyngeal aspirate specimen was collected (sample nr: HCoV-NL63). All routinely used tests on this sample for adenovirus, respiratory syncytial virus (RSV), influenza A and B, parainfluenza 1, 2 and 3, rhinovirus, HCoV-229E and HCoV-OC43 were negative. The clinical sample was subsequently inoculated onto a variety of cells including human fibroblast lung (HFL) cells, tertiary monkey kidney cells (tMK; Cynomolgus) and R-HeLa cells. A CPE was detected exclusively on tMK cells and first noted at eight days post-inoculation. The CPE was diffuse with a refractive appearance in the affected cells followed by cell detachment after 7 days. More pronounced CPE was observed upon passage onto LLC-MK2 cells. Besides overall cell rounding, moderate cell enlargement was observed. Additional subculturing on human endothelial lung cells, HFL, Rhabdomyosarcoma cells and Vero cells remained negative for CPE. Immunofluorescent assays to detect influenzavirus A and B, RSV, adenoviruses or parainfluenza virus types 1, 2 or 3 in the culture remained negative The culture supernatant of infected LLC-MK2 cells was subsequently analyzed by VIDISCA. As control we used the supernatant of uninfected LLC-MK2 cells. After the second PCR amplification step, several DNA fragments were present in the test sample but not in the control. These fragments were cloned and sequenced. A Blast search in GenBank revealed that 8 of 16 fragments had sequence similarity to the family of corona viruses with the highest homology the human corona virus 229E Cables 4 and 5).

Phylogenetic analysis of a 270 nt fragment of the replicase 1B region indicated that we identified a distinct new member of the coronavirus group 1. With the VIDISCA technique, 8 HCOV-163-specific fragments, named 163-2, 163-4, 163-9, 163-10, 163-11, 163-14, 163-15 and 163-18 were isolated, cloned, sequenced and aligned with the relevant sequences from GenBank. The Genbank accession number of the used sequences are: MHV (mouse hepatitis virus): AF201929; HCoV-229E: AF304460; PEDV (porcine epidemic diarrhea virus): AF353511; TGEV (transmissible gastroenteritis virus). AJ271965; SARS-CoV: AY278554; IBV (avian infectious bronchitis virus): NC_001451; BCoV (bovine coronavirus): NC_008045; FCoV (feline coronavirus): Y13921 and X80799; CCoV (canine coronavirus): AB105373 and A22732; PRCoV (porcine respiratory coronavirus): M94097; FIPV (feline infectious peritonitis virus): D32044. Position of the HCoV-NL63 fragments compared to HCoV-229E (AF304460): Replicase 1AB gene: 15156-15361, 16049-16182, 16190-16315, 18444-18550, Spike gene: 22124-22266; Nucleocapsid gene: 25667-25882 and 25887-25957; 3'UTR: 27052-27123. Branch lengths indicate the number of substitutions per sequence. From the most closely related species sequence identity scores were calculated (Tables 5 and 6).

Also the deduced amino acid sequence were aligned to the corresponding domains in the open reading frames of related corona (-like) viruses (Table 6).

The human corona viruses account for 10 to 30% of the common colds in man[7], and it is not unusual to find a coronavirus in a child with a respiratory illness. However, it is striking that the virus HCoV-NL63 was harvested from LLC-MK cells. Human Corona virus 229E and OC-43 are known for there inability to replicate on monkey kidney cells. Intriguingly, the newly identified human corona virus that is responsible for SARS is also able to replicate in monkey kidney cells[30].

Propagation of HCoV-NL63 in Cell Culture

A nasopharyngeal aspirate was collected 4 days after the onset of symptoms. The specimen was tested for the presence of adenovirus, RSV, influenza A, influenza B, and parainfluenza type 1, 2 an 3 using the Virus Respiratory Kit (Bartels: Trinity Biotech plc, Wicklow Ireland). In addition, PCR diagnosis for rhinoviruses, meta-pneumovirus and HCoV-OC43 and HCoV-229E were performed[2, 10]. The original nasopharyngeal aspirate was subsequently inoculated onto a variety of cell cultures including HFL cells, tMK cells and R-HeLa cells. The tubes were kept in a roller drum at 34° C. and observed every 3 to 4 days. Maintenance medium was replenished every 3 to 4 days. Two different types of medium were implemented: Optimem 1 (Gibco) without bovine fetal serum was used for the tMK cells and MEM Hanks'/Earle's medium (Gibco) with 3% bovine fetal serum was used for the remaining cell types. On the virus culture direct staining was performed with pools of fluorescent-labeled mouse antibodies against influenzavirus A and B, RSV and adenoviruses (Imagen, DAKO). Indirect staining was performed for parainfluenza virus types 1, 2 or 3 with mouse antibodies (Chemicon, Brunschwig, Amsterdam Netherlands) and subsequent staining with labeled rabbit anti-mouse antibodies (Imagen, DAKO).

Method to Detect HCoV-NL63 in Nasopharyngeal Swabs

For the diagnostic RT-PCR, nucleic acids were extracted by the Boom method[4] 4 from 50 μl virus supernatant or 50 μl suspended nasopharyngeal swab. The reverse transcription was performed as described above with the exception that 10 ng of reverse transcription primer repSZ-RT (Table 7) was used. The entire RT mixture was added to the first PCR mixture containing 100 ng of primer repSZ-1 and 100 ng of primer repSZ-3. The PCR reaction was performed according to the profile 5 min 95° C.; 20 cycles of: 1 min 95° C.–1 min 55° C.–2 min 72° C.; 10 min 72 ° C. A nested PCR was started using 5 μl of the first PCR with 100 ng of primer repSZ-2 and 100 ng of primer repSZ-4. Twenty-five PCR cycles were performed of the same profile as the first PCR.

Ten μl of the first and 10 μl of the nested PCR was analyzed by agarose gel electrophoresis (FIG. 2). Cloning and sequencing of the fragments was performed essentially as described above.

Method of Raising Polyclonal Antibodies

Appropriate domains within the HCoV-NL63 surface proteins (e.g. S-glycoprotein or HE-glycoprotein) can be selected and amplified with suitable oligonucleotides and RT-PCR. The corresponding purified viral antigens can be obtained by expression in a suitable host (e.g. *Yarrowia lipolytica* as previously described[38]). Female NZW rabbits (approx 4 kg) are primed with 0.5 to 5.0 mg of viral protein antigen preparation. The antigen is suspended in 0.5 ml. of phosphate buffered saline (pH 7.3) and emulsified in an equal volume of complete Freund's adjuvant (CFA). Freund's Adjuvant is a well-established adjuvant system that is appropriate for use in these experiments where small amounts of antigen are used, and where immunogenicity of the antigen (although likely) is unknown. Published guidelines for use will be followed, including limiting injection to 0.1 ml at each site, using CFA only for initial immunization dose. This antigen preparation (1 ml total volume) is injected subdermally in the loose skin on the backside of the rabbit's neck. This injection route is immunologically effective and minimizes the possibility of local inflammation associated with unilateral or bilateral flank injection (such ensuing flank inflammation can impair animal mobility). After resting for 3 weeks, one ml of blood will be removed from the ear artery for a test bleed. Antibodies will be boosted if titers of the desirable antibodies are judged to be too low. Rabbits with adequate antibody levels will be boosted subdermally 1.0 mg of antigen contained in CFA. Boosted animals will be bled after two weeks; i.e., 15 ml of blood will be taken from the ear artery using a heat lamp to dilate the blood vessel. The rabbit will be placed in a commercial restraint, tranquillized with xylazine not more than seven times in total after which the rabbit will be exsanguinated by cardiac puncture following anesthesia using xylazine/ketamine.

Method for Vaccine Production

For the production of a subunit vaccine the S-glycoprotein perhaps combined with the HE, M and N proteins, could be expressed in a suitable eukaryotic host (e.g. *Y. lipolytica* or LLC-MK2 cells) and purified using preferentially two small affinity tags (e.g. His-tag or the StrepII tag). After appropriate purification, the resulting viral proteins can be used as a subunit vaccine.

Alternatively the HCoV-NL63 virus can be propagated in a suitable cell line as described above and subsequently treated as described by Wu[11]. Briefly the virus is precipitated from culture medium with 20% polyethylene glycol 6000 and purified by ultracentrifugation at 80.000×g for 4 hours through a discontinuous 40-65% sucrose gradient followed by a linear 5 to 40% CsCl gradient for 4 hours at 120.000×g. The resulting virus preparation can be inactivated by beating for 30 minutes at 65° C. as described by Blondel[3].

Analysis of S Glycoprotein or Any of the HCOV-NL63 Viral Proteins Binding to an Immobilized Ligand (e.g. Antibody) in an Optical Biosensor Binding reactions were carried out in an IAsys two-channel resonant mirror biosensor at 20° C. (Affinity Sensors, Saxon Hill, Cambridge, United Kingdom) with minor modifications. Planar biotin surfaces, with which a signal of 600 arc s corresponds to 1 ng of bound protein/mm2, were derivatized with streptavidin according to the manufacturer's instructions. Controls showed that the viral proteins did not bind to streptavidin-derivatized biotin surfaces (result not shown). Biotinylated antibody was immobilized on planar streptavidin-derivatized surfaces, which were then washed with PBS. The distribution of the immobilized ligand and of the bound S-glycoprotein on the surface of the biosensor cuvette was inspected by the resonance scan, which showed that at all times these molecules were distributed uniformly on the sensor surface and therefore were not micro-aggregated. Binding assays were conducted in a final volume of 30 μl of PBS at 20±0.1° C. The ligate was added at a known concentration in 1 μl to 5 μl of PBS to the cuvette to give a final concentration of S-glycoprotein ranging from 14 to 70 nM. To remove residual bound ligate after the dissociation phase, and thus regenerate the immobilized ligand, the cuvette was washed three times with 50 μl of 2 M NaCl-10 mM Na2HPO4, pH 7.2, and three times with 50 μl of 20 mM HCl. Data were pooled from experiments carried out with different amounts of immobilized antibody (0.2, 0.6, and 1.2 ng/mm2). For the calculation of $k_{on}$, low concentrations of ligate (S-glycoprotein) were used, whereas for the measurement of $k_{off}$, higher concentrations of ligate were employed (1 μM) to avoid any rebinding artefacts. The binding parameters $k_{on}$ and $k_{off}$ were calculated from the association and dissociation phases of the binding reactions, respectively, using the non-linear curve-fitting FastFit software (Affinity Sensors) provided with the instrument. The dissociation constant ($K_d$) was calculated from the association and dissociation rate constants and from the extent of binding observed near equilibrium.

Example 2

Methods

Virus Isolation

The child, who was living in Amsterdam, was admitted to the hospital with complaints of coryza and conjunctivitis since 3 days. At admission she had shortness of breath and refused to drink. The patient's temperature was 89° C., the respiratory rate was 50 breaths/min with oxygen saturation of 96% and her pulse was 177 beats/min. Upon auscultation bilateral prolonged expirium and end-expiratory wheezing was found. A chest radiograph showed the typical features of bronchiolitis. The child was treated with salbutamol and ipratropium at the first day, followed by the use of salbutamol only for 5 days. The child was seen daily at the out patient clinic and the symptoms gradually decreased. A nasopharyngeal aspirate was collected 5 days after the onset of symptoms. The specimen was tested for the presence of RSV, adenovirus, influenza A and B virus, and parainfluenza virus type 1, 2 and 3 using the Virus Respiratory Kit (Bartels: Trinity Biotech plc, Wicklow Ireland). In addition, PCR tests for rhinoviruses, enterovirus, meta-pneumovirus and HCoV-OC43 and HCoV-229E were performed (2, 10). The original nasopharyngeal aspirate was inoculated onto a variety of cells. The cultures were kept in a roller drum at 34° C. and observed every 3 to 4 days. Maintenance medium was replenished every 3 to 4 days. Two different types of medium were implemented: Optimem 1 (InVitrogen, Breda, The Netherlands) without bovine fetal serum was used for the tMK cells and MEM Hanks'/Earle's medium (InVitrogen, Breda, The Netherlands) with 3% bovine fetal serum was used for the remaining cell types. Cell cultures that were infected with the aspirate specimen were stained for the presence of respiratory viruses after one week of incubation. Direct staining was performed with pools of fluorescent-labeled mouse antibodies against RSV and influenza A and B virus (Imagen, DakoCytomation Ltd, Cambridge, UK). Indirect staining was performed for adenoviruses and parainfluenza virus type 1, 2 or 3 with mouse antibodies (Chemicon International, Temecula, Calif.) and subsequent staining with FITC-labeled rabbit anti-mouse antibodies (Imagen, DakoCytomation Ltd, Cambridge, UK.

VIDISCA method

To remove residual cells and mitochondria, 110 μl of virus culture supernatant was spun down for 10 min at maximum speed in an eppendorf microcentrifuge (13500 rpm). To remove chromosomal DNA and mitochondrial DNA from the lysed cells, 100 μl was transferred to a fresh tube and treated with DNAse I for 45 min at 37° C. (Ambion, Huntingdon, UK). Nucleic acids were extracted as described by Boom et al. (4). A reverse transcription reaction was performed with random hexamer primers (Amersham Bioscience, Roosendaal, The Netherlands) and MMLV-RT (InVitrogen, Breda The Netherlands) while second strand DNA synthesis was carried out with Sequenase II (Amersham Bioscience, Roosendaal, The Netherlands). A phenol/chloroform extraction was followed by an ethanol precipitation. The cDNA-AFLP was performed essentially as described by Bachem et al (1) with some modifications. The dsDNA was digested with the HinP I and Mse I restriction enzymes (New England Biolabs, Beverly, Massachusetts). Mse I- and HinP I-anchors (see below) were subsequently added with 5U ligase enzyme (InVitrogen, Breda, The Netherlands) in the supplied ligase buffer for 2hrs at 37° C. The Mse I- and HinP I-anchors were prepared by mixing a top strand oligo (5'-CTCGTAGACT-GCGTACC-3' (SEQ. ID. NO: 3) for the Mse I anchor and 5'-GACGATGAGTCCTGAC-3' (SEQ. ID. NO: 4) for the HinP I anchor) with a bottom strand oligo (5'-TAGGTACG-CAGTC-3' (SEQ. ID. NO: 5) for the Mse I anchor and 5'-CG-GTCAGGACTCAT-3' (SEQ. ID. NO: 6) for the HinP I anchor) in a 1:40 dilution of ligase buffer. A 20 cycle PCR was performed with 10 μl of the ligation mixture, 100 ng HinP I standard primer (5'-GACGATGAGTCCTGACCGC-3' (SEQ. ID. NO: 7)) and 100 ng Mse I standard primer (5'-CTCGTAGACTGCGTACCTAA-3' (SEQ. ID. NO:8)). Five μl of this PCR product was used as input in the second "selective" amplification step with 100 ng HinPI-N primer and 100 ng MseI-N (the "N" denotes that the standard primers are extended with one nucleotide: G, A, T or C). The selective rounds of amplification were done with a "touch down PCR": 10 cycles of [60 sec 94° C-30 sec 65° C-1 min 72° C.] and the annealing temperature was reduced with 1 ° C. each cycle, followed by 23 cycles: [30 sec 94° C-30 sec 56 ° C-1 min 72° C.] and 1 cycle 10 min 72° C. The PCR products were analyzed on 4% Metaphor® agarose gels (Cambrex, Rockland, Maine) and the fragments of interest were cloned and sequenced using BigDye terminator reagents. Electrophoresis and data collection was performed on an ABI 377 instrument.

cDNA Library Construction and Full Genome Sequencing

The cDNA library was produced as described by Marra et al[17], with minor modifications. During reverse transcription only random hexamer primers were used and no oligo-dT primer, and the amplified cDNA was cloned into PCR2.1-TOPO TA clong vector. Colonies were picked and suspended in BHI media. The *E. coli* suspension was used as input in a PCR amplification using T7 and M13 RP for amplification. The PCR products were subsequently sequenced with the same primers that were used in the PCR-amplification and the BigDye terminator reagent. Electrophoresis and data collection was performed on an ABI 377 instrument. Sequences were assembled using the AutoAssembler DNA sequence Assembly software version 2.0.

Diagnostic RT-PCR

From 492 persons a total of 600 respiratory samples collected between December 2002 and August 2002. The kind of material ranged from oral/nasopharyngeal aspirate, throat swabs, bronchioalveolary lavages and sputum. The samples were collected for routine virus diagnostic screening of persons suffering from upper and lower respiratory tract disease. One hundred µl of the sample was used in a Boom extraction (4). The reverse transcription was performed with MMLV-RT (InVitrogen) using 10 ng or reverse transcription primer (repSZ-RT: 5'- CCACTATAAC-3' (SEQ. ID. NO: 9)). The entire RT mixture was added to the first PCR mixture containing 100 ng of primer repSZ-1 (5'-GTGATGCATAT-GCTAATTTG-3' (SEQ. ID. NO: 10)) and 100 ng of primer repSZ-3 (5'-CTCTTGCAGGTATAATCCTA-3' (SEQ. ID. NO: 11)). The PCR reaction was performed according to the profile 5min 95° C.; 20 cycles of: 1min 95° C.-1min 55° C.-2min 72° C.; 10 min 72 ° C. A nested PCR was started using 5 µl of the first PCR with 100 ng of primer repSZ-2 (5'-TTGGTAAACAAAAGATAACT-3' (SEQ. ID. NO: 12)) and 100 ng of primer repSZ-4 (5'-TCAATGCTATAAA-CAGTCAT-3' (SEQ. ID. NO: 13)). Twenty-five PCR cycles were performed of the same profile as the first PCR. Ten µl of the PCR products was analyzed by agarose gel electrophoresis. All positive samples were sequenced to confirm the presence of HCoV-NL63 in the sample.

Sequence Analysis

Sequences were compared to all sequences in the Genbank database using the BLAST tool of the NCBI web page: http://www.ncbi.nlm.nih.gov/blast. For phylogenetic analysis the sequences were aligned using the ClustalX software package with the following settings: Gap opening penalties: 10.00; Gap extension penalty 0.20; Delay divergent sequences switch at 30% and transition weight 0.5 (9). Phylogenetic analysis was carried out using the neighbor-joining method of the MEGA program (5) using the information of all fragments within one gene. The nucleotide distance matrix was generated either by Kimura's 2 parameter estimation or by the p-distance estimation (6). Bootstrap resampling (500 replicates) was employed to place approximate confidence limits on individual branches.

Results

Virus Isolation From a Child With Acute Respiratory Disease

In January 2003 a 7-month-old child appeared in the hospital with coryza, conjunctivitis and fever. Chest radiography showed typical features of bronchiolitis and a nasopharyngeal aspirate specimen was collected five days after the onset of disease (sample NL63). Diagnostic tests for respiratory syncytial virus (RSV), adenovirus, influenza A and B virus, parainfluenza virus type 1, 2 and 3, rhinovirus, enterovirus, HCoV-229E and HCoV-OC43 remained negative. The clinical sample was subsequently inoculated onto human fetal lung fibroblasts (HFL), tertiary monkey kidney cells (tMK; Cynomolgus monkey) and HeLa cells. CPE was detected exclusively on tMK cells and first noted at eight days post-inoculation. The CPE was diffuse with a refractive appearance in the affected cells followed by cell detachment after 7 days. More pronounced CPE was observed upon passage onto the monkey kidney cell line LLC-MK2 with overall cell rounding and moderate cell enlargement (FIG. 1). Additional subcultures on HFL, rhabdomyosarcoma cells and Vero cells remained negative for CPE. Immunofluorescent assays to detect RSV, adenovirus, influenza A and B virus, or parainfluenza virus type 1, 2 and 3 in the culture remained negative. Acid lability and chloroform sensitivity tests demonstrated that the virus is most likely enveloped and not a member of the picornavirus group[24].

Virus Discovery by the VIDISCA Method

Identification of unknown pathogens by molecular biology tools encounters the problem that the target sequence is not known and that genome specific PCR-primers cannot be designed. To overcome this problem we developed the VIDISCA method that is based on the cDNA-AFLP technique[4]. The advantage of VIDISCA is that prior knowledge of the sequence is not required as the presence of restriction enzyme sites is sufficient to guarantee amplification. The input sample can be either blood plasma/serum or culture supernatant. Whereas cDNA-AFLP starts with isolated mRNA, the VIDISCA technique begins with a treatment to selectively enrich for viral nucleic acid, which includes a centrifugation step to remove residual cells and mitochondria. In addition, a DNAse treatment is used to remove interfering chromosomal DNA and mitochondrial DNA from degraded cells, whereas viral nucleic acid is protected within the viral particle. Finally, by choosing frequently cutting restriction enzymes, the method is fine-tuned such that most viruses will be amplified. Using VIDISCA we were able to amplify viral nucleic acids from EDTA-plasma of a person with hepatitis B virus infection and a person with an acute parvovirus B19 infection. The technique can also detect HIV-1 in cell culture, demonstrating its capacity to identify both RNA and DNA viruses.

The supernatant of the CPE-positive culture NL63 was analyzed by VIDISCA. We used the supernatant of uninfected cells as a control. After the second PCR amplification step, unique and prominent DNA fragments were present in the test sample but not in the control. These fragments were cloned and sequenced. Twelve out of 16 fragments showed sequence similarity to members of the family of coronaviruses, but significant sequence divergence was apparent in all fragments. These results indicate that we identified a novel coronavirus (HCoV-NL63).

Detection of HCoV-NL63 in Patient Specimens

To demonstrate that HCoV-NL63 originated from the nasopharyngeal aspirate of the child, we designed a diagnostic RT-PCR that specifically detects HCoV-NL63. This test, based on unique sequences within the 1b gene, confirmed the presence of HCoV-NL63 in the clinical sample. The sequence of this PCR product was identical to that of the virus identified upon in vitro passage in LLC-MK2 cells (results not shown).

Having confirmed that the cultured coronavirus originated from the child, the question remains whether this is an isolated clinical case or whether HCoV-NL63 is circulating in humans. To address this question, we examined respiratory specimens of hospitalized persons and individuals visiting the outpatient clinic between December 2002 and August 2008 for the presence of HCoV-NL63. We identified 7 additional persons that carried HCoV-NL63. Sequence analysis of the PCR products indicated the presence of a few characteristic (and reproducible) point mutations in several samples, suggesting that several subgroups of NL63 may co-circulate. At least 5 of the HCoV-NL63-positive individuals suffered from a respiratory tract illness, the clinical data of 2 persons were not available. Including the index case, five patients were children less than 1 year old and 3 patients were adults. Two adults are likely to be immuno-suppressed, as one of them is a bone marrow transplant recipient, and the other is an HIV positive patient suffering from AIDS with very low CD4 cell counts. No clinical data of the third adult was available. Only 1 patient had a co-infection with RSV (nr 72), and the HIV-infected patient (nr 466) carried *Pneumocystis carinii*. No other respiratory agent was found in the other HCoV-NL63-positive patients, suggesting that the respiratory symptoms were caused by HCoV-NL63. All HCoV-NL63 positive samples were collected during the last winter season, with a detection frequency of 7% in January 2003. None of the 306 samples collected in the spring and summer of 2003 contained the virus (P<0.01, 2-tailed t-test).

Complete Genome Analysis of RCoV-NL63

The genomes of coronaviruses have a characteristic, genome organization. The 5' half contains the large 1a and 1b genes, encoding the non-structural polyproteins, followed by the genes coding for four structural proteins: spike (S), membrane (M), envelope (E) and the nucleocapsid (N) protein. Additional non-structural proteins are encoded either between 1b and the S gene, between the S and E gene, between the M and N gene or downstream of the N gene.

To determine whether the HCoV-NL63 genome organization shares these characteristics, we constructed a cDNA library with a purified virus stock as input material. A total of 475 genome fragments were analyzed, with an average coverage of 7 sequences per nucleotide. Specific PCRs were designed to fill in gaps and to sequence regions with low quality sequence data. Combined with 5'RACE (Rapid Amplification of cDNA Ends) and 3'RACE experiments the complete HCoV-NL63 genome sequence was resolved.

The genome of HCoV-NL63 is a 27,553-nucleotide RNA with a poly A tail. With a G-C content of 34% it has the lowest G-C content among the *coronaviridae*, which range from 37%-42%[25]. ZCurve software was used to identify ORFs[26] and the genome configuration is portrayed using the similarity with known coronaviruses (FIG. 6). The 1a and 1b genes encode the RNA polymerase and proteases that are essential for virus replication. A potential pseudoknot structure is present at position 12489, which may provide the −1 frameshift signal to translate the 1b polyprotein. Genes predicted to encode the S, E, M and N proteins are found in the 3' part of the genome. Short untranslated regions (UTRs) of 286 and 287 nucleotides are present at the 5' and 3+ termini, respectively. The hemagglutinin-esterase gene, which is present in some group 2 and group 3 coronaviruses, was not present. ORF 3 between the S and E gene probably encodes a single accessory non-structural protein.

The 1a and 1ab polyproteins are translated from the genomic RNA, but the remaining viral proteins are translated from subgenomic mRNAs (sg mRNA), each with a common 5' end derived from the 5' part of the genome (the 5' leader sequence) and 3' coterminal parts. The sg mRNA are made by discontinuous transcription during negative strand synthesis[27]. Discontinuous transcription requires base-pairing between cis-acting transcription regulatory sequences (TRSs), one located near the 5' part of the genome (the leader TRS) and others located upstream of the respective ORFs (the body TRSs)[28]. The cDNA bank that we used for sequencing contained copies of sg mRNA of the N protein, thus providing the opportunity to exactly map the leader sequence that is fused to all sg mRNAs. A leader of 72 nucleotides was identified at the 5' UTR. The leader TRS (5'-UCUCAACUAAAC-3' (SEQ. ID. NO: 14)) showed 11/12-nucleotide similarity with the body TRS upstream of the N gene. A putative TRS was also identified upstream of the S, ORF 3, E and M gene The sequence of HCoV-NL63 was aligned with the complete genomes of other coronaviruses. The percentage nucleotide identity was determined for each gene. For all genes except the M gene, the percentage identity was the highest with HCoV-229E. To confirm that HCoV-NL63 is a new member of the group 1 coronaviruses, phylogenetic analysis was performed using the nucleotide sequence of the 1A, 1B, S, M and N gene. For each gene analyzed, HCoV-NL63 clustered with the group 1 coronaviruses. The bootstrap values of the subgroup HCoV-NL63/HCoV-229E were 100 for the 1a, 1b and S gene. However, for the M and N gene the bootstrap values of this subcluster decreased (to 78 and 41 respectively) and a subcluster containing HCoV-229E, HCoV-NL63 and PEDV becomes apparent. A phylogenetic analysis could not be performed for the ORF 3 and E gene because the region varied too much between the different coronavirus groups or because the region was too small for analysis, respectively. Bootscan analysis by the Simplot software version 2.5[29] found no signs of recombination (results not shown).

The presence of a single non-structural protein gene between the S and E gene is noteworthy since almost all coronaviruses have 2 or more ORFs in this region, with the exception of PEDV and OC43[30,31]. Perhaps most remarkable is a large insert of 537 nucleotides in the 5'part of the S gene when compared to HCoV-229E. A Blast search found no similarity of this additional 179-amino acid domain of the spike protein to any coronavirus sequence or any other sequences deposited in GenBank.

TABLE 1 cDNA-AFLP oligonucleotides for virus discovery

| Oligo | Sequence |
| --- | --- |
| Top strand MSE adaptor | CTCGTAGACTGCGTACC (SEQ. ID. NO: 3) |
| Top strand for HinP1 adaptor | GACGATGAGTCCTGAC (SEQ. ID. NO: 4) |
| Bottom strand oligo for MSE adaptor | TAGGTACGCAGTC (SEQ. ID. NO: 5) |
| Bottom strand oligo for HinP1 adaptor | CGGTCAGGACTCAT (SEQ. ID. NO: 6) |
| HinPI standard primer | GACGATGAGTCCTGACCGC (SEQ. ID. NO: 7) |
| MseI standard primer | CTCGTAGACTGCGTACCTAA (SEQ. ID. NO: 8) |

TABLE 2

Oligonucleotide for PALM extension of the HCOV-NL68 Sequence

| Oligonucleotide name, | Application, | Sequence 5'-3' |
| --- | --- | --- |
| JZH2R | 1st PCR | GCTATCATCACAATGGACNNNNNG (SEQ. ID. NO: 15) |

TABLE 3

Nucleotide- and corresponding deduced amino acid sequences

| Fragment | Sequence |
|---|---|
| 163-2 | GTATTGTTTTTGTTGCTTGTGCCCATGCTGCTGTTGATTCCTTATGTGCAAAAGCTATGA<br>CTGTTTATAGCATTGATAAGTGTACTAGGATTATACCTGCAAGAGCTCGGGTTGAGTGTT<br>ATAGTGGCT (SEQ ID NO: 16) |
| 163-2<br>Translation | Replicase polyprotein 1a<br>IVFVACAHAAVDSLCAKAMTVYSIDKCTRIIPARARVECYSG<br>(SEQ ID NO: 17) |
| 163-4 | ATGGGTCTAGATATGGCTTGCAAACTTACTACAGTTACCTAACTTTTATTATGTTAGTA<br>ATGGTGGTAACAATTGCACTACGGCCGTTATGACCTATTCTAATTTTGGTATTTGTGCTG<br>ATGGTTCTTTGATTCCTGTTCGTCC (SEQ ID NO: 18) |
| 163-4<br>Translation | Spike protein<br>GSRYGLQNLLQLPNFYYVSNGGNNCTTAVMTYSNFGICADGSLIPVR<br>(SEQ ID NO: 19) |
| 163-9<br>(3'-UTR) | ATGATAAGGGTTTAGTCTTACACACAATGGTAGGCCAGTGATAGTAAAGTGTAAGTAATT<br>TGCTATCATAT (SEQ ID NO: 20) |
| 163-10 | ATGTCAGTGATGCATATGCTAATTTGGTTCCATATTACCAACTTATTGGTAAACAAAAGA<br>TAACTACAATACAGGGTCCTCCTGGTAGTGGTAAGTCACATTGTTCCATTGGACTTGGAT<br>TGTACTACCCAGGT (SEQ ID NO: 21) |
| 163-10<br>Translation | Replicase polyprotein 1ab<br>VSDAYANLVPYYQLIGKQKITTIQGPPGSGKSHCSIGLGLYYPG<br>(SEQ ID NO: 22) |
| 163-11 | ATCTAAACTAAACAAAATGGCTAGTGTAAATTGGGCCGATGACAGAGCTGCTAGGAAGAA<br>ATTTCCTCCTCCTTCATTTTACATGCCTCTTTTGGTTAGTTCTGATAAGGCACCATATAG<br>GGTCATTCCCAGGAATCTTGTCCCTATTGGTAAGGGTAATAAAGATGAGCAGATTGGTTA<br>TTGGAATGTTCAAGAGCGTTGGCGTAT (SEQ ID NO: 23) |
| 163-11<br>Translation | Nucleocapsid protein<br>SKLNKMASVNWADDRAARKKFPPPSFYMPLLVSSDKAPYRVIPRNLVPIGKGNKDEQIGY<br>WNVQERWR (SEQ ID NO: 24) |
| 163-14 | ACAAAAATTTGAATGAGGGTGTTCTTGAATCTTTTTCTGTTACACTTCTTGATAATCAAG<br>AAGATAAGTTTTGGTGTGAAGATTTTTATGCTAGTATGTATGAAAATTCTACAATATTGC<br>AAGCTGCTGGTTTATGTGTTGTTTGTGGTTCACAAACTGTACTTCGTTGTGGTGATTGTC<br>TGCGTAAGCCTATGTTGTGCACTAAAT (SEQ ID NO: 25) |
| 163-14<br>Translation | Rsplicase polyprotein 1ab<br>KNLNEGVLESFSVLLDNQEDKFWCEDFYASMYENSTILQAAGLCVVCGSQTVLRCGDCL<br>RKPMLCTK (SEQ ID NO: 26) |
| 163-15 | AGGGGGCAACGTGTTGATTTGCCTCCTAAAGTTCATTTTTATTACCTAGGTACTGGACCT<br>CATAAGGACCT (SEQ ID NO: 27) |
| 163-15<br>Translation | Nucleocapsid protein<br>RGQRVDLPPKVHFYYLGTGPHKD (SEQ ID NO: 28) |
| 163-18 | TAGTAGTTGTGTTACTCGTTGTAATATAGGTGGTGCTGTTTGTTCAAAACATGCAAATTT<br>GTATCAAAAATACGTTGAGGCATATAATACATTTACACAGGCAGGTT<br>(SEQ ID NO: 29) |
| 163-18<br>Translation | Replicase polyprotein 1ab<br>SSCVTRCNIGGAVCSKHANLYQKYVEAYNTFTQAG (SEQ ID NO: 30) |

TABLE 4

Identification of cDNA-AFLP fragments

| Fragment | Identification best Blast hit |
|---|---|
| 163-2 | replicase polyprotein 1ab [Human coronavirus 229E] |
| 163-4 | spike protein [Human coronavirus 229E] |
| 163-9 | 3'UTR Human coronavirus 229E |
| 163-10 | replicase polyprotein 1ab [Human coronavirus 229E] |
| 163-11 | replicase polyprotein 1ab [Human coronavirus 229E] |
| 163-14 | replicase polyprotein 1ab [Human coronavirus 229E] |
| 163-15 | nucleocapsid protein [Human coronavirus 229E] |
| 163-18 | replicase polyprotein 1ab [Human coronavirus 229E] |

TABLE 5

Pairwise nucleotide sequence homologies between the virus of the present invention and different corona (like) viruses in percentages sequence identity (%)

| Fragment | BcoV | MRV | HcoV | PEDV | TGE | SARS | IBV |
|---|---|---|---|---|---|---|---|
| Replicase 1AB 163-2 | 59.6 | 61.2 | 76.7 | 70.5 | 64.3 | 65.8 | 64.3 |
| Spike gene 163-4 | 31.7 | 26.5 | 64.6 | 48.9 | 45.4 | 33.7 | 25.9 |
| 3'UTR 163-9 | 29.5 | 34 | 81.9 | 53.6 | 50 | 31.5 | 38 |
| Replicase 1AB 163-10 | 55.2 | 57.4 | 82 | 73.8 | 69.4 | 64.1 | 65.1 |
| Nucleocapsid 163-11 | 25.5 | 23.8 | 54.9 | 51.5 | 44.6 | 28.3 | 27.6 |
| Replinase 1AB 163-14 | 52.1 | 52.1 | 78.7 | 72.9 | 76.3 | 52.6 | 58.4 |
| Nucleocapsid 163-15 | 29.5 | 35.2 | 71.8 | 63.3 | 60.5 | 25.8 | 45 |
| Replicase 1AB 163-18 | 67.2 | 65.4 | 72.8 | 65.4 | 61.6 | 68.2 | 57 |

TABLE 6

Pairwise deduced amino acid sequence homologies between different corona (like) viruses in percentages sequence identity (%)

| Fragment | BCoV | MHV | HcoV | PEDV | TGE | SARS | IBV |
|---|---|---|---|---|---|---|---|
| Replicase 1AB 163-2 | 55.8 | 53.4 | 88.3 | 79 | 60.4 | 67.4 | 55.8 |
| Spike gene 168-4 | ND | ND | 56.2 | ND | ND | ND | ND |
| Replicase 1AB 163-10 | 51.1 | 53.3 | 93.3 | 86.6 | 80 | 57.7 | 55.5 |
| Nucleocapsid 163-11 | ND | ND | 48.4 | ND | ND | ND | ND |
| Replicase 1AB 163-14 | 50.7 | 50.7 | 86.9 | 78.2 | 78.2 | 46.3 | 47.8 |
| Nucleocapsid 168-15 | ND | ND | 82.6 | ND | ND | ND | ND |
| Nucleocapsid 163-18 | 63.8 | 63.8 | 77.7 | 69.4 | 69.4 | 58.3 | 55.5 |

ND = Not Determined

TABLE 7

Oligos for Secific detection of HcoV-163

| Primer | Sequence |
|---|---|
| repSZ-RT | CCACTATAAC (SEQ. ID. NO: 9) |
| repSZ-1 | GTGATGCATATGCTAATTTG (SEQ. ID. NO: 10) |
| repSZ-2 | TTGGTAAACAAAAGATAACT (SEQ. ID. NO: 11) |
| repSZ-3 | CTCTTGCAGGTATAATCCTA (SEQ. ID. NO: 12) |
| repSZ-4 | TCAATGCTATAAACAGTCAT (SEQ. ID. NO: 13) |

TABLE 8

Molecule Features

| Start | End | Name | Description |
|---|---|---|---|
| 287 | 12439 | 1a | ORF-1a |
| 4081 | 4459 | | Pfam 01661 |
| 9104 | 10012 | | 3Cl protease |
| 12433 | 12439 | | Ribosomue slippery site |
| 12439 | 20475 | 1b | ORF-1b |
| 14166 | 14490 | | Pfam 00680 |
| 16162 | 16965 | | COG1112, Super family DNA and RNA helicase |
| 16237 | 16914 | | Pfam 01443 Viral helicase |
| 20472 | 24542 | 2 | ORF-2 S(pike)-gene |
| 21099 | 22619 | | S1 Pfam 01601 |
| 22625 | 24539 | | S2 Pfam 01601 |

TABLE 8-continued

Molecule Features

| Start | End | Name | Description |
|---|---|---|---|
| 24542 | 25219 | 3 | ORF-3 |
| 24551 | 25174 | | NS3b Pfam 03053 |
| 25200 | 25433 | 4 | ORF-4 Pfam 05780, Coronavirus NS4 E (envelope) protein |
| 25442 | 26122 | 5 | ORF-5 |
| 25442 | 26119 | | Matrix glycoprotein Pfam 01635 M-gene |
| 26133 | 27266 | 6 | ORF-6 |
| 26184 | 27256 | | Nucleocapaid Pfam 00937 N-gene |

Via a −1 frame shift at the ribosome slippery site the 1a ORF is extended to protein of 6729 amino acid residues referred to as 1ab. ORF 1a and 1ab encode two polyproteins that are proteolytically converted to 16 largely uncharacterized enzymes that are involved in RNA replication (for review seeSnijder, E. J., P. J. Bredenbeek, J. C. Dobbe, V. Thiel, J. Ziebuhr, L. L. Poon, Y. Guan, M. Rozanov, W. J. Spaan, and A. E. Gorbalenya. 2003. Unique and Conserved Features of Genome and Proteome of SARS-coronavirus, an Early Split-off From the Coronavirus Group 2 Lineage. J. Mol. Biol. 331:991-1004).

TABLE 9

Proteins from HcoV-NL63 ORFs

| ORF | Number of AA | Mw prediction | |
|---|---|---|---|
| 1a | 4060 | 451364 | Polyprotein |
| 1ab | 6729 | 752822 | Polyprotein |
| 2 | 1356 | 149841 | Spike |
| 3 | 225 | 25658 | |
| 4 | 77 | 9177 | Envelope |
| 5 | 226 | 25927 | Matrix |
| 6 | 377 | 42252 | Nucleocapsid |

The $M_w$ prediction does not take into account post-translational modification like glycosylation or cleavage of a signal sequence.

TABLE 10

Amplification oligonucleotides for HCoV-NL65 S, M and N encoding regions

| Primer | Sequence |
|---|---|
| S1 | ACAAGTTTGTACAAAAAAGCAGGCTTCAAACTTTCTTGATTTTGCTTGTTTTGCCCC (SEQ ID NO: 31) |
| S2 | ACCACTTTGTACAAGAAAGCTGGGTCTTGAACGTGGACCTTTTCAAATTCG (SEQ ID NO: 32) |
| M1 | ACAAGTTTGTACAAAAAAGCAGGCTTCTCTAATAGTAGTGTGCCTCTTTTAGAGG (SEQ ID NO: 33) |
| M2 | ACCACTTTGTACAAGAAAGCTGGGTCGATTAAATGAAGCAACTTCTC (SEQ ID NO: 34) |
| N1 | ACAAGTTTGTACAAAAAAGCAGGCTTCGCTAGTGTAAATTGGGCCGATG (SEQ ID NO: 35) |
| N2 | ACCACTTTGTACAAGAAAGCTGGGTCATGCAAAACCTCGTTGACAATTTCTATAATGGC (SEQ ID NO: 36) |

The S,M and N complementary sequences are indicated in bold print. The remainder of the PCR primers is composed of either in-frame attB1 or attB2 sites

TABLE 11

Overall full length genome DNA sequence identity

| | BCV | HC229E | IBV | SARS | TGV | HCoV-NL63 | HCoV-OC43 |
|---|---|---|---|---|---|---|---|
| BCV | 100 | 46 | 43 | 54 | 40 | 43 | 95 |
| HC229E | | 100 | 50 | 48 | 53 | 65 | 46 |
| IBV | | | 100 | 43 | 46 | 48 | 43 |

TABLE 11-continued

Overall full length genome DNA sequence identity

|       | BCV | HC229E | IBV | SARS | TGV | HCoV-NL63 | HCoV-OC43 |
|-------|-----|--------|-----|------|-----|-----------|-----------|
| SARS  |     |        |     | 100  | 40  | 43        | 53        |
| TGV   |     |        |     |      | 100 | 55        | 40        |
| HCoV-NL63 |     |    |     |      |     | 100       | 43        |
| OC43  |     |        |     |      |     |           | 100       |

Overall DNA sequence identity percentages of HCoV-NL63 compared to other coronaviruses. From the SimPlot graph (FIG. 7), comparing HCoV-NL63 (query) with SARS associated coronavirus and HCoV-229E, can be deduced that local sequence identity never exceeds 85%

TABLE 12

Overall DNA sequence identity Spike encoding region

|       | OC48 | NL63 | 229E | SARS |
|-------|------|------|------|------|
| OC43  | 100  | 46   | 40   | 44   |
| NL63  |      | 100  | 59   | 38   |
| 229E  |      |      | 100  | 41   |
| SARS  |      |      |      | 100  |

TABLE 13

Overall DNA sequence identity in 5'UTR

|       | OC43 | NL63 | 229E | SARS |
|-------|------|------|------|------|
| OC43  | 100  | 36   | 34   | 48   |
| NL63  |      | 100  | 74   | 33   |
| 229E  |      |      | 100  | 34   |
| SARS  |      |      |      | 100  |

BRIEF DESCRIPTION OF THE DRAWINGS

FIG. 1 cDNA-AFLP allows amplification of nucleic acids without any prior sequence information.

Figure 1:
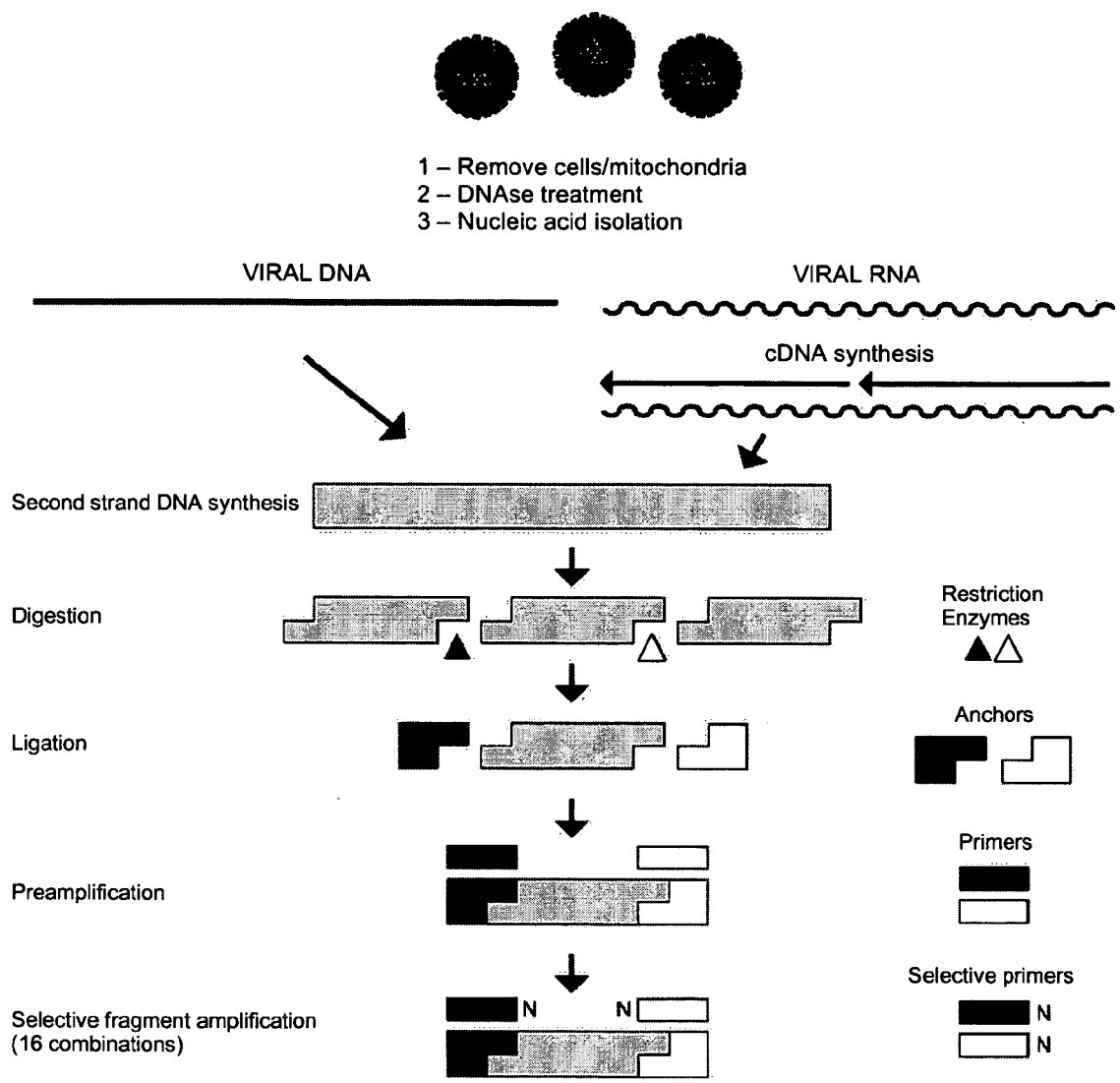
Figure 3:
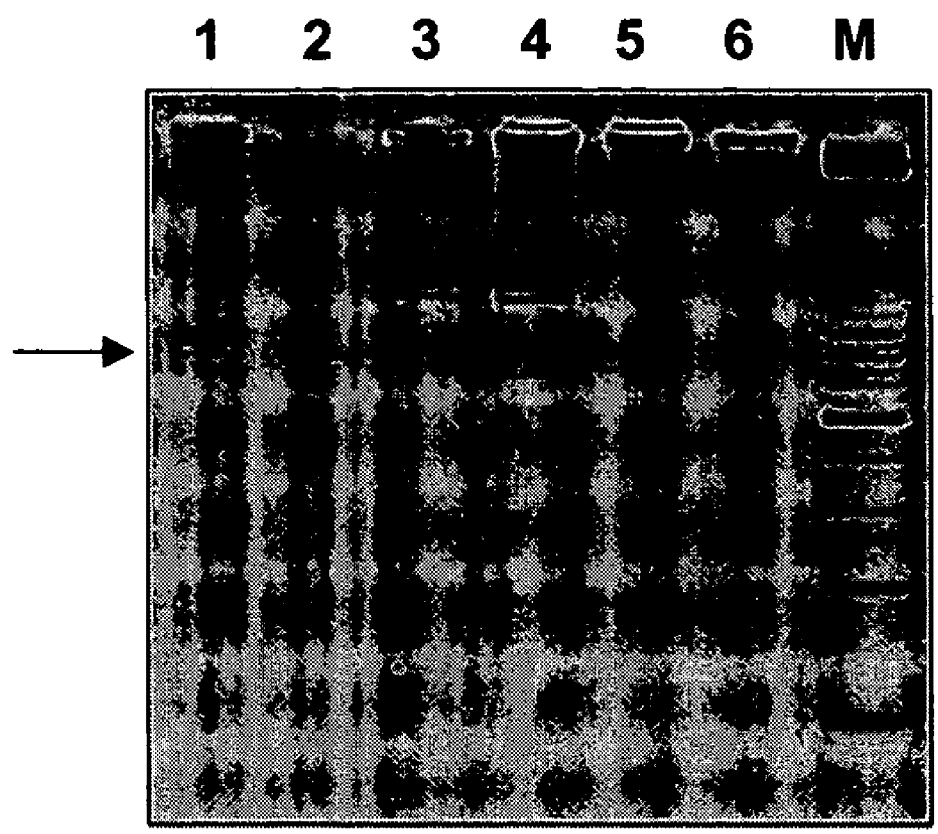
Figure 4:
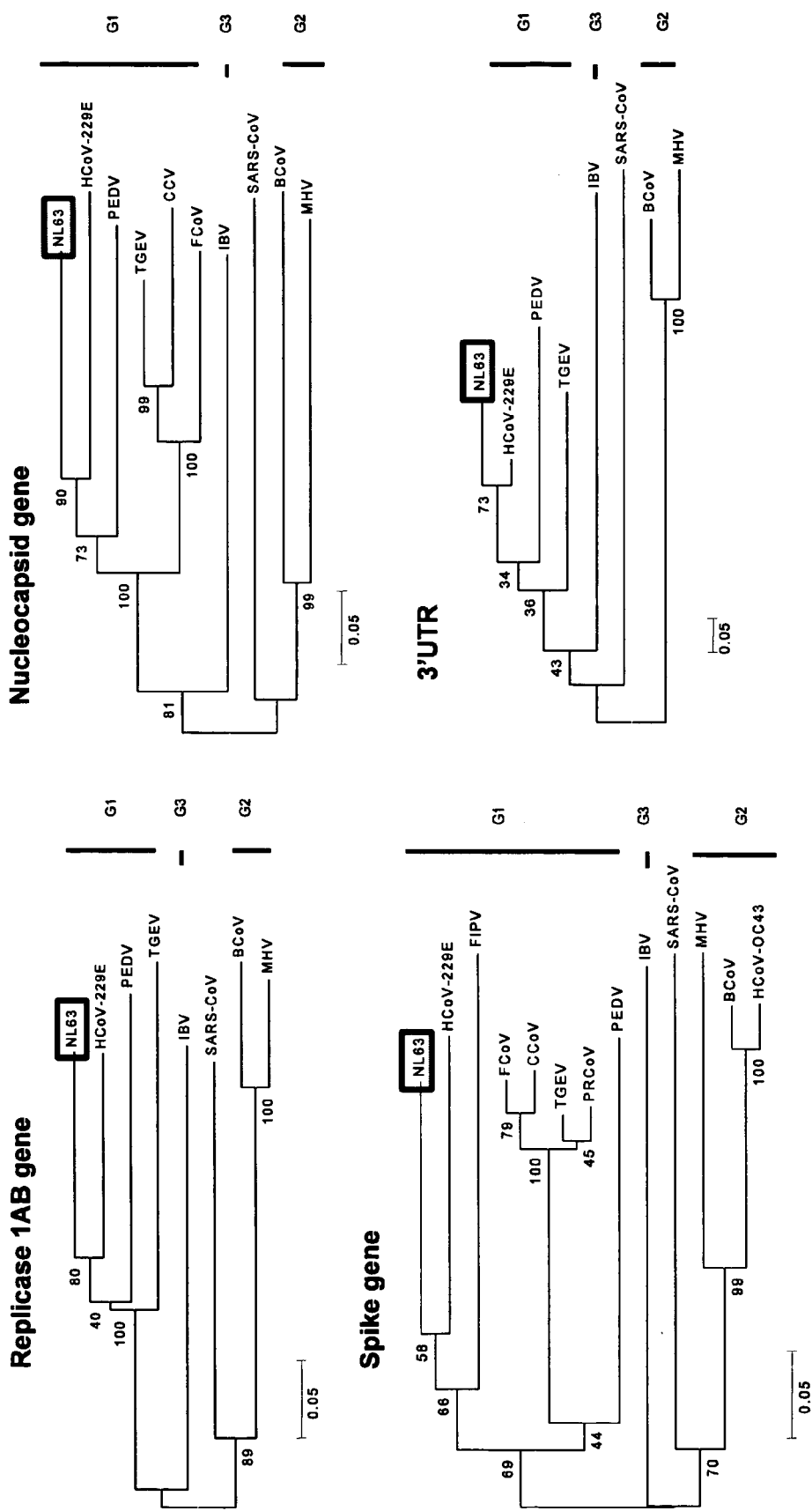
Figure 5:
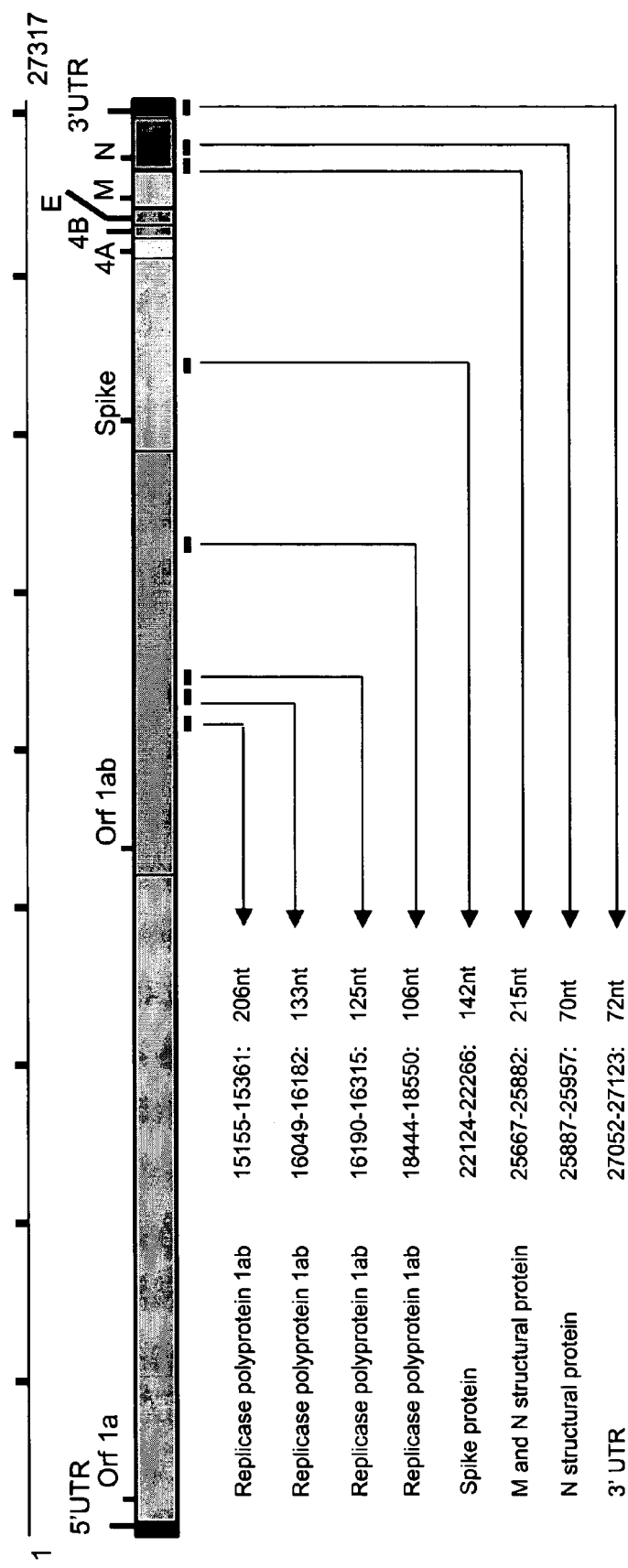
Figure 6:
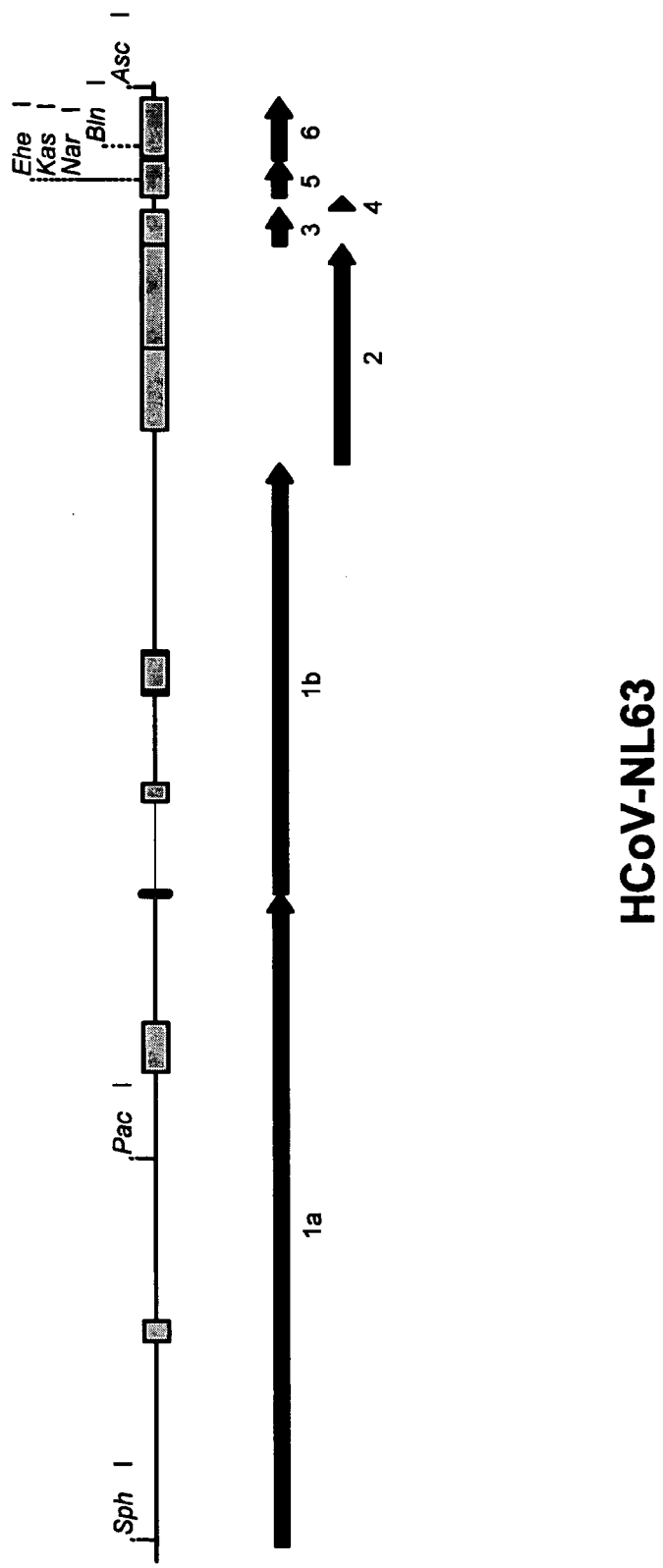
Figure 7:
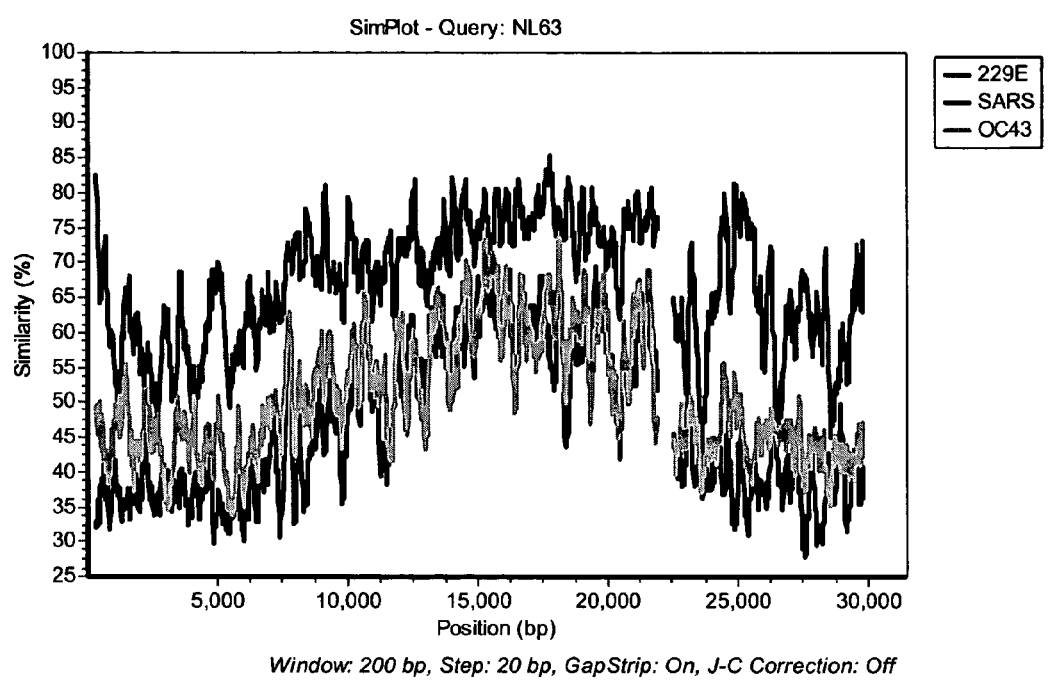
Figure 10:
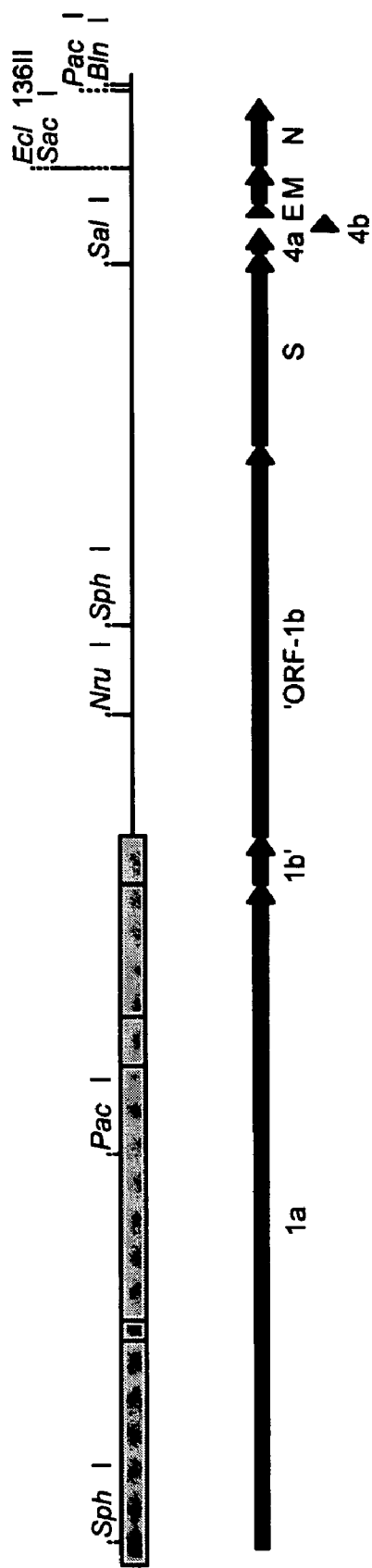
Figure 13:
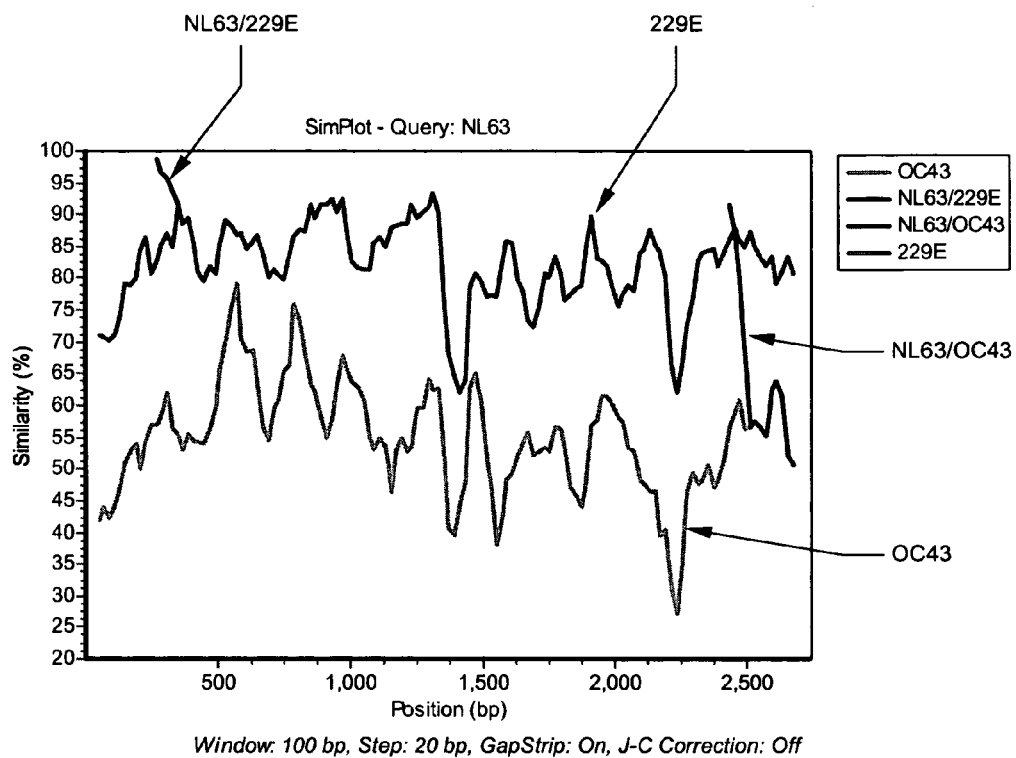
Figure 14:
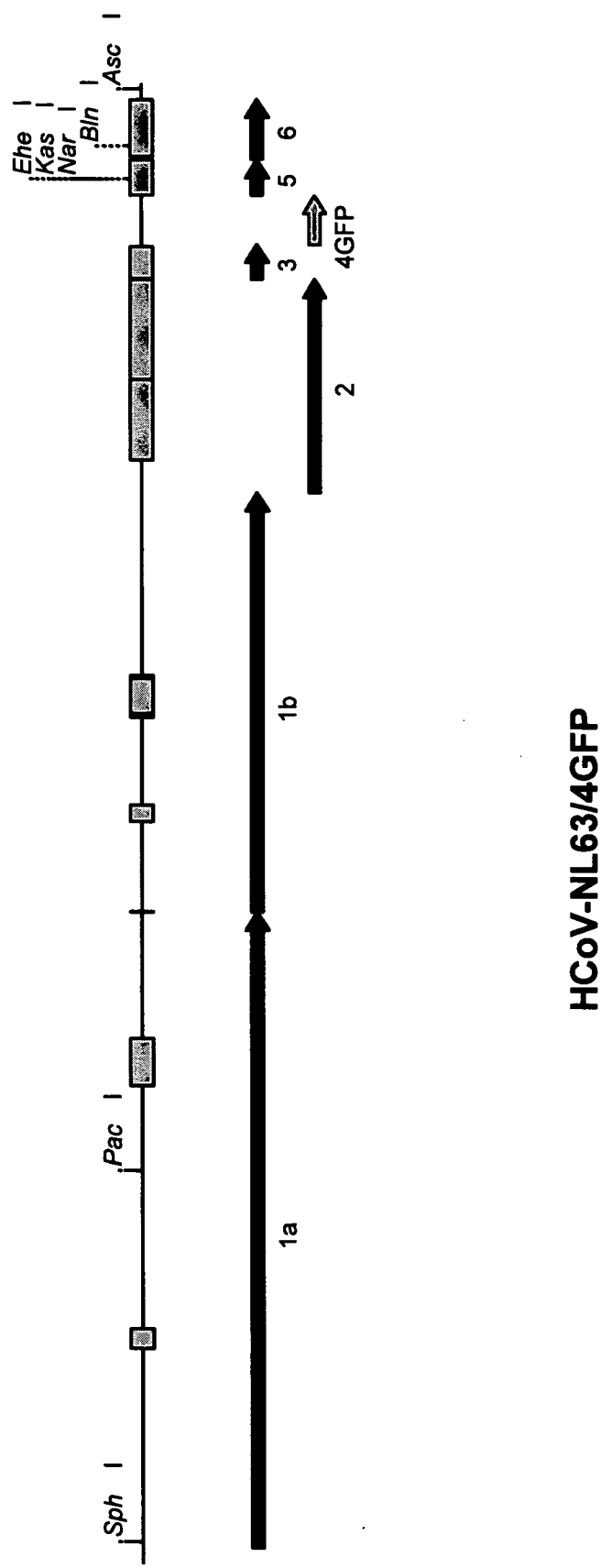
Figure 15:
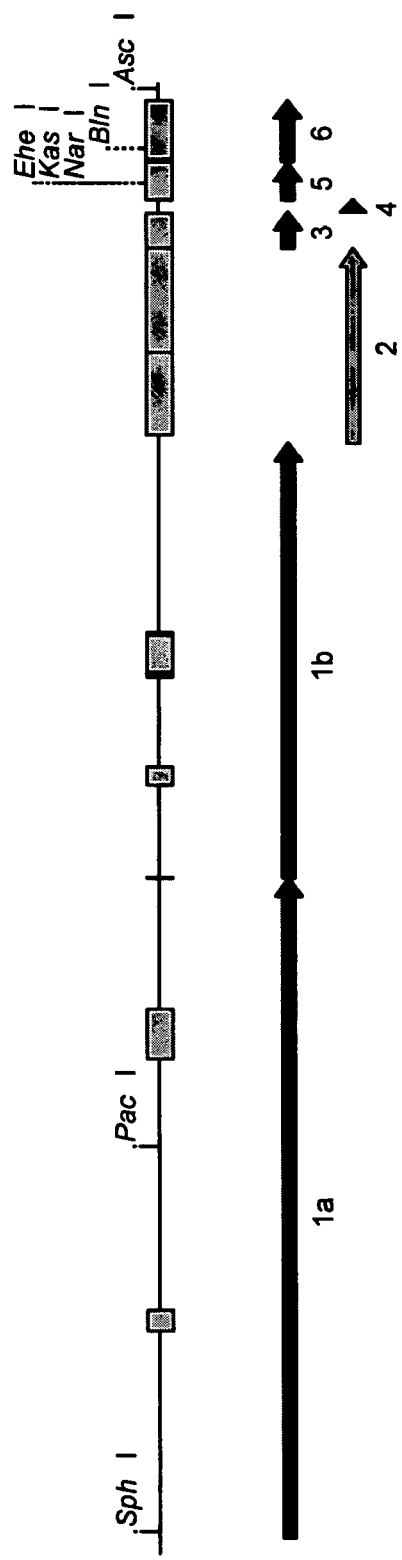

Culture supernatants from CPE-positive and uninfected cells are subjected to the cDNA-AFLP procedure. Amplification products derived from the CPE-positive culture which are not present in the uninfected control sample are cloned and sequenced.

FIG. 2

LLC-MK2 cells infected with HCoV-NL168.

Panel A and B are unstained cells while panel C and D are stained with haematoxilin eosin. The typical CPE of HCoV-NL163 is shown in panel A and C. The control uninfected LLC-MR cells are shown in panel B and D.

FIG. 3

VD-cDNA-AFLP PCR products visualized by Metaphors agarose gel electrophoreses.

The PCR products of 1 (HinP I-G and Mse I-A) of 16 primer pair combinations used during the selective amplification step. Lanes 1 and 2: duplicate PCR product of virus culture NL163; lanes 5 and 6 control supernatant of LLC-MK cells and in lane 7 and 8 the negative PCR control. Lanes M: 25 bp molecular weight marker (InVitrogen). The arrow indicates a new coronavirus fragment that was excised out of gel and sequenced.

FIG. 4

Phylogenetic analysis of the HCoV-163 sequences. G1, G2 and G3 denote the group 1, group 2 and group 3 coronavirus clusters. The Genbank accession number of the used sequences are: MHV (mouse hepatitis virus): AF201929; HCoV-229E: AF304460; PEDV (porcine epidemic diarrhea virus): AF353511; TGEV (transmissible gastroenteritis virus): AJ271965; SARS-CoV: AY278554; IBV (avian infectious bronchitis virus): NC_001451; BCoV (bovine coronavirus): NC_003045; FCoV (feline coronavirus): Y13921 and X80799; CCoV (canine coronavirus): AB105373 and A22732; PRCoV (porcine respiratory coronavirus): M94097; FIPV (feline infectious peritonitis virus): D32044. Position of the HCoV-163 fragments compared to HCoV-229E (AF304460): Replicase 1AB gene: 15155-15361, 16049-16182, 16190-16315, 18444-18550, Spike gene: 22124-22266; Nucleocapsid gene: 25667-25882 and 25887-25957; 3'UTR: 27052-27123. Branch lengths indicate the number of substitutions per sequence.

FIG. 5 schematic representation of Coronavirus and the location of the 163-fragments listed in table 3.

FIG. 6

Restriction map of HCoV-NL63'

Complete 27553 nt cDNA derivative of the ssRNA genome. Open reading frames (ORF) are depicted as numbered black arrows and the identified (PFAM) domains within these ORFs are indicated as gray boxes.

FIG. 7

Simplot analysis HcoV NL63 and other human Coronaviruses The gap in the comparison of HCoV NL63 to SARS, HCoV-OC43 and HCoV-229E is cause by a unique 537 in-frame insertion in the Spike protein encoding ORF (see elsewhere herein). Sigmaplot analysis is described in Lole, R. S., R C. Bollinger, R. S. Paranjape, D. Gadkari, S. S. Kulkarni, N. G. Novak, R. Ingersoll, H. W. Sheppard, and S. C. Ray. 1999. Full-length human immunodeficiency virus type 1 genomes from subtype C-infected seroconverters in India, with evidence of intersubtype recombination. J. Virol. 73:152-160.

FIG. 8

Expression constructs for HCoV-NL63 Spike and Matrix protein

Expression of a His and StrepII tagged Spike fusion protein can be induced by addition of IPTG to the bacterial growth medium. Through attB1/B2-mediated recombination, the S gene insert can be transferred to other commercially available expression vectors, facilitating protein production in other hosts.

Through an identical cloning procedure as for pGP7S, a Gateway compatible expression vector for HCoV-NL63 M-gene can be constructed. The plasmid directs IPTG inducible production of N and C-terminally affinity tagged Matrix fusion protein, allowing selective recovery of full-length fusion protein.

FIG. 9

Recombination site NL63-229E (SEq. ID. NO: 38)

NL63-derived sequences are in underlined bold black print and the 229E derived sequences are in gray bold print.

FIG. 10

Restriction map cDNA Clone NL63/229E hybrid The NL63 derived part is indicated as gray boxes and the 229E-derived region is indicated as a line. The junction between the two genomes is indicated by the succession of the two black arrows marked 1b' and ORF-1b indicating the hybrid 1b ORF.

A second chimeric genome was generated by a reciprocal recombination fusing nucleotide 19653 of HCoV-NL63 to nucleotide 20682 of HCoV-OC43 again creating a hybrid ORF 1b giving rise to a hybrid 1ab replicase polyprotein. Recombination occurred within the conserved sequence AATTATGG (SEQ. ID. NO: 37).

FIG. 11 Recombination site NL63/OC43 hybrid (SEQ. ID. NO: 39).

Figure 12:
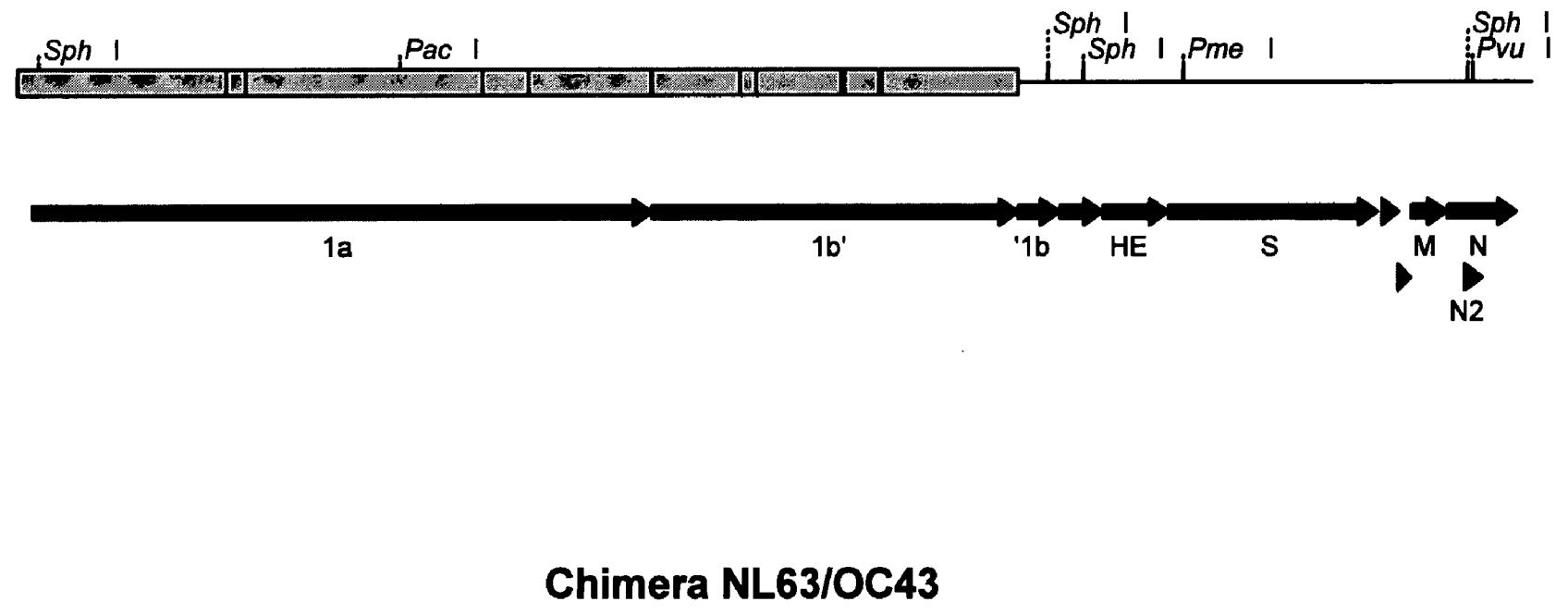

Again, NL63-derived region is in bold black underlined print and the OC43 derived sequences are in gray bold print. The resulting cDNA restriction map is depicted in FIG. 12

FIG. 12

Restriction map recombinant NL63/OC43 genome.

The NL63-derived part is indicated as gray boxes and the recombination site is depicted as the between the black arrows 1b' and 1b.

FIG. 13

Similarity plot deduced protein alignments of ORF1b from HCoV-NL63, HCoV-229E, HCoV-OC43 and the two hybrids NL63/229E and NL63/OC43.

FIG. 14

Green fluorescent protein expressing HcoV-NL63 derivative. Functional equivalent NL63/4GFP carries an in-frame C-terminal fusion of the E protein (ORF4) with a human codon optimised Green Fluorescent Protein (EGFP, Stratagene). Infected cells appear fluorescent after excitation of the 4-EGFP fusion protein. HCoV-NL63 can be used to elucidate the process of viral; infection and the translation of the polycistronic sub-genomic messengers.

FIG. 15

Restriction map of functional derivative NL63D2052021011.

This deletion derivative of NL63 lacks most of the insertion at the N-terminal end of the Spike protein. By deleting nucleotides 20520-21011 the unique domain is removed while retaining the predicted secretory signal sequence (Nielsen, H., J. Engelbrecht, S. Brunak, and G. Von Heijne. 1997. Identification of prokaryotic and eukarotic signal peptides and prediction of their cleavage sites. Protein Eng 10:1-6).

FIG. 16

Sequence variation in HCoV-NL63 from additional patient samples Direct sequencing of both strands of RT-PCR products from 6 patient samples revealed the presence of polymorphisms in the ORF 1a region. REF (SEQ. ID. NO: 40); 223 B (SEQ. ID. NO: 41); 246 B (SEQ. ID. NO: 42); 248 B (SEQ. ID. NO: 43); 251 B (SEQ. ID. NO: 44); 466 B (SEQ. ID. NO: 45); 496 B (SEQ. ID. NO: 46)

FIG. 17

HCoV-NL63 specific and generic human Coronavirus detection probes. Coronavirus polymerases generate several sub-genomic RNAs. The frequency of S. E, M and N protein encoding cDNA clones in the sequencing library of HCoV-NL63 and SARS (Snijder, E. J., P. J. Bredenbeek, J. C. Dobbe, V. Thiel, J. Ziebuhr, L. L. Poon, Y. Guan, M. Rozanov, W. J. Spaan, and A. E. Gorbalenya. 2003). Unique and conserved features of genome and proteome of SARS-coronavirus, an early split-off from the coronavirus group 2 lineage. J. Mol. Biol. 331:991-1004). Northern blot data demonstrate a high abundance of these sub-genomic RNAs in infected cells. Consequently, these genes are attractive targets for diagnostic tests.

Since the genomic and sub-genomic RNAs possess identical 3'ends, probes containing the N gene would hybridise to all of them (Table 8).

Through alignment of the full-length sequences of all human Coronaviruses a conserved region in ORF1b was identified, allowing their detection with a nested RT-PCR assay. Oligo NL63NF1 (SEQ. ID. NO: 47); Oligo NL63NR1 (SEQ. ID. NO: 48); Oligo NL63NF2 (SEQ. ID. NO: 49); Oligo NL63NR2 (SEQ. ID. NO: 50)

FIG. 18

Generic Coronavirus detection primers. Oligo COR1F (SEQ. ID. NO: 51); Oligo COR1R (Seq. ID. NO: 52), Oligo COR2F (SEQ. ID. NO: 53); Oligo COR2R (SEQ. ID. NO: 54)

FIG. 19

Nucleotide sequence an HcoV_NL63 (SEQ. ID. NO: 55)

FIG. 20

ORF 1a, replicase enzyme complex of an HcoV_NL63 (SEQ. ID. NO: 56)

FIG. 21

ORF 1 ab replicase polyprotein of an HcoV_NL63 (SEQ. ID. NO: 57). Adenosine diphosphate-ribose 1'-phosphate (SEQ. ID. NO: 58). 3CI$^{Pro}$ Coronavirus polyprotein processing endoprotease (SEQ. ID. NO: 59); RNA dependent RNA polymerase (pfam00680) (SEQ. ID. NO: 60); Exon 3' to 5' Exonuclease and helicase (SEQ. ID. NO: 61); XendoU (homolog of) polyU-specific endoribonuclease (SEQ. ID. NO: 62); 2'-O-MT 2:S-adenosylmethionine-dependnet ribose 2'-orthomethyltransferase (SEQ. ID. NO: 63

FIG. 22

The spike protein (ORF3) contains an N-terminal secretory signal sequence of 16 AA (indicated on the first line of the continuous sequence listed below). (Nielsen, H., J. Engelbrecht, S. Brunak, and G. Von Heijne. 1997. Identification of prokaryotic and eukaryotic signal peptides and prediction of their cleavage sites. Protein Eng 10:1-6)

FIG. 28

ORF-4 Coronavirus_NS4, Coronavirus non-structural protein 4. This family consists of several non-structural protein 4 (NS4) sequences or small membrane protein.

ORF-5. This family consists of various coronavirus matrix proteins that are transmembrane glycoproteins. The M protein or E1 glycoprotein is implicated in virus assembly. The E1 viral membrane protein is required for formation of the viral envelope and is transported via the Golgi complex. The matrix protein is predicted to contain an N-terminal secretory signal sequence (indicated in the first part of the continuous sequence) (Nielsen, H., J. Engelbrecht, S. Brunak, and G. Von Heijne. 1997. Identification of prokaryotic and eukaryotic signal peptides and prediction of their cleavage sites. Protein Eng 10:1-6.)

ORF-6 Pfam 00937, Coronavirus nucleocapsid protein. Structural protein forming complexes with the genomic RNA

REFERENCE LIST

1. Bachem, C. W., R. S. van der Hoeven, S. M. de Bruijn, D. Vreugdenhil, M. Zabeau, and R. G. Visser. 1996. Visualization of differential gene expression using a novel method of RNA fingerprinting based on AFLP: analysis of gene expression during potato tuber development. Plant J. 9:745-758.
2. Bestebroer, T. M., A. I. M. Bartelds, A. M. van Loon, H. Boswijk, K. Bijlsma, E. C. J. Claas, J. A. F. W. Kleijne, C. Verweij, M. W. Verweij-Uijterwaal, A. G. Wermenbol, and J. de Jong,. Virological NIVEL/RIVM-surveillance of respiratory virus infection in the season 1994/95. 245607002, 1-38. 1995. Bilthoven, RIVM. Virologische NIVEL/RIVM-surveillance van respiratoire virusinfecties in het seizoen 1994/95 RIVM. Ref Type: Report
3. Blondel, B., O. Akacem, R. Crainic, P. Couillin, and F. Horodniceanu. 1983. Detection by monoclonal antibodies of an antigenic determinant critical for poliovirus neutralization present on VP1 and on heat-inactivated virions. Virology 126:707-710.

4. Boom, R., C. J. Sol, M. M. Salimans, C. L. Jansen, P. M. Wertheim-van Dillen, and van der Noordaa J. 1990. Rapid and simple method for purification of nucleic acids. J. Clin. Microbiol. 28:495-503.
5. Kamur, S., Tamura, K., and Wei, M. Molecular Evolutionary Genetics Analysis (MEGA 2.0). 1993. Institute of Molecular Evolutionary Genetics, Pennsylvania State University, University Park. Ref Type: Computer Program
6. Kimura, M. 1980. A simple method for estimating evolutionary rates of base substitutions through comparative studies of nucleotide sequences. J. Mol. Evol. 16:111-120.
7. Kunkel, P. and G. Herrler. 1993. Structural and functional analysis of the surface protein of human coronavirus OC43. Virology 195:195-202.
8. Mounir, S., P. Labonte, and P. J. Talbot. 1993. Characterization of the nonstructural and spike proteins of the human respiratory coronavirus OC43: comparison with bovine enteric coronavirus. Adv. Exp. Med. Biol. 342:61-67.
9. Thompson, J. D., T. J. Gibson, F. Plewniak, F. Jeanmougin, and D. G. Higgins. 1997. The CLUSTAL_X windows interface: flexible strategies for multiple sequence alignment aided by quality analysis tools. Nucleic Acids Res. 25:4876-4882.
10. Van Den Hoogen, B. G., J. C. de Jong, J. Groen, T. Kuiken, R. de Groot, R. A. Fouchier, and A. D. Osterhaus. 2001. A newly discovered human pneumovirus isolated from young children with respiratory tract disease. Nat. Med. 7:719-724.
11. Wu, C. N., Y. C. Lin, C. Fann, N. S. Liao, S. R. Shih, and M. S. Ho. 2001. Protection against lethal enterovirus 71 infection in newborn mice by passive immunization with subunit VP1 vaccines and inactivated virus. Vaccine 20:895-904.
13. Almeida, J. D. and D. A. Tyrrell, The morphology of three previously uncharacterized human respiratory viruses that grow in organ culture. J Gen Virol 1, 175-178 (1967).
14. Thiel, V., J. Herold,, B. Schefle, and S. G. Siddell, Infectious RNA transcribed in vitro from a cDNA copy of the human coronavirus genome cloned in vaccinia virus. J Gen Virol 82, 1273-1281 (2001).
15. Hendley, J. O., H. B. Fishburne, and J. M. Gwaltney, Jr. Coronavirus infections in working adults. Eight-year study with 229 E and OC 43. Am Rev. Respir. Dis. 105, 805-811 (1972).
16. Mounir, S., P. Labonte, and P. J. Talbot, Characterization of the nonstructural and spike proteins of the human respiratory coronavirus OC43: comparison with bovine enteric coronavirus. Adv. Exp Med Biol 342, 61-67 (1993).
17. Kunkel, F. and G. Herrler, Structural and functional analysis of the surface protein of human coronavirus OC43. Virol. 195, 195-202 (1993).
18. Tyrrell, D. A. J. and M. L. Bynoe, Cultivation of novel type of common-cold virus in organ cultures. Br. Med J 1, 1467-1470 (1965).
19. Bradburne, A. F., M. L. Bynoe, and D. A. Tyrrell, Effects of a "new" human respiratory virus in volunteers. Br. Med J 3, 767-769 (1967).
20. Kapikian, A. Z. et al. Isolation from man of "avian infectious bronchitis virus-like" viruses (coronaviruses) similar to 229E virus, with some epidemiological observations. J Infect. Dis. 119, 282-290 (1969).
21. Ksiazek, T. G. et al. A novel coronavirus associated with severe acute respiratory syndrome. N Engl J Med 2003. May 15.; 348. (20):1953. –66. 348, 1953-1966 (2003).
22. Stohlman, S. A. and D. R. Hinton, Viral induced demyelination. Brain Pathol. 11, 92-106 (2001).
23. Jubelt, B. and J. R. Berger. Does viral disease underlie ALS? Lessons from the AIDS pandemic. Neurology 57, 945-946 (2001).
24. Shingadia, D., A. Bose, and R. Booy, Could a herpesvirus be the cause of Kawasaki disease? Lancet Infect. Dis. 2, 310-313 (2002).
25. Bachem, C. W. et al. Visualization of differential gene expression using a novel method of RNA fingerprinting based on AFLP: analysis of gene expression during potato tuber development. Plant J 9, 745-753 (1996).
26. Hamparian, V. V. Diagnostic procedures for viral, rickettsial and chlamydial infection. Lennette, E. H. & Schmidt, N. J. (eds.), pp. 562 (American Public Health Association, Washington, D.C., 1979).
27. Marra, M. A. et al. The Genome sequence of the SARS-associated coronavirus. Science 2003. May 30.; 300. (5624.):1899. –404. 300, 1399-1404 (2003).
28. McIntosh, K. et al. Coronavirus infection in acute lower respiratory tract disease of infants. J Infect. Dis. 130, 502-507 (1974).
29. Boivin, G. et al. Human metapneumovirus infections in hospitalized children. Emerg. Infect. Dis. 9, 634-640 (2003).
30. Rota, P. A. et al. Characterization of a novel coronavirus associated with severe acute respiratory syndrome. Science 300, 1394-1399 (2003).
31. Bestebroer, T. M. et al. Virological NIVEL/RIVM-surveillance of respiratory virus infection in the season 1994/95. 245607002, 1-38. 1995. Ref Type: Report
32. van den Hoogen, B. G. et al. A newly discovered human pneumovirus isolated from young children with respiratory tract disease. Nat. Med 7, 719-724 (2001).
34. Earley, E. M. and K. M. Johnson. 1988. The lineage of Vero, Vero 76 and its clone C1008 in the United States., p. 26-29. In B. Simizu and T. Terasima (eds.), Vero cells: origin, properties and biomedical applications. Chiba Univ, Tokyo.
35. Kamur, S., K Tamura, and M. Wei, Molecular Evolutionary Genetics Analysis (MEGA). (2.0). 1993. Institute of Molecular Evolutionary Genetics, Pennsylvania State University, University Park. Ref Type: Computer Program
36. Kimura, M. A simple method for estimating evolutionary rates of base substitutions through comparative studies of nucleotide sequences. J Mol Evol. 16, 111-120 (1980).
37. Fouchier, R. A., T. M. Bestebroer, S. Herfst, K. L. Van Der, G. F. Rimmelzwaan, and A. D. Osterhaus. 2000. Detection of influenza A viruses from different species by PCR amplification of conserved sequences in the matrix gene. J. Clin. Microbiol. 38:4096-4101.
38. Nicaud, J. M., C. Madzak, B. P. van den, C. Gysler, P. Duboc, P. Niederberger, and C. Gaillardin. 2002. Protein expression and secretion in the yeast Yarrowia lipolytica. FEM. Yeast Res. 2:371-379.
39. Guy, J. S., Breslin, J. J., Breubaus, B., Vivrette, S. & Smith, L. G. Characterization of a coronavirus isolated from a diarrheic foal. J Clin Microbiol. 38, 4523-4526 (2000).
40. Holmes, K. V. & Lai, M. M. C. Fields Virology. Fields, B. N., Knipe, D. M., Howley, P. M. & et al (eds.), pp. 1075-1093 (Lippincott-Raven Publishers, Philadelphia, 1996).
41. Hamre, D. & Procknow, J. J. A new virus isolated from the human respiratory tract. proc. soc. exp. biol. med. 121, 190-193 (1966).
42. McIntosh, K, Dees, J. H., Becker, W. B., Kapikian, A. Z. & Chanock, R. M. Recovery in tracheal organ cultures of novel viruses from patients with respiratory disease. Proc. Natl. Acad. Sci. U.S.A. 57, 933-940 (1967).

43. Peiris, J. S. et al. Clinical progression and viral load in a community outbreak of coronavirus-associated SARS pneumonia: a prospective study. lancet 361, 1767-1772 (2003).
44. Snijder, E. J. et al. Unique and conserved features of genome and proteome of SARS-coronavirus, an early split-off from the coronavirus group 2 lineage. J Mol Biol 331, 991-1004 (2003).
45. de Haan, C. A., Masters, P. S., Shen, X., Weiss, S. & Rottier, P. J. The group-specific murine coronavirus genes are not essential, but their deletion, by reverse genetics, is attenuating in the natural host. Virol. 296, 177-189 (2002).
46. Lai, M. M. & Cavanagh, D. The molecular biology of coronaviruses. Adv. Virus Res 48, 1-100 (1997).
47. Sawicki, S. G. & Sawicki, D. L. Coronaviruses use discontinuous extension for synthesis of subgenome-length negative strands. Adv. Exp Med Biol 380, 499-506 (1995).
48. van Marle, G. et al. Arterivirus discontinuous mRNA transcription is guided by base pairing between sense and antisense transcription-regulating sequences. Proc Natl Acad Sci U.S.A. 96, 12056-12061 (1999).
49. Chen, L. L., Ou, H. Y., Zhang, R. & Zhang, C. T. ZCURVE_CoV: a new system to recognize protein coding genes in coronavirus genomes, and its applications in analyzing SARS-CoV genomes. Biochem Biophys. Res Commun. 307, 382-388 (2003).
50. Liu, D. X. & Inglis, S. C. Internal entry of ribosomes on a tricistronic mRNA encoded by infectious bronchitis virus. J Virol 66, 6148-6154 (1992).
51. Thiel, V. & Siddell, S. G. Internal ribosome entry in the coding region of murine hepatitis virus mRNA 5. J Gen Virol 75 (Pt 11), 3041-3046 (1994).
52. Lole, K. S. et al. Full-length human immunodeficiency virus type 1 genomes from subtype C-infected seroconverters in India, with evidence of intersubtype recombination. J Virol 73, 152-160 (1999).
53. Vaughn, E. M., Halbur, P. G. & Paul, P. S. Sequence comparison of porcine respiratory coronavirus isolates reveals heterogeneity in the S, 3, and 3-1 genes. J Virol 69, 3176-3184 (1995).
54. Koren, G., S. Wing, S. Knowles, and E. Phillips. 2003. Ribavirin in the treatment of SARS: A new trick for an old drug? CMAJ. 168:1289-1292
55. Cinatl, J., B. Morgenstern, G. Bauer, P. Chandra, H. Rabenau, and H. W. Doerr. 2003. Glycyrrhizin, an active component of liquorice roots, and replication of SARS-associated coronavirus. Lancet 361:2045-2046.
56. Anand, K., J. Ziebuhr, P. Wadhwani, J. R. Mesters, and R. Hilgenfeld. 2003. Coronavirus main proteinase (3CLpro) structure: basis for design of anti-SARS drugs. Science 300:1763-1767.
57. Cinatl, J., B. Morgenstern, G. Bauer, P. Chandra, H. Rabenau, and H. W. Doerr. 2003. Treatment of BARS with human interferons. Lancet 362:293-294.
58. von Grotthuss, M., L. S. Wyrwicz, and L. Rychlewski. 2003. mRNA cap-1 methyltransferase in the SARS genome. Cell 113:701-702
59 Boivin, G., G. De Sarres, S. Cote, R. Gilca, Y. Abed, L. Rochette, M. G. Bergeron, and P. Dery. 2003. Human metapneumovirus infections in hospitalized children. Emerg. Infect. Dis. 9:634-640.

---

What is claimed is:

1. An isolated and/or recombinant nucleic acid sequence comprising a nucleic acid sequence at least 95% homologous to the entire sequence of SEQ ID NO: 55.

2. An isolated and/or recombinant nucleic acid sequence comprising a stretch of 100 consecutive nucleotides of the isolated and/or recombinant nucleic acid sequence of claim 1.

3. An isolated and/or recombinant nucleic acid sequence according to claim 1, encoding a proteinaceous molecule.

4. An isolated and/or recombinant virus comprising a nucleic acid sequence at least 95% homologous to the entire sequence of SEQ ID NO: 55.

5. The isolated and/or recombinant virus of claim 4, wherein said isolated and/or recombinant virus is capable of inducing a HCoV-NL63- related disease in a subject.

6. A vector comprising the isolated and/or recombinant nucleic acid sequence of claim 1.

7. A composition comprising the isolated and/or recombinant virus of claim 4 and a pharmaceutically acceptable carrier or excipient.

8. An isolated cell comprising the isolated and/or recombinant virus of claim 4.

9. The cell of claim 8, wherein said cell is a primate cell.

10. The cell of claim 8, wherein said cell is a kidney cell.

11. The cell of claim 9, wherein said cell is a monkey cell.

12. A gene delivery vehicle comprising the isolated and/or recombinant nucleic acid sequence of claim 1.

13. The isolated and/or recombinant virus of claim 4, wherein said isolated and/or recombinant virus has been attenuated.

14. An isolated and/or recombinant nucleic acid sequence comprising the entire sequence of SEQ ID NO: 55.

15. An isolated and/or recombinant nucleic acid sequence comprising a stretch of 100 consecutive nucleotides of the isolated and/or recombinant nucleic acid sequence of claim 14.

16. An isolated and/or recombinant nucleic acid sequence according to claim 14, wherein said sequence encodes a proteinaceous molecule.

17. An isolated and/or recombinant virus comprising the nucleic acid sequence of SEQ ID NO: 55.

18. The isolated and/or recombinant virus of claim 17, wherein said isolated and/or recombinant virus is capable of inducing a HCoV-NL63- related disease in a subject.

19. A vector comprising the isolated and/or recombinant nucleic acid sequence of claim 14.

20. A composition comprising the isolated and/or recombinant virus of claim 17, and a pharmaceutically acceptable carrier or excipient.

21. An isolated cell comprising the isolated and/or recombinant virus of claim 17.

22. The cell of claim 21, wherein said cell is a primate cell.

23. The cell of claim 21, wherein said cell is a kidney cell.

24. The cell of claim 22, wherein said cell is a monkey cell.

25. A gene delivery vehicle comprising the isolated and/or recombinant nucleic acid sequence of claim 14.

26. The isolated and/or recombinant virus of claim 17, wherein said isolated and/or recombinant virus has been attenuated.

* * * * *

UNITED STATES PATENT AND TRADEMARK OFFICE
CERTIFICATE OF CORRECTION

| | | |
|---|---|---|
| PATENT NO. | : 7,803,918 B2 | Page 1 of 1 |
| APPLICATION NO. | : 10/922232 | |
| DATED | : September 28, 2010 | |
| INVENTOR(S) | : Cornelia Maria van der Hoek | |

It is certified that error appears in the above-identified patent and that said Letters Patent is hereby corrected as shown below:

Title Page:

Item (75) Inventor:

Now reads: "Cornelia van der Hoek"

Should read: --Cornelia Maria van der Hoek--

Signed and Sealed this
Twenty-sixth Day of April, 2011

David J. Kappos
*Director of the United States Patent and Trademark Office*